(12) United States Patent
Osada

(10) Patent No.: US 11,510,915 B2
(45) Date of Patent: *Nov. 29, 2022

(54) ANTI-TUMOR EFFECT POTENTIATOR USING NOVEL BIPHENYL COMPOUND

(71) Applicant: TAIHO PHARMACEUTICAL CO., LTD., Tokyo (JP)

(72) Inventor: Akiko Osada, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/616,826

(22) PCT Filed: May 25, 2018

(86) PCT No.: PCT/JP2018/020101
§ 371 (c)(1),
(2) Date: Nov. 25, 2019

(87) PCT Pub. No.: WO2018/216795
PCT Pub. Date: Nov. 29, 2018

(65) Prior Publication Data
US 2021/0177826 A1    Jun. 17, 2021

(30) Foreign Application Priority Data
May 26, 2017    (JP) .............................. JP2017-104841

(51) Int. Cl.
| A61K 31/46 | (2006.01) |
| A61K 33/243 | (2019.01) |
| A61K 31/40 | (2006.01) |
| A61P 35/04 | (2006.01) |
| A61K 45/06 | (2006.01) |

(52) U.S. Cl.
CPC .............. *A61K 31/46* (2013.01); *A61K 31/40* (2013.01); *A61K 33/243* (2019.01); *A61K 45/06* (2013.01); *A61P 35/04* (2018.01)

(58) Field of Classification Search
CPC ..................................................... A61K 31/46
USPC ....................................................... 514/299
See application file for complete search history.

(56) References Cited

U.S. PATENT DOCUMENTS

| 6,933,315 | B2* | 8/2005 | Wang ..................... C07H 19/23 514/414 |
| 8,048,888 | B2* | 11/2011 | Wosikowski-Buters .................... A61K 31/555 514/266.4 |
| 8,455,477 | B2* | 6/2013 | Katz .......... A61P 3/10 514/210.18 |
| 9,834,521 | B2* | 12/2017 | Zech ..................... C07D 403/14 |
| 10,723,742 | B2* | 7/2020 | Yamashita ........... A61K 31/438 |
| 2006/0110383 | A1 | 5/2006 | Honjo et al. |
| 2012/0142028 | A1 | 6/2012 | Richardson et al. |
| 2012/0201832 | A1 | 8/2012 | Eckhardt et al. |
| 2013/0035377 | A1 | 2/2013 | Minucci et al. |
| 2013/0231342 | A1 | 9/2013 | Munoz et al. |
| 2016/0024024 | A1* | 1/2016 | Zech ..................... C07D 243/08 540/542 |
| 2016/0257662 | A1 | 9/2016 | McCall et al. |

FOREIGN PATENT DOCUMENTS

| EP | 3381896 A1 | 10/2018 |
| JP | 2012506238 A1 | 3/2012 |
| JP | 2012524280 A1 | 10/2012 |
| JP | 2013525318 A | 6/2013 |
| JP | 2013535460 A1 | 9/2013 |
| JP | 2016531121 A1 | 10/2016 |
| WO | 2004004771 A1 | 1/2004 |
| WO | 2010077624 A1 | 7/2010 |
| WO | 2014151761 A1 | 9/2014 |
| WO | 2015089192 A1 | 6/2015 |
| WO | 2015103060 A1 | 7/2015 |
| WO | 2015168466 A1 | 11/2015 |
| WO | 2016007727 A1 | 1/2016 |
| WO | 2016029262 A | 3/2016 |
| WO | 2016037005 A1 | 3/2016 |

(Continued)

OTHER PUBLICATIONS

Sundaresan, Protein Science (2002), 11:1330-1339. Published by Cold Spring Harbor Laboratory Press. 2002.*
Venkatesh, J. Pharm. Sci. 89, 145-154 (2000) (p. 146.*
J. G. Cannon, Chapter Nineteen in Burger's Medicinal Chemistry and Drug Discovery, Fifth Edition, vol. I: Principles and Practice, Wiley-Interscience 1995, pp. 783-802.*
Lynch , Expert Opinion on Therapeutic Targets, 2012, 16:12, 1239-1249.*
Simone, Oncology: Introduction, Cecil Textbook of Medicine, 20th Edition, 1996 vol. 1, pp. 1004-1010.*

(Continued)

*Primary Examiner* — Nizal S Chandrakumar
(74) *Attorney, Agent, or Firm* — Rothwell, Figg, Ernst & Manbeck, P.C.

(57) ABSTRACT

An antitumor formulation comprising a biphenyl compound having LSD1 inhibitory activity or a salt thereof and one or more other antitumor agents that are administered in combination, the compound being represented by Formula (I):

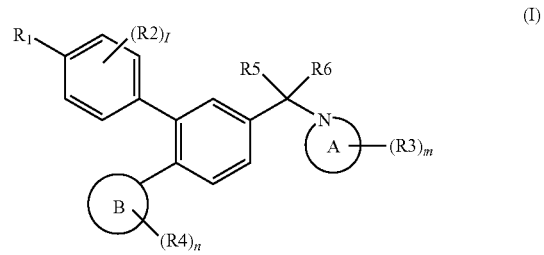

wherein ring A, ring B, R1 to R6, l, m, and n are as defined in the specification.

8 Claims, No Drawings

(56) References Cited

FOREIGN PATENT DOCUMENTS

| | | |
|---|---|---|
| WO | 2017013061 A1 | 1/2017 |
| WO | 2017090756 A1 | 6/2017 |
| WO | 2018216795 A1 | 11/2018 |
| WO | 2018216800 A1 | 11/2018 |
| WO | 2018221555 A1 | 12/2018 |

OTHER PUBLICATIONS

Amente et al., "The histone LSD1 demethylase in stemness and cancer transcription programs", Biochimica et Biophysica Acta, 2013, vol. 1829, No. 10, pp. 981-986.
Maes et al., "KDM1 histone lysine demethylases as targets for treatments of oncological and neurodegenerative disease", Epigenomics, 2015, vol. 7, No. 4, pp. 609-626.
Harris et al., "The Histone Demethylase KDM1A Sustains the Oncogenic Potential of MLL-AF9 Leukemia Stem Cells", Cancer Cell, 2012, vol. 21, No. 4, pp. 473-487.
Mohammad et al., A DNA Hypomethylation Signature Predicts Antitumor Activity of LSD1 Inhibitors in SCLC, Cancer Cell, 2015, vol. 28, No. 1, pp. 57-69.
Hill et al., "Inhibition of LSD1 reduces herpesvirus infection, shedding, and recurrence by promoting epigenetic suppression of viral genomes", Science Translational Medicine, 2014, vol. 6, No. 265, 265ra169.
Shi et al., "Lysine-specific demethylase 1 is a therapeutic target for fetal hemoglobin induction", Nature Medicine, 2013, vol. 19, No. 3, pp. 291-294.
Kawagishi et al., "TPC-144, a novel reversible LSD1 inhibitor, exhibited strong antitumor activity in preclinical models of AML and SCLC", The European Journal of Cancer , 2016, vol. 68, Supplment 1, pp. S86-S87, 258.
Singh et al., Inhibition of LSD1 sensitizes glioblastoma cells to histone deachthlase inhibitors, Neuro-Oncology, 2011, vol. 13, No. 8, pp. 894-903.
Fiskus et al., Highly effective combination of LSD1 (KDM1A) antagonist and pan-histone deacetylase inhibitor against human AML cells, Leukemia, 2014, vol. 28, No. 11, pp. 2155-2164.
Rosenbaum, "A Novel Immunohistochemical and Molecular Maker for Neuroendocrine and Neuroepithelial Neoplasms", American Journal of Clinical Pathlogy, 2015, vol. 144, No. 4, pp. 579-591.
Takagi, "LSD1 Inhibitor T-3775440 Inhibits SCLC Cell Proliferation by Disrupting LSD1 Interactions with Snag Domain Proteins INSM1 and GFI1B", Cancer Research, 2017, vol. 77, No. 17, pp. 4652-4662.
Breslin et al., "Neuroendocrine differentiation factor, IA-1, is a transcriptional repressor and contains a specific DNA-binding domain: identification of consensus IA-1 binding sequence", Nucleic Acids Research, 2002, vol. 30, No. 4.
Lan et al., "Structure, expression, and biological function of INSM1 transcription factor in neuroendocrine differentiation", FASEB Journal, 2009, 23(7): 2024-2033.
Lin et al., "Requirement of the Histone Demethylase LSD1 in Snai1-mediated Transcriptional Repression during Epithelial-Mesenchymal Transition", Oncogene, 2010, 29(35): 4896-4904.
Saleque et al., "Epigenetic Regulation of Hematopoietic Differentiation by Gfi-1 and Gfi-1b is Mediated by the Cofactors CoREST and LSD1", Molecular Cell, 2007, 27(49), 562-572.
Welcker et al., "Insm1 controls development of pituitary endocrine cells and requires a SNAG domain for function and for recruitment of histone-modifying factors", Development, 2013, 140(24), 4947-4958.
Lan et al., "IA-1, a New Marker for Neuroendocrine Differentiation in Human Lung Cancer Cell Lines", Cancer Research, 1993, 53(18), 4169-4171.
Crombie et al., "Synthesis and evaluation of azabicyclo [3.2. 1] octane derivatives as potent mixed vasopressin antagonists", Bioorganic & Medicinal Chemistry Letters, 20 (2010), pp. 3742-3745.

First Examination Report for the corresponding IN patent application No. 201817022113, dated Jul. 29, 2019, 6 pgs.
Wu et al., 3-(Piperidin-4-ylmethoxy)pyridine Containing Compounds are Potent Inhibitors of Lysine Specific Demethylase 1, Journal of Medicinal Chemistry, 2016, vol. 59, No. 1, pp. 253-263.
Ye et al., "The LSD1 inhibitor INCB059872 is synergistic with ATRA in models of non-APL acute myelogenous leukemia", Cancer Research 76(14 Suppl), Abstract 4696, 2016.
Maiques-Diaz et al.,"LSD1: biolojic roles and therapeutic targeting", Epigenomics, 2016, 8(8), pp. 1103-1116.
Wang et al., "Identification of an INSM1-binding site in the insulin promoter:negative regulation of the insulin gene transcription", J. Endocrinol 2008, 198(1), pp. 29-39.
Official Action of the corresponding RU Patent Application No. 2019144056.
Santa Cruz Biotechnology Inc., INSM1 (A-8): sc-271408, 2015, 1 page.
Extended European Search Report for European Patent Application No. 18809220.9 dated Jan. 27, 2021, 7 pages.
Sergeev, "Short Course of Molecular Pharmacology", 1975, p. 10, 4 pages (Machine Translation).
Kholodov et al., Clinical Pharmacokinetics, 1985, pp. 83-98, 134-138, 160, 378-380, 52 pages (Machine Translation).
Russian Office Action issued in 2019144056 dated Dec. 8, 2021 with translation (11 pages).
ClinicalTrials.gov Identifier: NCT02177812, Jun. 28, 2019, Retrieved from the internet:<URL:https://clinicaltrials.gov/ct2/show/study/NCT02177812>, A Phase I Dose Escalation Study of GSK2879552 in Subjects With Acute Myeloid Leukemia (AML), 17 pages.
Somervaille et al., Safety, Phamacokinetics (PK), Pharmacodynamics (PD) and Preliminary Activity in Acute Leukemia of Ory-1001, a First-in-Class Inhibitor of Lysine-Specific Histone Demethylase 1A (LSD1/KDM1A): Initial Results from a First-in Human Phase 1 Study, Blood, 2016, 128 (22): 4060.
ClinicalTrials.gov Identifier: NCT03132324, Apr. 27, 2017, Retrieved from the internet <URL:https://clinicaltrials.gov/ct2/show/study/NCT03132324>, A Study to Evaluate Safety, Pharmacokinetic, and Biological Activity of INCB059872 in Subjects With Sickle Cell Disease, 7 pages.
Hollebecque et al., Phase I study of CC-90011 in patients with advanced solid tumours (STs) and relapsed/refractory non-hodgkin lymphoma (R/R NHL), Annals of Oncology, vol. 30, Issue Supplement_5, 2019, mdz256.003, https://doi.org/10.1093/annonc/mdz256.003, 1 page.
Japanese Journal of Clinical Medicine, Recent Advances Science and Care of Leukemia (II), 74(extra No. 10 (1112)), 2016, pp. 100-104.
Russo et al., "All-trans retinoic acid (ATRA) in patients with chronic myeloid leukemia in the chronic phase", Leukemia, 1998, 12, pp. 449-454.
Database EMBASE on STN, AN 0050300062, DN 70306324, Haematologica, 2010, vol. 95, Supp. SUPPL. 2. pp. 58. Abstract No. 0143, 13 pages.
International Search Report of PCT/JP2020/042410, dated Jan. 19, 2021, 10 pages.
Fang et al., "LSD1/KDM1A inhibitors in clinical trials:advances and prospects", J. Hematol. Oncol., 2019, 12: 129.
Majello et al., "Expanding the Role of the Histone Lysine-SpecificDemethylase LSD1 in Cancer", Cancers (Basel), 2019, 11, 324.
Chen et al., "Lysine-specific histone demethylase 1 (LSD1): A potential molecular target for tumor therapy", Crit. Rev. Eukaryot. Gene Expr, 22(1): 53-59, 2012.
Zhang et al., "Targeting LSD1 for acute myeloid leukemia (AML) treatment", Pharmacol. Res, 164, 2021, 105335.
Topalian et al., "Safety, Activity, and Immune Correlates of Anti-PD-1 Antibody in Cancer", N. Engl. J. Med., 2012, vol. 366, No. 26, pp. 2443-2454.
ClinicalTrials.gov Identifier: NCT02959437, Nov. 9, 2016, Retrieved from the internet:<URL:http://www.clinicaltrials.gov/ct2/show/NCT02959437[retrieved on Jan. 4, 2021], Azacitidine Combined with Pembrolizumab and Epacadostat in Subjects with Advanced Solid Tumors (Echo-206), 13 pages.

(56) References Cited

OTHER PUBLICATIONS

Sundaresan, "Towards a general model for protein-substrate stereoselectivity", Protein Science (2002), 11:1330-1339. Published by Cold Spring Harbor Laboratory Press. 2002.
Venkatesh, "Role of the Development Scientist in Compound Lead Selection and Optimization" J. Pharm. Sci. 89, 145-154 (2000) p. 146.
J. G. Cannon, "Analog Design", Chapter Nineteen in Burger's Medicinal Chemistry and Drug Discovery, Fifth Edition, vol. I: Principles and Practice, Wiley-Interscience 1995, pp. 783-802.
Lynch, "LSD1 inhibition: a therapeutic strategy in cancer?", Expert Opinion on Therapeutic Targets, 2012, 16:12, 1239-1249.
Non-final office action issued in U.S. Appl. No. 16/616,826 dated Dec. 2, 2021, 25 pages.

\* cited by examiner

ANTI-TUMOR EFFECT POTENTIATOR USING NOVEL BIPHENYL COMPOUND

CROSS REFERENCE TO RELATED APPLICATION

This application is a 35 U.S.C. 371 National Phase Entry Application from PCT/JP2018/020101, filed May 25, 2018, which claims the benefit of Japanese Patent Application No. 2017-104841 filed on May 26, 2017 the disclosures of which are incorporated herein in their entirety by reference.

TECHNICAL FIELD

The present invention relates to an antitumor formulation comprising a combination of a biphenyl compound or a salt thereof and one or more other antitumor agents, and an antitumor effect potentiator for the one or more other antitumor agents.

BACKGROUND ART

Histone methylation modification is one of the epigenetic mechanisms, which regulate gene expressions. Histone methylation modification regulates various processes including cellular maintenance, growth, and differentiation.

LSD1 (KDM1A), one of the enzymes that regulate histone methylation modification, is an FAD (flavin adenine dinucleotide)-dependent histone demethylase, and mainly demethylates the lysine residue at position 4 (K4) and the lysine residue at position 9 (K9) on histone H3 (Non-patent Literature (NPL) 1). With such functions, LSD1 is believed to positively or negatively regulate various gene transcriptions, and regulate stem cell self-renewal and cell differentiation in each normal tissue.

In general, abnormalities in cell self-renewal capacity or differentiation are believed to lead to cell cancerization. Thus, aberrant control of LSD1, which plays a key role in these processes, can possibly cause cell cancerization. In fact, in terms of various solid and blood cancers, many reports have been made regarding the correlation of overexpression of LSD1 and their prognosis (NPL 2). Further, in cell lines from carcinomas or in non-clinical models, LSD1 inhibition has been reported to have resulted in induction of cellular differentiation, growth inhibition, and an in vivo antitumor effect (NPL 3 and NPL 4), which strongly suggests that LSD1 serves as one of the important target molecules in cancer therapy. These carcinomas in which LSD1 is involved, such as small-cell lung cancer (SCLC) and acute myelocytic leukemia (AML), have an extremely short lifetime, and existing therapeutic methods cannot achieve a satisfactory therapeutic effect.

Accordingly, LSD1 inhibitory drugs are expected to provide effective therapeutic means based on novel mechanisms to treat intractable cancers, for which no therapeutic methods currently exist.

Further, according to some reports, LSD1, which is involved in neuron programs and functions, can also possibly serve as a target in the treatment of diseases other than cancers, such as Alzheimer's disease, Huntington's disease, Rett syndrome, and other cranial nerve diseases (NPL 2); Herpesvirus infections, in which LSD1 function has been implicated (NPL 5); and sickle cell diseases (NPL 6).

There are some reports regarding antitumor effects of combinations of LSD1 inhibitors with other antitumor agents. For example, an antitumor effect of a combination of LSD1 inhibitor SP2509 with histone deacetylase inhibitor panobinostat on acute myelocytic leukemia has been reported (NPL 7). In addition, an antitumor effect of a combination of LSD1 inhibitor INCB059872 with all-trans retinoic acid (ATRA) on acute myelocytic leukemia has been reported (NPL 8).

CITATION LIST

Non-Patent Literature

NPL 1: Biochim. Biophys. Acta, 1829 (10), pp. 981-986 (2013)
NPL 2: Epigenomics, 7 (4), pp. 609-626 (2015)
NPL 3: Cancer Cell, 21 (4), pp. 473-487 (2012)
NPL 4: Cancer Cell, 28 (1), pp. 57-69 (2015)
NPL 5: Sci. Transl. Med., 6 (265), 265ra169 (2014)
NPL 6: Nat. Med., 19 (3), pp. 291-294 (2013)
NPL 7: Leukemia, 28(11), pp. 2155-2164 (2014)
NPL 8: Cancer Res., 74 (14 Suppl) Abstract, 4696 (2016)

SUMMARY OF INVENTION

Technical Problem

An object of the present invention is to provide a method for potentiating an antitumor effect using a compound or a salt thereof that potently inhibits LSD1.

Solution to Problem

The present inventors conducted extensive research to achieve the above object, and found that a compound represented by the following Formula (I) or a salt thereof has excellent antitumor effect potentiating action in combined use with one or more other compounds having an antitumor effect (other antitumor agents). The present invention has been accomplished based on this finding.

More specifically, the present invention provides the following:

Item 1. An antitumor formulation comprising a biphenyl compound represented by Formula (I) or a salt thereof and one or more other antitumor agents that are administered in combination:

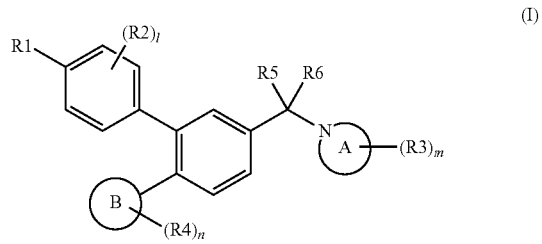

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;

R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl) oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.
Item 2. The antitumor formulation according to Item 1, wherein the biphenyl compound satisfies the following conditions in Formula (I):
ring A represents pyrrolidinyl, piperidinyl, piperazinyl, azepanyl, diazepanyl,

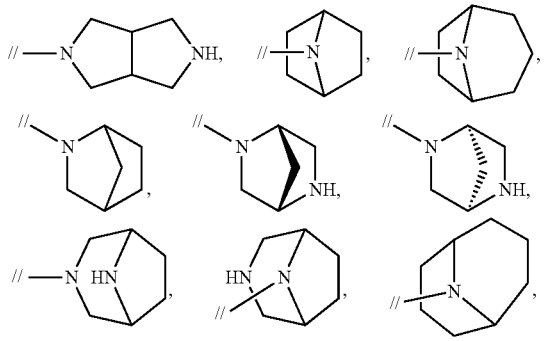

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl;
ring B represents phenyl, naphthyl, pyridyl, pyrazolopyridyl, pyrazolopyrimidinyl, indolyl, indolinyl, 2-oxo-indolinyl, indazolyl, benzoimidazolyl, benzoisoxazolyl, benzothiazolyl, benzotriazolyl, imidazopyridinyl, quinolinyl, isoquinolinyl, quinazolinyl, quinoxalinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl;
R1 represents nitro or cyano;
R2 represents fluorine, and is present at the ortho position relative to R1 on the phenyl;
R3 represents amino, methylamino, ethylamino, isopropylamino, dimethylamino, cyclobutylamino, or methyl (when two or more R3s are present, R3s may be identical or different);
R4 represents fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropyl, phenylcarbamoyl cyclopropyl, benzyloxy, dimethylamino, carbamoyl, methylcarbamoyl, or dimethylcarbamoyl (when two or more R4s are present, R4s may be identical or different);
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
n represents an integer of 0 to 3; and
when n is 2 to 3, two to three R4s may be identical or different.
Item 3. The antitumor formulation according to Item 1 or 2, wherein the biphenyl compound is selected from the following (1) to (7):
(1) 4-[5-[(3S)-3-aminopyrrolidine-1-carbonyl]-2-[2-fluoro-4-(2-hydroxy-2-methyl-propyl)phenyl]phenyl]-2-fluoro-benzonitrile;
(2) 4-[5-[(3-endo)-3-amino-8-azabicyclo[3.2.1]octane-8-carbonyl]-2-[2-fluoro-4-(2-hydroxy-2-methyl-propyl) phenyl]phenyl]-2-fluoro-benzonitrile;
(3) 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile-isomer-B;
(4) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
(5) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
(6) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X;
(7) 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.
Item 4. The antitumor formulation according to any one of Items 1 to 3, wherein the one or more other antitumor agents are at least one member selected from antimetabolites, antitumor antibiotics, molecular target drugs, platinum-based drugs, and plant alkaloid-based drugs.

Item 5. The antitumor formulation according to any one of Items 1 to 3, wherein the one or more other antitumor agents are at least one member selected from cytarabine, azacitidine, decitabine, guadecitabine, daunorubicin, tretinoin (ATRA), RG7388, carboplatin, cisplatin, paclitaxel, irinotecan (SN-38), and etoposide.

Item 6. An antitumor effect potentiator for one or more other antitumor agents, the antitumor effect potentiator comprising as an active ingredient a biphenyl compound represented by Formula (I) or a salt thereof:

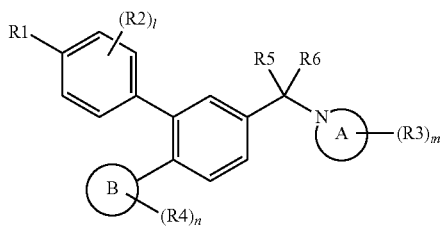

(I)

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl) oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 7. An antitumor agent comprising a biphenyl compound or a salt thereof for treating a cancer patient administered one or more other antitumor agents, wherein the biphenyl compound is represented by Formula (I):

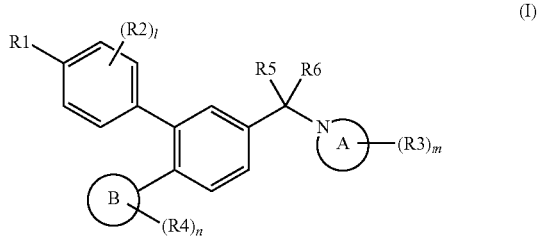

(I)

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl) oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;

when n is 2 to 5, two to five R4s may be identical or different.

Item 8. An antitumor formulation comprising a combination of a biphenyl compound or a salt thereof and one or more other antitumor agents, wherein the biphenyl compound is represented by Formula (I):

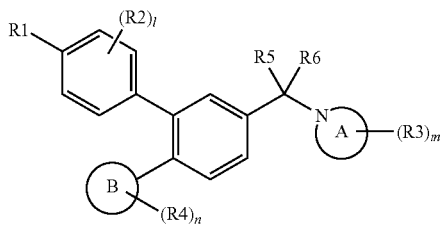

(I)

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 9. A pharmaceutical composition for the prevention and/or treatment of a tumor, the composition comprising a biphenyl compound represented by Formula (I) or a salt thereof and one or more other antitumor agents:

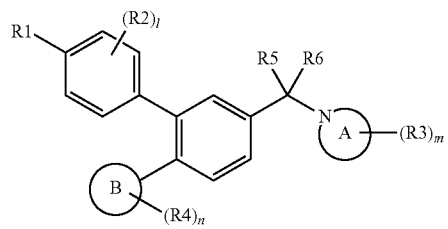

(I)

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 10. A biphenyl compound represented by Formula (I) or a salt thereof for potentiating an antitumor effect of one or more other antitumor agents:

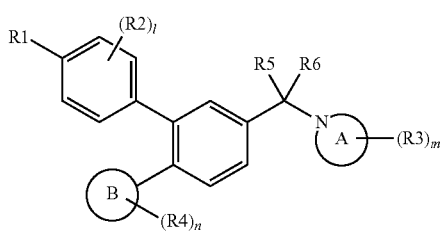

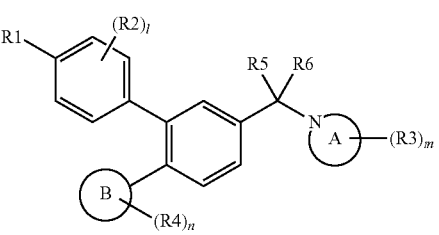

wherein ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;

ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;

R1 represents nitro or cyano;

R2 represents halogen;

R3 represents amino, mono- or di(C1-C6 alkyl)amino, (C3-C7 cycloalkyl)amino, or C1-C6 alkyl;

R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;

when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;

R5 and R6 may be identical or different, and each represent hydrogen or C1-C6 alkyl; R5 and R6 may otherwise form oxo or thioxo together;

when R5 and R6 are identical or different, and each represent hydrogen or C1-C6 alkyl, at least one of R5 and R6 is hydrogen;

l represents an integer of 0 to 2;

m represents an integer of 0 to 2;

n represents an integer of 0 to 5;

when l is 2, two R2s may be identical or different;

when m is 2, two R3s may be identical or different;

when n is 2 to 5, two to five R4s may be identical or different.

Item 11. Use of a biphenyl compound represented by Formula (I) or a salt thereof for potentiating an antitumor effect of one or more other antitumor agents:

Item 12. Use of a biphenyl compound represented by Formula (I) or a salt thereof for the production of an antitumor effect potentiator for one or more other antitumor agents:

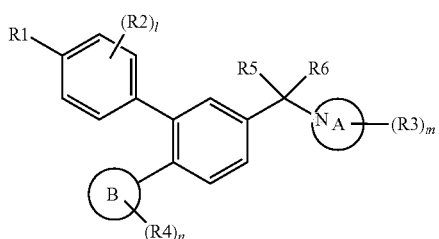 (I)

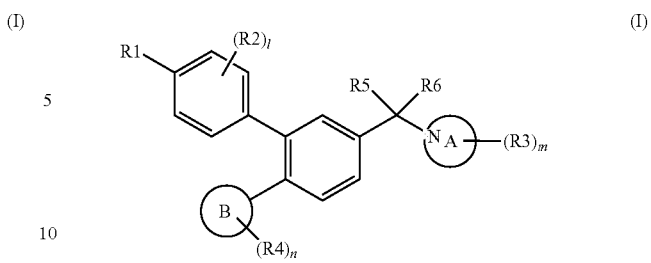 (I)

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 13. A method for preventing and/or treating a tumor, comprising administering a combination of a biphenyl compound represented by Formula (I) or a salt thereof and one or more other antitumor agents in an amount effective for prevention and/or treatment to a patient:

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 14. A method for preventing and/or treating a tumor, comprising administering a biphenyl compound represented by Formula (I) or a salt thereof in an amount effective for prevention and/or treatment to a cancer patient administered one or more other antitumor agents:

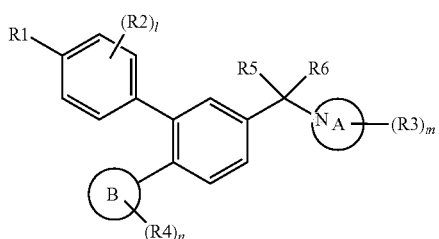 (I)

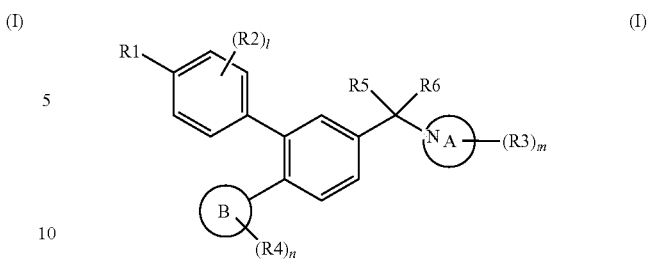 (I)

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl) oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 15. A method for potentiating an antitumor effect, comprising administering a biphenyl compound represented by Formula (I) or a salt thereof in an amount effective for prevention and/or treatment to a cancer patient administered one or more other antitumor agents:

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl) oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l represents an integer of 0 to 2;
m represents an integer of 0 to 2;
n represents an integer of 0 to 5;
when l is 2, two R2s may be identical or different;
when m is 2, two R3s may be identical or different;
when n is 2 to 5, two to five R4s may be identical or different.

Item 16. A product as a combined preparation to be used simultaneously, sequentially, or at an interval upon prevention and/or treatment of a tumor, the product comprising a biphenyl compound or a salt thereof and one or more other antitumor agents, wherein the biphenyl compound is represented by Formula (I):

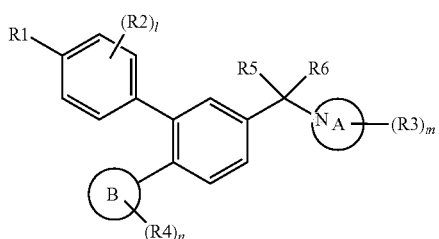
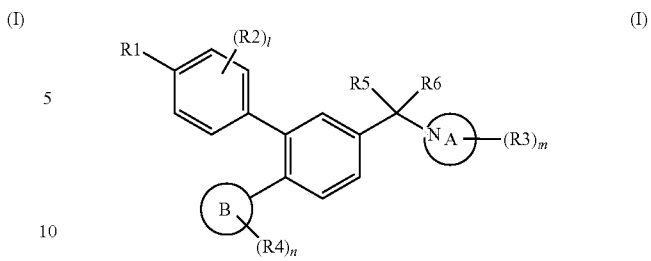

wherein ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;

ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;

R1 represents nitro or cyano;

R2 represents halogen;

R3 represents amino, mono- or di(C1-C6 alkyl)amino, (C3-C7 cycloalkyl)amino, or C1-C6 alkyl;

R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;

when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;

R5 and R6 may be identical or different, and each represent hydrogen or C1-C6 alkyl; R5 and R6 may otherwise form oxo or thioxo together;

when R5 and R6 are identical or different, and each represent hydrogen or C1-C6 alkyl, at least one of R5 and R6 is hydrogen;

l represents an integer of 0 to 2;

m represents an integer of 0 to 2;

n represents an integer of 0 to 5;

when l is 2, two R2s may be identical or different;

when m is 2, two R3s may be identical or different;

when n is 2 to 5, two to five R4s may be identical or different.

Item 17. A combination of a biphenyl compound represented by Formula (I) or a salt thereof and one or more other antitumor agents:

wherein ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;

ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;

R1 represents nitro or cyano;

R2 represents halogen;

R3 represents amino, mono- or di(C1-C6 alkyl)amino, (C3-C7 cycloalkyl)amino, or C1-C6 alkyl;

R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;

when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;

R5 and R6 may be identical or different, and each represent hydrogen or C1-C6 alkyl; R5 and R6 may otherwise form oxo or thioxo together;

when R5 and R6 are identical or different, and each represent hydrogen or C1-C6 alkyl, at least one of R5 and R6 is hydrogen;

l represents an integer of 0 to 2;

m represents an integer of 0 to 2;

n represents an integer of 0 to 5;

when l is 2, two R2s may be identical or different;

when m is 2, two R3s may be identical or different;

when n is 2 to 5, two to five R4s may be identical or different.

Advantageous Effects of Invention

The present invention enables cancer therapy that achieves an excellent antitumor effect while suppressing occurrence of side effects.

DESCRIPTION OF EMBODIMENTS

In the present invention, the LSD1 inhibitor that provides excellent synergism with one or more other antitumor agents is a biphenyl compound represented by the following Formula (I) or a salt thereof.

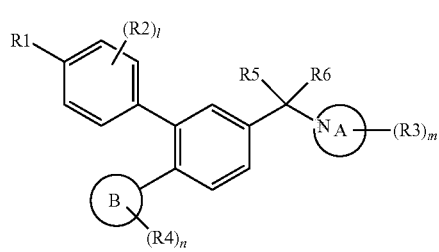

wherein ring A, ring B, R1 to R6, l, m, and n are as defined above.

In the present specification, unless otherwise specified, examples of the "substituent" include halogen, hydroxy, cyano, nitro, alkyl, hydroxyalkyl, halogenoalkyl, cycloalkyl, hydroxycycloalkyl, cycloalkyl-alkyl, aralkyl, alkenyl, alkynyl, alkoxy, halogenoalkoxy, cycloalkoxy, cycloalkyl-alkoxy, unsaturated hydrocarbon ring-alkoxy, alkylthio, cycloalkyl-alkylthio, amino, mono- or di-alkylamino, cycloalkylamino, cycloalkyl-alkylamino, acyl, acyloxy, oxo, carboxy, alkoxycarbonyl, aralkyloxycarbonyl, carbamoyl that may be substituted with an unsaturated hydrocarbon ring, saturated or unsaturated heterocyclic group, unsaturated hydrocarbon ring (e.g., aromatic hydrocarbon), saturated heterocyclic oxy, and the like. The number of the substituents, when present, is typically one, two, or three.

In the present specification, examples of the "halogen" include fluorine, chlorine, bromine, iodine, and the like, with fluorine, chlorine, bromine, or iodine being preferable, and fluorine or chlorine being more preferable.

In the present specification, the "alkyl" may be straight or branched. Examples include C1-C6 alkyl, such as methyl, ethyl, n-propyl, isopropyl, n-butyl, isobutyl, sec-butyl, tert-butyl, n-pentyl, isopentyl, tert-pentyl, and n-hexyl.

In the present specification, examples of the "hydroxyalkyl" include the above-listed alkyl groups that have at least one hydroxy group (e.g., one or two hydroxy groups). Specific examples include hydroxymethyl, 2-hydroxyethyl, 1-hydroxyethyl, 3-hydroxypropyl, 2-hydroxypropyl, 1-methyl-2-hydroxyethyl, 4-hydroxybutyl, 2,2-dimethyl-2-hydroxyethyl, 5-hydroxypentyl, 3,3-dimethyl-3-hydroxypropyl, 6-hydroxyhexyl, dihydroxymethyl, 1,2-dihydroxyethyl, 2,3-dihydroxypropyl, 3,4-dihydroxybutyl, 4,5-dihydroxypentyl, 5,6-dihydroxyhexyl, and the like, with hydroxyalkyl having one hydroxy group being preferable.

In the present specification, the "halogenoalkyl" is straight or branched C1-C6 alkyl having 1 to 13 halogen atoms (halogeno C1-C6 alkyl). Examples include halogeno C1-C6 alkyl, such as fluoromethyl, difluoromethyl, trifluoromethyl, trichloromethyl, fluoroethyl, 1,1,1-trifluoroethyl, monofluoro-n-propyl, perfluoro-n-propyl, and perfluoroisopropyl, with halogeno C1-C4 alkyl being preferable, and halogeno C1-C4 alkyl having 1 to 7 halogen atoms being more preferable.

In the present specification, specific examples of the "cycloalkyl" include C3-C7 cycloalkyl, such as cyclopropyl, cyclobutyl, cyclopentyl, cyclohexyl, and cycloheptyl.

In the present specification, examples of the "hydroxycycloalkyl" include the above-listed C3-C7 cycloalkyl groups that have at least one hydroxy group (e.g., one or two hydroxy groups). Specific examples include 1-hydroxycyclopropyl, 2-hydroxycyclopropyl, 1-hydroxycyclobutyl, 3-hydroxycyclobutyl, 1-hydroxycyclopentyl, 3,4-dihydroxycyclopentyl, 1-hydroxycyclohexyl, 4-hydroxycyclohexyl, 1-hydroxycycloheptyl, and the like, with hydroxycycloalkyl having one hydroxy group being preferable.

In the present specification, examples of the "cycloalkyl-alkyl" include C3-C7 cycloalkyl-substituted C1-C4 alkyl, such as cyclopropylmethyl, cyclobutylmethyl, cyclopentylmethyl, cyclohexylmethyl, and cycloheptylmethyl.

In the present specification, examples of the "aralkyl" include C7-C13 aralkyl, such as benzyl, phenethyl, naphthylmethyl, and fluorenylmethyl.

In the present specification, the "alkenyl" may be straight, branched, or cyclic, and refers to unsaturated hydrocarbon having at least one double bond (e.g., one or two double bonds). Examples include C2-C6 alkenyl, such as vinyl, allyl, 1-propenyl, 2-methyl-2-propenyl, isopropenyl, 1-butenyl, 2-butenyl, 3-butenyl, isobutenyl, 2-pentenyl, 3-pentenyl, 4-pentenyl, 2-methyl-2-butenyl, 3-methyl-2-butenyl, 5-hexenyl, 1-cyclopentenyl, 1-cyclohexenyl, and 3-methyl-3-butenyl.

In the present specification, the "alkynyl" may be straight, branched, or cyclic, and refers to unsaturated hydrocarbon having at least one triple bond (e.g., one or two triple bonds). Examples include C2-C6 alkynyl, such as ethynyl, 1-propynyl, 2-propynyl, 1-butynyl, 2-butynyl, 3-butynyl, and 1-methyl-2-propynyl.

In the present specification, the "alkoxy" may be straight or branched. Examples include C1-C6 alkoxy, such as methoxy, ethoxy, n-propoxy, isopropoxy, n-butoxy, isobutoxy, sec-butoxy, tert-butoxy, pentyloxy, isopentyloxy, and hexyloxy.

In the present specification, the "halogenoalkoxy" refers to straight or branched C1-C6 alkoxy having 1 to 13 halogen atoms (halogeno C1-C6 alkoxy). Examples include halogeno C1-C6 alkoxy, such as fluoromethoxy, difluoromethoxy, trifluoromethoxy, trichloromethoxy, fluoroethoxy, 1,1,1-trifluoroethoxy, monofluoro-n-propoxy, perfluoro-n-propoxy, and perfluoro-isopropoxy, with halogeno C1-C4 alkoxy being preferable, and halogeno C1-C4 alkoxy having 1 to 7 halogen atoms being more preferable.

In the present specification, examples of the "cycloalkoxy" include C3-C7 cycloalkoxy, such as cyclopropoxy, cyclobutoxy, cyclopentyloxy, cyclohexyloxy, and cycloheptyloxy.

In the present specification, examples of the "cycloalkyl-alkoxy" include C3-C7 cycloalkyl-substituted C1-C4 alkoxy, such as cyclopropylmethoxy, cyclobutylmethoxy, cyclopentylmethoxy, cyclohexylmethoxy, and cycloheptylmethoxy.

In the present specification, the "alkylthio" may be straight or branched. Examples include C1-C6 alkylthio, such as methylthio, ethylthio, n-propylthio, isopropylthio, n-butylthio, isobutylthio, tert-butylthio, n-pentylthio, isopentylthio, and hexylthio.

In the present specification, examples of the "cycloalkyl-alkylthio" include C3-C7 cycloalkyl-substituted C1-C4 alkylthio, such as cyclopropylmethylthio, cyclobutylmethylthio, cyclopentylmethylthio, cyclohexylmethylthio, and cycloheptylmethylthio.

In the present specification, examples of the "monoalkylamino" include amino monosubstituted with straight or branched C1-C6 alkyl, such as methylamino, ethylamino, n-propylamino, isopropylamino, n-butylamino, isobutylamino, tert-butylamino, n-pentylamino, isopentylamino, and hexylamino.

In the present specification, examples of the "dialkylamino" include amino disubstituted with the same or different straight or branched C1-C6 alkyl groups, such as dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, and methylisopropylamino.

In the present specification, examples of the "cycloalkylamino" include amino having one or two cycloalkyl groups mentioned above. Specific examples include N-cyclopropylamino, N,N-dicyclopropylamino, N-cyclobutylamino, N-cyclopentylamino, N-cyclohexylamino, N-cycloheptylamino, and the like.

In the present specification, examples of the "cycloalkylalkylamino" include C3-C7 cycloalkyl-substituted C1-C4 alkylamino, such as cyclopropylmethylamino, cyclobutylmethylamino, cyclopentylmethylamino, cyclohexylmethylamino, and cycloheptylmethylamino.

In the present specification, the "acyl" refers to alkylcarbonyl or arylcarbonyl.

In the present specification, examples of the "alkylcarbonyl" include straight or branched (C1-C6 alkyl)carbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl.

In the present specification, examples of the "arylcarbonyl" include (C6-C13 aryl)carbonyl, such as phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl.

In the present specification, the "acylamino" refers to alkylcarbonylamino or arylcarbonylamino.

In the present specification, examples of the "alkylcarbonylamino" include straight or branched (C1-C6 alkyl)carbonylamino, such as methylcarbonylamino, ethylcarbonylamino, n-propylcarbonylamino, isopropylcarbonylamino, n-butylcarbonylamino, isobutylcarbonylamino, tert-butylcarbonylamino, n-pentylcarbonylamino, isopentylcarbonylamino, and hexylcarbonylamino.

In the present specification, examples of the "arylcarbonylamino" include (C6-C13 aryl)carbonylamino, such as phenylcarbonylamino, naphthylcarbonylamino, fluorenylcarbonylamino, anthrylcarbonylamino, biphenylylcarbonylamino, tetrahydronaphthylcarbonylamino, chromanylcarbonylamino, 2,3-dihydro-1,4-dioxanaphthalenylcarbonylamino, indanylcarbonylamino, and phenanthrylcarbonylamino.

In the present specification, the "acyloxy" refers to alkylcarbonyloxy or arylcarbonyloxy.

In the present specification, examples of the "alkylcarbonyloxy" include straight or branched (C1-C6 alkyl)carbonyloxy, such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy.

In the present specification, examples of the "arylcarbonyloxy" include (C6-C13 aryl)carbonyloxy, such as phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

In the present specification, the "alkoxycarbonyl" may be straight or branched. Examples include (C1-C6 alkoxy)carbonyl, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, and hexyloxycarbonyl.

In the present specification, examples of the "aralkyloxycarbonyl" include (C7-C13 aralkyl)oxycarbonyl, such as benzyloxycarbonyl, phenethyloxycarbonyl, naphthylmethyloxycarbonyl, and fluorenylmethyloxycarbonyl.

In the present specification, the "saturated heterocyclic group" refers to a monocyclic or polycyclic saturated heterocyclic group having one or more (preferably 1 to 3) heteroatoms selected from nitrogen, oxygen, and sulfur. Specific examples include morpholinyl, pyrrolidinyl, piperidinyl, piperazinyl, azepanyl, diazepanyl, tetrahydrofuranyl, tetrahydropyranyl, tetrahydrothiophenyl, thiazolidinyl, oxazolidinyl, and the like.

In the present specification, the "unsaturated heterocyclic group" refers to a monocyclic or polycyclic, completely or partially unsaturated heterocyclic group having one or more (preferably 1 to 3) heteroatoms selected from nitrogen, oxygen, and sulfur. Specific examples include imidazolyl, thienyl, furyl, pyrrolyl, oxazolyl, isoxazolyl, thiazolyl, isothiazolyl, thiadiazolyl, pyrazolyl, triazolyl, tetrazolyl, pyridyl, pyrazyl, pyrimidinyl, pyridazinyl, pyrazolopyridyl, pyrazolopyrimidinyl, indolyl, isoindolyl, indazolyl, triazolopyridyl, benzoimidazolyl, benzoxazolyl, benzoisoxazolyl, benzothiazolyl, benzothienyl, benzofuranyl, 1,3-dihydroisobenzofuranyl, purinyl, benzotriazolyl, imidazopyridinyl, quinolinyl, isoquinolinyl, quinazolinyl, quinoxalinyl, phthalazinyl, methylenedioxyphenyl, ethylenedioxyphenyl, dihydrobenzofuranyl, and the like.

In the present specification, examples of the "unsaturated hydrocarbon" include a monocyclic or polycyclic C5-14 hydrocarbon ring having at least one unsaturated bond (e.g., 1 to 8 unsaturated bonds), and the like. The "unsaturated hydrocarbon" is preferably aromatic hydrocarbon, or monocyclic or bicyclic 5- to 14-membered unsaturated hydrocarbon.

In the present specification, examples of the "aromatic hydrocarbon" include C6-C14 aromatic hydrocarbons, such as phenyl, naphthyl, anthracenyl, phenanthryl, fluorenyl, and tetrahydronaphthyl.

In the present specification, examples of the "monocyclic or bicyclic 5- to 14-membered unsaturated hydrocarbon" include cyclopentadienyl, phenyl, naphthyl, tetrahydronaphthyl, azulenyl, heptalenyl, and the like.

In the present specification, examples of the "monocyclic 5- to 10-membered unsaturated hydrocarbon" include cyclopentadienyl, phenyl, cyclooctatetraenyl, and the like.

In the present specification, the "saturated heterocyclic oxy" refers to saturated heterocyclic oxy having a heteroatom selected from nitrogen, oxygen, and sulfur. Specific examples include morpholinyloxy, 1-pyrrolidinyloxy, piperidinyloxy, piperazinyloxy, 4-methyl-1-piperazinyloxy, tetrahydrofuranyloxy, tetrahydropyranyloxy, tetrahydrothiophenyloxy, thiazolidinyloxy, and oxazolidinyloxy, with saturated heterocyclic oxy having 1 to 3 heteroatoms selected from nitrogen, oxygen, and sulfur being preferable.

In the present specification, the term "CA-CB" used in the description of a group indicates that the group has A- to B-number of carbon atoms. For example, "C1-C6 alkyl" refers to alkyl having 1 to 6 carbon atoms, and "C6-C14 aromatic hydrocarbon oxy" refers to oxy to which C6-C14 aromatic hydrocarbon is bonded. Further, the term "A- to B-membered" indicates that the number of atoms (number of ring members) that constitute a ring is A to B. For example, "4- to 10-membered nitrogen-containing saturated heterocyclic group" refers to a nitrogen-containing saturated heterocyclic group containing 4 to 10 ring members.

In the compound represented by Formula (I), ring A refers to a nitrogen-containing saturated heterocyclic group that may be crosslinked or spirocyclic. As shown in Formula (I) above, the nitrogen on ring A is bonded to carbonyl, carbothionyl or methylene.

Examples of the monocyclic nitrogen-containing saturated heterocyclic group in the "monocyclic, bridged cyclic, or spirocyclic nitrogen-containing saturated heterocyclic group" represented by ring A include monocyclic nitrogen-containing saturated heterocyclic groups, such as pyrrolidinyl, piperidinyl, piperazinyl, azepanyl, and diazepanyl. The monocyclic nitrogen-containing saturated heterocyclic group is preferably a monocyclic nitrogen-containing saturated heterocyclic group having 1 to 3 nitrogen atoms, 0 to 1 sulfur atoms, and 0 to 2 oxygen atoms as heteroatoms, more preferably a monocyclic nitrogen-containing saturated heterocyclic group having 1 to 2 nitrogen atoms as heteroatoms, more preferably a monocyclic 4- to 10-membered nitrogen-containing saturated heterocyclic group having 1 to 2 nitrogen atoms as heteroatoms, more preferably pyrrolidinyl, piperidinyl, piperazinyl, azepanyl, or diazepanyl, more preferably pyrrolidinyl, piperidinyl, azepanyl, or diazepanyl, more preferably pyrrolidinyl or diazepanyl, and more preferably pyrrolidinyl.

Examples of the bridged cyclic nitrogen-containing saturated heterocyclic group in the "monocyclic, bridged cyclic, or spirocyclic nitrogen-containing saturated heterocyclic group" represented by ring A include

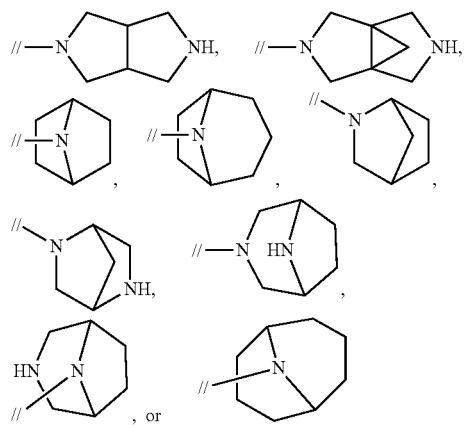

and the like. The bridged cyclic nitrogen-containing saturated heterocyclic group is preferably

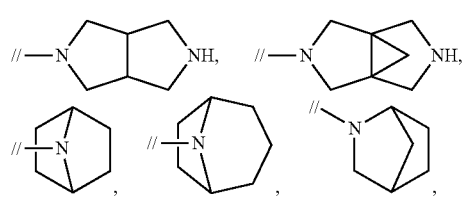

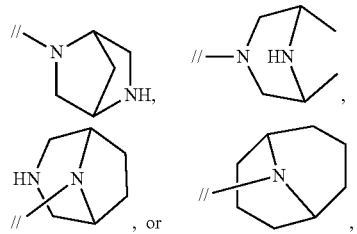

more preferably

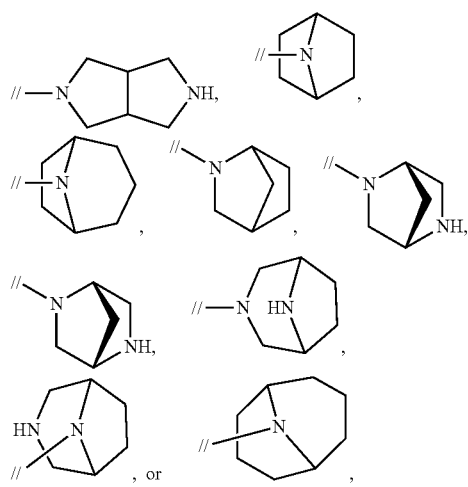

more preferably

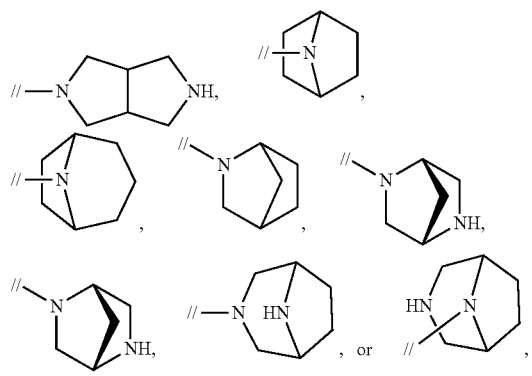

more preferably

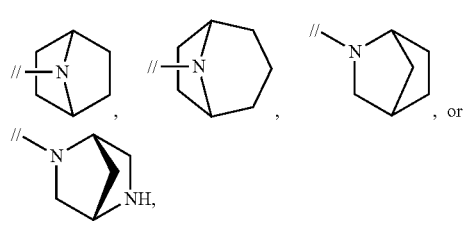

and more preferably

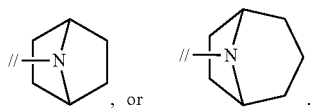
, or

Examples of the spirocyclic nitrogen-containing saturated heterocyclic group in the "monocyclic, bridged cyclic, or spirocyclic nitrogen-containing saturated heterocyclic group" represented by ring A include spirocyclic groups having 0 to 2 oxygen atoms in which any two of 4- to 7-membered nitrogen-containing saturated heterocyclic rings are bonded to each other. The spirocyclic nitrogen-containing saturated heterocyclic group is preferably a 7- to 12-membered spirocyclic group having 2 nitrogen atoms and 0 to 1 oxygen atoms in which any two of 4- to 7-membered nitrogen-containing saturated heterocyclic rings are bonded to each other, more preferably diazaspiroheptanyl, diazaspirooctanyl, diazaspirononanyl, diazaspirodecanyl, diazaspiroundecanyl, oxadiazaspiroheptanyl, oxadiazaspirooctanyl, oxadiazaspirononanyl, oxadiazaspirodecanyl, or oxadiazaspiroundecanyl, more preferably diazaspirooctanyl, diazaspirononanyl, diazaspirodecanyl, or oxadiazaspirononanyl, more preferably 2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[3.5]decanyl, or 9-oxa-diazaspiro[3.5]nonanyl, more preferably 2,7-diazaspiro[3.4]octanyl, 3,7-diazaspiro[3.4] octanyl, 2,7-diazaspiro[3.5]nonanyl, 2,8-diazaspiro[3.5] nonanyl, or 9-oxa-diazaspiro[3.5]nonanyl, more preferably 2,7-diazaspiro[3.4]octanyl, 3,7-diazaspiro[3.4]octanyl, or 2,8-diazaspiro[3.5]nonanyl, and more preferably 2,8-diazaspiro[3.5]nonanyl.

The "monocyclic, bridged cyclic, or spirocyclic nitrogen-containing saturated heterocyclic group" represented by ring A is preferably a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms, more preferably a monocyclic 4- to 10-membered nitrogen-containing saturated heterocyclic group having 1 to 2 nitrogen atoms as heteroatoms, a bridged cyclic nitrogen-containing saturated heterocyclic group, such as

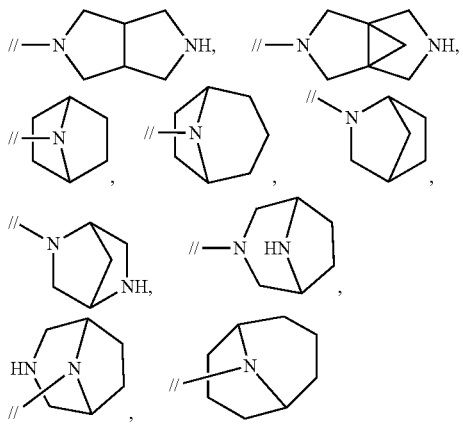

or a spirocyclic group having 0 to 2 oxygen atoms in which any two of 4- to 7-membered nitrogen-containing saturated heterocyclic rings are bonded to each other, more preferably a monocyclic 4- to 10-membered nitrogen-containing saturated heterocyclic group having 1 to 2 nitrogen atoms as heteroatoms, a bridged cyclic nitrogen-containing saturated heterocyclic group, such as

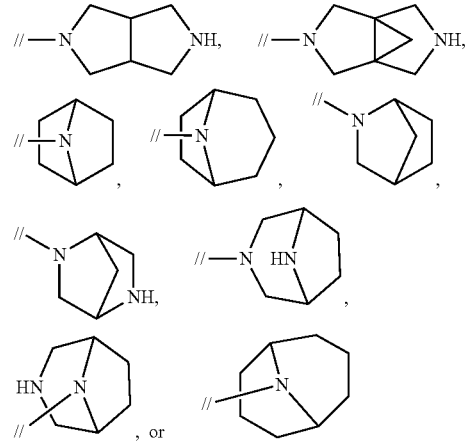

or a 7- to 12-membered spirocyclic group having 2 nitrogen atoms and 0 to 1 oxygen atoms in which any two of 4- to 7-membered nitrogen-containing saturated heterocyclic rings are bonded to each other, more preferably pyrrolidinyl, piperidinyl, piperazinyl, azepanyl, diazepanyl,

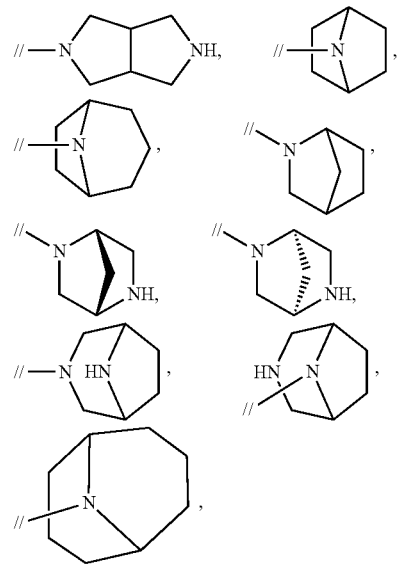

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, more preferably pyrrolidinyl, piperidinyl, azepanyl, diazepanyl,

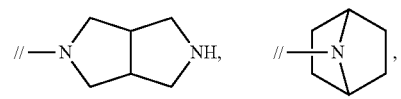

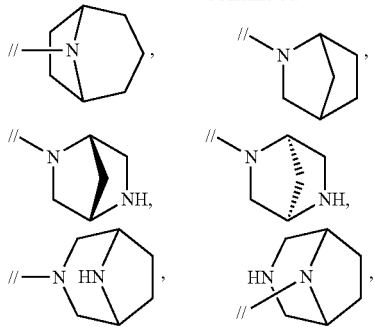

2,7-diazaspiro[3.4]octanyl, 3,7-diazaspiro[3.4]octanyl, 2,7-diazaspiro[3.5]nonanyl, 2,8-diazaspiro[3.5]nonanyl, or 9-oxa-diazaspiro[3.5]nonanyl, more preferably pyrrolidinyl,

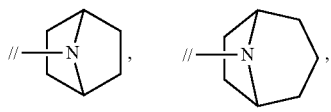

or 2,8-diazaspiro[3.5]nonanyl, more preferably pyrrolidinyl,

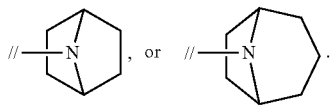

In the compound represented by Formula (I), ring B represents monocyclic or bicyclic unsaturated hydrocarbon, or a monocyclic or bicyclic unsaturated heterocyclic group that may be substituted with oxo.

The "monocyclic or bicyclic unsaturated hydrocarbon" represented by ring B is preferably monocyclic or bicyclic 5- to 14-membered unsaturated hydrocarbon, more preferably phenyl or naphthyl, and more preferably phenyl.

The "monocyclic or bicyclic unsaturated heterocyclic group" represented by ring B refers to a monocyclic or bicyclic, completely or partially unsaturated heterocyclic group having a heteroatom selected from nitrogen, oxygen, and sulfur, preferably a 5- to 14-membered monocyclic or bicyclic completely unsaturated heterocyclic group or partially unsaturated heterocyclic group having 0 to 4 nitrogen atoms, 0 to 2 sulfur atoms, and 0 to 3 oxygen atoms as heteroatoms and having at least one of nitrogen, sulfur, and oxygen, more preferably imidazolyl, thienyl, furyl, pyrrolyl, oxazolyl, isoxazolyl, thiazolyl, isothiazolyl, thiadiazolyl, pyrazolyl, triazolyl, tetrazolyl, pyridyl, pyrazyl, pyrimidinyl, pyridazinyl, pyrazolopyridyl, pyrazolopyrimidinyl, indolyl, isoindolyl, indolinyl, indazolyl, triazolopyridyl, benzoimidazolyl, benzoxazolyl, benzoisoxazolyl, benzothiazolyl, benzotriazolyl, benzothienyl, benzofuranyl, purinyl, imidazopyridinyl, quinolinyl, isoquinolinyl, quinazolinyl, quinoxalinyl, phthalazinyl, methylenedioxyphenyl, ethylenedioxyphenyl, dihydrobenzofuranyl, 1,3-dihydroisobenzofuranyl, dihydrobenzoxazolyl (e.g., 2,3-dihydrobenzo[d]oxazolyl), dihydrobenzooxazinyl (e.g., 3,4-dihydro-2H-benzo[b][1,4]oxazinyl), benzodioxolyl (e.g., benzo[d][1,3]dioxolyl), dihydrobenzodioxynyl (e.g., 2,3-dihydrobenzo[b][1,4]dioxynyl), or dihydrobenzothiazolyl (e.g., 2,3-dihydrobenzo[d]thiazolyl), more preferably pyridyl, pyrazolopyridyl, pyrazolopyrimidinyl, indolyl, indolinyl, indazolyl, benzoimidazolyl, benzoisoxazolyl, benzothiazolyl, benzotriazolyl, imidazopyridinyl, quinolinyl, isoquinolinyl, quinoxalinyl, quinazolinyl, phthalazinyl, dihydrobenzoxazolyl, 1,3-dihydroisobenzofuranyl, dihydrobenzooxazinyl, benzodioxolyl, dihydrobenzodioxynyl, or dihydrobenzothiazolyl, more preferably pyridyl, pyrazolopyridyl, indolyl, indolinyl, indazolyl, benzoimidazolyl, benzoisoxazolyl, benzotriazolyl, quinolinyl, dihydrobenzoxazolyl, 1,3-dihydroisobenzofuranyl, dihydrobenzooxazinyl, or dihydrobenzothiazolyl, more preferably indolyl, indazolyl, benzoisoxazolyl, or benzotriazolyl, and more preferably benzotriazolyl. The monocyclic or bicyclic unsaturated heterocyclic group represented by ring B may be substituted with oxo. Examples of the monocyclic or bicyclic unsaturated heterocyclic group that is substituted with oxo include 2-oxo-indolinyl,

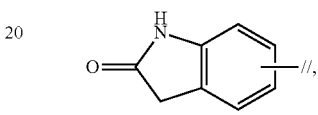

2-oxo-2,3-dihydrobenzo[d]oxazolyl,

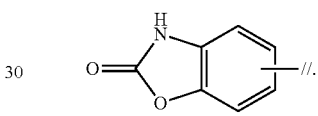

2-oxo-2,3-dihydrobenzo[d]thiazolyl,

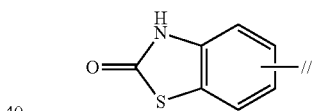

and the like. The monocyclic or bicyclic unsaturated heterocyclic group that is substituted with oxo is preferably 2-oxo-indolinyl, 2-oxo-2,3-dihydrobenzo[d]oxazolyl, or 2-oxo-2,3-dihydrobenzo[d]thiazolyl, and more preferably 2-oxo-2,3-dihydrobenzo[d]oxazolyl or 2-oxo-2,3-dihydrobenzo[d]thiazolyl.

Ring B is preferably monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen, more preferably phenyl, naphthyl, pyridyl, pyrazolopyridyl, pyrazolopyrimidinyl, indolyl, indolinyl, 2-oxo-indolinyl, indazolyl, benzoimidazolyl, benzoisoxazolyl, benzothiazolyl, benzotriazolyl, imidazopyridinyl, quinolinyl, isoquinolinyl, quinazolinyl, quinoxalinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl, more preferably phenyl, naphthyl, pyridyl, pyrazolopyridyl, indolyl, indolinyl, indazolyl, benzoimidazolyl, benzoisoxazolyl, benzotriazolyl, quinolinyl, 2-oxo-2,3-dihydrobenzo[d]oxazolyl, 1,3-dihydroisobenzofuranyl, dihydrobenzooxazinyl, or 2-oxo-2,3-dihydrobenzo[d]thiazolyl, more preferably phenyl, indolyl, indazolyl, benzoisoxazolyl, or benzotriazolyl, and more preferably benzotriazolyl.

In the compound represented by Formula (I), R1 represents nitro or cyano, and preferably cyano.

In the compound represented by Formula (I), R2 represents halogen, and preferably fluorine. When two or more R2s are present, R2s may be identical or different.

In the compound represented by Formula (I), 1 is an integer of 0 to 2, and preferably an integer of 0 to 1.

In the compound represented by Formula (I), R3 represents substituted or unsubstituted amino, C1-C6 alkyl, halogen, cyano, oxo, hydroxy, carbamoyl, sulfo, C1-C6 alkoxy, or amino (C1-C6 alkyl). When two or more R3s are present, R3s may be identical or different.

The "C1-C6 alkyl" represented by R3 may be straight or branched. Examples include methyl, ethyl, n-propyl, isopropyl, n-butyl, isobutyl, tert-butyl, n-pentyl, isopentyl, hexyl, and the like, with C1-C4 alkyl being preferable, and methyl being more preferable.

Examples of the "mono(C1-C6 alkyl)amino" represented by R3 include methylamino, ethylamino, n-propylamino, isopropylamino, n-butylamino, isobutylamino, tert-butylamino, n-pentylamino, isopentylamino, hexylamino, and the like, with mono(C1-C4 alkyl)amino being preferable, and methylamino, ethylamino, or isopropylamino being more preferable.

Examples of the "di(C1-C6 alkyl)amino" represented by R3 include dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, methylisopropylamino, and the like. The "di(C1-C6 alkyl)amino" is preferably dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, or methylisopropylamino, more preferably di(C1-C4 alkyl)amino, and more preferably dimethylamino.

Examples of the "(C3-C7 cycloalkyl)amino" represented by R3 include (C3-C7 cycloalkyl)amino, such as cyclopropylamino, cyclobutylamino, cyclopentylamino, cyclohexylamino, and cycloheptylamino. The "(C3-C7 cycloalkyl)amino" is preferably cyclopropylamino, cyclobutylamino, cyclopentylamino, cyclohexylamino, or cycloheptylamino, and more preferably cyclobutylamino.

R3 is preferably substituted or unsubstituted amino, C1-C6 alkyl, halogen, cyano, oxo, hydroxy, carbamoyl, sulfo, C1-C6 alkoxy, or amino(C1-C6 alkyl), more preferably amino that may be substituted with one to two C1-C6 alkyl or C3-C7 cycloalkyl groups, C1-C6 alkyl, halogen, cyano, oxo, hydroxy, carbamoyl, sulfo, C1-C6 alkoxy, or amino(C1-C6 alkyl), more preferably amino, mono- or di(C1-C6 alkyl)amino, (C3-C7 cycloalkyl)amino, or C1-C6 alkyl, more preferably amino, methylamino, ethylamino, isopropylamino, dimethylamino, cyclobutylamino, or methyl, more preferably amino or methyl, and more preferably amino.

In the compound represented by Formula (I), m is an integer of 0 to 2, and preferably an integer of 0 to 1.

In the compound represented by Formula (I), R4 represents halogen, hydroxy, nitro, cyano, amino, carboxy, (C2-C7 acyl)amino, (C2-C7 acyl)oxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, substituted or unsubstituted carbamoyl, substituted or unsubstituted C2-C6 alkynyl, substituted or unsubstituted (C1-C6 alkyl)carbonyl, substituted or unsubstituted 4- to 14-membered nitrogen-containing saturated heterocyclic group, or substituted or unsubstituted C6-C14 aromatic hydrocarbon. When two or more R4s are present, R4s may be identical or different.

In the present invention, when at least one R4 represents substituted C1-C8 alkyl, substituted C2-C6 alkenyl, substituted C1-C6 alkoxy, substituted C3-C7 cycloalkyl, or substituted carbamoyl, examples of the substituents include halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, (C1-C6 alkoxy) (C1-C6 alkyl), and the like. When two or more of the substituents are present, the substituents may be identical or different.

The "C1-C8 alkyl" in the "substituted or unsubstituted C1-C8 alkyl" represented by R4 is preferably methyl, ethyl, n-propyl, isopropyl, n-butyl, isobutyl, sec-butyl, tert-butyl, pentyl, hexyl, heptyl, or octyl, more preferably C1-C6 alkyl, more preferably methyl, ethyl, n-propyl, isopropyl, n-butyl, isobutyl, sec-butyl, tert-butyl, pentyl, or hexyl, and more preferably methyl, ethyl, n-propyl, isopropyl, n-butyl, isobutyl, sec-butyl, or tert-butyl.

The substituent in the "substituted or unsubstituted C1-C8 alkyl" represented by R4 may be, for example, the substituents mentioned above, preferably halogen, amino, hydroxy, carboxy, carbamoyl, alkylcarbamoyl, acylamino, alkoxy, hydroxycycloalkyl, or acyloxy, more preferably halogen, amino, hydroxy, carboxy, carbamoyl, (C1-C6 alkyl)carbamoyl, (C2-C7 acyl)amino, C1-C6 alkoxy, C3-C7 cycloalkyl, hydroxy(C3-C7 cycloalkyl), or (C2-C7 acyl)oxy, more preferably halogen, amino, hydroxy, carboxy, carbamoyl, (C1-C6 alkyl)carbamoyl, (C1-C6 alkyl)carbonylamino, C1-C6 alkoxy, C3-C7 cycloalkyl, hydroxy(C3-C7 cycloalkyl), or (C1-C6 alkyl)carbonyloxy, and more preferably fluorine, amino, hydroxy, carboxy, carbamoyl, methylcarbamoyl, dimethylcarbamoyl, acetylamino, methoxy, hydroxycyclopropyl, or methylcarbonyloxy.

The "substituted or unsubstituted C1-C8 alkyl" represented by R4 is preferably unsubstituted C1-C8 alkyl, or C1-C8 alkyl that may be substituted with halogen, amino, hydroxy, carboxy, carbamoyl, (C1-C6 alkyl)carbamoyl, (C1-C6 alkyl)carbonylamino, C1-C6 alkoxy, C3-C7 cycloalkyl, hydroxy(C3-C7 cycloalkyl), or (C1-C6 alkyl)carbonyloxy, more preferably methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, or methylcarbonyloxyethyl, more preferably methyl, ethyl, n-propyl, tert-butyl, difluoromethyl, hydroxyethyl, hydroxymethylpropyl, hydroxymethylbutyl, hydroxyethylbutyl, carbamoylmethyl, methylcarbamoylmethyl, dimethylcarbamoylmethyl, methoxyethyl, hydroxycyclopropylmethyl, hydroxycyclobutylmethyl, or methylcarbonyloxyethyl, more preferably methyl, difluoromethyl, hydroxymethylpropyl, hydroxymethylbutyl, hydroxycyclobutylmethyl, methoxyethyl, or hydroxycyclobutylmethyl, and more preferably methyl, difluoromethyl, hydroxymethylpropyl, hydroxyethylbutyl, or hydroxycyclobutylmethyl.

The "substituted or unsubstituted C2-C6 alkenyl" represented by R4 is preferably unsubstituted C2-C6 alkenyl, more preferably vinyl, allyl, 1-propenyl, 2-methyl-2-propenyl, isopropenyl, 1-, 2- or 3-butenyl, isobutenyl, 2-, 3-, or 4-pentenyl, 2-methyl-2-butenyl, 3-methyl-2-butenyl, 5-hexenyl, 1-cyclopentenyl, 1-cyclohexenyl, or 3-methyl-3-butenyl, and more preferably isobutenyl.

Examples of the "C2-C6 alkynyl" in the "substituted or unsubstituted C2-C6 alkynyl" represented by R4 include ethynyl, 1- or 2-propynyl, 1-, 2- or 3-butynyl, 1-methyl-2-propynyl, and the like. The "substituted or unsubstituted C2-C6 alkynyl" is preferably unsubstituted C2-C6 alkynyl.

The "C1-C6 alkoxy" in the "substituted or unsubstituted C1-C6 alkoxy" represented by R4 is preferably methoxy, ethoxy, n-propoxy, isopropoxy, n-butoxy, isobutoxy, sec-butoxy, tert-butoxy, pentyloxy, or hexyloxy, and more preferably methoxy, ethoxy, n-propoxy, isopropoxy, n-butoxy, isobutoxy, sec-butoxy, and tert-butoxy.

The substituent in the "substituted or unsubstituted C1-C6 alkoxy" represented by R4 may be, for example, those mentioned above, and is preferably hydroxy or 5- to 14-membered unsaturated hydrocarbon, more preferably hydroxy or monocyclic 5- to 10-membered unsaturated hydrocarbon, and more preferably hydroxy or phenyl.

The "substituted or unsubstituted C1-C6 alkoxy" represented by R4 is preferably C1-C6 alkoxy that may be substituted with hydroxy or 5- to 14-membered unsaturated hydrocarbon, more preferably C1-C6 alkoxy that may be substituted with hydroxy or monocyclic 5- to 10-membered unsaturated hydrocarbon, more preferably C1-C6 alkoxy that may be substituted with hydroxy or phenyl, and more preferably methoxy, hydroxypropoxy, or benzyloxy.

The "substituted or unsubstituted C3-C7 cycloalkyl" represented by R4 is preferably C3-C7 cycloalkyl that may be substituted with hydroxyalkyl, alkoxyalkyl, hydroxycycloalkyl, or unsaturated hydrocarbon carbamoyl, more preferably C3-C7 cycloalkyl that may be substituted with hydroxy(C1-C4 alkyl), (C1-C4 alkoxy)(C1-C4 alkyl), hydroxy(C3-C7 cycloalkyl), or (C6-C14 aromatic hydrocarbon)carbamoyl, more preferably C3-C7 cycloalkyl that may be substituted with hydroxy(C1-C4 alkyl), (C1-C4 alkoxy)(C1-C4 alkyl), hydroxy(C3-C7 cycloalkyl), or phenylcarbamoyl, more preferably cyclopropyl, hydroxymethyl cyclopropyl, methoxymethyl cyclopropyl, hydroxycyclopropyl cyclopropyl, or phenylcarbamoyl cyclopropyl, more preferably cyclopropyl or hydroxymethyl cyclopropyl, and more preferably cyclopropyl.

The "mono- or di(C1-C6 alkyl)amino" represented by R4 is preferably methylamino, ethylamino, n-propylamino, isopropylamino, n-butylamino, isobutylamino, tert-butylamino, n-pentylamino, isopentylamino, hexylamino, dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, or methylisopropylamino, more preferably methylamino, ethylamino, n-propylamino, isopropylamino, n-butylamino, isobutylamino, tert-butylamino, dimethylamino, diethylamino, di(n-propyl)amino, diisopropylamino, di(n-butyl)amino, diisobutylamino, di(tert-butyl)amino, methylethylamino, or methylisopropylamino, and more preferably dimethylamino.

The "substituted or unsubstituted carbamoyl" represented by R4 is preferably carbamoyl that may be substituted with alkyl, more preferably carbamoyl that may be substituted with C1-C6 alkyl, and more preferably carbamoyl, methylcarbamoyl, or dimethylcarbamoyl.

Examples of the alkylcarbonyl in the "substituted or unsubstituted (C1-C6 alkyl)carbonyl" represented by R4 include straight or branched (C1-C6 alkyl)carbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl.

Examples of the "nitrogen-containing saturated heterocyclic group" in the "substituted or unsubstituted 4- to 14-membered nitrogen-containing saturated heterocyclic group" represented by R4 include morpholinyl, azetidinyl, pyrrolidinyl, piperidinyl, piperazinyl, and the like.

Examples of the "substituted or unsubstituted C6-C14 aromatic hydrocarbon" represented by R4 include C6-C14 aromatic hydrocarbon that may be substituted with methyl, such as phenyl, toluyl, xylyl, naphthyl, anthracenyl, phenanthryl, fluorenyl, and tetrahydronaphthyl.

R4 is preferably halogen, hydroxy, nitro, cyano, amino, carboxy, (C2-C7 acyl)amino, (C2-C7 acyl)oxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, substituted or unsubstituted carbamoyl, substituted or unsubstituted C2-C6 alkynyl, substituted or unsubstituted (C1-C6 alkyl)carbonyl, substituted or unsubstituted 4- to 14-membered nitrogen-containing saturated heterocyclic group, or substituted or unsubstituted C6-C14 aromatic hydrocarbon, more preferably halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl, more preferably halogen, nitro, cyano, carboxy, C1-C6 alkyl that may be substituted with halogen, amino, hydroxy, carboxy, carbamoyl, (C1-C6 alkyl)carbamoyl, (C1-C6 alkyl)carbonylamino, C1-C6 alkoxy, C3-C7 cycloalkyl, hydroxy(C3-C7 cycloalkyl), or (C1-C6 alkyl)carbonyloxy, C2-C6 alkenyl, C1-C6 alkoxy that may be substituted with hydroxy or monocyclic 5- to 10-membered unsaturated hydrocarbon, C3-C7 cycloalkyl that may be substituted with hydroxy, hydroxy(C1-C4 alkyl), (C1-C4 alkoxy)(C1-C4 alkyl), hydroxy(C3-C7 cycloalkyl), or (C6-C14 aromatic hydrocarbon)-substituted carbamoyl, mono- or di(C1-C6 alkyl)amino, or carbamoyl that may be substituted with C1-C6 alkyl, more preferably fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropyl, phenylcarbamoyl cyclopropyl, benzyloxy, dimethylamino, carbamoyl, methylcarbamoyl, or dimethylcarbamoyl, more preferably fluorine, chlorine, bromine, nitro, cyano, carboxy, methyl, ethyl, n-propyl tert-butyl, difluoromethyl, hydroxyethyl, hydroxymethylpropyl, hydroxymethylbutyl, hydroxyethylbutyl, carbamoylmethyl, methylcarbamoylmethyl, dimethylcarbamoylmethyl, methoxyethyl, hydroxycyclopropylmethyl, hydroxycyclobutylmethyl, methylcarbonyloxyethyl, methoxy, cyclopropyl, hydroxymethyl cyclopropyl, dimethylamino, carbamoyl, methylcarbamoyl, or dimethylcarbamoyl, more preferably fluorine, chlorine, bromine, cyano, methyl, difluoromethyl, hydroxymethylpropyl, hydroxymethylbutyl, hydroxyethylbutyl, methoxyethyl, hydroxycyclobutylmethyl, or cyclopropyl, and more preferably fluorine, chlorine, bromine, cyano, methyl, difluoromethyl, hydroxymethylpropyl, hydroxyethylbutyl, or hydroxycyclobutylmethyl.

In the compound represented by Formula (I), n is an integer of 0 to 5, and preferably an integer of 0 to 3.

In the compound represented by Formula (I), R5 and R6 may be identical or different, and each represent hydrogen or C1-C6 alkyl; R5 and R6 may otherwise form oxo or thioxo together. When R5 and R6 are identical or different, and each represent hydrogen or C1-C6 alkyl, at least one of R5 and R6 is hydrogen.

The "C1-C6 alkyl" represented by R5 and R6 may be straight or branched. Examples include methyl, ethyl, n-propyl, isopropyl, n-butyl, isobutyl, tert-butyl, n-pentyl, isopentyl, hexyl, and the like, with C1-C4 alkyl being preferable, and methyl being more preferable.

R5 and R6 are preferably identical or different, and each represent hydrogen or C1-C6 alkyl; R5 and R6 may otherwise form oxo or thioxo together. When R5 and R6 are identical or different, and each represent hydrogen or C1-C6 alkyl, at least one of R5 and R6 is hydrogen; more preferably, they are hydrogen, or may form oxo together.

As the biphenyl compound represented by Formula (I), preferred is a compound represented by Formula (I) or a salt thereof, wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, mono- or di(C1-C6 alkyl)amino, (C3-C7 cycloalkyl)amino, or C1-C6 alkyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy) (C1-C6 alkyl); when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l is an integer of 0 to 2;
m is an integer of 0 to 2;
n is an integer of 0 to 5;
when l is 2, two R2s may be identical or different;
when m is 2, two R3s may be identical or different;
when n is 2 to 5, two to five R4s may be identical or different.

More preferred is a compound represented by Formula (I) or a salt thereof, wherein
ring A represents pyrrolidinyl, piperidinyl, piperazinyl, azepanyl, diazepanyl,

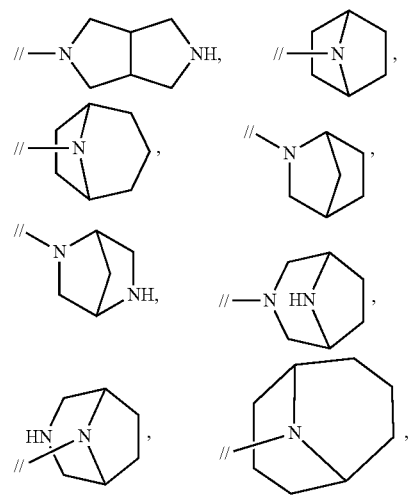

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, methylamino, ethylamino, isopropylamino, dimethylamino, cyclobutylamino, or methyl;
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl;
when at least one R4 is substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, a monocyclic 5- to 10-membered unsaturated hydrocarbon, carbamoyl that may be substituted with C1-C6 alkyl or monocyclic 5- to 10-membered unsaturated hydrocarbon, C2-C7 acyl, amino that may be substituted with C1-C6 alkyl or C2-C7 acyl, C3-C7 cycloalkyl that may be substituted with hydroxy, or (C1-C6 alkoxy) (C1-C6 alkyl);

when two or more of the substituents are present, the substituents may be identical or different;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l is an integer of 0 to 2;
m is an integer of 0 to 2;
n is an integer of 0 to 5;
when l is 2, two R2s may be identical or different;
when m is 2, two R3s may be identical or different;
when n is 2 to 5, two to five R4s may be identical or different.

More preferred is a compound represented by Formula (I) or a salt thereof, wherein
ring A represents pyrrolidinyl, piperidinyl, piperazinyl, azepanyl, and diazepanyl,

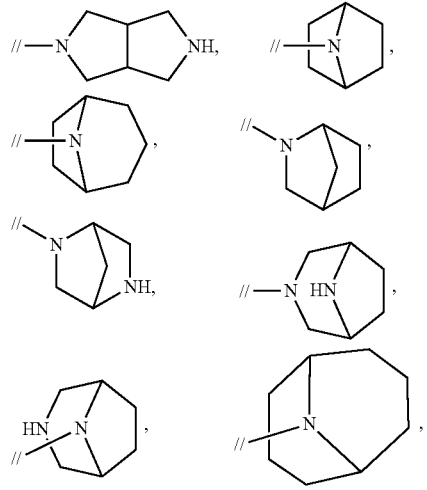

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl;
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen;
R1 represents nitro or cyano;
R2 represents halogen;
R3 represents amino, methylamino, ethylamino, isopropylamino, dimethylamino, cyclobutylamino, or methyl;
R4 represents halogen, nitro, cyano, carboxy, C1-C8 alkyl that may be substituted with halogen, amino, hydroxy, carboxy, carbamoyl, (C1-C6 alkyl)carbamoyl, (C1-C6 alkyl)carbonylamino, C1-C6 alkoxy, (C1-C6 alkyl)carbonyl, C3-C7 cycloalkyl, hydroxy(C3-C7 cycloalkyl), or (C1-C6 alkyl)carbonyloxy, C2-C6 alkenyl, C1-C6 alkoxy that may be substituted with hydroxy or monocyclic 5- to 10-membered unsaturated hydrocarbon, C3-C7 cycloalkyl that may be substituted with hydroxy, hydroxy(C1-C4 alkyl), (C1-C4 alkoxy)(C1-C4 alkyl), hydroxy(C3-C7 cycloalkyl), or (C6-C14 aromatic hydrocarbon)-substituted carbamoyl, mono- or di(C1-C6 alkyl)amino, or carbamoyl that may be substituted with C1-C6 alkyl;
R5 and R6 may be identical or different, and each represent hydrogen or C1-C6 alkyl; R5 and R6 may otherwise form oxo or thioxo together;
when R5 and R6 are identical or different, and each represent hydrogen or C1-C6 alkyl, at least one of R5 and R6 is hydrogen;
l is an integer of 0 to 2;
m is an integer of 0 to 2;
n is an integer of 0 to 5;
when l is 2, two R2s may be identical or different;
when m is 2, two R3s may be identical or different;
when n is 2 to 5, two to five R4s may be identical or different.

More preferred is a compound represented by Formula (I) or a salt thereof, wherein
ring A represents pyrrolidinyl, piperidinyl, piperazinyl, azepanyl, diazepanyl,

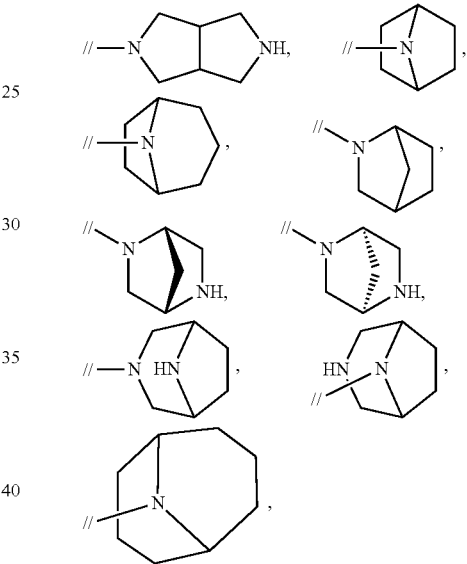

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl;
ring B represents phenyl, naphthyl, pyridyl, pyrazolopyridyl, pyrazolopyrimidinyl, indolyl, indolinyl, 2-oxo-indolinyl, indazolyl, benzoimidazolyl, benzoisoxazolyl, benzothiazolyl, benzotriazolyl, imidazopyridinyl, quinolinyl, isoquinolinyl, quinoxalinyl, quinazolinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl;
R1 represents nitro or cyano;
R2 represents fluorine, and is present at the ortho position relative to R1 on the phenyl;
R3 represents amino, methylamino, ethylamino, isopropylamino, dimethylamino, cyclobutylamino, or methyl (when two or more R3s are present, R3s may be identical or different);
R4 represents fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxyethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropyl, phenylcarbamoyl cyclopropyl, benzyloxy, dimethylamino, carbamoyl, methylcarbamoyl, or dimethylcarbamoyl;

R5 and R6 may be identical or different, and each represent hydrogen or C1-C6 alkyl; R5 and R6 may otherwise form oxo or thioxo together;

when R5 and R6 are identical or different, and each represent hydrogen or C1-C6 alkyl, at least one of R5 and R6 is hydrogen, l is an integer of 0 to 2,
m is an integer of 0 to 2, and
n is an integer of 0 to 3;
when m is 2, two R3s may be identical or different;
when n is 2 to 3, two to three R4s may be identical or different.

More preferred is a compound represented by Formula (I) or a salt thereof, wherein
ring A represents pyrrolidinyl, piperidinyl, azepanyl, diazepanyl,

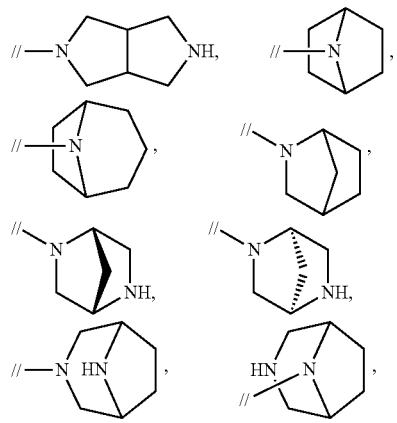

2,7-diazaspiro[3.4]octanyl, 3,7-diazaspiro[3.4]octanyl, 2,7-diazaspiro[3.5]nonanyl, 2,8-diazaspiro[3.5]nonanyl, or 9-oxa-diazaspiro[3.5]nonanyl;

ring B represents phenyl, naphthyl, pyridyl, pyrazolopyridyl, indolyl, indolinyl, indazolyl, benzoimidazolyl, benzoisoxazolyl, benzotriazolyl, quinolinyl, 2-oxo-2,3-dihydrobenzo[d]oxazolyl, 1,3-dihydroisobenzofuranyl, dihydrobenzooxazinyl, or 2-oxo-2,3-dihydrobenzo[d]thiazolyl;

R1 represents cyano;
R2 represents fluorine, and is present at the ortho position relative to R1 on the phenyl;
R3 represents amino, methylamino, ethylamino, isopropylamino, dimethylamino, cyclobutylamino, or methyl (when two or more R3s are present, R3s may be identical or different);
R4 represents fluorine, chlorine, bromine, nitro, cyano, carboxy, methyl, ethyl, n-propyl, tert-butyl, difluoromethyl, hydroxyethyl, hydroxymethylpropyl, hydroxymethylbutyl, hydroxyethylbutyl, carbamoylmethyl, methylcarbamoylmethyl, dimethylcarbamoylmethyl, methoxyethyl, hydroxycyclopropylmethyl, hydroxycyclobutylmethyl, methylcarbonyloxyethyl, methoxy, cyclopropyl, hydroxymethylcyclopropyl, dimethylamino, carbamoyl, methylcarbamoyl, or dimethylcarbamoyl;

R5 and R6 may be identical or different, and each represent hydrogen or C1-C6 alkyl; R5 and R6 may otherwise form oxo or thioxo together;

when R5 and R6 are identical or different, and each represent hydrogen or C1-C6 alkyl, at least one of R5 and R6 is hydrogen;

l is an integer of 0 to 2;
m is an integer of 0 to 2;
n is an integer of 0 to 3;
when m is 2, two R3s may be identical or different;
when n is 2 to 3, two to three R4s may be identical or different.

More preferred is a compound represented by Formula (I) or a salt thereof, wherein
ring A represents pyrrolidinyl,

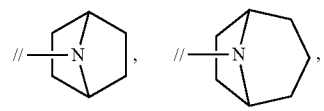

or 2,8-diazaspiro[3.5]nonanyl;
ring B represents phenyl, indolyl, indazolyl, benzoisoxazolyl, or benzotriazolyl;
R1 represents cyano;
R2 represents fluorine, and is present at the ortho position relative to R1 on the phenyl;
R3 represents amino or methyl (when two or more R3s are present, R3s may be identical or different);
R4 represents fluorine, chlorine, bromine, cyano, methyl, difluoromethyl, hydroxymethylpropyl, hydroxymethylbutyl, hydroxyethylbutyl, methoxyethyl, hydroxycyclobutylmethyl, or cyclopropyl;
R5 and R6 may represent hydrogen or form oxo together;
l is an integer of 0 to 2;
m is an integer of 0 to 2;
n is an integer of 0 to 3;
when m is 2, two R3s may be identical or different;
when n is 2 to 3, two to three R4s may be identical or different.

More preferred is a compound represented by Formula (I) or a salt thereof, wherein ring A represents pyrrolidinyl,

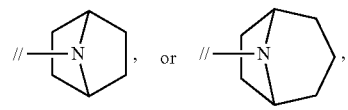

ring B represents phenyl, indolyl, indazolyl, benzoisoxazolyl, or benzotriazolyl;
R1 represents cyano;
R2 represents fluorine, and is present at the ortho position relative to R1 on the phenyl;
R3 represents amino (when two or more R3s are present, R3s may be identical or different);
R4 represents fluorine, chlorine, bromine, cyano, methyl, difluoromethyl, hydroxymethylpropyl, hydroxyethylbutyl, or hydroxycyclobutylmethyl;
R5 and R6 may represent hydrogen or form oxo together;

l is an integer of 0 to 2;
m is an integer of 0 to 2;
n is an integer of 0 to 3;
when m is 2, two R3s may be identical or different;
when n is 2 to 3, two to three R4s may be identical or different.

More preferred is a compound represented by Formula (I) or a salt thereof, wherein ring A represents pyrrolidinyl,

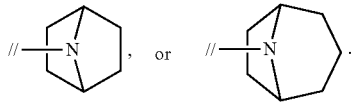

ring B represents phenyl or benzotriazolyl;
R1 represents cyano;
R2 represents fluorine, and is present at the ortho position relative to R1 on the phenyl;
R3 represents amino (when two or more R3s are present, R3s may be identical or different);
R4 represents fluorine, bromine, hydroxymethylpropyl, or hydroxyethylbutyl;
R5 and R6 may represent hydrogen or form oxo together;
l is an integer of 0 to 2;
m is an integer of 0 to 2;
n is an integer of 0 to 3;
when m is 2, two R3s may be identical or different;
when n is 2 to 3, two to three R4s may be identical or different.

In an embodiment of the present invention, preferred as the biphenyl compound represented by Formula (I) is a compound represented by Formula (I) or a salt thereof, wherein
ring A represents a monocyclic or bridged cyclic 4- to 8-membered nitrogen-containing saturated heterocyclic group having 1 to 3 nitrogen atoms as heteroatoms;
ring B represents monocyclic 5- to 8-membered unsaturated hydrocarbon or a bicyclic 8- to 14-membered unsaturated heterocyclic group having 1 to 4 nitrogen atoms as heteroatoms;
R1 represents cyano;
R2 represents halogen;
R3 represents amino;
R4 represents halogen or C1-C8 alkyl that may be substituted with hydroxy; when two or more of the substituents are present, the substituents may be identical or different;
R5 and R6 may represent hydrogen or form oxo together;
l is an integer of 0 to 2;
m is an integer of 0 to 2;
n is an integer of 0 to 3;
when l is 2, two R2s may be identical or different;
when m is 2, two R3s may be identical or different;
when n is 2 to 3, two to three R4s may be identical or different.

More preferred is a compound represented by Formula (I) or a salt thereof, wherein ring A represents pyrrolidinyl;

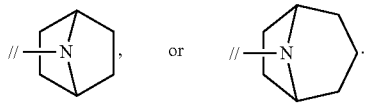

ring B represents phenyl or benzotriazolyl;
R1 represents cyano;
R2 represents halogen;
R3 represents amino;
R4 represents halogen or C1-C8 alkyl that may be substituted with hydroxy; when two or more of the substituents are present, the substituents may be identical or different;
R5 and R6 may represent hydrogen or form oxo together;
l is an integer of 0 to 2;
m is an integer of 0 to 2;
n is an integer of 0 to 3;
when l is 2, two R2s may be identical or different;
when m is 2, two R3s may be identical or different;
when n is 2 to 3, two to three R4s may be identical or different.

More preferred is a compound represented by Formula (I) or a salt thereof, wherein ring A represents pyrrolidinyl,

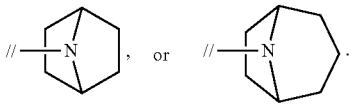

ring B represents phenyl or benzotriazolyl;
R1 represents cyano;
R2 represents fluorine;
R3 represents amino;
R4 represents fluorine, bromine, or hydroxy(C1-C8 alkyl); when two or more of the substituents are present, the substituents may be identical or different;
R5 and R6 may represent hydrogen or form oxo together;
l is an integer of 0 to 2;
m is an integer of 0 to 1;
n is an integer of 0 to 3;
when l is 2, two R2s may be identical or different;
when n is 2 to 3, two to three R4s may be identical or different.

More preferred is a compound represented by Formula (I) or a salt thereof, wherein ring A represents pyrrolidinyl,

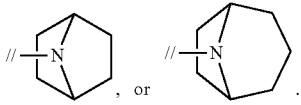

ring B represents phenyl or benzotriazolyl;
R1 represents cyano;
R2 represents fluorine;
R3 represents amino;
R4 represents fluorine, bromine, hydroxymethylpropyl, or hydroxyethylbutyl; when two or more of the substituents are present, the substituents may be identical or different,
R5 and R6 may represent hydrogen or form oxo together;
l is an integer of 0 to 2;
m is an integer of 0 to 1;
n is an integer of 0 to 3;
when l is 2, two R2s may be identical or different;
when n is 2 to 3, two to three R4s may be identical or different.

Specific examples of the biphenyl compounds according to the present invention include, but are not limited to, Example compounds 1 to 295 produced in the Examples below.

The following are examples of preferable biphenyl compounds:

4-[5-[(3S)-3-aminopyrrolidine-1-carbonyl]-2-[2-fluoro-4-(2-hydroxy-2-methyl-propyl)phenyl]phenyl]-2-fluoro-benzonitrile;

4-[5-[(3-endo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile;

5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile-isomer-B;

5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;

5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;

5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X;

5'-((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.

Next, the methods for producing the compounds of the present invention are described.

The biphenyl compound represented by Formula (I) may be produced, for example, through the production methods below or the methods described in the Examples. However, the methods for producing the biphenyl compound represented by Formula (I) are not limited to these reaction examples.

In steps 1 to 9, in the formulas, L1, L2, and L3 each individually represent a leaving group, $NH_2$, or OH, W represents hydroxy, C1-C6 alkoxy, or

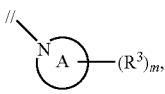

Q1 represents L1 or

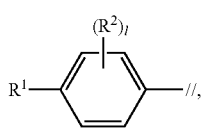

Q2 represents L2 or

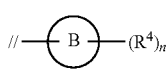

and X represents oxygen or sulfur, and E1 represents hydrogen or substituted or unsubstituted C1-C6 alkyl, wherein when E1 is substituted or unsubstituted C1-C6 alkyl, E1, taken together with the BOO, may form a ring. Ring A, ring B, R1, R2, R3, R4, R5, R6, l, m, and n are as defined above. Further, R5a represents C1-C6 alkyl.

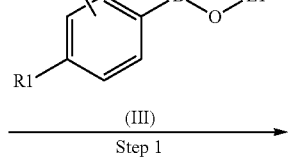

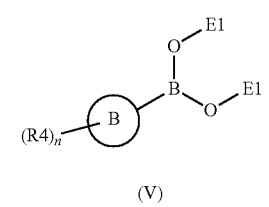

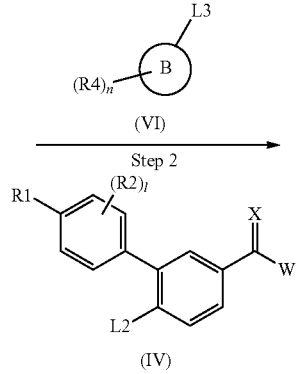

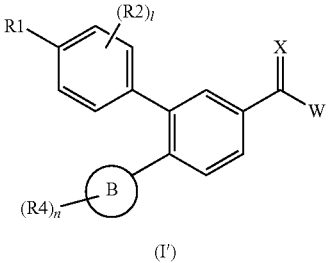

Step 1: Suzuki Reaction

This step represents a method for producing a compound represented by Formula (IV) through a Suzuki reaction using a compound represented by Formula (II).

This step may be performed in accordance with a commonly known method (e.g., the method disclosed in Chemical Reviews, Vol. 95, p. 2457, 1995). Protection of a substituent, removal or conversion of the protecting group, and conversion of leaving groups L1, L2, and L3 can be suitably performed.

Examples of the leaving groups represented by L1, L2, and L3 include halogen, such as chlorine, bromine, and iodine; organic sulfonyloxy groups, such as trifluoromethylsulfonyloxy and p-tolylsulfonyloxy; and the like.

The amount of the aromatic boronic acid or aromatic boronic acid ester (III) used may be 0.5 to 10 moles, and preferably 0.8 to 3 moles, per mole of the compound represented by Formula (II).

Examples of transition metal catalysts include palladium catalysts, such as palladium acetate, tetrakis(triphenylphosphine)palladium, 1,1'-bis(diphenylphosphino)ferrocene-palladium(II) dichloride, bis(dibenzylideneacetone)dipalladium(0), and tris(dibenzylideneacetone)dipalladium(0); nickel catalysts, such as nickel chloride; and the like.

As necessary, a ligand may be added. Examples of ligands include triphenylphosphine, tricyclohexylphosphine, (diphenylphosphino)ferrocene, 2-dicyclohexylphosphino-2',4',6'-triisopropylbiphenyl, Silica-SMAP, and the like. The amount of the transition metal catalyst used varies depending on the type of catalyst. The amount of the transition metal catalyst used is usually 0.0001 to 1 mole, and preferably 0.01 to 0.5 moles, per mole of the compound represented by Formula (II). The amount of the ligand used is usually 0.0001 to 4 moles, and preferably 0.01 to 2 moles, per mole of the compound represented by Formula (II).

Examples of bases include organic amines, such as triethylamine; alkali metal salts, such as sodium carbonate, potassium carbonate, cesium carbonate, sodium phosphate, tripotassium phosphate, sodium hydroxide, and potassium hydroxide; alkali metal alkoxides, such as sodium methoxide, sodium ethoxide, sodium tert-butoxide, and potassium tert-butoxide; and the like. The amount of the base used is usually 0.1 to 10 moles, and preferably 1 to 5 moles, per mole of the compound represented by Formula (II).

The solvent is not limited as long as it does not adversely affect the reaction. Examples include toluene, acetonitrile, 1,2-dimethoxyethane, tetrahydrofuran, 1,4-dioxane, ethanol, N,N-dimethylformamide, water, mixed solvents thereof, and the like. The reaction time is 0.1 to 7 days, and preferably 0.5 to 24 hours. The reaction temperature is 0° C. to the boiling temperature of the solvent, and preferably 20° C. to 160° C.

The thus-obtained compound represented by Formula (IV) can be subjected to the subsequent step after or without isolation or purification by known isolation and purification means, such as concentration, vacuum concentration, crystallization, solvent extraction, reprecipitation, and chromatography.

It is also possible to first perform a reaction for converting L2 into

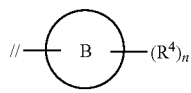

by reacting the compound represented by Formula (V) or (VI) with the compound represented by Formula (II), as in step 2 described below.

Step 2: Suzuki Reaction

This step represents a method for producing a compound represented by Formula (I') through a Suzuki reaction using the compound represented by Formula (IV).

This step can be performed as in step 1. When L2 (if the reaction for converting L2 into

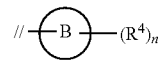

is performed first, then L1) is a boronic acid or a boronic acid ester derivative, compound (VI) is used for the reaction.

L3 in (VI) is the same as L1 and L2 in step 1, and the amount of (VI) used is usually 1 to 10 moles, and preferably 1 to 5 moles, per mole of the compound represented by Formula (IV).

Step 3: Boronic Acid Esterification Reaction

This step represents a method for producing a compound represented by Formula (IX), in which L2 has been converted into a boronic acid ester through a boronic acid esterification reaction, using a compound represented by Formula (IV) and diborane compound (VIII) in the presence of a transition metal catalyst and a base, optionally using a ligand.

The amount of diborane compound (VIII) used is 1 to 10 moles, and preferably 1 to 5 moles, per mole of the compound represented by Formula (IV).

The transition metal catalyst may be the same as in step 1.

As a base, potassium acetate, sodium acetate, and the like may be used, in addition to those mentioned in step 1.

The ligand may be the same as in step 1, with Silica-SMAP being preferable.

The solvent may be the same as in step 1.

The reaction temperature is usually 0 to 200° C., and preferably 50 to 160° C. The reaction time is usually 5 minutes to 3 days, preferably 5 minutes to 10 hours.

Before performing step 3, it is possible to first introduce into a compound represented by Formula (II); afterward, a boronic acid esterification reaction with respect to L1 may be performed as in step 3.

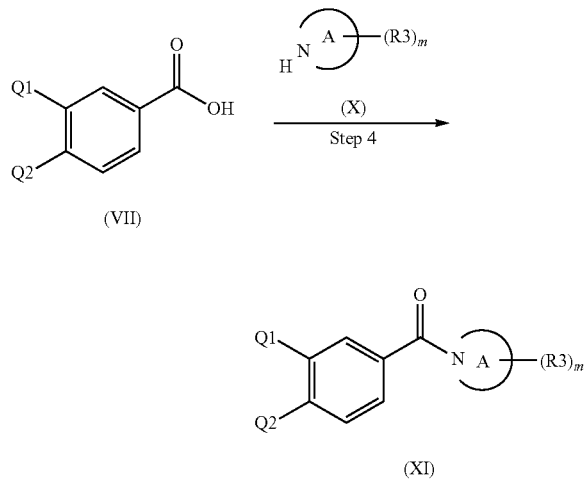

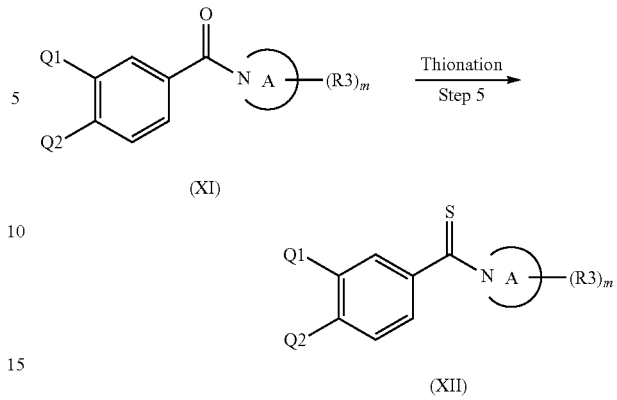

Step 4: Amidation Reaction

This step represents a method for producing a compound represented by Formula (XI) through an amidation reaction using a carboxylic acid compound represented by Formula (VII), an amine compound represented by Formula (X), and a condensation agent.

The amount of amine compound (X) used is 0.5 to 10 moles, and preferably 0.8 to 5 moles, per mole of the compound represented by Formula (VII).

Examples of condensation agents include benzotriazol-1-yloxy-trisdimethylaminophosphonium salts, 4-(4,6-dimethoxy-1,3,5-triazin-2-yl)-4-methylmorpholinium chloride, a combination of 1-ethyl-3-(3-dimethylaminopropyl)carbodiimide and 1-hydroxybenzotriazole, O-(7-azabenzotriazol-1-yl)-N,N,N',N'-tetramethyluronium hexafluorophosphate, and the like. The amount added is usually 1 to 100 moles, and preferably 1 to 5 moles, per mole of the compound represented by Formula (VII).

A base is optionally added during the above reaction. Examples of bases include organic bases, such as triethylamine, diisopropylethylamine, and pyridine; and inorganic bases, such as potassium carbonate. The amount added is usually 1 to 100 moles, preferably 1 to 10 moles, per mole of the compound represented by Formula (VII).

The solvent is not particularly limited, and any solvent that does not adversely affect the reaction can be used. Examples of the solvent include toluene, chloroform, tetrahydrofuran, N,N-dimethylformamide, dimethylacetamide, N-methylpyrrolidin-2-one, mixed solvent thereof, and the like.

The reaction temperature is usually −78 to 200° C., and preferably 0 to 50° C. The reaction time is usually 5 minutes to 3 days, preferably 5 minutes to 10 hours.

The thus-obtained compound represented by Formula (XI) can be subjected to the subsequent step after or without isolation or purification by known isolation and purification means, such as concentration, vacuum concentration, crystallization, solvent extraction, reprecipitation, and chromatography.

Step 5: Thionation Reaction

This step represents a method for producing a thioamide compound represented by Formula (XII) through a reaction that uses a compound represented by Formula (XI) and a thionation reagent.

Examples of thionation reagents include Lawesson's reagent and the like. The amount of this reagent added may be 1 to 10 moles, and preferably 1 to 5 moles, per mole of the compound represented by Formula (XI).

The solvent may be the same as in step 1.

The reaction temperature is usually 0 to 200° C., and preferably 0 to 100° C. The reaction time is usually 5 minutes to 3 days, and preferably 5 minutes to 10 hours.

The thus-obtained compound represented by Formula (XII) can be subjected to the subsequent step after or without isolation or purification by known isolation and purification means, such as concentration, vacuum concentration, crystallization, solvent extraction, reprecipitation, and chromatography.

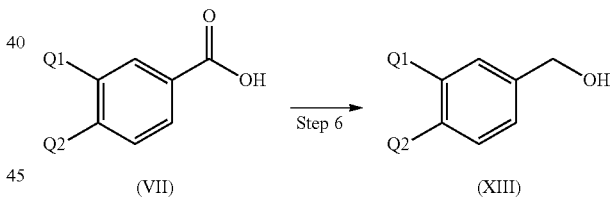

Step 6: Reaction of Reduction to Primary Alcohol

This step represents a method for producing a primary alcohol compound (XIII) by a reaction using the carboxylic acid compound represented by Formula (VII) and a reducing agent. Examples of reducing agents include borane, lithium aluminum hydride, and the like. Further, sodium borohydride, lithium borohydride and the like are also exemplified after the formation of the active ester in the system. Examples of active esterification agents include WSC HCl and the like used together with HATU and HOBt. The amount of the reducing agent to be added is usually 1 to 10 moles, and preferably 1 to 5 moles, per mole of the compound represented by Formula (VII). The amount of the active esterification agent to be added is usually 1 to 10 moles, and preferably 1 to 5 moles, per mole of the compound represented by Formula (VII). The solvent may be the same as in step 1. The reaction temperature is usually 0 to 200° C., and preferably 0 to 100° C. The reaction time is usually 5 minutes to 3 days, preferably 5 minutes to 10 hours.

The thus-obtained compound represented by Formula (XIII) can be subjected to the subsequent step after or without isolation or purification by known isolation and purification means, such as concentration, vacuum concentration, crystallization, solvent extraction, reprecipitation, and chromatography.

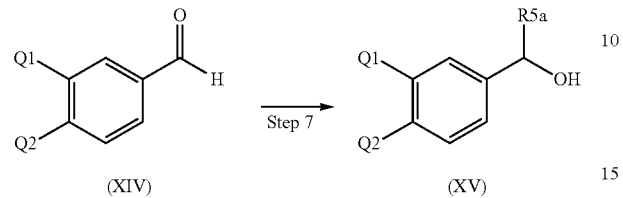

(XIV)    (XV)

Step 7: Alkylation Reaction

This step represents a method for producing a secondary alcohol compound (XV) through a reaction that uses an aldehyde compound represented by Formula (XIV) and an alkyl metal reagent. Examples of alkyl metal reagents include alkyl lithium, alkyl magnesium reagents, and the like. The amount of the alkyl metal reagent to be added is usually 1 to 10 moles, and preferably 1 to 5 moles, per mole of the compound represented by Formula (XIV). The solvent may be the same as in step 5. The reaction temperature is usually −78 to 200° C., and preferably −78 to 0° C. The reaction time is usually 5 minutes to 3 days, preferably 5 minutes to 10 hours.

The thus-obtained compound represented by Formula (XV) can be subjected to the subsequent step after or without isolation or purification by known isolation and purification means, such as concentration, vacuum concentration, crystallization, solvent extraction, reprecipitation, and chromatography.

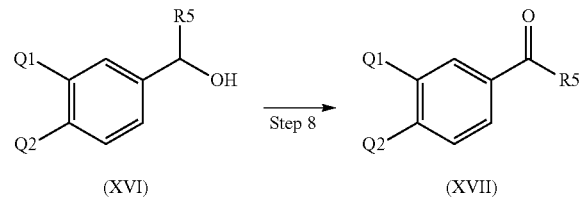

(XVI)    (XVII)

Step 8: Reaction of Oxidation to Aldehyde or Ketone

This step represents a method for producing an aldehyde or ketone compound represented by Formula (XVII) using an alcohol compound represented by Formula (XVI) and an oxidant.

Examples of oxidants include manganese dioxide, tetrapropylammonium perruthenate, sulfur trioxide pyridine complex, Dess-Martin periodinane, pyridinium chlorochromate, and the like. The amount of the oxidant to be added is usually 1 to 10 moles, and preferably 1 to 5 moles, per mole of the compound represented by Formula (XVI). The solvent may be the same as in step 5. The reaction temperature is usually −78 to 200° C., and preferably 0 to 100° C. The reaction time is usually 5 minutes to 3 days, preferably 5 minutes to 10 hours. The thus-obtained compound represented by Formula (XVII) can be subjected to the subsequent step after or without isolation or purification by known isolation and purification means, such as concentration, vacuum concentration, crystallization, solvent extraction, reprecipitation, and chromatography.

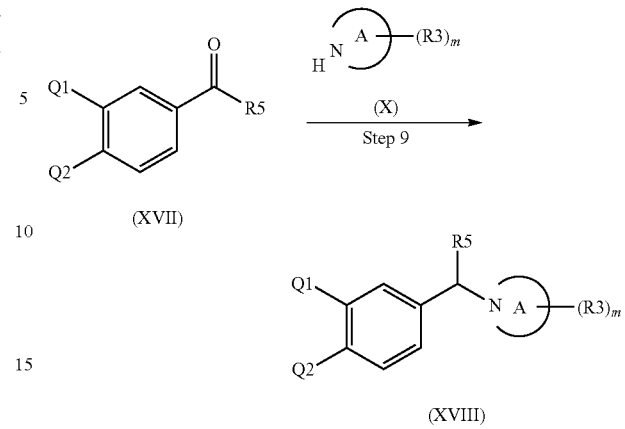

(XVII)

(XVIII)

Step 9: Reductive Amination Reaction

This step represents a method for producing a compound represented by Formula (XVIII) using an amine compound represented by Formula (X) and a reducing agent with the aldehyde or ketone compound represented by Formula (XVII).

Examples of reducing agents include sodium triacetoxyborohydride, sodium cyanoborohydride, sodium borohydride, and the like. The amount of the reducing agent to be added is usually 1 to 10 moles, and preferably 1 to 5 moles, per mole of the compound represented by Formula (XVII).

The solvent is not particularly limited, and any solvent that does not interfere with the reaction can be used. Examples of solvents include toluene, chloroform, tetrahydrofuran, dichloromethane, methanol, ethanol, and the like; as well as a mixed solvent thereof.

The thus-obtained compound represented by Formula (XVIII) can be subjected to the subsequent step after or without isolation or purification by known isolation and purification means, such as concentration, vacuum concentration, crystallization, solvent extraction, reprecipitation, and chromatography.

The conversion of substituents W and X, and leaving groups L1, L2, and L3, may be suitably performed.

In any of steps 1 to 9, protection of a substituent, and removal or conversion of the protecting group, can be suitably performed. For example, for functional groups such as amino, imino, hydroxy, carboxy, carbonyl, and amide groups, as well as functional groups having an active proton, such as indole, protected reagents can be used, or a protecting group can be introduced into such a functional group according to a usual method; afterward, the protecting group can be removed in an appropriate step in each production method.

The protecting group of an amino group or protecting group of an imino group is not particularly limited, insofar as it has a protecting function. Examples of such protecting groups include aralkyl groups, such as benzyl, p-methoxybenzyl, 3,4-dimethoxybenzyl, o-nitrobenzyl, p-nitrobenzyl, benzhydryl, trityl, and cumyl; lower alkanoyl groups, such as formyl, acetyl, propionyl, butyryl, pivaloyl, trifluoroacetyl, and trichloroacetyl; benzoyl; arylalkanoyl groups, such as phenylacetyl and phenoxyacetyl; lower alkoxycarbonyl groups, such as methoxycarbonyl, ethoxycarbonyl, propyloxycarbonyl, and tert-butoxycarbonyl; aralkyloxycarbonyl groups, such as p-nitrobenzyloxycarbonyl and phenethyloxycarbonyl; lower alkylsilyl groups, such as trimethylsilyl and tert-butyldimethylsilyl; tetrahydropyranyl;

trimethylsilylethoxymethyl; lower alkylsulfonyl groups, such as methylsulfonyl, ethylsulfonyl, and tert-butylsulfonyl; lower alkylsulfinyl groups, such as tert-butylsulfinyl; arylsulfonyl groups, such as benzenesulfonyl and toluenesulfonyl; and imido groups, such as phthalimido. In particular, trifluoroacetyl, acetyl, tert-butoxycarbonyl, benzyloxycarbonyl, trimethylsilylethoxymethyl, cumyl, and the like are preferable.

The protecting group of a hydroxy group is not particularly limited insofar as it has a protecting function. Examples of such protecting groups include lower alkyl groups, such as methyl, ethyl, propyl, isopropyl, and tert-butyl; lower alkylsilyl groups, such as trimethylsilyl and tert-butyldimethylsilyl; lower alkoxymethyl groups, such as methoxymethyl and 2-methoxyethoxymethyl; tetrahydropyranyl; trimethylsilylethoxymethyl; aralkyl groups, such as benzyl, p-methoxybenzyl, 2,3-dimethoxybenzyl, o-nitrobenzyl, p-nitrobenzyl, and trityl; and acyl groups, such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The protecting group of a carboxy group is not particularly limited insofar as it has a protecting function. Examples of such protecting groups include lower alkyl groups, such as methyl, ethyl, propyl, isopropyl, and tert-butyl; halo-lower-alkyl groups, such as 2,2,2-trichloroethyl; lower alkenyl groups, such as allyl; trimethylsilylethoxymethyl; and aralkyl groups, such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The protecting group of a carbonyl group is not particularly limited insofar as it has a protecting function. Examples of such protecting groups include ethylene ketal, trimethylene ketal, dimethyl ketal, ethylene acetal, trimethylene acetal, dimethyl acetal, and like ketals and acetals.

The protecting group of an amide group or the protecting group of a functional group having an active proton, such as indole, is not particularly limited, insofar as it has a protecting function. Examples of such protecting groups include lower alkyl groups, such as methyl, ethyl, propyl, isopropyl, and tert-butyl; lower alkylsilyl groups, such as trimethylsilyl and tert-butyldimethylsilyl; lower alkoxymethyl groups, such as methoxymethyl and 2-methoxyethoxymethyl; tetrahydropyranyl; trimethylsilylethoxymethyl; aralkyl groups, such as benzyl, p-methoxybenzyl, 2,3-dimethoxybenzyl, o-nitrobenzyl, p-nitrobenzyl, and trityl; and acyl groups, such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The method for removing such a protecting group may vary depending on the type of protecting group, stability of the target compound, etc. For example, the following methods can be used: solvolysis using an acid or a base according to the method disclosed in a publication (Protective Groups in Organic Synthesis, third edition, T. W. Green, John Wiley & Sons (1999)) or a similar method, i.e., a method comprising reacting with 0.01 moles or a large excess of an acid, preferably trifluoroacetic acid, formic acid, or hydrochloric acid, or an equimolar to large excessive molar amount of a base, preferably potassium hydroxide or calcium hydroxide; chemical reduction using a metal hydride complex etc.; or catalytic reduction using a palladium-carbon catalyst, Raney nickel catalyst, etc.

The biphenyl compound represented by Formula (I) can be easily isolated and purified by common isolation and purification means. Examples of such means include solvent extraction, recrystallization, preparative reversed-phase high-performance liquid chromatography, column chromatography, preparative thin-layer chromatography, and the like.

When the biphenyl compound represented by Formula (I) has isomers such as optical isomers, stereoisomers, rotational isomers, and tautomers, any of the isomers and mixtures thereof is included within the scope of the compound, unless otherwise specified. For example, when the biphenyl compound represented by Formula (I) has optical isomers, the optical isomer separated from a racemic mixture is also included within the scope of the compound, unless otherwise specified. Each of such isomers can be obtained as a single compound by known synthesis and separation means (e.g., concentration, solvent extraction, column chromatography, and recrystallization).

As stated above, unless otherwise specified, the biphenyl compound represented by Formula (I) includes all of the enantiomers and mixtures thereof. The biphenyl compound represented by Formula (I) may be a mixture of R and S enantiomers. Such a mixture may be a mixture comprising 90% or more, 95% or more, or 99% or more of R enantiomer; a mixture comprising 90% or more, 95% or more, or 99% or more of S enantiomer; or the like.

Methods for chiral resolution include, for example: a diastereomer method of causing a chiral resolving agent to act on the biphenyl compound represented by Formula (I) to form a salt, and resolving one of the enantiomers using a solubility difference etc. of the obtained salt; a preferential crystallization method of adding one of the enantiomers to a supersaturated solution of a racemate as a seed for crystallization; and column chromatography such as HPLC using a chiral column. A chiral resolving agent that can be used in the diastereomer method can be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and a-methylbenzylamine. One of the enantiomers of the biphenyl compound represented by Formula (I) alone can be obtained not only by obtaining the biphenyl compound represented by Formula (I) as a mixture of enantiomers and then conducting chiral resolution as above, but also by obtaining one enantiomer of the biphenyl compound represented by Formula (I) through chiral resolution as above or by other methods, and using it as a synthetic raw material of the biphenyl compound represented by Formula (I). Furthermore, methods for obtaining one of the enantiomers of the biphenyl compound represented by Formula (I) or its raw material compound include a method of preferentially obtaining one of the enantiomers by adjusting reaction conditions for a catalyst or the like in a reaction step of generating asymmetric carbon.

The biphenyl compound represented by Formula (I) or a salt thereof may be in the form of crystals. Single crystals and polymorphic crystal mixtures are included within the scope of the compound or a salt thereof. Such crystals can be produced by crystallization according to a crystallization method known per se in the art. The biphenyl compound represented by Formula (I) or a salt thereof may be a solvate (e.g., a hydrate) or a non-solvate. Any of such forms are included within the scope of the biphenyl compound represented by Formula (I) or a salt thereof. Compounds labeled with an isotope (e.g., $^3$H, $^{14}$C, $^{35}$S, and $^{125}$I) are also included within the scope of the biphenyl compound represented by Formula (I) or a salt thereof.

The salts of the biphenyl compound represented by Formula (I) or of the intermediates thereof refer to common salts used in the field of organic chemistry. The salts are preferably pharmaceutically acceptable salts. Examples of such salts include base addition salts to a carboxy group when the compound has a carboxy group, and acid addition salts to an amino or basic heterocyclic group when the compound has an amino or basic heterocyclic group.

Examples of base addition salts include alkali metal salts, such as sodium salts and potassium salts; alkaline earth metal salts, such as calcium salts and magnesium salts; ammonium salts; and organic amine salts, such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts, such as hydrochloride, sulfate, nitrate, phosphate, and perchlorate; organic acid salts, such as acetate, formate, maleate, fumarate, tartrate, citrate, ascorbate, and trifluoroacetate; and sulfonates such as methanesulfonate, isethionate, benzenesulfonate, and p-toluenesulfonate.

Due to their excellent LSD1 inhibitory activity, the biphenyl compound represented by Formula (I) or a salt thereof is useful as a pharmaceutical preparation for preventing and treating, preferably treating, LSD1-related diseases.

Using the biphenyl compound represented by Formula (I) or a salt thereof in combination with one or more other antitumor agents potentiates the antitumor effect. The form of a combination of the biphenyl compound represented by Formula (I) or a salt thereof and one or more other antitumor agents may be a single preparation (i.e., a combination drug) or two or more separate preparations to be administered in combination.

In the present invention, the antitumor effect can be evaluated as, for example, reduced tumor volume, tumor growth stasis, or prolonged survival time.

An embodiment provides an antitumor formulation comprising a combination of the biphenyl compound represented by Formula (I) or a salt thereof and one or more other antitumor agents. Another embodiment provides an antitumor effect potentiator for an antitumor agent, the potentiator comprising the biphenyl compound represented by Formula (I) or a salt thereof as an active ingredient.

The other antitumor agents are not particularly limited. Examples thereof include antimetabolites, antitumor antibiotics, molecular target drugs, platinum-based drugs, and plant alkaloid-based drugs.

Examples of antimetabolites include 5-fluorouracil (5-FU), 5-fluoro-2'-deoxyuridine (FdUrd), tegafur, combination drugs of tegafur and uracil (e.g., UFT), combination drugs of tegafur, gimeracil, and oteracil (e.g., TS-1), pemetrexed, trifluridine, combination drugs of trifluridine and tipiracil hydrochloride (e.g., Lonsurf), gemcitabine, capecitabine, nelarabine, clofarabine, cytarabine, DNA methylation inhibitors (such as azacitidine, decitabine, and guadecitabine), and the like, with cytarabine or DNA methylation inhibitors, such as azacitidine, decitabine, and guadecitabine, being preferable, and cytarabine, azacitidine, decitabine, or guadecitabine being more preferable.

Examples of antitumor antibiotics include daunorubicin, doxorubicin, amrubicin, idarubicin, epirubicin, and like anthracycline-based antitumor antibiotics, mitomycin C, bleomycin, and the like, with anthracycline-based antitumor antibiotics being preferable, and daunorubicin being more preferable.

Examples of molecular target drugs include all-trans retinoic acid or derivatives thereof, human MDM2 (mouse double minute 2) (HDM2; human double minute 2) inhibitors, and HDAC inhibitors.

The all-trans retinoic acid or a derivative thereof is preferably tretinoin (ATRA) or tamibarotene, and more preferably tretinoin (ATRA).

The human MDM2 (HDM2) inhibitor is preferably RG7388 (RO5503781), AMG-232, DS-3032b, RG7112 (RO5045337), SAR405838, or MK-8242, and more preferably RG7388.

Examples of HDAC inhibitors include vorinostat, panobinostat, romidepsin, belinostat, and the like.

The molecular target drug is preferably all-trans retinoic acid or a derivative thereof, a human MDM2 (HDM2) inhibitor, or an HDAC inhibitor, and more preferably tretinoin (ATRA) or RG7388.

Examples of platinum-based drugs include oxaliplatin, carboplatin, cisplatin, nedaplatin, and the like, with carboplatin or cisplatin being preferable.

Examples of plant alkaloid-based drugs include microtubule inhibitors, such as paclitaxel, docetaxel, vinblastine, vincristine, vindesine, vinorelbine, and eribulin, and topoisomerase inhibitors, such as irinotecan (SN-38), nogitecan, and etoposide, with taxane microtubule inhibitors such as paclitaxel and docetaxel or topoisomerase inhibitors such as irinotecan (SN-38), nogitecan, and etoposide being preferable, and paclitaxel, irinotecan (SN-38), or etoposide being more preferable.

The one or more other antitumor agents are preferably an antimetabolite, an antitumor antibiotic, a molecular target drug, a platinum-based drug, or a plant alkaloid-based drug, more preferably an antimetabolite, an antitumor antibiotic, all-trans retinoic acid or a derivative thereof, a human MDM2 (HDM2) inhibitor, an HDAC inhibitor, a platinum-based drug, or a plant alkaloid-based drug, more preferably an antimetabolite, an antitumor antibiotic, all-trans retinoic acid or a derivative thereof, a human MDM2 (HDM2) inhibitor, a platinum-based drug, or a plant alkaloid-based drug, more preferably an antimetabolite, an antitumor antibiotic, all-trans retinoic acid or a derivative thereof, a human MDM2 (HDM2) inhibitor, a platinum-based drug, a topoisomerase inhibitor, or a taxane microtubule inhibitor, more preferably cytarabine, a DNA methylation inhibitor, an anthracycline-based antitumor antibiotic, all-trans retinoic acid or a derivative thereof, a platinum-based drug, a topoisomerase inhibitor, or a taxane microtubule inhibitor, and more preferably cytarabine, azacitidine, decitabine, guadecitabine, daunorubicin, tretinoin (ATRA), RG7388, carboplatin, cisplatin, paclitaxel, irinotecan (SN-38), or etoposide.

The tumor targeted in the present invention is not particularly limited as long as the antitumor effect is potentiated. The tumor is preferably a tumor in which the biphenyl compound represented by Formula (I) or a salt thereof exerts an antitumor effect, and more preferably LSD1-related malignant tumors.

Examples of the "LSD1-related malignant tumors" include malignant tumors whose incidence can be reduced, and whose symptoms can be remitted, relieved, and/or completely cured by eliminating, suppressing, and/or inhibiting LSD1 function. The type of malignant tumor to be treated by the compound or a salt thereof of the present invention is not particularly limited. Examples of such malignant tumors include head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, myelodysplastic syndrome, chronic myeloproliferative disease, malignant lymphoma, multiple myeloma, skin cancer, brain tumor, mesothelioma, and the like. Preferable examples include lung cancers (e.g., non-small cell lung cancer and small cell lung cancer), leukemia, and myelodysplastic syndromes.

When the biphenyl compound or a salt thereof and one or more other antitumor agents are used as a pharmaceutical preparation, a pharmaceutical carrier can be added, if required, thereby forming one or more suitable dosage forms according to prevention and treatment purposes. Examples of the dosage form(s) include oral preparations, injections, suppositories, ointments, patches, and the like. In the case of the biphenyl compound or a salt thereof, oral preparations are preferable. Such dosage forms can be formed by methods conventionally known to persons skilled in the art.

The administration schedule of the biphenyl compound represented by Formula (I) or a salt thereof and one or more other antitumor agents is suitably selected within the range in which an antitumor effect is potentiated. The active ingredients may be administered simultaneously or separately at intervals. When they are administered separately, the order of administration is not limited.

The biphenyl compound represented by Formula (I) or a salt thereof and one or more other antitumor agents may be formulated into multiple dosage forms, or may be formulated into a single dosage form (i.e., formulated as a combination drug), based on the administration form and administration schedule of each active ingredient. Further, preparations may be produced and sold in a single package suitable for combined use, or preparations may be produced and sold in separate packages.

As the pharmaceutical carrier, various conventional organic or inorganic carrier materials used as preparation materials may be blended as an excipient, binder, disintegrant, lubricant, or coating agent in solid preparations; or as a solvent, solubilizing agent, suspending agent, isotonizing agent, pH adjuster, buffer, or soothing agent in liquid preparations. Moreover, pharmaceutical preparation additives, such as antiseptics, antioxidants, colorants, taste-masking or flavoring agents, and stabilizers, may also be used, if required.

When oral solid preparations are prepared, an excipient, a binder, a disintegrant, a lubricant, a colorant, a taste-masking or flavoring agent, etc., may be added; and the resulting mixture may be formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid a-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, stearic acid salt sodium, magnesium stearate, borax, polyethylene glycol, and the like. Examples of colorants include titanium oxide, iron oxide, and the like. Examples of taste-masking or flavoring agents include sucrose, bitter orange peel, citric acid, tartaric acid, and the like.

When liquid preparations for oral administration are prepared, a taste-masking agent, a buffer, a stabilizer, a flavoring agent, etc., may be added; and the resulting mixture may be formulated into oral liquid preparations, syrups, elixirs, or the like by ordinary methods.

In this case, the same taste-masking or flavoring agent as those mentioned above may be used. Examples of the buffer include sodium citrate and the like, and examples of the stabilizer include tragacanth, gum arabic, gelatin, and the like. As necessary, these preparations for oral administration may be coated according to methods known in the art with an enteric coating or other coating for the purpose of, for example, persistence of effects. Examples of such coating agents include hydroxypropyl methylcellulose, ethyl cellulose, hydroxymethyl cellulose, hydroxypropyl cellulose, polyoxyethylene glycol, and Tween 80 (registered trademark).

When injections are prepared, a pH adjuster, a buffer, a stabilizer, an isotonizing agent, a topical anesthetic, etc., may be added; and the resulting mixture may be formulated into subcutaneous, intramuscular, and intravenous injections by ordinary methods.

Examples of usable pH adjusters and buffers include sodium citrate, sodium acetate, sodium phosphate, and the like. Examples of usable stabilizers include sodium pyrosulfite, EDTA, thioglycolic acid, and thiolactic acid. Examples of usable topical anesthetics include procaine hydrochloride, lidocaine hydrochloride, and the like. Examples of usable isotonizing agents include sodium chloride, glucose, D-mannitol, glycerin, and the like.

The preparations of the one or more other antitumor agents also include drug delivery system (DDS) preparations for them. For example, "paclitaxel" includes albumin-bound paclitaxel (e.g., Abraxane), paclitaxel micelles (e.g., NK105), and the like; and "cisplatin" includes cisplatin micelles (e.g., NC-6004) and the like.

The amount of the biphenyl compound to be incorporated in each of such dosage unit forms depends on the condition of the patient to whom the compound is administered, the dosage form, etc. In general, in the case of an oral agent, an injection, and a suppository, the amount of the biphenyl compound is preferably 0.05 to 1000 mg, 0.01 to 500 mg, and 1 to 1000 mg, respectively, per dosage unit form.

The daily dose of the biphenyl compound in such a dosage form depends on the condition, body weight, age, gender, etc., of the patient, and cannot be generalized. For example, the daily dose of the biphenyl compound for an adult (body weight: 50 kg) may be usually 0.05 to 5000 mg, and preferably 0.1 to 1000 mg; and is preferably administered in one dose, or in two to three divided doses, per day.

EXAMPLES

The present invention is described below in more detail with reference to Examples. However, the scope of the present invention is not limited to these Examples. The present invention is fully described below by way of Examples; however, it is understood that various changes and modifications by a skilled artisan are possible. Therefore, such changes and modifications are included in the present invention as long as they do not depart from the scope of the invention.

The various reagents used in the Examples were obtained from commercial suppliers, unless otherwise specified. For silica gel column chromatography, a SNAP-Ultra (registered trademark) silica prepacked column produced by Biotage was used. Alternatively, for basic silica gel column chromatography, a KP-NH (registered trademark) prepacked column produced by Biotage was used. NMR spectra were measured by using an AL400 (400 MHz; produced by JEOL), a Mercury 400 (400 MHz; produced by Agilent Technologies, Inc.), or a 500-MHz Bruker Avance III HD NMR Spectrometer (500 MHz; Bruker). When the deuterated solvent contained tetramethylsilane, tetramethylsilane was used as the internal reference. Otherwise, an NMR solvent was used as the internal reference. All of the δ values are shown in ppm. The microwave reaction was performed using an Initiator produced by Biotage.

LCMS spectra were measured using an Acquity SQD (quadrupole) produced by Waters Corporation under the following conditions.
Column: Acquity UPLC (registered trademark) BEH C18, 2.1×50 mm, 1.7 μm (produced by Waters Corporation)
MS detection: ESI positive
UV detection: 254 and 280 nm
Column flow rate: 0.5 mL/min
Mobile phase: Water/acetonitrile (0.1% formic acid)
Injection volume: 1 μL
Gradient (Table 1)
Time (min) Water Acetonitrile
0 95 5
0.1 95 5
2.1 5 95
3.0 STOP Preparative reversed-phase HPLC purification was performed under the following conditions using a preparative separation system available from Gilson, Inc.
Column: Xselect CSH Prep C18 5 μm OBD (19×50 mm)+ (19×100 mm), produced by Waters Corporation
UV detection: 254 nm
Column flow rate: 18 mL/min
Mobile phase: Water/acetonitrile (0.1% formic acid)
Injection volume: 0.1 to 0.5 mL The symbols stand for the following.
s: Singlet
d: Doublet
t: Triplet
q: Quartet
dd: Double doublet
dt: Double triplet
td: Triple doublet
tt: Triple triplet
ddd: Double double doublet
ddt: Double double triplet
dtd: Double triple doublet
tdd: Triple double doublet
m: Multiplet
br: Broad
brs: Broad singlet
THF: Tetrahydrofuran
DMF: N,N-dimethylformamide
DME: 1,2-Dimethoxyethane
DMSO: Dimethylsulfoxide
HATU: O-(7-azabenzotriazol-1-yl)-N,N,N',N'-tetramethyluronium hexafluorophosphate
TEA: Triethylamine
WSC HCl: 1-Ethyl-3-(3-dimethylaminopropyl)carbodiimide hydrochloride
t-BuOH: Tertiary butanol
DMAP: N,N-dimethylaminopyridine
$Pd(PPh_3)_4$: Tetrakis(triphenylphosphine)palladium(0)
$Pd(dba)_2$: Bis(dibenzylideneacetone)palladium(0)
$PCy_3$: Tricyclohexylphosphine
TFA: Trifluoroacetic acid
$Pd(OAc)_2$: Palladium acetate
KOAc: Potassium acetate
$PdCl_2(dppf)$: [1,1'-Bis(diphenylphosphino)ferrocene]palladium(II) dichloride
$PdCl_2(dppf)CH_2Cl_2$: [1,1'-Bis(diphenylphosphino)ferrocene]palladium(II) dichloride dichloromethane complex
DMEAD: Di-2-methoxyethyl azodicarboxylate
$PPh_3$: Triphenylphosphine
DMA: Dimethylacetamide
MeMgBr: Methylmagnesium bromide
EtMgBr: Ethylmagnesium bromide
MTBE: Methyltertiary-butyl ether
DCM: Dichloromethane
$Boc_2O$: Di-tert-butyl dicarbonate
NBS: N-bromosuccinimide
X-phos: 2-dicyclohexylphosphino-2',4',6'-triisopropylbiphenyl
MeOH: Methanol
EtOH: Ethanol
IPE: Diisopropyl ether
TBAF: Tetrabutylammonium fluoride
$Pd_2(dba)_3$: Tris(dibenzylideneacetone)dipalladium(0)
$PdCl_2(PPh_3)_2$: Bistriphenylphosphine palladium chloride
S-Phos: 2-Dicyclohexylphosphino-2,6-dimethoxybiphenyl
HOBt: 1-Hydroxybenzotriazole
Pd/C: Palladium on carbon
NMP: N-methyl-2-pyrrolidinone.

Example 1: Synthesis of 4-[5-[(3S)-3-aminopyrrolidine-1-carbonyl]-2-(p-tolyl)phenyl]benzonitrile Step 1

3-Bromo-4-chloro-benzoic acid (19 g) was dissolved in DMF (160 mL). At 25° C., DMAP (20 g) and WSC HCl (31 g) were added thereto, followed by the addition of t-BuOH (38 mL). The resulting mixture was stirred at room temperature overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl 3-bromo-4-chloro-benzoate.

Step 2

The tert-butyl 3-bromo-4-chloro-benzoate (1.3 g) obtained in step 1 above was dissolved in 1,4-dioxane (8.7 mL). At room temperature, (4-cyanophenyl)boronic acid (768 mg), $Pd(PPh_3)_4$ (151 mg), and a 2 M $Na_2CO_3$ aqueous solution (5.4 mL) were added thereto, and the reaction mixture was stirred in a microwave reactor at 120° C. for 30 minutes. The reaction mixture was then vacuum-concentrated, and the residue was purified by silica gel column chromatography (mobile phase: hexane/ethyl acetate) to give tert-butyl 4-chloro-3-(4-cyanophenyl) benzoate.

Step 3

The tert-butyl 4-chloro-3-(4-cyanophenyl)benzoate (1.1 g) obtained in step 2 above was dissolved in 1,4-dioxane (17 mL). At room temperature, p-tolylboronic acid (932 mg), $Pd(dba)_2$ (157 mg), tripotassium phosphate (1.5 g), and a solution of 1 M $PCy_3$ in THF (0.57 mL) were added thereto, and the reaction mixture was stirred in a microwave reactor at 160° C. for 30 minutes. After the addition of chloroform, the insoluble matter was filtered off, and the solvent was distilled off. The residue was purified by silica gel column chromatography (mobile phase: hexane/ethyl acetate), and the solvent was distilled off. The residue was dissolved in TFA (2 mL). The solvent was distilled off. Ethyl acetate was added thereto, and the mixture was washed sequentially with water and saturated brine. After the organic layer was dried over anhydrous sodium sulfate, the solvent was distilled off to give 3-(4-cyanophenyl)-4-(p-tolyl)benzoic acid.
Step 4

The 3-(4-cyanophenyl)-4-(p-tolyl)benzoic acid (10 mg) obtained in step 3 above, tert-butyl N-[(3S)-pyrrolidin-3-yl] carbamate (6 mg), and HATU (24 mg) were dissolved in THF (0.5 mL). At room temperature, TEA (0.013 mL) was added thereto, followed by stirring at 50° C. overnight. The reaction mixture was vacuum-concentrated, and the solvent was distilled off. The residue was purified by silica gel column chromatography (mobile phase: hexane/ethyl acetate) to give tert-butyl N-[(3S)-1-[3-(4-cyanophenyl)-4-(p-tolyl)benzoyl]pyrrolidin-3-yl]carbamate.
Step 5

The tert-butyl N-[(3S)-1-[3-(4-cyanophenyl)-4-(p-tolyl) benzoyl]pyrrolidin-3-yl]carbamate (15 mg) obtained in step 4 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 2: Synthesis of 4-[5-[(3S)-3-aminopyrrolidine-1-carbothioyl]-2-(p-tolyl)phenyl]benzonitrile The 4-[5-[(3S)-3-aminopyrrolidine-1-carbonyl]-2-(p-tolyl)phenyl]benzonitrile (6 mg) obtained in Example 1 (step 5) was dissolved in THF (0.8 mL). At room temperature, Lawesson's reagent (3.8 mg) was added thereto, followed by stirring at room temperature for 30 minutes. Chloroform was added thereto, and the mixture was partitioned with sodium bicarbonate water. After the organic layer was dried over anhydrous sodium sulfate, the solvent was distilled off. The residue was purified by reversed-phase HPLC (mobile phase: water/acetonitrile) to give the title compound.

Example 3: Synthesis of 4-[5-(4-aminopiperidine-1-carbonyl)-2-(p-tolyl)phenyl]benzonitrile Step 1

The 3-(4-cyanophenyl)-4-(p-tolyl)benzoic acid (20 mg) obtained in Example 1 (step 3) was dissolved in THF (1 mL). At room temperature, tert-butyl N-(4-piperidyl)carbamate (13 mg), HATU (49 mg), and TEA (0.027 mL) were added thereto, followed by stirring at 50° C. overnight. The reaction mixture was vacuum-concentrated, and the solvent was distilled off. The residue was purified by silica gel column chromatography (mobile phase: hexane/ethyl acetate) to give tert-butyl N-[1-[3-(4-cyanophenyl)-4-(p-tolyl)benzoyl]-4-piperidyl]carbamate.
Step 2

The tert-butyl N-[1-[3-(4-cyanophenyl)-4-(p-tolyl)benzoyl]-4-piperidyl]carbamate (30 mg) obtained in step 1 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 4: Synthesis of 4-[5-(2,8-diazaspiro[3.5] nonane-2-carbonyl)-2-(p-tolyl)phenyl]benzonitrile The procedure of steps 1 to 5 in Example 1 was conducted using tert-butyl 2,8-diazaspiro[3.5]nonane-8-carboxylate hydrochloride instead of tert-butyl N-[(3S)-pyrrolidin-3-yl] carbamate to give the title compound.

Example 5: Synthesis of 4-[5-(2,7-diazaspiro[3.4] octane-7-carbonyl)-2-(p-tolyl)phenyl]benzonitrile The procedure of steps 1 to 5 in Example 1 was conducted using tert-butyl 2,7-diazaspiro[3.4]octane-2-carboxylate instead of tert-butyl N-[(3S)-pyrrolidin-3-yl]carbamate to give the title compound.

Example 6: Synthesis of 4-[5-(3,8-diazaspiro[4.4] nonane-8-carbonyl)-2-(p-tolyl)phenyl]benzonitrile The procedure of steps 1 to 5 in Example 1 was conducted using tert-butyl 3,8-diazaspiro[4.4]nonane-8-carboxylate instead of tert-butyl N-[(3S)-pyrrolidin-3-yl]carbamate to give the title compound.

Example 7: Synthesis of 4-[5-[(3-exo)-3-amino-8-azabicyclo[3.2.1]octane-8-carbonyl]-2-(p-tolyl)phenyl]benzonitrile Step 1

3-Bromo-4-chloro-benzoic acid (500 mg) was dissolved in DMA (5.3 mL). At room temperature, HATU (1 g), TEA (0.59 mL), and tert-butyl N-[(3-exo)-8-azabicyclo[3.2.1] octan-3-yl]carbamate (480 mg) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ ethyl acetate) to give tert-butyl N-[(3-exo)-8-(3-bromo-4-chloro-benzoyl)-8-azabicyclo[3.2.1]octan-3-yl]carbamate.
Step 2

The tert-butyl N-[(3-exo)-8-(3-bromo-4-chloro-benzoyl)-8-azabicyclo[3.2.1]octan-3-yl]carbamate (200 mg) obtained in step 1 above was dissolved in 1,4-dioxane (2.3 mL). At room temperature, (4-cyanophenyl)boronic acid (60 mg), Pd(PPh$_3$)$_4$ (16 mg), and a 2 M Na$_2$CO$_3$ aqueous solution (1.1 mL) were added thereto, and the reaction mixture was stirred in a microwave reactor at 120° C. for 30 minutes. The solvent was distilled off, and the residue was purified by silica gel column chromatography (mobile phase: hexane/ ethyl acetate) to give tert-butyl N-[(3-exo)-8-[4-chloro-3-(4-cyanophenyl)benzoyl]-8-azabicyclo[3.2.1]octan-3-yl]carbamate.
Step 3

The tert-butyl N-[(3-exo)-8-[4-chloro-3-(4-cyanophenyl) benzoyl]-8-azabicyclo[3.2.1]octan-3-yl]carbamate (15 mg) obtained in step 2 above was dissolved in 1,4-dioxane (0.322 mL). At room temperature, p-tolylboronic acid (5.3 mg), Pd(dba)$_2$ (0.93 mg), a solution of 1 M PCy$_3$ in THF (0.003 mL), and tripotassium phosphate (21 mg) were added thereto, and the reaction mixture was stirred in a microwave reactor at 160° C. for 30 minutes. The solvent was distilled off, and the residue was purified by silica gel column chromatography (mobile phase: hexane/ethyl acetate) to give tert-butyl N-[(3-exo)-8-[3-(4-cyanophenyl)-4-(p-tolyl) benzoyl]-8-azabicyclo[3.2.1]octan-3-yl]carbamate.

Step 4

The tert-butyl N-[(3-exo)-8-[3-(4-cyanophenyl)-4-(p-tolyl)benzoyl]-8-azabicyclo[3.2.1]octan-3-yl]carbamate (15 mg) obtained in step 3 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 8: Synthesis of 4-[5-[(3S)-3-amino-3-methyl-pyrrolidine-1-carbonyl]-2-(p-tolyl)phenyl]benzonitrile The procedure of steps 1 to 5 in Example 1 was conducted using tert-butyl N-[(3S)-3-methylpyrrolidin-3-yl]carbamate instead of tert-butyl N-[(3S)-pyrrolidin-3-yl]carbamate to give the title compound.

Example 9: Synthesis of 4-[5-[(3S)-3-aminopyrrolidine-1-carbonyl]-2-(2-chloro-4-methyl-phenyl)phenyl]benzonitrile Step 1

3-Bromo-4-chloro-benzoic acid (10 g) was dissolved in DMA (85 mL). At room temperature, HATU (24 g), TEA (12 mL), and tert-butyl N-[(3S)-pyrrolidin-3-yl]carbamate (8.7 g) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-(3-bromo-4-chloro-benzoyl)pyrrolidin-3-yl]carbamate.

Step 2

The tert-butyl N-[(3S)-1-(3-bromo-4-chloro-benzoyl)pyrrolidin-3-yl]carbamate (2.2 g) obtained in step 1 above was dissolved in 1,4-dioxane (13.6 mL). At room temperature, 4-(4,4,5,5-tetramethyl-1,3,2-dioxaborolan-2-yl)benzonitrile (1.5 g), Pd(PPh$_3$)$_4$ (189 mg), and a 2 M Na$_2$CO$_3$ aqueous solution (6.8 mL) were added thereto, and the reaction mixture was stirred in a microwave reactor at 120° C. for 30 minutes. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-[4-chloro-3-(4-cyanophenyl)benzoyl]pyrrolidin-3-yl]carbamate.

Step 3

The tert-butyl N-[(3S)-1-[4-chloro-3-(4-cyanophenyl)benzoyl]pyrrolidin-3-yl]carbamate (500 mg) obtained in step 2 above was dissolved in 1,4-dioxane (9.8 mL). At room temperature, Pd(OAc)$_2$ (26 mg), KOAc (346 mg), bis(pinacolato)diboron (596 mg), and Silica-SMAP (150 mg, produced by Wako Pure Chemical Industries, Ltd.) were added thereto, followed by stirring at 160° C. overnight. The mixture was passed through Celite, and the filtrate was vacuum-concentrated. The residue was purified by silica gel column chromatography (mobile phase: hexane/ethyl acetate) to give tert-butyl N-[(3S)-1-[3-(4-cyanophenyl)-4-(4,4,5,5-tetramethyl-1,3,2-dioxaborolan-2-yl)benzoyl]pyrrolidin-3-yl]carbamate.

Step 4

The tert-butyl N-[(3S)-1-[3-(4-cyanophenyl)-4-(4,4,5,5-tetramethyl-1,3,2-dioxaborolan-2-yl)benzoyl]pyrrolidin-3-yl]carbamate (15 mg) obtained in step 3 above, 1-bromo-2-chloro-4-methyl-benzene (12 mg), and Pd(PPh$_3$)$_4$ (1.7 mg) were suspended in 1,4-dioxane (1.5 mL). At room temperature, a 2 M Na$_2$CO$_3$ aqueous solution (0.7 mL) was added thereto, followed by stirring at 120° C. for 30 minutes. After the reaction mixture was filtrated, the solvent was distilled off to give tert-butyl N-[(3S)-1-[4-(2-chloro-4-methyl-phenyl)-3-(4-cyanophenyl)benzoyl]pyrrolidin-3-yl]carbamate.

Step 5

The tert-butyl N-[(3S)-1-[4-(2-chloro-4-methyl-phenyl)-3-(4-cyanophenyl)benzoyl]pyrrolidin-3-yl]carbamate (15 mg) obtained in step 4 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 10: Synthesis of 4-[5-[(3S)-3-aminopyrrolidine-1-carbonyl]-2-(3-chloro-4-methyl-phenyl)phenyl]benzonitrile The procedure of steps 1 to 5 in Example 9 was conducted using 4-bromo-2-chloro-1-methyl-benzene instead of 1-bromo-2-chloro-4-methyl-benzene to give the title compound.

Example 11: Synthesis of 4-[5-[(3S)-3-aminopyrrolidine-1-carbonyl]-2-[3-fluoro-4-(trifluoromethyl)phenyl]phenyl]benzonitrile The procedure of steps 1 to 5 in Example 9 was conducted using 4-bromo-2-fluoro-1-(trifluoromethyl)benzene instead of 1-bromo-2-chloro-4-methyl-benzene to give the title compound.

Example 12: Synthesis of 4-[5-[(3S)-3-aminopyrrolidine-1-carbonyl]-2-(4-methyl-2-nitro-phenyl)phenyl]benzonitrile Step 1

The tert-butyl N-[(3S)-1-[4-chloro-3-(4-cyanophenyl)benzoyl]pyrrolidin-3-yl]carbamate (15 mg) obtained in Example 9 (step 2), 4-methyl-2-nitrophenylboronic acid pinacol ester (18 mg), Pd(dba)$_2$ (1.6 mg), a solution of 1 M PCy$_3$ in THF (0.003 mL), and tripotassium phosphate (15 mg) were added thereto, and the reaction mixture was stirred in a microwave reactor at 160° C. for 30 minutes. The solvent was distilled off, and the residue was purified by silica gel column chromatography (mobile phase: hexane/ethyl acetate) to give tert-butyl N-[(3S)-1-[3-(4-cyanophenyl)-4-(4-methyl-2-nitro-phenyl)benzoyl]pyrrolidin-3-yl]carbamate.

Step 2

The tert-butyl N-[(3S)-1-[3-(4-cyanophenyl)-4-(4-methyl-2-nitro-phenyl)benzoyl]pyrrolidin-3-yl]carbamate (10 mg) obtained in step 1 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 13: Synthesis of 4-[5-[(3S)-3-aminopyrrolidine-1-carbonyl]-2-[4-(difluoromethyl)phenyl]phenyl]benzonitrile The procedure of steps 1 to 5 in Example 9 was conducted using 1-bromo-4-(difluoromethyl)benzene instead of 1-bromo-2-chloro-4-methyl-benzene to give the title compound.

Example 14: Synthesis of 4-[5-[(3S)-3-aminopyrrolidine-1-carbonyl]-2-[4-(trifluoromethyl)phenyl]phenyl]benzonitrile The procedure of steps 1 to 2 in Example 12 was conducted using [4-(trifluoromethyl)phenyl]boronic acid instead of 4-methyl-2-nitrophenylboronic acid pinacol ester to give the title compound.

Example 15: Synthesis of 4-[5-[(3S)-3-aminopyrrolidine-1-carbonyl]-2-(2-fluoro-4-methyl-phenyl)phenyl]benzonitrile Step 1
The tert-butyl N-[(3S)-1-[4-chloro-3-(4-cyanophenyl)benzoyl]pyrrolidin-3-yl]carbamate (1.7 g) obtained in Example 9 (step 2) was dissolved in 1,4-dioxane (20 mL). At room temperature, (2-fluoro-4-methyl-phenyl)boronic acid (980 mg), Pd(dba)$_2$ (110 mg), a solution of 1 M PCy$_3$ in THF (0.4 mL), and tripotassium phosphate (2.5 g) were added thereto, and the reaction mixture was stirred in a microwave reactor at 160° C. for 45 minutes. The mixture was purified by NH-silica gel and washed with methanol/ethyl acetate, and the solvent was distilled off to give tert-butyl N-[(3S)-1-[3-(4-cyanophenyl)-4-(2-fluoro-4-methyl-phenyl)benzoyl]pyrrolidin-3-yl]carbamate.
Step 2
The tert-butyl N-[(3S)-1-[3-(4-cyanophenyl)-4-(2-fluoro-4-methyl-phenyl)benzoyl]pyrrolidin-3-yl]carbamate (1.7 g) obtained in step 1 above was dissolved in TFA (44 mL), followed by stirring for 10 minutes. The solvent was distilled off, and the residue was purified by reversed-phase HPLC (mobile phase: water/acetonitrile) to give the title compound.

Example 16: Synthesis of 4-[5-[(3S)-3-aminopyrrolidine-1-carbonyl]-2-(p-tolyl)phenyl]-2-fluoro-benzonitrile Step 1
The tert-butyl N-[(3S)-1-(3-bromo-4-chloro-benzoyl)pyrrolidin-3-yl]carbamate (14 g) obtained in Example 9 (step 1) was dissolved in 1,4-dioxane (87 mL). At room temperature, (4-cyano-3-fluoro-phenyl)boronic acid (6.3 g), Pd(PPh$_3$)$_4$ (1.2 g), and a 2 M Na$_2$CO$_3$ aqueous solution (44 mL) were added thereto, followed by stirring at 90° C. overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-[4-chloro-3-(4-cyano-3-fluoro-phenyl)benzoyl]pyrrolidin-3-yl]carbamate.
Step 2
The tert-butyl N-[(3S)-1-[4-chloro-3-(4-cyano-3-fluoro-phenyl)benzoyl]pyrrolidin-3-yl]carbamate (48 mg) obtained in step 1 above was dissolved in 1,4-dioxane (0.5 mL). At room temperature, p-tolylboronic acid (29 mg), Pd(dba)$_2$ (3.1 mg), a solution of 1 M PCy$_3$ in THF (0.005 mL), and tripotassium phosphate (68 mg) were added thereto, and the reaction mixture was stirred in a microwave reactor at 160° C. for 45 minutes. The mixture was purified by NH-silica gel and washed with methanol/ethyl acetate, and the solvent was distilled off to give tert-butyl N-[(3S)-1-[3-(4-cyano-3-fluoro-phenyl)-4-(p-tolyl)benzoyl]pyrrolidin-3-yl]carbamate.
Step 3
TFA (1.2 mL) was added to the tert-butyl N-[(3S)-1-[3-(4-cyano-3-fluoro-phenyl)-4-(p-tolyl)benzoyl]pyrrolidin-3-yl]carbamate (48 mg) obtained in step 2 above, followed by stirring for 10 minutes. The solvent was distilled off, and the residue was purified by reversed-phase HPLC (mobile phase: water/acetonitrile) to give the title compound.

Example 17: Synthesis of 4-[5-[(3-endo)-3-amino-8-azabicyclo[3.2.1]octane-8-carbonyl]-2-(p-tolyl)phenyl]-2-fluoro-benzonitrile Step 1
3-Bromo-4-chloro-benzoic acid (700 mg) was dissolved in THF (15 mL). At room temperature, HATU (1.2 g), TEA (0.83 mL), and tert-butyl N-[(3-endo)-8-azabicyclo[3.2.1]octan-3-yl]carbamate (700 mg) were added thereto, followed by stirring at 50° C. for 1 hour. The solvent was distilled off, and the residue was purified by silica gel column chromatography (mobile phase: hexane/ethyl acetate) to give tert-butyl N-[(3-endo)-8-(3-bromo-4-chloro-benzoyl)-8-azabicyclo[3.2.1]octan-3-yl]carbamate.
Step 2
The tert-butyl N-[(3-endo)-8-(3-bromo-4-chloro-benzoyl)-8-azabicyclo[3.2.1]octan-3-yl]carbamate (1.2 g) obtained in step 1 above was dissolved in 1,4-dioxane (6.7 mL). At room temperature, (4-cyano-3-fluoro-phenyl)boronic acid (461 mg), PdCl$_2$(dppf) (58 mg), and a 2 M Na$_2$CO$_3$ aqueous solution (3.3 mL) were added thereto, followed by stirring at 95° C. overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3-endo)-8-[4-chloro-3-(4-cyano)-3-fluoro-phenyl)benzoyl]-8-azabicyclo[3.2.1]octan-3-yl]carbamate.
Step 3
The tert-butyl N-[(3-endo)-8-[4-chloro-3-(4-cyano-3-fluoro-phenyl)benzoyl]-8-azabicyclo[3.2.1]octan-3-yl]carbamate (17 mg) obtained in step 2 above was dissolved in 1,4-dioxane (0.5 mL). At room temperature, p-tolylboronic acid (9.6 mg), Pd(dba)$_2$ (1.6 mg), tripotassium phosphate (15 mg), and a solution of 1 M PCy$_3$ in THF (0.004 mL) were added thereto, and the mixture was stirred in a microwave reactor at 160° C. for 30 minutes. The reaction mixture was filtered through NH-silica gel, and the solvent of the filtrate was distilled off to give tert-butyl N-[(3-endo)-8-[3-(4-cyano-3-fluoro-phenyl)-4-(p-tolyl)benzoyl]-8-azabicyclo[3.2.1]octan-3-yl]carbamate.
Step 4
The tert-butyl N-[(3-endo)-8-[3-(4-cyano-3-fluoro-phenyl)-4-(p-tolyl)benzoyl]-8-azabicyclo[3.2.1]octan-3-yl]carbamate (15 mg) obtained in step 3 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 18: Synthesis of 4-[5-[(3-exo)-3-amino-8-azabicyclo[3.2.1]octane-8-carbonyl]-2-(1-methylindol-5-yl)phenyl]-2-fluoro-benzonitrile Step 1

The tert-butyl N-[(3-exo)-8-(3-bromo-4-chloro-benzoyl)-8-azabicyclo[3.2.1]octan-3-yl]carbamate (300 mg) obtained in Example 7 (step 1) was dissolved in 1,4-dioxane (1.7 mL). At room temperature, (4-cyano-3-fluoro-phenyl)boronic acid (123 mg), PdCl$_2$(dppf) (17 mg), and a 2 M Na$_2$CO$_3$ aqueous solution (0.85 mL) were added thereto, and the reaction mixture was stirred in a microwave reactor at 120° C. for 30 minutes. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3-exo)-8-[4-chloro-3-(4-cyano-3-fluoro-phenyl)benzoyl]-8-azabicyclo[3.2.1]octan-3-yl]carbamate.

Step 2

The tert-butyl N-[(3-exo)-8-[4-chloro-3-(4-cyano-3-fluoro-phenyl)benzoyl]-8-azabicyclo[3.2.1]octan-3-yl]carbamate (10 mg) obtained in step 1 above was dissolved in 1,4-dioxane (0.5 mL). At room temperature, (1-methylindol-5-yl)boronic acid (7.2 mg), Pd(dba)$_2$ (0.9 mg), tripotassium phosphate (8.8 mg), and a solution of 1 M PCy$_3$ in THF (0.002 mL) were added thereto, and the reaction mixture was stirred in a microwave reactor at 160° C. for 30 minutes. The reaction mixture was filtered through NH-silica gel, and the solvent of the filtrate was distilled off. The residue was purified by silica gel column chromatography (mobile phase: hexane/ethyl acetate) to give tert-butyl N-[(3-exo)-8-[3-(4-cyano-3-fluoro-phenyl)-4-(1-methylindol-5-yl)benzoyl]-8-azabicyclo[3.2.1]octan-3-yl]carbamate.

Step 3

The tert-butyl N-[(3-exo)-8-[3-(4-cyano-3-fluoro-phenyl)-4-(1-methylindol-5-yl)benzoyl]-8-azabicyclo[3.2.1]octan-3-yl]carbamate (15 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 19: Synthesis of 4-[5-[(3S)-3-aminopyrrolidine-1-carbonyl]-2-(p-tolyl)phenyl]-2,6-difluoro-benzonitrile Step 1

4-Bromo-3-chloro-benzoic acid (2 g) was dissolved in DMA (17 mL). At room temperature, HATU (4.8 g), TEA (2.4 mL), and tert-butyl N-[(3S)-pyrrolidin-3-yl]carbamate (1.7 g) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-(4-bromo-3-chloro-benzoyl)pyrrolidin-3-yl]carbamate.

Step 2

The tert-butyl N-[(3S)-1-(4-bromo-3-chloro-benzoyl)pyrrolidin-3-yl]carbamate obtained in step 1 above was dissolved in 1,4-dioxane (10.6 mL). At room temperature, Pd(PPh$_3$)$_4$ (147 mg), a 2 M Na$_2$CO$_3$ aqueous solution (5.3 mL), and p-tolylboronic acid (693 mg) were added thereto, and the reaction mixture was stirred in a microwave reactor at 120° C. for 30 minutes. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-[3-chloro-4-(p-tolyl)benzoyl]pyrrolidin-3-yl]carbamate.

Step 3

The tert-butyl N-[(3S)-1-[3-chloro-4-(p-tolyl)benzoyl]pyrrolidin-3-yl]carbamate (666 mg) obtained in step 2 above was dissolved in 1,4-dioxane (16 mL). At room temperature, Pd(OAc)$_2$ (36 mg), KOAc (473 mg), bis(pinacolato)diboron (815 mg), and a solution of 1 M PCy$_3$ in THF (0.24 mL) were added thereto. After degassing and nitrogen substitution, the mixture was stirred at 80° C. overnight. The reaction mixture was passed through Celite, and the solvent of the filtrate was distilled off. The residue was purified by silica gel column chromatography (mobile phase: hexane/ethyl acetate) to give tert-butyl N-[(3S)-1-[4-(p-tolyl)-3-(4,4,5,5-tetramethyl-1,3,2-dioxaborolan-2-yl)benzoyl]pyrrolidin-3-yl]carbamate.

Step 4

The tert-butyl N-[(3S)-1-[4-(p-tolyl)-3-(4,4,5,5-tetramethyl-1,3,2-dioxaborolan-2-yl)benzoyl]pyrrolidin-3-yl]carbamate (15 mg) obtained in step 3 above, 4-bromo-2,6-difluoro-benzonitrile (12.9 mg), and Pd(PPh$_3$)$_4$ (1.7 mg) were suspended in 1,4-dioxane (1.5 mL). At room temperature, a 2 M Na$_2$CO$_3$ aqueous solution (0.7 mL) was added thereto, and the reaction mixture was stirred in a microwave reactor at 120° C. for 30 minutes. The reaction mixture was filtrated, and the solvent was distilled off to give tert-butyl N-[(3S)-1-[3-(4-cyano-3,5-difluoro-phenyl)-4-(p-tolyl)benzoyl]pyrrolidin-3-yl]carbamate.

Step 5

The tert-butyl N-[(3S)-1-[3-(4-cyano-3,5-difluoro-phenyl)-4-(p-tolyl)benzoyl]pyrrolidin-3-yl]carbamate (15 mg) obtained in step 4 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 20: Synthesis of 4-[5-[(3S)-3-aminopyrrolidine-1-carbonyl]-2-[2-fluoro-4-(2-methoxyethyl)phenyl]phenyl]-2-fluoro-benzonitrile Step 1

1-Bromo-2-fluoro-4-(2-methoxyethyl)benzene (4.5 g) was suspended in 1,4-dioxane (48 mL), followed by stirring. Then, bis(pinacolato)diboron (7.4 g), KOAc (3.8 g), and PdCl$_2$(dppf) (0.71 g) were added thereto, followed by stirring at 90° C. overnight. Ethyl acetate was added thereto, the mixture was passed through Celite, and the filtrate was washed sequentially with water and saturated brine. After the organic layer was dried over anhydrous sodium sulfate, the solvent was distilled off. The residue was purified by silica gel column chromatography (mobile phase: hexane/ethyl acetate) to give 2-[2-fluoro-4-(2-methoxyethyl)phenyl]-4,4,5,5-tetramethyl-1,3,2-dioxaborolane.

Step 2

The tert-butyl N-[(3S)-1-[4-chloro-3-(4-cyano-3-fluoro-phenyl)benzoyl]pyrrolidin-3-yl]carbamate (150 mg) obtained in Example 16 (step 1), the 2-[2-fluoro-4-(2-methoxyethyl)phenyl]-4,4,5,5-tetramethyl-1,3,2-dioxaborolane (189 mg) obtained in step 1 above, Pd(dba)$_2$ (15 mg), tripotassium phosphate (144 mg), and a solution of 1 M PCy$_3$ in THF (0.034 mL) were dissolved in 1,4-dioxane (3.8 mL). The reaction mixture was stirred in a microwave reactor at 160° C. for 45 minutes. The reaction mixture was filtered through NH-silica gel, and the solvent of the filtrate was distilled off. The residue was purified by silica gel column chromatography (mobile phase: hexane/ethyl acetate) to give tert-butyl N-[(3S)-1-[3-(4-cyanophenyl)-4-[2-fluoro-4-(2-methoxyethyl)phenyl]benzoyl]pyrrolidin-3-yl]carbamate.

Step 3

The tert-butyl N-[(3S)-1-[3-(4-cyanophenyl)-4-[2-fluoro-4-(2-methoxyethyl)phenyl]benzoyl]pyrrolidin-3-yl]carbamate (150 mg) obtained in step 2 above was dissolved in TFA (10 mL), and the progress of the reaction was confirmed with LCMS, followed by vacuum concentration. The residue was purified by reversed-phase HPLC (mobile phase: water/acetonitrile) to give the title compound.

Example 21: Synthesis of 4-[5-[(3-endo)-3-amino-8-azabicyclo[3.2.1]octane-8-carbonyl]-2-(2-fluoro-4-methyl-phenyl)phenyl]-2-fluoro-benzonitrile The procedure of steps 1 to 4 in Example 17 was conducted using (2-fluoro-4-methyl-phenyl)boronic acid instead of p-tolylboronic acid to give the title compound.

Example 22: Synthesis of 4-[5-[(3-endo)-3-amino-8-azabicyclo[3.2.1]octane-8-carbonyl]-2-[2-fluoro-4-(2-methoxyethyl)phenyl]phenyl]-2-fluoro-benzonitrile Step 1

The tert-butyl 3-bromo-4-chloro-benzoate (1.00 g) obtained in Example 1 (step 1) was dissolved in 1,4-dioxane (8.6 mL). At room temperature, (4-cyano-3-fluoro-phenyl)boronic acid (509 mg), Pd(PPh$_3$)$_4$ (119 mg), and a 2 M Na$_2$CO$_3$ aqueous solution (4.3 mL) were added thereto, and the reaction mixture was stirred in a microwave reactor at 120° C. for 30 minutes. The reaction mixture was filtrated, and the solvent was distilled off. The residue was purified by silica gel column chromatography (mobile phase: hexane/ethyl acetate) to give tert-butyl 4-chloro-3-(4-cyano-3-fluoro-phenyl)benzoate.

Step 2

The tert-butyl 4-chloro-3-(4-cyano-3-fluoro-phenyl)benzoate (1.00 g) obtained in step 1 above was dissolved in 1,4-dioxane (15 mL). At room temperature, the 2-[2-fluoro-4-(2-methoxyethyl)phenyl]-4,4,5,5-tetramethyl-1,3,2-dioxaborolane (1.69 g) obtained in Example 20 (step 1), Pd(dba)$_2$ (138 mg), tripotassium phosphate (1.28 g), and a solution of 1 M PCy$_3$ in THF (0.30 mL) were added thereto, and the reaction mixture was stirred in a microwave reactor at 160° C. for 30 minutes. After the addition of chloroform, the insoluble matter was filtered off, and the solvent was distilled off. The residue was purified by silica gel column chromatography (mobile phase: hexane/ethyl acetate), and the solvent was distilled off. The residue was dissolved in TFA (2 mL), and the solvent was distilled off. Ethyl acetate was added thereto, and the mixture was washed sequentially with water and saturated brine. After the organic layer was dried over anhydrous sodium sulfate, the solvent was distilled off to give 3-(4-cyano-3-fluoro-phenyl)-4-[2-fluoro-4-(2-methoxyethyl)phenyl]benzoic acid.

Step 3

The 3-(4-cyano-3-fluoro-phenyl)-4-[2-fluoro-4-(2-methoxyethyl)phenyl]benzoic acid (10 mg) obtained in step 2 above, tert-butyl N-[(3-endo)-8-azabicyclo[3.2.1]octan-3-yl]carbamate (5.8 mg), and HATU (19 mg) were dissolved in THF (0.5 mL). At room temperature, TEA (0.007 mL) was added thereto, followed by stirring at 50° C. overnight. The reaction mixture was vacuum-concentrated, and the solvent was distilled off. The residue was purified by silica gel column chromatography (mobile phase: hexane/ethyl acetate) to give tert-butyl N-[(3-endo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate.

Step 4

The tert-butyl N-[(3-endo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate (10.9 mg) obtained in step 3 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 23: Synthesis of 4-[5-[(3-exo)-3-amino-8-azabicyclo[3.2.1]octane-8-carbonyl]-2-(6-fluoro-1-methyl-indol-5-yl)phenyl]-2-fluoro-benzonitrile Step 1

The tert-butyl N-[(3-exo)-8-[4-chloro-3-(4-cyano-3-fluoro-phenyl)benzoyl]-8-azabicyclo[3.2.1]octan-3-yl]carbamate (270 mg) obtained in Example 18 (step 1) was dissolved in 1,4-dioxane (2.8 mL). At room temperature, Pd(OAc)$_2$ (2.5 mg), KOAc (164 mg), bis(pinacolato)diboron (283 mg), and Silica-SMAP (4.6 mg) were added thereto, followed by stirring at 150° C. overnight. The mixture was passed through Celite, and the filtrate was vacuum-concentrated. The residue was purified by silica gel column chromatography (mobile phase: hexane/ethyl acetate) to give tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate.

Step 2

The tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (10 mg) obtained in step 1 above, 5-bromo-6-fluoro-1-methyl-indole (4.8 mg), and PdCl$_2$(dppf) (0.71 mg) were suspended in 1,4-dioxane (0.5 mL). At room temperature, tripotassium phosphate (11 mg) was added thereto, followed by stirring at 125° C. for 45 minutes. After the reaction mixture was filtrated, the solvent was distilled off to give tert-butyl N-[(3-exo)-8-[3-(4-cyano-3-fluoro-phenyl)-4-(6-fluoro-1-methyl-indol-5-yl)benzoyl]-8-azabicyclo[3.2.1]octan-3-yl]carbamate.

Step 3

The tert-butyl N-[(3-exo)-8-[3-(4-cyano-3-fluoro-phenyl)-4-(6-fluoro-1-methyl-indol-5-yl)benzoyl]-8-azabicyclo[3.2.1]octan-3-yl]carbamate (8 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 24: Synthesis of 4-[5-[(3-exo)-3-amino-8-azabicyclo[3.2.1]octane-8-carbonyl]-2-(6-fluoro-1-methyl-indazol-5-yl)phenyl]-2-fluoro-benzonitrile Step 1

The tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (10 mg) obtained in Example 23 (step 1) was dissolved in 1,4-dioxane (0.5 mL). At room temperature, 5-bromo-6-fluoro-1-methyl-indazole (4.8 mg), PdCl$_2$(dppf) (0.71 mg), and tripotassium phosphate (11 mg) were added thereto, and the mixture was stirred in a microwave reactor at 125° C. for 45 minutes. The reaction mixture was filtrated, and the solvent was distilled off to give tert-butyl N-[(3-exo)-8-[3-(4-cyano-3-fluoro-phenyl)-4-(6-fluoro-1-methyl-indazol-5-yl)benzoyl]-8-azabicyclo[3.2.1]octan-3-yl]carbamate.

Step 2

The tert-butyl N-[(3-exo)-8-[3-(4-cyano-3-fluoro-phenyl)-4-(6-fluoro-1-methyl-indazol-5-yl)benzoyl]-8-azabicyclo[3.2.1]octan-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 25: Synthesis of 4-[5-[(3S)-3-amino-3-methyl-pyrrolidine-1-carbonyl]-2-[2-fluoro-4-(2-methoxyethyl)phenyl]phenyl]-2-fluoro-benzonitrile Step 1

The 3-(4-cyano-3-fluoro-phenyl)-4-[2-fluoro-4-(2-methoxyethyl)phenyl]benzoic acid (10 mg) obtained in Example 22 (step 2) and tert-butyl N-[(3S)-3-methylpyrrolidin-3-yl]carbamate (5.1 mg) were dissolved in THF (0.5 mL). At room temperature, TEA (0.011 mL) and HATU (19 mg) were added thereto, followed by stirring at 50° C. overnight. The reaction mixture was vacuum-concentrated, and the solvent was distilled off to give tert-butyl N-[(3S)-1-[3-(4-cyano-3-fluoro-phenyl)-4-[2-fluoro-4-(2-methoxyethyl)phenyl]benzoyl]-3-methyl-pyrrolidin-3-yl]carbamate.

Step 2

The tert-butyl N-[(3S)-1-[3-(4-cyano 3 fluoro-phenyl)-4-[2-fluoro-4-(2-methoxyethyl)phenyl]benzoyl]-3-methyl-pyrrolidin-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 26: Synthesis of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile Step 1

The 3-(4-cyano-3-fluoro-phenyl)-4-[2-fluoro-4-(2-methoxyethyl)phenyl]benzoic acid (10 mg) obtained in Example 22 (step 2), and tert-butyl N-[(3-exo)-8-azabicyclo[3.2.1]octan-3-yl]carbamate (5.8 mg) were dissolved in THF (0.5 mL). At room temperature, TEA (0.011 mL) and HATU (19 mg) were added thereto, followed by stirring at 50° C. overnight. The reaction mixture was vacuum-concentrated, and the solvent was distilled off to give tert-butyl N-[(3-exo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate.

Step 2

The tert-butyl N-[(3-exo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 27: Synthesis of 4-[5-(3,8-diazabicyclo[3.2.1]octane-8-carbonyl)-2-[2-fluoro-4-(2-methoxyethyl)phenyl]phenyl]-2-fluoro-benzonitrile The procedure of steps 1 to 4 in Example 22 was conducted using tert-butyl 3,8-diazabicyclo[3.2.1]octane-3-carboxylic acid instead of tert-butyl N-[(3-endo)-8-azabicyclo[3.2.1]octan-3-yl]carbamate to give the title compound.

Example 28: Synthesis of 4-[5-[(3-exo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile Step 1

Methyl 2-(4-bromo-3-fluoro-phenyl)acetate (500 mg) was dissolved in THF (2.2 mL). At −30° C., a solution of 3 M MeMgBr in ether (5.40 mL) was added thereto dropwise, followed by stirring at room temperature overnight. The reaction mixture was introduced into an aqueous ammonium chloride solution, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: ethyl acetate/hexane=10%→50%) to give 1-(4-bromo-3-fluoro-phenyl)-2-methyl-propan-2-ol.

Step 2

The tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (68 mg) obtained in Example 23 (step 1), the 1-(4-bromo-3-fluoro-phenyl)-2-methyl-propan-2-ol (107 mg) obtained in step 1 above, and Pd(PPh$_3$)$_4$ (6.42 mg) were suspended in 1,4-dioxane (0.93 mL). At room temperature, a 2 M Na$_2$CO$_3$ aqueous solution (0.46 mL) was added thereto, followed by stirring at 125° C. for 45 minutes. After the reaction mixture was filtrated, the solvent was distilled off to give tert-butyl N-[(3-exo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate.

Step 3

The tert-butyl N-[(3-exo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate (90 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 29: Synthesis of 4-[5-[(3S)-3-aminopyrrolidine-1-carbonyl]-2-[4-(hydroxymethyl)phenyl]phenyl]benzonitrile Step 1

[4-(4,4,5,5-Tetramethyl-1,3,2-dioxaborolan-2-yl)phenyl]methanol (500 mg) and DMAP (26 mg) were dissolved in THF (7.1 mL), followed by the addition of TEA (0.74 mL). At room temperature, acetylchloride (0.23 mL) was added thereto, followed by stirring for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give [4-(4,4,5,5-tetramethyl-1,3,2-dioxaborolan-2-yl)phenyl]methyl acetate.

Step 2

The tert-butyl N-[(3S)-1-[4-chloro-3-(4-cyanophenyl)benzoyl]pyrrolidin-3-yl]carbamate (100 mg) obtained in Example 9 (step 2) and the [4-(4,4,5,5-tetramethyl-1,3,2-dioxaborolan-2-yl)phenyl]methyl acetate (130 mg) obtained in step 1 above were dissolved in 1,4-dioxane (1.2 mL). At room temperature, Pd(dba)$_2$ (6.8 mg), tripotassium phosphate (100 mg), and a solution of 1 M PCy$_3$ in THF (0.02 mL) were added thereto, and the mixture was stirred in a microwave reactor at 160° C. for 1 hour. The reaction mixture was filtered through NH-silica gel, and the solvent of the filtrate was distilled off. The residue was purified by silica gel column chromatography (mobile phase: ethyl acetate/hexane=30%→100%) to give [4-[4-[(3S)-3-(tert-butoxycarbonylamino)pyrrolidine-1-carbonyl]-2-(4-cyanophenyl)phenyl]phenyl]methyl acetate.

Step 3

The [4-[4-[(3S)-3-(tert-butoxycarbonylamino)pyrrolidine-1-carbonyl]-2-(4-cyanophenyl)phenyl]phenyl]methyl acetate (100 mg) obtained in step 2 above was dissolved in MeOH (2 mL). At room temperature, K$_2$CO$_3$ (65 mg) was added thereto, followed by stirring at room temperature for 30 minutes. Chloroform was added thereto, the mixture was washed sequentially with a saturated aqueous ammonium chloride solution and saturated brine, and dried over anhydrous sodium sulfate, and the solvent was distilled off. The residue was purified by silica gel column chromatography (mobile phase: ethyl acetate/hexane=40%→100%) to give tert-butyl N-[(3S)-1-[3-(4-cyanophenyl)-4-[4-(hydroxymethyl)phenyl]benzoyl]pyrrolidin-3-yl]carbamate.

Step 4

The tert-butyl N-[(3S)-1-[3-(4-cyanophenyl)-4-[4-(hydroxymethyl)phenyl]benzoyl]pyrrolidin-3-yl]carbamate (15 mg) obtained in step 3 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 30: Synthesis of 4-[5-[(3S)-3-aminopyrrolidine-1-carbonyl]-2-[4-(2-methoxyethyl)phenyl]phenyl]benzonitrile Step 1

1-Bromo-4-(2-methoxyethyl)benzene (450 mg) was dissolved in 1,4-dioxane (5.2 mL). Then, bis(pinacolato)diboron (797 mg), KOAc (411 mg), and PdCl$_2$(dppf) (77 mg) were added thereto, followed by stirring at 90° C. overnight. Ethyl acetate was added thereto, the mixture was passed through Celite, and the filtrate was washed sequentially with water and saturated brine. After the organic layer was dried over anhydrous sodium sulfate, the solvent was distilled off. The residue was purified by silica gel column chromatography (mobile phase: ethyl acetate/hexane=2%→20%) to give 2-[4-(2-methoxyethyl)phenyl]-4,4,5,5-tetramethyl-1,3,2-dioxaborolane.

Step 2

The tert-butyl N-[(3S)-1-[4-chloro-3-(4-cyanophenyl)benzoyl]pyrrolidin-3-yl]carbamate (300 mg) obtained in Example 9 (step 2) and the 2-[4-(2-methoxyethyl)phenyl]-4,4,5,5-tetramethyl-1,3,2-dioxaborolane (369 mg) obtained in step 1 above were dissolved in 1,4-dioxane (2 mL). At room temperature, Pd(dba)$_2$ (32 mg), tripotassium phosphate (300 mg), and a solution of 1 M PCy$_3$ in THF (0.07 mL) were added thereto, and the mixture was stirred in a microwave reactor at 160° C. for 45 minutes. The reaction mixture was passed through Celite, and the solvent of the filtrate was distilled off. The residue was purified by reversed-phase HPLC (mobile phase: water/acetonitrile) to give tert-butyl N-[(3S)-1-[3-(4-cyanophenyl)-4-[4-(2-methoxyethyl)phenyl]benzoyl]pyrrolidin-3-yl]carbamate.

Step 3

The tert-butyl N-[(3S)-1-[3-(4-cyanophenyl)-4-[4-(2-methoxyethyl)phenyl]benzoyl]pyrrolidin-3-yl]carbamate (15 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 31: Synthesis of 4-[5-[(3S)-3-aminopyrrolidine-1-carbonyl]-2-[4-(2-hydroxyethyl)phenyl]phenyl]benzonitrile The procedure of steps 1 to 4 in Example 29 was conducted using 2-[4-(4,4,5,5-tetramethyl-1,3,2-dioxaborolan-2-yl)phenyl]ethanol instead of [4-(4,4,5,5-tetramethyl-1,3,2-dioxaborolan-2-yl)phenyl]methanol to give the title compound.

Example 32: Synthesis of 4-[5-[(3S)-3-aminopyrrolidine-1-carbonyl]-2-[4-(3-hydroxypropyl)phenyl]phenyl]benzonitrile The procedure of steps 1 to 4 in Example 29 was conducted using 3-[4-(4,4,5,5-tetramethyl-1,3,2-dioxaborolan-2-yl)phenyl]propan-1-ol instead of [4-(4,4,5,5-tetramethyl-1,3,2-dioxaborolan-2-yl)phenyl]methanol to give the title compound.

Example 33: Synthesis of 4-[5-[(3S)-3-aminopyrrolidine-1-carbonyl]-2-[4-[1-(hydroxymethyl)cyclopropyl]phenyl]phenyl]benzonitrile The procedure of steps 1 to 5 in Example 9 was conducted using (1-(4-bromophenyl)cyclopropyl)methanol instead of 1-bromo-2-chloro-4-methyl-benzene to give the title compound.

Example 34: Synthesis of 4-[5-[(3S)-3-aminopyrrolidine-1-carbonyl]-2-[4-(2-hydroxy-2-methyl-propyl)phenyl]phenyl]benzonitrile The procedure of steps 1 to 5 in Example 9 was conducted using 1-(4-bromophenyl)-2-methylpropan-2-ol instead of 1-bromo-2-chloro-4-methyl-benzene to give the title compound.

Example 35: Synthesis of 4-[5-[(3S)-3-aminopyrrolidine-1-carbonyl]-2-[4-(2-hydroxypropoxy)phenyl]phenyl]benzonitrile Step 1

The procedure of step 1 in Example 12 was conducted using (4-benzyloxyphenyl)boronic acid instead of 4-methyl-2-nitrophenylboronic acid pinacol ester to give tert-butyl N-[(3S)-1-[4-(4-benzyloxyphenyl)-3-(4-cyanophenyl)benzoyl]pyrrolidin-3-yl]carbamate.

Step 2

The tert-butyl N-[(3S)-1-[4-(4-benzyloxyphenyl)-3-(4-cyanophenyl)benzoyl]pyrrolidin-3-yl]carbamate (800 mg) obtained in step 1 above and palladium hydroxide-carbon (160 mg) were suspended in EtOH (20 mL), and hydrogen substitution was carried out, followed by stirring at room temperature for 6 hours. The reaction mixture was passed through Celite, and the solvent was distilled off. The residue was purified by silica gel column chromatography (mobile phase: hexane/ethyl acetate) to give tert-butyl N-[(3S)-1-[3-(4-cyanophenyl)-4-(4-hydroxyphenyl)benzoyl]pyrrolidin-3-yl]carbamate.

Step 3

The tert-butyl N-[(3S)-1-[3-(4-cyanophenyl)-4-(4-hydroxyphenyl)benzoyl]pyrrolidin-3-yl]carbamate (15 mg) obtained in step 2 above was dissolved in DMF (0.5 mL). At room temperature, $K_2CO_3$ (6.4 mg) and 2-methyloxirane (5.4 mg) were added thereto, followed by stirring at 120° C. for 2 hours. Ethyl acetate was added thereto, the resulting mixture was washed sequentially with water and saturated brine, and dried over anhydrous sodium sulfate, and the solvent was distilled off. The residue was purified by silica gel column chromatography (mobile phase: hexane/ethyl acetate) to give tert-butyl N-[(3S)-1-[3-(4-cyanophenyl)-4-[4-(2-hydroxypropoxy)phenyl]benzoyl]pyrrolidin-3-yl]carbamate.

Step 4

The tert-butyl N-[(3S)-1-[3-(4-cyanophenyl)-4-[4-(2-hydroxypropoxy)phenyl]benzoyl]pyrrolidin-3-yl]carbamate (15 mg) obtained in step 3 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 36: Synthesis of 4-[5-[(3S)-3-aminopyrrolidine-1-carbonyl]-2-(2-fluoro-4-methyl-phenyl)phenyl]-2-fluoro-benzonitrile The procedure of steps 1 to 3 in Example 16 was conducted using (2-fluoro-4-methyl-phenyl)boronic acid instead of p-tolylboronic acid to give the title compound.

Example 37: Synthesis of 4-[5-[(3S)-3-aminopyrrolidine-1-carbonyl]-2-[2-fluoro-4-(2-hydroxy-2-methyl-propyl)phenyl]phenyl]-2-fluoro-benzonitrile Step 1

The tert-butyl N-[(3S)-1-[4-chloro-3-(4-cyano-3-fluoro-Phenyl)benzoyl]pyrrolidin-3-yl]carbamate (4 g) obtained in Example 16 (step 1) was dissolved in 1,4-dioxane (45 mL). At room temperature, Pd(OAc)$_2$ (0.40 g), KOAc (2.7 g), bis(pinacolato)diboron (4.6 g), and Silica-SMAP (0.72 g) were added thereto, followed by stirring at 150° C. for 18 hours. The reaction mixture was filtrated, and the solvent was distilled off. The residue was purified by silica gel column chromatography (mobile phase: hexane/ethyl acetate) to give tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate.

Step 2

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (30 mg) obtained in step 1 above and the 1-(4-bromo-3-fluoro-phenyl)-2-methyl-propan-2-ol (28 mg) obtained in Example 28 (step 1) were dissolved in 1,4-dioxane (0.8 mL). At room temperature, Pd(PPh$_3$)$_4$ (3.2 mg) and a 2 M Na$_2$CO$_3$ aqueous solution (0.4 mL) were added thereto, and the mixture was stirred in a microwave reactor at 120° C. for 30 minutes. The reaction mixture was filtrated, and the solvent was distilled off. Ethyl acetate was added thereto, the resulting mixture was washed sequentially with water and saturated brine, and dried over anhydrous sodium sulfate, and the solvent was distilled off. The residue was purified by silica gel column chromatography (mobile phase: chloroform/methanol) to give tert-butyl N-[(3S)-1-[3-(4-cyano-3-fluoro-phenyl)-4-[2-fluoro-4-(2-hydroxy-2-methyl-propyl)phenyl]benzoyl]pyrrolidin-3-yl]carbamate.

Step 3

The tert-butyl N-[(3S)-1-[3-(4-cyano-3-fluoro-phenyl)-4-[2-fluoro-4-(2-hydroxy-2-methyl-propyl)phenyl]benzoyl]pyrrolidin-3-yl]carbamate (20 mg) obtained in step 2 above was dissolved in MeOH (1 mL). At room temperature, a 12 M HCl aqueous solution (1 mL) was added thereto, followed by stirring at room temperature for 30 minutes. The reaction mixture was neutralized by the addition of water (1 mL) and a 2 M aqueous sodium hydroxide solution (6 mL). Chloroform was added thereto, the mixture was washed sequentially with water and saturated brine, and dried over anhydrous sodium sulfate. Thereafter, the solvent was distilled off to give the title compound.

Example 38: Synthesis of 2-fluoro-4-[2-[2-fluoro-4-(2-methoxyethyl)phenyl]-5-(9-oxa-2,6-diazaspiro[3.5]nonane-2-carbonyl)phenyl]benzonitrile The procedure of steps 1 to 4 in Example 22 was conducted using tert-butyl 9-oxa-2,6-diazaspiro[3.5]nonane-6-carboxylic acid instead of tert-butyl N-[(3-endo)-8-azabicyclo[3.2.1]octan-3-yl]carbamate to give the title compound.

Example 39: Synthesis of 4-[5-(2,3,3a,4,6,6a-hexahydro-1H-pyrrolo[3,4-c]pyrrole-5-carbonyl)-2-[2-fluoro-4-(2-methoxyethyl)phenyl]phenyl]-2-fluoro-benzonitrile The procedure of steps 1 to 4 in Example 22 was conducted using tert-butyl 2,3,3a,4,6,6a-hexahydro-1H-pyrrolo[3,4-c]pyrrole-5-carboxylic acid instead of tert-butyl N-[(3-endo)-8-azabicyclo[3.2.1]octan-3-yl]carbamate to give the title compound.

Example 40: 4-[5-[(3S)-3-aminopyrrolidine-1-carbonyl]-2-[4-(2-hydroxy-2-methyl-propyl)phenyl]phenyl]-2-fluoro-benzonitrile The procedure of steps 1 to 3 in Example 37 was conducted using 1-(4-bromophenyl)-2-methylpropan-2-ol instead of 1-(4-bromo-3-fluoro-phenyl)-2-methyl-propan-2-ol to give the title compound.

Example 41: Synthesis of 4-[5-[(3-endo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile Step 1

The tert-butyl 4-chloro-3-(4-cyano-3-fluoro-phenyl)benzoate (300 mg) obtained in Example 22 (step 1) was dissolved in 1,4-dioxane (5 mL). At room temperature, Pd(OAc)$_2$ (40 mg), KOAc (300 mg), bis(pinacolato)diboron (500 mg), and Silica-SMAP (50 mg) were added thereto, followed by stirring at 100° C. for 26 hours. The reaction mixture was filtrated, and the solvent was distilled off. The residue was purified by silica gel column chromatography (mobile phase: hexane/ethyl acetate) to give tert-butyl 3-(4-cyano-3-fluoro-phenyl)-4-(4,4,5,5-tetramethyl-1,3,2-dioxaborolan-2-yl)benzoate.

Step 2

The tert-butyl 3-(4-cyano-3-fluoro-phenyl)-4-(4,4,5,5-tetramethyl-1,3,2-dioxaborolan-2-yl)benzoate (100 mg) obtained in step 1 above was dissolved in DCM (1.2 mL). At room temperature, TFA (1.00 mL) was added thereto, followed by stirring at room temperature for 30 minutes. The reaction mixture was vacuum-concentrated, and the solvent was distilled off. Chloroform was added thereto, the mixture was washed with water and dried over anhydrous sodium sulfate, and the solvent was distilled off to give 3-(4-cyano-3-fluoro-phenyl)-4-(4,4,5,5-tetramethyl-1,3,2-dioxaborolan-2-yl)benzoic acid.

Step 3

The 3-(4-cyano-3-fluoro-phenyl)-4-(4,4,5,5-tetramethyl-1,3,2-dioxaborolan-2-yl)benzoic acid (500 mg) obtained in step 2 above and tert-butyl N-[(3-endo)-8-azabicyclo[3.2.1]octan-3-yl]carbamate (308 mg) were dissolved in THF (4.5 mL). At room temperature, TEA (0.57 mL) and HATU (1 g) were added thereto, followed by stirring at 50° C. for 1 hour. The reaction mixture was vacuum-concentrated, and the residue was purified by silica gel column chromatography (mobile phase: hexane/ethyl acetate) to give tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate.

Step 4

The tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (30 mg) obtained in step 3 above and the 1-(4-bromo-3-fluoro-phenyl)-2-methyl-propan-2-ol (19 mg) obtained in Example 28 (step 1) were dissolved in 1,4-dioxane (0.5 mL). At room temperature, Pd(PPh$_3$)$_4$ (18 mg) and a 2 M Na$_2$CO$_3$ aqueous solution (0.3 mL) were added thereto, and the mixture was stirred in a microwave reactor at 120° C. for 30 minutes. The supernatant of the reaction mixture was collected and filtered through NH-silica gel, and the solvent was distilled off to give tert-butyl-N-[(3-endo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate.

Step 5

The tert-butyl-N-[(3-endo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate (15 mg) obtained in step 4 above was dissolved in MeOH (0.5 mL). At room temperature, a 12 M HCl aqueous solution (0.5 mL) was added thereto, followed by stirring at room temperature for 30 minutes. Then, water and a 2 M aqueous sodium hydroxide solution (3 mL) were added thereto, and the mixture was partitioned and extracted with chloroform. After the organic layer was dried over anhydrous sodium sulfate, the solvent was distilled off. The residue was purified by reversed-phase HPLC (mobile phase: water/acetonitrile) to give the title compound.

Example 42: Synthesis of 4-[5-[(3S)-3-(methylamino)pyrrolidine-1-carbonyl]-2-(p-tolyl)phenyl]benzonitrile The procedure of steps 1 to 5 in Example 1 was conducted using (S)-tert-butyl methyl(pyrrolidin-3-yl)carbamate instead of tert-butyl N-[(3S)-pyrrolidin-3-yl]carbamate to give the title compound.

Example 43: Synthesis of 4-[5-[(3S)-3-aminopyrrolidine-1-carbonyl]-2-(4-benzyloxyphenyl)phenyl]benzonitrile The procedure of steps 1 to 5 in Example 9 was conducted using 1-(benzyloxy)-4-bromobenzene instead of 1-bromo-2-chloro-4-methyl-benzene to give the title compound.

Example 44: Synthesis of 1-[4-[4-[(3S)-3-aminopyrrolidine-1-carbonyl]-2-(4-cyanophenyl)phenyl]phenyl]-N-phenyl-cyclopropanecarboxamide The procedure of steps 1 to 5 in Example 9 was conducted using 1-(4-bromophenyl)-N-phenylcyclopropanecarboxamide instead of 1-bromo-2-chloro-4-methyl-benzene to give the title compound.

Example 45: Synthesis of 2-[4-[4-[(3S)-3-aminopyrrolidine-1-carbonyl]-2-(4-cyanophenyl)phenyl]phenyl]ethyl acetate Step 1

The procedure of step 1 in Example 29 was conducted using 2-(4-(4,4,5,5-tetramethyl-1,3,2-dioxaborolan-2-yl)phenyl)ethanol instead of [4-(4,4,5,5-tetramethyl-1,3,2-dioxaborolan-2-yl)phenyl]methanol to give 4-(4,4,5,5-tetramethyl-1,3,2-dioxaborolan-2-yl)phenethyl acetate.

Step 2

The procedure of steps 1 to 2 in Example 12 was conducted using the 4-(4,4,5,5-tetramethyl-1,3,2-dioxaborolan-2-yl)phenethyl acetate obtained in step 1 above instead of 4-methyl-2-nitrophenylboronic acid pinacol ester to give the title compound.

Example 46: Synthesis of 4-[2-[4-(2-hydroxyethyl)phenyl]-5-[(3S)-3-(methylamino)pyrrolidine-1-carbonyl]phenyl]benzonitrile Step 1

The procedure of steps 1 to 5 in Example 1 was conducted using the 4-(4,4,5,5-tetramethyl-1,3,2-dioxaborolan-2-yl)phenethyl acetate obtained in Example 45 (step 1) instead of p-tolylboronic acid, and using (S)-tert-butyl methyl(pyrrolidin-3-yl)carbamate instead of tert-butyl N-[(3S)-pyrrolidin-3-yl]carbamate to give 2-[4-[2-(4-cyanophenyl)-4-[(3S)-3-(methylamino)pyrrolidine-1-carbonyl]phenyl]phenyl]ethyl acetate.

Step 2

The procedure of step 3 in Example 29 was conducted using the 2-[4-[2-(4-cyanophenyl)-4-[(3S)-3-(methylamino)pyrrolidine-1-carbonyl]phenyl]phenyl]ethyl acetate obtained in step 1 above instead of [4-[4-[(3S)-3-(tert-butoxycarbonylamino)pyrrolidine-1-carbonyl]-2-(4-cyanophenyl)phenyl]phenyl]methyl acetate to give the title compound.

Example 47: Synthesis of 4-[2-[4-(2-methoxyethyl)phenyl]-5-[(3S)-3-(methylamino)pyrrolidine-1-carbonyl]phenyl]benzonitrile Step 1

The procedure of steps 1 to 5 in Example 1 was conducted using (4-(2-methoxyethyl)phenyl)boronic acid instead of p-tolylboronic acid, and using (S)-tert-butyl methyl(pyrrolidin-3-yl)carbamate instead of tert-butyl N-[(3S)-pyrrolidin-3-yl]carbamate to give the title compound.

Example 48: Synthesis of 4-[5-[(3S)-3-(dimethylamino)pyrrolidine-1-carbonyl]-2-[4-[1-(hydroxymethyl)cyclopropyl]phenyl]phenyl]benzonitrile The procedure of steps 1 to 4 in Example 1 was conducted using [4-[1-(hydroxymethyl)cyclopropyl]phenyl]boronic acid instead of p-tolylboronic acid, and using (S)—N,N-dimethylpyrrolidin-3-amine instead of tert-butyl N-[(3S)-pyrrolidin-3-yl]carbamate to give the title compound.

Example 49: Synthesis of 4-[5-[(3S)-3-aminopyrrolidine-1-carbonyl]-2-(3-fluoro-4-methyl-phenyl)phenyl]benzonitrile The procedure of steps 1 to 2 in Example 12 was conducted using (3-fluoro-4-methyl-phenyl)boronic acid instead of 4-methyl-2-nitrophenylboronic acid pinacol ester to give the title compound.

Example 50: Synthesis of 4-[5-[(3S)-3-aminopyrrolidine-1-carbonyl]-2-(4-chlorophenyl)phenyl]benzonitrile The procedure of steps 1 to 5 in Example 9 was conducted using 1-bromo-4-chloro-benzene instead of 1-bromo-2-chloro-4-methyl-benzene to give the title compound.

Example 51: Synthesis of 4-[5-[(3S)-3-aminopyrrolidine-1-carbonyl]-2-(4-bromophenyl)phenyl]benzonitrile The procedure of steps 1 to 5 in Example 9 was conducted using 1,4-dibromobenzene instead of 1-bromo-2-chloro-4-methyl-benzene to give the title compound.

Example 52: Synthesis of 5'-((1S,4S)-2,5-diazabicyclo[2.2.1]heptane-2-carbonyl)-4''-methyl-[1,1':2',1''-terphenyl]-4-carbonitrile The procedure of steps 1 to 5 in Example 1 was conducted using tert-butyl (1S,4S)-2,5-diazabicyclo[2.2.1]heptane-2-carboxylate instead of tert-butyl N-[(3S)-pyrrolidin-3-yl]carbamate to give the title compound.

Example 53: Synthesis of 4-[2-[4-(2-aminoethyl)phenyl]-5-[(3S)-3-aminopyrrolidine-1-carbonyl]phenyl]benzonitrile Step 1

The tert-butyl N-[(3S)-1-[3-(4-cyanophenyl)-4-(4,4,5,5-tetramethyl-1,3,2-dioxaborolan-2-yl)benzoyl]pyrrolidin-3-yl]carbamate (50 mg) obtained in Example 9 (step 3) was dissolved in 1,4-dioxane (0.48 mL). At room temperature, 2-(4-bromophenyl)ethanamine (29 mg), Pd(PPh$_3$)$_4$ (3.4 mg), and a 2 M Na$_2$CO$_3$ aqueous solution (0.24 mL) were added thereto, and the mixture was stirred in a microwave reactor at 120° C. for 30 minutes. The residue was purified by silica gel column chromatography (mobile phase: hexane/ethyl acetate) to give tert-butyl N-[(3S)-1-[4-[4-(2-aminoethyl)phenyl]-3-(4-cyanophenyl)benzoyl]pyrrolidin-3-yl]carbamate.

Step 2

The tert-butyl N-[(3S)-1-[4-[4-(2-aminoethyl)phenyl]-3-(4-cyanophenyl)benzoyl]pyrrolidin-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 54: Synthesis of 4-[5-[(3S)-3-aminopyrrolidine-1-carbonyl]-2-(4-iodophenyl)phenyl]benzonitrile The procedure of steps 1 to 5 in Example 9 was conducted using 1,4-diiodobenzene instead of 1-bromo-2-chloro-4-methyl-benzene to give the title compound.

Example 55: Synthesis of N-[2-[4-[4-[(3S)-3-aminopyrrolidine-1-carbonyl]-2-(4-cyanophenyl)phenyl]phenyl]ethyl]acetamide The tert-butyl N-[(3S)-1-[4-[4-(2-aminoethyl)phenyl]-3-(4-cyanophenyl)benzoyl]pyrrolidin-3-yl]carbamate (15 mg) obtained in Example 53 (step 1) was dissolved in THF. At room temperature, TEA (0.02 mL) and then acetylchloride (4.6 mg) were added thereto, followed by stirring at room temperature for 1 hour. TFA was added to the residue, and the progress of the reaction was confirmed with LCMS, followed by vacuum concentration. The residue was purified by reversed-phase HPLC (mobile phase: water/acetonitrile) to give the title compound.

Example 56: Synthesis of 4-[5-[(3S)-3-aminopyrrolidine-1-carbonyl]-2-(4-propylphenyl)phenyl]benzonitrile The procedure of steps 1 to 2 in Example 12 was conducted using (4-propylphenyl)boronic acid instead of 4-methyl-2-nitrophenylboronic acid pinacol ester to give the title compound.

Example 57: Synthesis of 4-[5-[(3S)-3-aminopyrrolidine-1-carbonyl]-2-(2-naphthyl)phenyl]benzonitrile The procedure of steps 1 to 2 in Example 12 was conducted using 2-naphthyl boronic acid instead of 4-methyl-2-nitrophenylboronic acid pinacol ester to give the title compound.

Example 58: Synthesis of 4-[2-[4-[1-(hydroxymethyl)cyclopropyl]phenyl]-5-[(3S)-3-(methylamino)pyrrolidine-1-carbonyl]phenyl]benzonitrile The procedure of steps 1 to 5 in Example 1 was conducted using [4-[1-(hydroxymethyl)cyclopropyl]phenyl]boronic acid instead of p-tolylboronic acid, and using (S)-tert-butyl methyl(pyrrolidin-3-yl)carbamate instead of tert-butyl N-[(3S)-pyrrolidin-3-yl]carbamate to give the title compound.

Example 59: Synthesis of 4-[5-[(3S)-3-aminopyrrolidine-1-carbonyl]-2-[4-[(1-hydroxycyclopropyl)methyl]phenyl]phenyl]benzonitrile The procedure of steps 1 to 5 in Example 9 was conducted using 1-[(4-bromophenyl)methyl]cyclopropanol instead of 1-bromo-2-chloro-4-methyl-benzene to give the title compound.

Example 60: Synthesis of 4-[5-[(3S)-3-aminopyrrolidine-1-carbonyl]-2-[4-(2-methylprop-1-enyl)phenyl]phenyl]benzonitrile The procedure of steps 1 to 5 in Example 9 was conducted using 1-bromo-4-(2-methylprop-1-enyl)benzene instead of 1-bromo-2-chloro-4-methyl-benzene to give the title compound.

Example 61: Synthesis of 4-[5-[(3S)-3-aminopyrrolidine-1-carbonyl]-2-[4-(3-hydroxy-3-methyl-butyl)phenyl]phenyl]benzonitrile The procedure of steps 1 to 5 in Example 9 was conducted using 4-(4-bromophenyl)-2-methyl-butan-2-ol instead of 1-bromo-2-chloro-4-methyl-benzene to give the title compound.

Example 62: Synthesis of 4-[5-[(3S)-3-aminopyrrolidine-1-carbonyl]-2-[4-[2-(1-hydroxycyclopropyl)ethyl]phenyl]phenyl]benzonitrile The procedure of steps 1 to 5 in Example 9 was conducted using 1-[2-(4-bromophenyl)ethyl]cyclopropanol instead of 1-bromo-2-chloro-4-methyl-benzene to give the title compound.

Example 63: Synthesis of 4-[5-[(3S)-3-aminopyrrolidine-1-carbonyl]-2-[4-(2-hydroxyethyl)phenyl]phenyl]-2-fluoro-benzonitrile The procedure of steps 1 to 3 in Example 37 was conducted using 2-(4-bromophenyl)ethanol instead of 1-(4-bromo-3-fluoro-phenyl)-2-methyl-propan-2-ol to give the title compound.

Example 64: Synthesis of 4-[5-[(3S)-3-aminopyrrolidine-1-carbonyl]-2-[2-fluoro-4-(2-hydroxy-2-methyl-propyl)phenyl]phenyl]benzonitrile The procedure of steps 1 to 5 in Example 9 was conducted using the 1-(4-bromo-3-fluoro-phenyl)-2-methyl-propan-2-ol obtained in Example 28 (step 1) instead of 1-bromo-2-chloro-4-methyl-benzene to give the title compound.

Example 65: Synthesis of 4-[5-[(3S)-3-aminopyrrolidine-1-carbonyl]-2-[4-(3-hydroxy-3-methyl-butyl)phenyl]phenyl]-2-fluoro-benzonitrile The procedure of steps 1 to 3 in Example 16 was conducted using 2-methyl-4-[4-(4,4,5,5-tetramethyl-1,3,2-dioxaborolan-2-yl)phenyl]butan-2-ol instead of p-tolylboronic acid to give the title compound.

Example 66: Synthesis of 4-[5-[(3S)-3-aminopyrrolidine-1-carbonyl]-2-[4-[1-(methoxymethyl)cyclopropyl]phenyl]phenyl]benzonitrile The procedure of steps 1 to 5 in Example 9 was conducted using 1-bromo-4-[1-(methoxymethyl)cyclopropyl]benzene instead of 1-bromo-2-chloro-4-methyl-benzene to give the title compound.

Example 67: Synthesis of 4-[5-[(3S)-3-aminopyrrolidine-1-carbonyl]-2-[2-fluoro-4-[(1-hydroxycyclopropyl)methyl]phenyl]phenyl]benzonitrile Step 1

Methyl-2-(4-bromo-3-fluoro-phenyl)acetate (500 mg) and titanium isopropoxide (0.84 mL) were dissolved in THF (5 mL). At 0° C., a solution of 3 M EtMgBr in diethyl ether (1.9 mL) was added thereto dropwise, followed by stirring at room temperature overnight. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-[(4-bromo-3-fluoro-phenyl)methyl]cyclopropanol.

Step 2

The procedure of steps 1 to 5 in Example 9 was conducted using the 1-[(4-bromo-3-fluoro-phenyl)methyl]cyclopropanol obtained in step 1 above instead of 1-bromo-2-chloro-4-methyl-benzene to give the title compound.

Example 68: Synthesis of 4-[5-[(3S)-3-aminopyrrolidine-1-carbonyl]-2-[4-[1-(1-hydroxycyclopropyl)cyclopropyl]phenyl]phenyl]benzonitrile Step 1

The procedure of step 1 in Example 67 was conducted using methyl 1-(4-bromophenyl)cyclopropanecarboxylic acid instead of methyl-2-(4-bromo-3-fluoro-phenyl)acetate to give 1-[1-(4-bromophenyl)cyclopropyl]cyclopropanol.

Step 2

The procedure of steps 1 to 5 in Example 9 was conducted using the 1-[1-(4-bromophenyl)cyclopropyl]cyclopropanol obtained in step 1 above instead of 1-bromo-2-chloro-4-methyl-benzene to give the title compound.

Example 69: Synthesis of 4-[5-[(3S)-3-aminopyrrolidine-1-carbonyl]-2-[4-(2-methoxyethyl)phenyl]phenyl]-2-fluoro-benzonitrile The procedure of steps 1 to 3 in Example 16 was conducted using the 2-[4-(2-methoxyethyl)phenyl]-4,4,5,5-tetramethyl-1,3,2-dioxaborolane obtained in Example 30 (step 1) instead of p-tolylboronic acid to give the title compound.

Example 70: Synthesis of 4-[5-[(3S)-3-aminopyrrolidine-1-carbonyl]-2-[2-fluoro-4-(2-hydroxyethyl)phenyl]phenyl]benzonitrile The procedure of steps 1 to 5 in Example 9 was conducted using 2-(4-bromo-3-fluoro-phenyl)ethanol instead of 1-bromo-2-chloro-4-methyl-benzene to give the title compound.

Example 71: Synthesis of 4-[5-[(3S)-3-aminopyrrolidine-1-carbonyl]-2-[2-fluoro-4-(2-methoxyethyl)phenyl]phenyl]benzonitrile The procedure of steps 1 to 5 in Example 9 was conducted using 1-bromo-2-fluoro-4-(2-methoxyethyl)benzene instead of 1-bromo-2-chloro-4-methyl-benzene to give the title compound.

Example 72: Synthesis of 4-[5-[(3S)-3-aminopyrrolidine-1-carbonyl]-2-[4-(2-hydroxy-1,1-dimethyl-ethyl)phenyl]phenyl]benzonitrile The procedure of steps 1 to 5 in Example 9 was conducted using 2-(4-bromophenyl)-2-methyl-propan-1-ol instead of 1-bromo-2-chloro-4-methyl-benzene to give the title compound.

Example 73: Synthesis of 4-[5-[(3S)-3-aminopyrrolidine-1-carbonyl]-2-[4-(2-fluoroethyl)phenyl]phenyl]benzonitrile The procedure of steps 1 to 5 in Example 9 was conducted using 1-bromo-4-(2-fluoroethyl)benzene instead of 1-bromo-2-chloro-4-methyl-benzene to give the title compound.

Example 74: Synthesis of 4-[5-(2,7-diazaspiro[3.4]octane-7-carbonyl)-2-[2-fluoro-4-(2-methoxyethyl)phenyl]phenyl]-2-fluoro-benzonitrile The procedure of steps 1 to 4 in Example 22 was conducted using tert-butyl 2,7-diazaspiro[3.4]octane-2-carboxylic acid instead of tert-butyl N-[(3-endo)-8-azabicyclo[3.2.1]octan-3-yl]carbamate to give the title compound.

Example 75: Synthesis of 4-[5-(2,8-diazaspiro[3.5]nonane-2-carbonyl)-2-[2-fluoro-4-(2-methoxyethyl)phenyl]phenyl]-2-fluoro-benzonitrile The procedure of steps 1 to 4 in Example 22 was conducted using tert-butyl 2,8-diazaspiro[3.5]nonane-8-carboxylic acid instead of tert-butyl N-[(3-endo)-8-azabicyclo[3.2.1]octan-3-yl]carbamate to give the title compound.

Example 76: Synthesis of 4-[5-(2,7-diazaspiro[3.4]octane-7-carbonyl)-2-[2-fluoro-4-(2-hydroxy-2-methyl-propyl)phenyl]phenyl]-2-fluoro-benzonitrile The procedure of steps 1 to 5 in Example 41 was conducted using tert-butyl 2,7-diazaspiro[3.4]octane-2-carboxylic acid instead of tert-butyl N-[(3-endo)-8-azabicyclo[3.2.1]octan-3-yl]carbamate to give the title compound.

Example 77: Synthesis of 4-[5-(2,8-diazaspiro[3.5]nonane-2-carbonyl)-2-[2-fluoro-4-(2-hydroxy-2-methyl-propyl)phenyl]phenyl]-2-fluoro-benzonitrile The procedure of steps 1 to 5 in Example 41 was conducted using tert-butyl 2,8-diazaspiro[3.5]nonane-8-carboxylic acid instead of tert-butyl N-[(3-endo)-8-azabicyclo[3.2.1]octan-3-yl]carbamate to give the title compound.

Example 78: Synthesis of 4-[5-(3,8-diazaspiro[4.5]decane-8-carbonyl)-2-[2-fluoro-4-(2-methoxyethyl)phenyl]phenyl]-2-fluoro-benzonitrile hydrochloride The procedure of steps 1 to 4 in Example 22 was conducted using tert-butyl 3,8-diazaspiro[4.5]decane-3-carboxylic acid instead of tert-butyl N-[(3-endo)-8-azabicyclo[3.2.1]octan-3-yl]carbamate to give the title compound.

Example 79: Synthesis of 4-[5-(2,8-diazaspiro[3.5]nonane-8-carbonyl)-2-[2-fluoro-4-(2-methoxyethyl)phenyl]phenyl]-2-fluoro-benzonitrile The procedure of steps 1 to 4 in Example 22 was conducted using tert-butyl 2,8-diazaspiro[3.5]nonane-2-carboxylic acid instead of tert-butyl N-[(3-endo)-8-azabicyclo[3.2.1]octan-3-yl]carbamate to give the title compound.

Example 80: Synthesis of 4-[5-(1,4-diazepane-1-carbonyl)-2-[2-fluoro-4-(2-methoxyethyl)phenyl]phenyl]-2-fluoro-benzonitrile hydrochloride The procedure of steps 1 to 4 in Example 22 was conducted using tert-butyl-1,4-diazepane-1-carboxylic acid instead of tert-butyl N-[(3-endo)-8-azabicyclo[3.2.1]octan-3-yl]carbamate to give the title compound.

Example 81: Synthesis of 4-[5-(3,7-diazaspiro[3.4]octane-7-carbonyl)-2-[2-fluoro-4-(2-methoxyethyl)phenyl]phenyl]-2-fluoro-benzonitrile The procedure of steps 1 to 4 in Example 22 was conducted using tert-butyl-3,7-diazaspiro[3.4]octane-3-carboxylic acid instead of tert-butyl N-[(3-endo)-8-azabicyclo[3.2.1]octan-3-yl]carbamate to give the title compound.

Example 82: Synthesis of 4-[5-[(1S,4S)-2,5-diazabicyclo[2.2.1]heptane-2-carbonyl]-2-[2-fluoro-4-(2-methoxyethyl)phenyl]phenyl]-2-fluoro-benzonitrile The procedure of steps 1 to 4 in Example 22 was conducted using tert-butyl (1S,4S)-2,5-diazabicyclo[2.2.1]heptane-2-carboxylic acid instead of tert-butyl N-[(3-endo)-8-azabicyclo[3.2.1]octan-3-yl]carbamate to give the title compound.

Example 83: Synthesis of 4-[5-(3,7-diazaspiro[3.5]nonane-7-carbonyl)-2-[2-fluoro-4-(2-methoxyethyl)phenyl]phenyl]-2-fluoro-benzonitrile The procedure of steps 1 to 4 in Example 22 was conducted using tert-butyl 3,7-diazaspiro[3.5]nonane-3-carboxylic acid instead of tert-butyl N-[(3-endo)-8-azabicyclo[3.2.1]octan-3-yl]carbamate to give the title compound.

Example 84: Synthesis of 4-[5-(2,7-diazaspiro[3.5]nonane-2-carbonyl)-2-[2-fluoro-4-(2-methoxyethyl)phenyl]phenyl]-2-fluoro-benzonitrile The procedure of steps 1 to 4 in Example 22 was conducted using tert-butyl 2,7-diazaspiro[3.5]nonane-7-carboxylic acid hydrochloride instead of tert-butyl N-[(3-endo)-8-azabicyclo[3.2.1]octan-3-yl]carbamate to give the title compound.

Example 85: Synthesis of 4-[5-[(1R,4R)-2,5-diazabicyclo[2.2.1]heptane-2-carbonyl]-2-[2-fluoro-4-(2-methoxyethyl)phenyl]phenyl]-2-fluoro-benzonitrile The procedure of steps 1 to 4 in Example 22 was conducted using tert-butyl (1R,4R)-2,5-diazabicyclo[2.2.1]

heptane-2-carboxylic acid instead of tert-butyl N-[(3-endo)-8-azabicyclo[3.2.1]octan-3-yl]carbamate to give the title compound.

Example 86: Synthesis of 2-fluoro-4-[2-[2-fluoro-4-(2-methoxyethyl)phenyl]-5-[(1S,4S)-5-methyl-2,5-diazabicyclo[2.2.1]heptane-2-carbonyl]phenyl]benzonitrile The procedure of steps 1 to 4 in Example 22 was conducted using (1S,4S)-2-methyl-2,5-diazabicyclo[2.2.1]heptane instead of tert-butyl N-[(3-endo)-8-azabicyclo[3.2.1]octan-3-yl]carbamate to give the title compound.

Example 87: Synthesis of 2-fluoro-4-[2-[2-fluoro-4-(2-methoxyethyl)phenyl]-5-[(1R,4R)-5-methyl-2,5-diazabicyclo[2.2.1]heptane-2-carbonyl]phenyl]benzonitrile The procedure of steps 1 to 4 in Example 22 was conducted using (1R,4R)-2-methyl-2,5-diazabicyclo[2.2.1]heptane instead of tert-butyl N-[(3-endo)-8-azabicyclo[3.2.1]octan-3-yl]carbamate to give the title compound.

Example 88: Synthesis of 4-[5-(3,8-diazabicyclo[3.2.1]octane-3-carbonyl)-2-[2-fluoro-4-(2-methoxyethyl)phenyl]phenyl]-2-fluoro-benzonitrile The procedure of steps 1 to 4 in Example 22 was conducted using tert-butyl 3,8-diazabicyclo[3.2.1]octane-8-carboxylic acid) instead of tert-butyl N-[(3-endo)-8-azabicyclo[3.2.1]octan-3-yl]carbamate to give the title compound.

Example 89: Synthesis of 4-[5-[(3S)-3-aminopyrrolidine-1-carbonyl]-2-(1,3-benzothiazol-5-yl)phenyl]-2-fluoro-benzonitrile The procedure of steps 1 to 3 in Example 16 was conducted using 1,3-benzothiazol-5-yl boronic acid instead of p-tolylboronic acid to give the title compound.

Example 90: Synthesis of 4-[5-[(3S)-3-aminopyrrolidine-1-carbonyl]-2-(1-methylpyrazolo[3,4-b]pyridin-5-yl)phenyl]-2-fluoro-benzonitrile The procedure of steps 1 to 3 in Example 16 was conducted using (1-methylpyrazolo[3,4-b]pyridin-5-yl)boronic acid instead of p-tolylboronic acid to give the title compound.

Example 91: Synthesis of 4-[5-[(3S)-3-aminopyrrolidine-1-carbonyl]-2-(1-methylbenzimidazol-5-yl)phenyl]-2-fluoro-benzonitrile The procedure of steps 1 to 3 in Example 37 was conducted using 5-bromo-1-methyl-benzimidazole instead of 1-(4-bromo-3-fluoro-phenyl)-2-methyl-propan-2-ol to give the title compound.

Example 92: Synthesis of 4-[5-[(3S)-3-aminopyrrolidine-1-carbonyl]-2-(1-methylindazol-5-yl)phenyl]-2-fluoro-benzonitrile The procedure of steps 1 to 3 in Example 16 was conducted using (1-methylindazol-5-yl)boronic acid instead of p-tolylboronic acid to give the title compound.

Example 93: Synthesis of 4-[5-[(3S)-3-aminopyrrolidine-1-carbonyl]-2-(2-methylindazol-5-yl)phenyl]-2-fluoro-benzonitrile The procedure of steps 1 to 3 in Example 16 was conducted using 2-methyl-5-(4,4,5,5-tetramethyl-1,3,2-dioxaborolan-2-yl)indazole instead of p-tolylboronic acid to give the title compound.

Example 94: Synthesis of 4-[5-[(3S)-3-aminopyrrolidine-1-carbothioyl]-2-[2-fluoro-4-(2-methoxyethyl)phenyl]phenyl]-2-fluoro-benzonitrile The procedure of Example 2 was conducted using the 4-[5-[(3S)-3-aminopyrrolidine-1-carbonyl]-2-[2-fluoro-4-(2-methoxyethyl)phenyl]phenyl]-2-fluoro-benzonitrile obtained in Example 20 (step 3) instead of 4-[5-[(3S)-3-aminopyrrolidine-1-carbonyl]-2-(p-tolyl)phenyl]benzonitrile to give the title compound.

Example 95: Synthesis of 4-[5-[(3S)-3-aminopyrrolidine-1-carbonyl]-2-(6-fluoro-1-methyl-benzimidazol-5-yl)phenyl]-2-fluoro-benzonitrile The procedure of steps 1 to 3 in Example 37 was conducted using 5-bromo-6-fluoro-1-methyl-benzimidazole instead of 1-(4-bromo-3-fluoro-phenyl)-2-methyl-propan-2-ol to give the title compound.

Example 96: Synthesis of 4-[5-[(3S)-3-aminopyrrolidine-1-carbonyl]-2-(6-fluoro-1-methyl-benzotriazol-5-yl)phenyl]-2-fluoro-benzonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (15 mg) obtained in Example 37 (step 1) was dissolved in 1,4-dioxane (0.5 mL). At room temperature, 5-bromo-6-fluoro-1-methyl-benzotriazole (9.7 mg), PdCl$_2$(dppf) (1.0 mg), and tripotassium phosphate (18 mg) were added thereto, and the mixture was stirred in a microwave reactor at 125° C. for 30 minutes. Ethyl acetate was added thereto, and the mixture was put on NH-silica gel and washed with ethyl acetate/methanol. The solvent was distilled off to give tert-butyl N-[(3S)-1-[3-(4-cyano-3-fluoro-phenyl)-4-(6-fluoro-1-methyl-benzotriazol-5-yl)benzoyl]pyrrolidin-3-yl]carbamate.

Step 2

The tert-butyl N-[(3S)-1-[3-(4-cyano-3-fluoro-phenyl)-4-(6-fluoro-1-methyl-benzotriazol-5-yl)benzoyl]pyrrolidin-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 97: Synthesis of 4-[5-[(3-exo)-3-amino-8-azabicyclo[3.2.1]octane-8-carbonyl]-2-(4-fluorophenyl)phenyl]benzonitrile The procedure of steps 1 to 3 in Example 23 was conducted using 1-bromo-4-fluorobenzene instead of 5-bromo-6-fluoro-1-methyl-indole to give the title compound.

Example 98: Synthesis of 4-[5-[(3-exo)-3-amino-8-azabicyclo[3.2.1]octane-8-carbonyl]-2-(4-chlorophenyl)phenyl]benzonitrile The procedure of steps 1 to 3 in Example 23 was conducted using 1-bromo-4-chloro-benzene instead of 5-bromo-6-fluoro-1-methyl-indole to give the title compound.

Example 99: Synthesis of [(3S)-3-aminopyrrolidin-1-yl]-[3-(4-nitrophenyl)-4-(p-tolyl)phenyl]methanone The procedure of steps 1 to 5 in Example 19 was conducted using 1-bromo-4-nitro-benzene instead of 4-bromo-2,6-difluoro-benzonitrile to give the title compound.

Example 100: Synthesis of 4-[5-[(3S)-3-aminopyrrolidine-1-carbonyl]-2-[6-(dimethylamino)-3-pyridyl]phenyl]-2-fluoro-benzonitrile The procedure of steps 1 to 3 in Example 37 was conducted using 5-bromo-N,N-dimethylpyridin-2-amine instead of 1-(4-bromo-3-fluoro-phenyl)-2-methyl-propan-2-ol to give the title compound.

Example 101: Synthesis of 4-[5-[(3S)-3-aminopyrrolidine-1-carbonyl]-2-(1-methylbenzotriazol-5-yl)phenyl]-2-fluoro-benzonitrile The procedure of steps 1 to 3 in Example 37 was conducted using 5-bromo-1-methyl-benzotriazole instead of 1-(4-bromo-3-fluoro-phenyl)-2-methyl-propan-2-ol to give the title compound.

Example 102: Synthesis of 4-[5-[(3S)-3-aminopyrrolidine-1-carbonyl]-2-(6,7-difluoro-1-methyl-benzimidazol-5-yl)phenyl]-2-fluoro-benzonitrile The procedure of steps 1 to 3 in Example 37 was conducted using 5-bromo-6,7-difluoro-1-methyl-benzimidazole instead of 1-(4-bromo-3-fluoro-phenyl)-2-methyl-propan-2-ol to give the title compound.

Example 103: Synthesis of 4-[5-[(3S)-3-aminopyrrolidine-1-carbonyl]-2-(1,2-dimethylbenzimidazol-5-yl)phenyl]-2-fluoro-benzonitrile The procedure of steps 1 to 3 in Example 37 was conducted using 5-bromo-1,2-dimethyl-benzimidazole instead of 1-(4-bromo-3-fluoro-phenyl)-2-methyl-propan-2-ol to give the title compound.

Example 104: Synthesis of 4-[5-[(3-exo)-3-amino-8-azabicyclo[3.2.1]octane-8-carbonyl]-2-(2-naphthyl)phenyl]-2-fluoro-benzonitrile The procedure of steps 1 to 3 in Example 23 was conducted using 2-bromonaphthalene instead of 5-bromo-6-fluoro-1-methyl-indole to give the title compound.

Example 105: Synthesis of 4-[5-[(3-exo)-3-amino-8-azabicyclo[3.2.1]octane-8-carbonyl]-2-(8-fluoro-7-quinolyl)phenyl]-2-fluoro-benzonitrile The procedure of steps 1 to 3 in Example 23 was conducted using 7-bromo-8-fluoroquinoline instead of 5-bromo-6-fluoro-1-methyl-indole to give the title compound.

Example 106: Synthesis of 4-[5-[(3-exo)-3-amino-8-azabicyclo[3.2.1]octane-8-carbonyl]-2-(4-methyl-2,3-dihydro-1,4-benzoxazin-7-yl)phenyl]-2-fluoro-benzonitrile The procedure of steps 1 to 3 in Example 23 was conducted using 7-bromo-4-methyl-3,4-dihydro-2H-benzo[b][1,4]oxazine instead of 5-bromo-6-fluoro-1-methyl-indole to give the title compound.

Example 107: Synthesis of 4-[5-[(3-exo)-3-amino-8-azabicyclo[3.2.1]octane-8-carbonyl]-2-(7-quinonyl)phenyl]-2-fluoro-benzonitrile The procedure of steps 1 to 3 in Example 23 was conducted using 7-bromoquinoline instead of 5-bromo-6-fluoro-1-methyl-indole to give the title compound.

Example 108: Synthesis of 4-[5-[(3-exo)-3-amino-8-azabicyclo[3.2.1]octane-8-carbonyl]-2-(6-fluoro-1-methyl-benzimidazol-5-yl)phenyl]-2-fluoro-benzonitrile The procedure of steps 1 to 3 in Example 23 was conducted using 5-bromo-6-fluoro-1-methyl-benzimidazole instead of 5-bromo-6-fluoro-1-methyl-indole to give the title compound.

Example 109: Synthesis of 4-[5-[(3-exo)-3-amino-8-azabicyclo[3.2.1]octane-8-carbonyl]-2-(6-fluoro-1-methyl-benzotriazol-5-yl)phenyl]-2-fluoro-benzonitrile The procedure of steps 1 to 3 in Example 23 was conducted using 5-bromo-6-fluoro-1-methyl-benzotriazole instead of 5-bromo-6-fluoro-1-methyl-indole to give the title compound.

Example 110: Synthesis of 4-[5-[(3-exo)-3-amino-8-azabicyclo[3.2.1]octane-8-carbonyl]-2-(4-fluoro-1-methyl-indazol-5-yl)phenyl]-2-fluoro-benzonitrile The procedure of steps 1 to 3 in Example 23 was conducted using 5-bromo-4-fluoro-1-methyl-indazole instead of 5-bromo-6-fluoro-1-methyl-indole to give the title compound.

Example 111: Synthesis of 4-[5-[(3-exo)-3-amino-8-azabicyclo[3.2.1]octane-8-carbonyl]-2-(2-methyl-indazol-5-yl)phenyl]benzonitrile The procedure of steps 1 to 3 in Example 23 was conducted using 5-bromo-2-methyl-2H-indazole instead of 5-bromo-6-fluoro-1-methyl-indole to give the title compound.

Example 112: Synthesis of 2-fluoro-4-[2-[2-fluoro-4-(2-methoxyethyl)phenyl]-5-[(3-exo)-3-(isopropylamino)-8-azabicyclo[3.2.1]octane-8-carbonyl]phenyl]benzonitrile Acetone (0.002 mL) was added at 25° C. to a solution of the 4-[5-[(3-exo)-3-amino-8-azabicyclo[3.2.1]octane-8-carbonyl]-2-[2-fluoro-4-(2-methoxyethyl)phenyl]-2-fluoro-benzonitrile obtained in Example 26 (step 2) in dichloromethane (0.05 mL). Subsequently, NaBH(OAc)$_3$ (8.45 mg) was added thereto, followed by stirring at room temperature for 1 hour. MeOH was added thereto, and the solvent was distilled off. Then, the residue was purified by reversed-phase HPLC (mobile phase: water/acetonitrile) to give the title compound.

Example 113: Synthesis of 2-fluoro-4-[2-[2-fluoro-4-(2-hydroxy-2-methyl-propyl)phenyl]-5-[(3-exo)-3-(isopropylamino)-8-azabicyclo[3.2.1]octane-8-carbonyl]phenyl]benzonitrile The procedure of Example 112 was conducted using the 4-[5-[(3-exo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile obtained in Example 28 (step 3) instead of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile to give the title compound.

Example 114: Synthesis of 4-[5-[(3S)-3-(ethylamino)pyrrolidine-1-carbonyl]-2-(6-fluoro-1-methyl-benzotriazol-5-yl)phenyl]-2-fluoro-benzonitrile Step 1
The tert-butyl N-[(3S)-1-[3-(4-cyano-3-fluoro-phenyl)-4-(6-fluoro-1-methyl-benzotriazol-5-yl)benzoyl]pyrrolidin-3-yl]carbamate (10 mg) obtained in Example 96 (step 1) was dissolved in THF (0.5 mL). At room temperature, sodium hydride (0.85 mg), and then iodoethane (5.58 mg) were added thereto, the mixture was stirred at 50° C. overnight, and the solvent was distilled off to give (S)-tert-butyl (1-(4'-cyano-3'-fluoro-6-(6-fluoro-1-methyl-1H-benzo[d][1,2,3]triazol-5-yl)-[1,1'-biphenyl]-3-carbonyl)pyrrolidin-3-yl)(ethyl)carbamate. The thus obtained product was used in the next step without purification.
Step 2
The procedure of step 2 in Example 26 was conducted using the (S)-tert-butyl (1-(4'-cyano-3'-fluoro-6-(6-fluoro-1-methyl-1H-benzo[d][1,2,3]triazol-5-yl)-[1,1'-biphenyl]-3-carbonyl)pyrrolidin-3-yl) (ethyl)carbamate obtained in step 1 above instead of [(3-exo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate to give the title compound.

Example 115: Synthesis of 2-fluoro-4-[2-(6-fluoro-1-methyl-benzotriazol-5-yl)-5-[(3S)-3-(isopropylamino)pyrrolidine-1-carbonyl]phenyl]benzonitrile The procedure of Example 112 was conducted using the 4-[5-[(3S)-3-aminopyrrolidine-1-carbonyl]-2-(6-fluoro-1-methyl-benzotriazol-5-yl)phenyl]-2-fluoro-benzonitrile obtained in Example 96 (step 2) instead of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile to give the title compound.

Example 116: Synthesis of 4-[5-[(3S)-3-(cyclobutylamino)pyrrolidine-1-carbonyl]-2-(6-fluoro-1-methyl-benzotriazol-5-yl)phenyl]-2-fluoro-benzonitrile The procedure of Example 112 was conducted using the 4-[5-[(3S)-3-aminopyrrolidine-1-carbonyl]-2-(6-fluoro-1-methyl-benzotriazol-5-yl)phenyl]-2-fluoro-benzonitrile obtained in Example 96 (step 2) instead of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile, and using cyclobutanone instead of acetone to give the title compound.

Example 117: Synthesis of 4-[5-[(3S)-3-aminopyrrolidine-1-carbonyl]-2-(1-methylindolin-5-yl)phenyl]-2-fluoro-benzonitrile The procedure of steps 1 to 3 in Example 37 was conducted using 5-bromo-1-methyl-indoline instead of 1-(4-bromo-3-fluoro-phenyl)-2-methyl-propan-2-ol to give the title compound.

Example 118: Synthesis of 4-[5-[(3S)-3-aminopyrrolidine-1-carbonyl]-2-(4-methyl-2,3-dihydro-1,4-benzoxazin-7-yl)phenyl]-2-fluoro-benzonitrile The procedure of steps 1 to 3 in Example 37 was conducted using 7-bromo-4-methyl-3,4-dihydro-2H-benzo[b][1,4]oxazine instead of 1-(4-bromo-3-fluoro-phenyl)-2-methyl-propan-2-ol to give the title compound.

Example 119: Synthesis of 4-[5-[(3S)-3-aminopyrrolidine-1-carbonyl]-2-(3-methyl-2-oxo-1,3-benzoxazol-6-yl)phenyl]-2-fluoro-benzonitrile The procedure of steps 1 to 3 in Example 37 was conducted using 6-bromo-3-methyl-1,3-benzooxazol-2-one instead of 1-(4-bromo-3-fluoro-phenyl)-2-methyl-propan-2-ol to give the title compound.

Example 120: Synthesis of 4-[5-[(3S)-3-aminopyrrolidine-1-carbonyl]-2-(3-methyl-2-oxo-1,3-benzothiazol-6-yl)phenyl]-2-fluoro-benzonitrile The procedure of steps 1 to 3 in Example 37 was conducted using 6-bromo-3-methyl-1,3-benzothiazol-2-one instead of 1-(4-bromo-3-fluoro-phenyl)-2-methyl-propan-2-ol to give the title compound.

Example 121: Synthesis of 4-[5-[(3S)-3-aminopyrrolidine-1-carbonyl]-2-(2,3-dihydro-1,4-benzodioxin-6-yl)phenyl]-2-fluoro-benzonitrile The procedure of steps 1 to 3 in Example 16 was conducted using 2,3-dihydro-1,4-benzodioxan-6-yl boronic acid instead of p-tolylboronic acid to give the title compound.

Example 122: Synthesis of 4-[5-[(3S)-3-aminopyrrolidine-1-carbonyl]-2-(1,3-benzodioxol-5-yl)phenyl]-2-fluoro-benzonitrile The procedure of steps 1 to 3 in Example 16 was conducted using 1,3-benzodioxol-5-yl boronic acid instead of p-tolylboronic acid to give the title compound.

Example 123: Synthesis of 4-[5-[(3-endo)-3-amino-8-azabicyclo[3.2.1]octane-8-carbonyl]-2-(6-fluoro-1-methyl-indol-5-yl)phenyl]-2-fluoro-benzonitrile The procedure of steps 1 to 5 in Example 41 was conducted using 5-bromo-6-fluoro-1-methyl-indole instead of 1-(4-bromo-3-fluoro-phenyl)-2-methyl-propan-2-ol to give the title compound.

Example 124: Synthesis of 4-[5-[(3-endo)-3-amino-8-azabicyclo[3.2.1]octane-8-carbonyl]-2-(6-fluoro-1-methyl-indazol-5-yl)phenyl]-2-fluoro-benzonitrile The procedure of steps 1 to 5 in Example 41 was conducted using 5-bromo-6-fluoro-1-methyl-indazole instead of 1-(4-bromo-3-fluoro-phenyl)-2-methyl-propan-2-ol to give the title compound.

Example 125: Synthesis of 4-[5-[(3-endo)-3-amino-8-azabicyclo[3.2.1]octane-8-carbonyl]-2-(6-fluoro-1-methyl-benzotriazol-5-yl)phenyl]-2-fluoro-benzonitrile The procedure of steps 1 to 5 in Example 41 was conducted using 5-bromo-6-fluoro-1-methyl-benzotriazole instead of 1-(4-bromo-3-fluoro-phenyl)-2-methyl-propan-2-ol to give the title compound.

Example 126: Synthesis of 4-[5-[(3-endo)-3-amino-8-azabicyclo[3.2.1]octane-8-carbonyl]-2-(6,7-difluoro-1-methyl-benzimidazol-5-yl)phenyl]-2-fluoro-benzonitrile The procedure of steps 1 to 5 in Example 41 was conducted using 5-bromo-6,7-difluoro-1-methyl-benzimidazole instead of 1-(4-bromo-3-fluoro-phenyl)-2-methyl-propan-2-ol to give the title compound.

Example 127: Synthesis of 4-[5-[(3-exo)-3-amino-9-azabicyclo[3.3.1]nonane-9-carbonyl]-2-[2-fluoro-4-(2-methoxyethyl)phenyl]phenyl]-2-fluoro-benzonitrile The procedure of steps 1 to 4 in Example 22 was conducted using tert-butyl N-[(3-exo)-9-azabicyclo[3.3.1]nonan-3-yl]carbamate instead of tert-butyl N-[(3-endo)-8-azabicyclo[3.2.1]octan-3-yl]carbamate to give the title compound.

Example 128: Synthesis of 4-[5-[(3-endo)-3-amino-8-azabicyclo[3.2.1]octane-8-carbonyl]-2-(4-methyl-2,3-dihydro-1,4-benzoxazin-7-yl)phenyl]-2-fluoro-benzonitrile The procedure of steps 1 to 5 in Example 41 was conducted using 7-bromo-4-methyl-3,4-dihydro-2H-benzo[b][1,4]oxazine instead of 1-(4-bromo-3-fluoro-phenyl)-2-methyl-propan-2-ol to give the title compound.

Example 129: Synthesis of 4-[5-[(3-endo)-3-amino-9-azabicyclo[3.3.1]nonane-9-carbonyl]-2-[2-fluoro-4-(2-methoxyethyl)phenyl]phenyl]-2-fluoro-benzonitrile The procedure of steps 1 to 4 in Example 22 was conducted using tert-butyl N-[(3-endo)-9-azabicyclo[3.3.1]nonan-3-yl]carbamate instead of tert-butyl N-[(3-endo)-8-azabicyclo[3.2.1]octan-3-yl]carbamate to give the title compound.

Example 130: Synthesis of 4-[5-[(3-endo)-3-amino-8-azabicyclo[3.2.1]octane-8-carbonyl]-2-(6-fluoro-1-methyl-benzimidazol-5-yl)phenyl]-2-fluoro-benzonitrile The procedure of steps 1 to 5 in Example 41 was conducted using 5-bromo-6-fluoro-1-methyl-benzimidazole instead of 1-(4-bromo-3-fluoro-phenyl)-2-methyl-propan-2-ol to give the title compound.

Example 131: Synthesis of 4-[5-[(3-endo)-3-amino-8-azabicyclo[3.2.1]octane-8-carbonyl]-2-[6-(dimethylamino)-3-pyridyl]phenyl]-2-fluoro-benzonitrile The procedure of steps 1 to 5 in Example 41 was conducted using 5-bromo-N,N-dimethylpyridin-2-amine instead of 1-(4-bromo-3-fluoro-phenyl)-2-methyl-propan-2-ol to give the title compound.

Example 132: Synthesis of 4-[5-[(3-endo)-3-amino-8-azabicyclo[3.2.1]octane-8-carbonyl]-2-(1,3,3-trimethyl-2-oxo-indolin-5-yl)phenyl]-2-fluoro-benzonitrile The procedure of steps 1 to 5 in Example 41 was conducted using 5-bromo-1,3,3-trimethyl-indolin-2-one instead of 1-(4-bromo-3-fluoro-phenyl)-2-methyl-propan-2-ol to give the title compound.

Example 133: Synthesis of 4-[5-[(3-endo)-3-amino-8-azabicyclo[3.2.1]octane-8-carbonyl]-2-(3-methyl-2-oxo-1,3-benzothiazol-6-yl)phenyl]-2-fluoro-benzonitrile The procedure of steps 1 to 5 in Example 41 was conducted using 6-bromo-3-methyl-1,3-benzothiazol-2-one instead of 1-(4-bromo-3-fluoro-phenyl)-2-methyl-propan-2-ol to give the title compound.

Example 134: Synthesis of (S)-5'-(3-aminopyrrolidine-1-carbonyl)-3-fluoro-2'-(6-fluoro-1-methyl-1H-indol-5-yl)-[1,1'-biphenyl]-4-carbonitrile The procedure of steps 1 to 3 in Example 37 was conducted using 5-bromo-6-fluoro-1-methyl-1H-indole instead of 1-(4-bromo-3-fluoro-phenyl)-2-methyl-propan-2-ol to give the title compound.

Example 135: Synthesis of (S)-5'-(3-aminopyrrolidine-1-carbonyl)-3-fluoro-2'-(6-fluoro-1-methyl-1H-indazol-5-yl)-[1,1'-biphenyl]-4-carbonitrile The procedure of steps 1 to 3 in Example 37 was conducted using 5-bromo-6-fluoro-1-methyl-1H-indazole instead of 1-(4-bromo-3-fluoro-phenyl)-2-methyl-propan-2-ol to give the title compound.

Example 136: Synthesis of 5'-((3-endo)-3-amino-8-azabicyclo[3.2.1]octane-8-carbonyl)-3-fluoro-2'-(6-fluoro-1-(2-hydroxy-2-methylpropyl)-1H-indol-5-yl)-[1,1'-biphenyl]-4-carbonitrile Step 1

5-Bromo-6-fluoro-1H-indole (50 mg) was dissolved in DMF (0.78 mL). At room temperature, $Cs_2CO_3$ (151 mg) and 2,2-dimethyloxirane (42 μL) were added thereto, followed by stirring at 90° C. for 16 hours. The reaction was quenched with a saturated $NH_4Cl$ aqueous solution, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indol-1-yl)-2-methyl-propan-2-ol.

Step 2

The procedure of steps 1 to 5 in Example 41 was conducted using the 1-(5-bromo-6-fluoro-indol-1-yl)-2-methyl-propan-2-ol obtained in step 1 above instead of 1-(4-bromo-3-fluoro-phenyl)-2-methyl-propan-2-ol to give the title compound.

Example 137: Synthesis of 5'-((3-endo)-3-amino-8-azabicyclo[3.2.1]octane-8-carbonyl)-2'-(1,3-dihydroisobenzofuran-5-yl)-3-fluoro-[1,1'-biphenyl]-4-carbonitrile The procedure of steps 1 to 5 in Example 41 was conducted using 5-bromo-1,3-dihydroisobenzofuran instead of 1-(4-bromo-3-fluoro-phenyl)-2-methyl-propan-2-ol to give the title compound.

Example 138: Synthesis of 5'-((3-endo)-3-amino-8-azabicyclo[3.2.1]octane-8-carbonyl)-3-fluoro-2'-(3-isopropyl-2-oxo-2,3-dihydrobenzo[d]thiazol-6-yl)-[1,1'-biphenyl]-4-carbonitrile Step 1

6-Bromo-3H-1,3-benzothiazol-2-one (100 mg) was dissolved in DMF (0.87 mL). At room temperature, potassium carbonate (90 mg) was added thereto, followed by stirring at 0° C. for 15 minutes. At room temperature, 2-bromopropane (0.082 mL) was added thereto, followed by stirring at 100° C. for 3 hours. The reaction was quenched with a saturated NH$_4$Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 6-bromo-3-isopropyl-1,3-benzothiazol-2-one.

Step 2

The procedure of steps 1 to 5 in Example 41 was conducted using the 6-bromo-3-isopropyl-1,3-benzothiazol-2-one obtained in step 1 above instead of 1-(4-bromo-3-fluoro-phenyl)-2-methyl-propan-2-ol to give the title compound.

Example 139: Synthesis of 5'-((3-endo)-3-amino-8-azabicyclo[3.2.1]octane-8-carbonyl)-2'-(1-(tert-butyl)-6-fluoro-1H-benzo[d][1,2,3]triazol-5-yl)-3-fluoro-[1,1'-biphenyl]-4-carbonitrile The procedure of steps 1 to 5 in Example 41 was conducted using 5-bromo-1-(tert-butyl)-6-fluoro-1H-benzo[d][1,2,3]triazole instead of 1-(4-bromo-3-fluoro-phenyl)-2-methyl-propan-2-ol to give the title compound.

Example 140: Synthesis of (S)-5'-(3-aminopyrrolidine-1-carbonyl)-2'-(1,3-dihydroisobenzofuran-5-yl)-3-fluoro-[1,1'-biphenyl]-4-carbonitrile The procedure of steps 1 to 3 in Example 37 was conducted using 5-bromo-1,3'-dihydroisobenzofuran instead of 1-(4-bromo-3-fluoro-phenyl)-2-methyl-propan-2-ol to give the title compound.

Example 141: Synthesis of (S)-5'-(3-aminopyrrolidine-1-carbonyl)-3-fluoro-2'-(5-fluoro-3-methyl-2-oxo-2,3-dihydrobenzo[d]thiazol-6-yl)-[1,1'-biphenyl]-4-carbonitrile Step 1

5-Fluoro-3H-1,3-benzothiazol-2-one (200 mg) was suspended in MeCN (1 mL). At room temperature, NBS (231 mg) was added thereto, followed by stirring at room temperature for 1 hour. The solvent was vacuum-concentrated, and the residue was purified by silica gel column chromatography (mobile phase: hexane/ethyl acetate) to give 6-bromo-5-fluoro-3H-1,3-benzothiazol-2-one.

Step 2

The 6-bromo-5-fluoro-3H-1,3-benzothiazol-2-one (100 mg) obtained in step 1 above was dissolved in DMF (1.3 mL). At room temperature, potassium carbonate (84 mg) was added thereto, followed by stirring at 0° C. for 15 minutes. At room temperature, iodomethane (0.050 mL) was added thereto, followed by stirring at room temperature for 0.5 hours. The reaction was quenched with a saturated NH$_4$Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 6-bromo-5-fluoro-3-methyl-1,3-benzothiazol-2-one.

Step 3

The procedure of steps 1 to 3 in Example 37 was conducted using the 6-bromo-5-fluoro-3-methyl-1,3-benzothiazol-2-one obtained in step 2 above instead of 1-(4-bromo-3-fluoro-phenyl)-2-methyl-propan-2-ol to give the title compound.

Example 142: Synthesis of 5'-((3-endo)-3-amino-8-azabicyclo[3.2.1]octane-8-carbonyl)-3-fluoro-2'-(6-fluoro-1-(2-hydroxy-2-methylpropyl)-1H-indazol-5-yl)-[1,1'-biphenyl]-4-carbonitrile Step 1

5-Bromo-6-fluoro-1H-indazole (94 mg) was dissolved in DMF (1.5 mL). At room temperature, cesium carbonate (285 mg) and 2,2-dimethyloxirane (0.078 mL) were added thereto, followed by stirring at 90° C. for 16 hours. The reaction was quenched with a saturated NH$_4$Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indazol-1-yl)-2-methyl-propan-2-ol.

Step 2

The procedure of steps 1 to 5 in Example 41 was conducted using the 1-(5-bromo-6-fluoro-indazol-1-yl)-2-methyl-propan-2-ol obtained in step 1 above instead of 1-(4-bromo-3-fluoro-phenyl)-2-methyl-propan-2-ol to give the title compound.

Example 143: Synthesis of 4-[5-[(1S,3R,4R)-rel-3-amino-7-azabicyclo[2.2.1]heptane-7-carbonyl]-2-[2-fluoro-4-(2-methoxyethyl)phenyl]phenyl]-2-fluoro-benzonitrile Step 1 tert-Butyl (1S,3R,4R)-rel-3-amino-7-azabicyclo[2.2.1]heptane-7-carboxylate (50 mg) was dissolved in THF (1.2 mL). At 0° C., TEA (0.066 mL) and 2-nitrobenzene sulfonyl chloride (57 mg) were added thereto, followed by stirring at room temperature for 1 hour. Ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate), and the solvent was distilled off. The residue was dissolved in a 4 N hydrochloric acid-ethyl acetate solution (2 mL), followed by stirring at room temperature for 30 minutes. The reaction mixture was vacuum-concentrated to give N-[(1S,3R,4R)-rel-7-azabicyclo[2.2.1]heptan-3-yl]-2-nitrobenzenesulfonamide hydrochloride.

Step 2

The procedure of step 3 in Example 22 was conducted using the N-[(1S,3R,4R)-rel-7-azabicyclo[2.2.1]heptan-3-yl]-2-nitrobenzenesulfonamide hydrochloride obtained in step 1 above instead of tert-butyl N-[(3-endo)-8-azabicyclo[3.2.1]octan-3-yl]carbamate to give N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2-nitrobenzenesulfonamide.

Step 3

The N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2-nitrobenzenesulfonamide (20 mg) obtained in step 2 above was dissolved in DMF (0.5 mL). At room temperature, $K_2CO_3$ (21 mg) and 4-mercaptobenzoic acid (12 mg) were added thereto, followed by stirring at 40° C. for 12 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 144: Synthesis of 5'-((3-endo)-3-amino-8-azabicyclo[3.2.1]octane-8-carbonyl)-2'',3,3''-trifluoro-4''-methyl-[1,1':2',1''-terphenyl]-4-carbonitrile The procedure of steps 1 to 5 in Example 41 was conducted using 1-bromo-2,3-difluoro-4-methyl-benzene instead of 1-(4-bromo-3-fluoro-phenyl)-2-methyl-propan-2-ol to give the title compound.

Example 145: Synthesis of 5'-((3-endo)-3-amino-8-azabicyclo[3.2.1]octane-8-carbonyl)-2'-(6,7-difluoro-1-methyl-1H-benzo[d][1,2,3]triazol-5-yl)-3-fluoro-[1,1'-biphenyl]-4-carbonitrile Step 1

The tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (200 mg) obtained in step 3 in Example 41 and 5-bromo-6,7-difluoro-1-methyl-benzotriazole (129 mg) were dissolved in 1,4-dioxane (1.74 mL). At room temperature, Pd(dba)$_2$ (16.0 mg), X-phos (26.5 mg), and tripotassium phosphate (221 mg) were added thereto, and the mixture was stirred in a microwave reactor at 125° C. for 1 hour. The reaction mixture was filtrated, and the solvent was distilled off. The residue was purified by silica gel column chromatography (mobile phase: ethyl acetate/hexane) to give tert-butyl N-[(3-endo)-8-[3-(4-cyano-3-fluoro-phenyl)-4-(6,7-difluoro-1-methyl-benzotriazol-5-yl)benzoyl]-8-azabicyclo[3.2.1]octan-3-yl]carbamate.

Step 2

The tert-butyl N-[(3-endo)-8-[3-(4-cyano-3-fluoro-phenyl)-4-(6,7-difluoro-1-methyl-benzotriazol-5-yl)benzoyl]-8-azabicyclo[3.2.1]octan-3-yl]carbamate (210 mg) obtained in step 1 above was dissolved in MeOH (1.60 mL). At room temperature, a 4 N hydrochloric acid-ethyl acetate solution (2.40 mL) was added thereto, followed by stirring at room temperature for 1 hour. The reaction mixture was vacuum-concentrated, and the solvent was distilled off. The residue was purified by reversed-phase HPLC (mobile phase: water/acetonitrile) to give the title compound.

Example 146: Synthesis of (S)-5'-(3-aminopyrrolidine-1-carbonyl)-3-fluoro-2'-(6-fluoro-1-(2-hydroxy-2-methylpropyl)-1H-indol-5-yl)-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (60 mg) obtained in step 1 of Example 37 and the 1-(5-bromo-6-fluoro-indol-1-yl)-2-methyl-propan-2-ol (48.1 mg) obtained in step 1 of Example 136 were dissolved in 1,4-dioxane (0.50 mL). At room temperature, Pd(dba)$_2$ (3.22 mg), X-phos (5.34 mg), and tripotassium phosphate (71.4 mg) were added thereto, and the mixture was stirred in a microwave reactor at 125° C. for 1 hour. The reaction mixture was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-[6-fluoro-1-(2-hydroxy-2-methyl-propyl)indol-5-yl]benzoyl]pyrrolidin-3-yl]carbamate.

Step 2

The tert-butyl N-[(3S)-1-[3-(4-cyano-3-fluoro-phenyl)-4-[6-fluoro-1-(2-hydroxy-2-methyl-propyl)indol-5-yl]benzoyl]pyrrolidin-3-yl]carbamate (68.0 mg) obtained in step 1 above was dissolved in MeOH (1.0 mL). At room temperature, 12 N hydrochloric acid (1.0 mL) was added thereto, followed by stirring at room temperature for 1 hour. A 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 147: Synthesis of (S)-5'-(3-aminopyrrolidine-1-carbonyl)-3-fluoro-2'-(6-fluoro-1-(2-hydroxy-2-methylpropyl)-1H-indazol-5-yl)-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (70 mg) obtained in step 1 of Example 37 and the 1-(5-bromo-6-fluoro-indazol-1-yl)-2-methyl-propan-2-ol (56.3 mg) obtained in step 1 of Example 142 were dissolved in 1,4-dioxane (0.50 mL). At room temperature, Pd(dba)₂ (3.76 mg), X-phos (6.23 mg), and tripotassium phosphate (83.3 mg) were added thereto, and the mixture was stirred in a microwave reactor at 125° C. for 1 hour. The reaction mixture was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-[6-fluoro-1-(2-hydroxy-2-methyl-propyl)indazol-5-yl]benzoyl]pyrrolidin-3-yl]carbamate.

Step 2

The tert-butyl N-[(3S)-1-[3-(4-cyano-3-fluoro-phenyl)-4-[6-fluoro-1-(2-hydroxy-2-methyl-propyl)indazol-5-yl]benzoyl]pyrrolidin-3-yl]carbamate (70.0 mg) obtained in step 1 above was dissolved in MeOH (1.0 mL). At room temperature, 12 N hydrochloric acid (1.0 mL) was added thereto, followed by stirring at room temperature for 1 hour. A 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 148: Synthesis of 5'-((3-endo)-3-amino-8-azabicyclo[3.2.1]octane-8-carbonyl)-3-fluoro-2'-(quinoxalin-6-yl)-[1,1'-biphenyl]-4-carbonitrile The procedure of steps 1 to 5 in Example 41 was conducted using 6-bromoquinoxaline instead of 1-(4-bromo-3-fluoro-phenyl)-2-methyl-propan-2-ol to give the title compound.

Example 149: Synthesis of 5'-((3-endo)-3-amino-8-azabicyclo[3.2.1]octane-8-carbonyl)-3-fluoro-2'-(isoquinolin-6-yl)-[1,1'-biphenyl]-4-carbonitrile The procedure of steps 1 to 5 in Example 41 was conducted using 6-bromoisoquinoline instead of 1-(4-bromo-3-fluoro-phenyl)-2-methyl-propan-2-ol to give the title compound.

Example 150: Synthesis of 5'-((3-endo)-3-amino-8-azabicyclo[3.2.1]octane-8-carbonyl)-3-fluoro-2'-(isoquinolin-7-yl)-[1,1'-biphenyl]-4-carbonitrile The procedure of steps 1 to 5 in Example 41 was conducted using 7-bromoisoquinoline instead of 1-(4-bromo-3-fluoro-phenyl)-2-methyl-propan-2-ol to give the title compound.

Example 151: Synthesis of 5'-((3-endo)-3-amino-8-azabicyclo[3.2.1]octane-8-carbonyl)-3-fluoro-2'-(quinolin-6-yl)-[1,1'-biphenyl]-4-carbonitrile The procedure of steps 1 to 5 in Example 41 was conducted using 6-bromoquinoline instead of 1-(4-bromo-3-fluoro-phenyl)-2-methyl-propan-2-ol to give the title compound.

Example 152: Synthesis of 5'-((3-endo)-3-amino-8-azabicyclo[3.2.1]octane-8-carbonyl)-3-fluoro-2'-(quinazolin-7-yl)-[1,1'-biphenyl]-4-carbonitrile The procedure of steps 1 to 5 in Example 41 was conducted using 7-bromoquinazolin instead of 1-(4-bromo-3-fluoro-phenyl)-2-methyl-propan-2-ol to give the title compound.

Example 153: Synthesis of 5'-((3-endo)-3-amino-8-azabicyclo[3.2.1]octane-8-carbonyl)-3-fluoro-2'-(quinazolin-6-yl)-[1,1'-biphenyl]-4-carbonitrile The procedure of steps 1 to 5 in Example 41 was conducted using 6-bromoquinazolin instead of 1-(4-bromo-3-fluoro-phenyl)-2-methyl-propan-2-ol to give the title compound.

Example 154: Synthesis of 5'-((3-endo)-3-amino-8-azabicyclo[3.2.1]octane-8-carbonyl)-3-fluoro-2'-(phthalazin-6-yl)-[1,1'-biphenyl]-4-carbonitrile The procedure of steps 1 to 5 in Example 41 was conducted using 6-bromophthalazine instead of 1-(4-bromo-3-fluoro-phenyl)-2-methyl-propan-2-ol to give the title compound.

Example 155: Synthesis of 5'-((1R,2R,4S)-rel-2-amino-7-azabicyclo[2.2.1]heptane-7-carbonyl)-2'',3-difluoro-4''-(2-methoxyethyl)-[1,1':2',1''-terphenyl]-4-carbonitrile-isomer-B Step 1 tert-Butyl (1S,3R,4R)-rel-3-amino-7-azabicyclo[2.2.1]heptane-7-carboxylate (550 mg) was dissolved in THF (13.0 mL). At 0° C., TEA (0.720 mL) and 2,4-dinitrobenzene sulfonyl chloride (829 mg) were added thereto, followed by stirring at room temperature for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give tert-butyl (1S,3R,4R)-rel-3-[(2,4-dinitrophenyl)sulfonylamino]-7-azabicyclo[2.2.1]heptane-7-carboxylate.

Step 2

The tert-butyl (1S,3R,4R)-rel-3-[(2,4-dinitrophenyl)sulfonylamino]-7-azabicyclo[2.2.1]heptane-7-carboxylate (440 mg) obtained in step 1 above was subjected to chiral separation using SFC (device: Thar SFC prep 80 system, column: CHIRALPAK IE 20×250 mm, flow rate: 50 g/min, mobile phase: CO2/MeOH=90/10) to give (1S,3R,4R)-rel-3-[(2,4-dinitrophenyl)sulfonylamino]-7-azabicyclo[2.2.1]heptane-7-carboxylate-isomer-A (faster isomer) and (1S,3R,4R)-rel-3-[(2,4-dinitrophenyl)sulfonylamino]-7-azabicyclo[2.2.1]heptane-7-carboxylate-isomer-B (slower isomer).

Each isomer was analyzed under the following HPLC conditions.
Column: CHIRALPAK IE 4.6×150 mm
Mobile phase: hexane (0.1% triethylamine)/ethanol=85/15
Flow rate: 1.0 mL/min
Retention time of each isomer:
(1S,3R,4R)-rel-3-[(2,4-dinitrophenyl)sulfonylamino]-7-azabicyclo[2.2.1]heptane-7-carboxylate-isomer-A: 10.903 min (faster isomer)
(1S,3R,4R)-rel-3-[(2,4-dinitrophenyl)sulfonylamino]-7-azabicyclo[2.2.1]heptane-7-carboxylate-isomer-B: 14.028 min (slower isomer)

Step 3

The (1S,3R,4R)-rel-3-[(2,4-dinitrophenyl)sulfonylamino]-7-azabicyclo[2.2.1]heptane-7-carboxylate-isomer-B (200 mg) obtained in step 2 above was dissolved in ethyl acetate (1.00 mL). At room temperature, a 4 N hydrochloric acid-ethyl acetate solution (2.00 mL) was added thereto, followed by stirring at room temperature for 2 hours. The reaction mixture was vacuum-concentrated to give N-((1R,2R,4S)-rel-7-azabicyclo[2.2.1]heptan-2-yl)-2,4-dinitrobenzenesulfonamide-isomer-B hydrochloride.

Step 4

The 3-(4-cyano-3-fluoro-phenyl)-4-[2-fluoro-4-(2-methoxyethyl)phenyl]benzoic acid (8 mg) obtained in step 2 of Example 22 and the N-((1R,2R,4S)-rel-7-azabicyclo[2.2.1]heptan-2-yl)-2,4-dinitrobenzenesulfonamide-isomer-B hydrochloride (8.47 mg) obtained in step 3 above were dissolved in THF (0.30 mL). At room temperature, TEA (8.49 μL) and HATU (15.5 mg) were added thereto, followed by stirring at 50° C. for 1 hour. The solvent was distilled off under reduced pressure. The residue was purified by silica gel column chromatography (mobile phase: hexane/ethyl acetate) to give N-[(1S,3R,4R)-rel-7-[3-(4-cyano-3-fluoro-phenyl)-4-[2-fluoro-4-(2-methoxyethyl) phenyl]benzoyl]-7-azabicyclo[2.2.1]heptan-3-yl]-2,4-dinitrobenzenesulfonamide-isomer-B.

Step 5

The N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2,4-dinitrobenzenesulfonamide-isomer-B (14.5 mg) obtained in step 4 above was dissolved in DCM (1 mL). At 0° C., mercaptoacetic acid (2.83 μL) and TEA (7.49 μL) were added thereto, followed by stirring at room temperature for 2 hours. Chloroform was added thereto, the mixture was washed with a 4 N aqueous sodium hydroxide solution, and dried over anhydrous sodium sulfate, and the solvent was distilled off. The residue was purified by reversed-phase HPLC (mobile phase: water/acetonitrile) to give the title compound.

Example 156: Synthesis of 5'-((1R,2R,4S)-rel-2-amino-7-azabicyclo[2.2.1]heptane-7-carbonyl)-2'',3-difluoro-4''-(2-methoxyethyl)-[1,1':2',1''-terphenyl]-4-carbonitrile-isomer-A Step 1

The (1S,3R,4R)-rel-3-[(2,4-dinitrophenyl)sulfonylamino]-7-azabicyclo[2.2.1]heptane-7-carboxylate-isomer-A (200 mg) obtained in step 2 of Example 155 was dissolved in ethyl acetate (1.00 mL). At room temperature, a 4 N hydrochloric acid-ethyl acetate solution (2.00 mL) was added thereto, followed by stirring at room temperature for 2 hours. The reaction mixture was vacuum-concentrated to give N-((1R,2R,4S)-rel-7-azabicyclo[2.2.1]heptan-2-yl)-2,4-dinitrobenzenesulfonamide-isomer-A hydrochloride.

Step 2

The 3-(4-cyano-3-fluoro-phenyl)-4-[2-fluoro-4-(2-methoxyethyl)phenyl]benzoic acid (8 mg) obtained in step 2 of Example 22 and the N-((1r,2r,4s)-rel-7-azabicyclo[2.2.1]heptan-2-yl)-2,4-dinitrobenzenesulfonamide-isomer-A hydrochloride (8.47 mg) obtained in step 1 above were dissolved in THF (0.30 mL). At room temperature, TEA (8.49 μL) and HATU (15.5 mg) were added thereto, followed by stirring at 50° C. for 1 hour. The solvent was distilled off under reduced pressure. The residue was purified by silica gel column chromatography (mobile phase: hexane/ethyl acetate) to give N-[(1S,3R,4R)-rel-7-[3-(4-cyano-3-fluoro-phenyl)-4-[2-fluoro-4-(2-methoxyethyl) phenyl]benzoyl]-7-azabicyclo[2.2.1]heptan-3-yl]-2,4-dinitrobenzenesulfonamide-isomer-A.

Step 3

The N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2,4-dinitrobenzenesulfonamide-isomer-A (14.5 mg) obtained in step 2 above was dissolved in DCM (1 mL). At 0° C., mercaptoacetic acid (2.83 μL) and TEA (7.49 μL) were added thereto, followed by stirring at room temperature for 2 hours. Chloroform was added thereto, the mixture was washed with a 4 N aqueous sodium hydroxide solution, and dried over anhydrous sodium sulfate, and the solvent was distilled off. The residue was purified by reversed-phase HPLC (mobile phase: water/acetonitrile) to give the title compound.

Example 157: Synthesis of 5'-((3-endo)-3-amino-8-azabicyclo[3.2.1]octane-8-carbonyl)-3-fluoro-2'-(3-methylimidazo[1,5-a]pyridin-7-yl)-[1,1'-biphenyl]-4-carbonitrile The procedure of steps 1 to 5 in Example 41 was conducted using 7-bromo-3-methyl-imidazo[1,5-a]pyridine instead of 1-(4-bromo-3-fluoro-phenyl)-2-methyl-propan-2-ol to give the title compound.

Example 158: Synthesis of 5'-((3-endo)-3-amino-8-azabicyclo[3.2.1]octane-8-carbonyl)-3-fluoro-2'-(3-methylpyrazolo[1,5-a]pyrimidin-6-yl)-[1,1'-biphenyl]-4-carbonitrile The procedure of steps 1 to 5 in Example 41 was conducted using 6-bromo-3-methyl-pyrazolo[1,5-a]pyrimidine instead of 1-(4-bromo-3-fluoro-phenyl)-2-methyl-propan-2-ol to give the title compound.

Example 159: Synthesis of 5'-((3-endo)-3-amino-8-azabicyclo[3.2.1]octane-8-carbonyl)-3-fluoro-2'-(6-fluoro-2-(2-hydroxy-2-methylpropyl)-2H-indazol-5-yl)-[1,1'-biphenyl]-4-carbonitrile Step 1

5-Bromo-6-fluoro-1H-indazole (94 mg) was dissolved in DMF (1.5 mL). At room temperature, cesium carbonate (285 mg) and 2,2-dimethyloxirane (0.078 mL) were added thereto, followed by stirring at 90° C. for 16 hours. The reaction was quenched with a saturated NH$_4$Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indazol-2-yl)-2-methyl-propan-2-ol.

Step 2

The procedure of steps 1 to 5 in Example 41 was conducted using the 1-(5-bromo-6-fluoro-indazol-2-yl)-2-methyl-propan-2-ol obtained in step 1 above instead of 1-(4-bromo-3-fluoro-phenyl)-2-methyl-propan-2-ol to give the title compound.

Example 160: Synthesis of 5'-((3-endo)-3-amino-8-azabicyclo[3.2.1]octane-8-carbonyl)-2'-(1-ethyl-6-fluoro-1H-benzo[d][1,2,3]triazol-5-yl)-3-fluoro-[1,1'-biphenyl]-4-carbonitrile The procedure of steps 1 to 5 in Example 41 was conducted using 5-bromo-1-ethyl-6-fluoro-benzotriazole instead of 1-(4-bromo-3-fluoro-phenyl)-2-methyl-propan-2-ol to give the title compound.

Example 161: Synthesis of 5'-((3-endo)-3-amino-8-azabicyclo[3.2.1]octane-8-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile Step 1

1-(2,3-Difluoro-6-nitro-anilino)-2-methyl-propan-2-ol (6.20 g) was dissolved in DMF (84.0 mL). At room temperature, NBS (5.80 g) was added thereto, followed by stirring at 90° C. for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(4-bromo-2,3-difluoro-6-nitro-anilino)-2-methyl-propan-2-ol.

Step 2

The 1-(4-bromo-2,3-difluoro-6-nitro-anilino)-2-methyl-propan-2-ol (5.67 g) obtained in step 1 above was dissolved in ethanol (87.2 mL). At room temperature, ammonium chloride (5.67 g), iron (5.67 g), and water (87.2 mL) were added thereto, followed by stirring at 60° C. overnight. The reaction mixture was passed through Celite and washed with ethyl acetate. The filtrate was vacuum-concentrated, ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(6-amino-4-bromo-2,3-difluoro-anilino)-2-methyl-propan-2-ol.

Step 3

The 1-(6-amino-4-bromo-2,3-difluoro-anilino)-2-methyl-propan-2-ol (4.36 g) obtained in step 2 above was dissolved in water (28.4 mL) and THF (28.4 mL). At 0° C., 12 N hydrochloric acid (28.4 mL) and sodium nitrite (1.80 g) were added thereto, followed by stirring at room temperature for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(5-bromo-6,7-difluoro-benzotriazol-1-yl)-2-methyl-propan-2-ol.

Step 4

The tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (50 mg) obtained in step 3 of Example 41 and the 1-(5-bromo-6,7-difluoro-benzotriazol-1-yl)-2-methyl-propan-2-ol (39.9 mg) obtained in step 3 above were dissolved in 1,4-dioxane (0.50 mL). At room temperature, Pd(dba)$_2$ (2.50 mg), X-phos (4.14 mg), and tripotassium phosphate (55.3 mg) were added thereto, and the mixture was stirred in a microwave reactor at 125° C. for 1 hour. The reaction mixture was filtrated, and the solvent was distilled off. The residue was purified by silica gel column chromatography (mobile phase: chloroform/methanol) to give tert-butyl N-[(3-endo)-8-[3-(4-cyano-3-fluoro-phenyl)-4-[6,7-difluoro-1-(2-hydroxy-2-methyl-propyl)benzotriazol-5-yl]benzoyl]-8-azabicyclo[3.2.1]octan-3-yl]carbamate.

Step 5

The tert-butyl N-[(3-endo)-8-[3-(4-cyano-3-fluoro-phenyl)-4-[6,7-difluoro-1-(2-hydroxy-2-methyl-propyl)benzotriazol-5-yl]benzoyl]-8-azabicyclo[3.2.1]octan-3-yl]carbamate (55.0 mg) obtained in step 4 above was dissolved in MeOH (1.0 mL). At room temperature, 12 N hydrochloric acid (1.0 mL) was added thereto, followed by stirring at room temperature for 1 hour. A 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 162: Synthesis of (S)-5'-(3-aminopyrrolidine-1-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (100 mg) obtained in step 1 of Example 37 and the 1-(5-bromo-6,7-difluoro-benzotriazol-1-yl)-2-methyl-propan-2-ol (85.8 mg) obtained in step 3 of Example 161 were dissolved in 1,4-dioxane (0.934 mL). At room temperature, Pd(dba)$_2$ (5.37 mg), X-phos (8.90 mg), and tripotassium phosphate (119 mg) were added thereto, and the mixture was stirred in a microwave reactor at 125° C. for 1 hour. The reaction mixture was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-[6,7-difluoro-1-(2-hydroxy-2-methyl-propyl)benzotriazol-5-yl]benzoyl]pyrrolidin-3-yl]carbamate.

Step 2

The tert-butyl N-[(3S)-1-[3-(4-cyano-3-fluoro-phenyl)-4-[6,7-difluoro-1-(2-hydroxy-2-methyl-propyl)benzotriazol-5-yl]benzoyl]pyrrolidin-3-yl]carbamate (99.8 mg) obtained in step 1 above was dissolved in MeOH (1.0 mL). At room temperature, 12 N hydrochloric acid (1.0 mL) was added thereto, followed by stirring at room temperature for 1 hour. Then, a 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 163: Synthesis of 2'',3-difluoro-4''-(2-methoxyethyl)-5'-(piperazine-1-carbonyl)-[1,1':2',1''-terphenyl]-4-carbonitrile The procedure of steps 1 to 4 in Example 22 was conducted using tert-butyl piperazine-1-carboxylate instead of tert-butyl N-[(3-endo)-8-azabicyclo[3.2.1]octan-3-yl]carbamate to give the title compound.

Example 164: Synthesis of (R)-5'-(3-aminopiperidine-1-carbonyl)-2'',3-difluoro-4''-(2-methoxyethyl)-[1,1':2',1''-terphenyl]-4-carbonitrile The procedure of steps 1 to 4 in Example 22 was conducted using tert-butyl N-[(3R)-3-piperidyl]carbamate instead of tert-butyl N-[(3-endo)-8-azabicyclo[3.2.1]octan-3-yl]carbamate to give the title compound.

Example 165: Synthesis of 5'-(4-aminoazepan-1-carbonyl)-2'',3-difluoro-4''-(2-methoxyethyl)-[1,1':2',1''-terphenyl]-4-carbonitrile The procedure of steps 1 to 4 in Example 22 was conducted using tert-butyl N-(azepan-4-yl)carbamate instead of tert-butyl N-[(3-endo)-8-azabicyclo[3.2.1]octan-3-yl]carbamate to give the title compound.

Example 166: Synthesis of 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (500 mg) obtained in step 1 of Example 41 and the 1-(4-bromo-3-fluoro-phenyl)-2-methyl-propan-2-ol (379 mg) obtained in step 1 of Example 28 were dissolved in 1,4-dioxane (5.9 mL). At room temperature, Pd(dba)$_2$ (68 mg), X-phos (113 mg), and tripotassium phosphate (752 mg) were added thereto, followed by stirring at 100° C. overnight. The solvent was distilled off, and the residue was purified by silica gel column chromatography (mobile phase: hexane/ethyl acetate) to give tert-butyl 3-(4-cyano-3-fluoro-phenyl)-4-[2-fluoro-4-(2-hydroxy-2-methyl-propyl)phenyl]benzoate.

Step 2

The tert-butyl 3-(4-cyano-3-fluoro-phenyl)-4-[2-fluoro-4-(2-hydroxy-2-methyl-propyl)phenyl]benzoate (300 mg) obtained in step 1 above was dissolved in THF (0.9 mL). At 0° C., 12 N hydrochloric acid (0.9 mL) was added thereto, followed by stirring at room temperature for 2 hours. Then, MTBE was added thereto, the mixture was washed with water and dried over anhydrous sodium sulfate, and the solvent was distilled off to give 3-(4-cyano-3-fluoro-phenyl)-4-[2-fluoro-4-(2-hydroxy-2-methyl-propyl)phenyl]benzoic acid.

Step 3

The 3-(4-cyano-3-fluoro-phenyl)-4-[2-fluoro-4-(2-hydroxy-2-methyl-propyl)phenyl]benzoic acid (10 mg) obtained in step 2 above and the N-((1R,2R,4S)-rel-7-azabicyclo[2.2.1]heptan-2-yl)-2,4-dinitrobenzenesulfonamide-isomer-B hydrochloride (10.2 mg) obtained in step 3 of Example 155 were dissolved in THF (0.12 mL). At room temperature, TEA (0.014 mL) and HATU (18.7 mg) were added thereto, followed by stirring at 50° C. for 1 hour. The reaction mixture was vacuum-concentrated, and the residue was purified by silica gel column chromatography (mobile phase: hexane/ethyl acetate) to give N-[(1S,3R,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide-isomer-B.

Step 4

The N-[(1S,3R,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide-isomer-B (15 mg) obtained in step 3 above was dissolved in DCM (0.2 mL). At 0° C., mercaptoacetic acid (2 μL) and TEA (8.6 μL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 167: Synthesis of (S)-5'-(3-aminopyrrolidine-1-carbonyl)-2'-(6,7-difluoro-1-methyl-1H-benzo[d][1,2,3]triazol-5-yl)-3-fluoro-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (60 mg) obtained in step 1 of Example 37 and 5-bromo-6,7-difluoro-1-methyl-benzotriazole (41.7 mg) were dissolved in 1,4-dioxane (0.56 mL). At room temperature, Pd(dba)$_2$ (3.22 mg), X-phos (5.34 mg), and tripotassium phosphate (71.4 mg) were added thereto, and the mixture was stirred in a microwave reactor at 125° C. for 1 hour. The reaction mixture was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-(6,7-difluoro-1-methyl-benzotriazol-5-yl)benzoyl]pyrrolidin-3-yl]carbamate.

Step 2

The tert-butyl N-[(3S)-1-[3-(4-cyano-3-fluoro-phenyl)-4-(6,7-difluoro-1-methyl-benzotriazol-5-yl)benzoyl]pyrrolidin-3-yl]carbamate (20 mg) obtained in step 1 above was dissolved in TFA (0.40 mL), followed by stirring at room temperature for 5 minutes. After the completion of the reaction was confirmed by LCMS, DMSO (1.60 mL) was added thereto, and purification was performed by reversed-phase HPLC (mobile phase: water/acetonitrile) to give the title compound.

Example 168: Synthesis of 5'-((3-endo)-3-amino-8-azabicyclo[3.2.1]octane-8-carbonyl)-3-fluoro-2'-(6-fluoro-1-propyl-1H-benzo[d][1,2,3]triazol-5-yl)-[1,1'-biphenyl]-4-carbonitrile The procedure of steps 1 to 5 in Example 41 was conducted using 5-bromo-6-fluoro-1-propyl-benzotriazole instead of 1-(4-bromo-3-fluoro-phenyl)-2-methyl-propan-2-ol to give the title compound.

Example 169: Synthesis of (S)-5'-(3-aminopyrrolidine-1-carbonyl)-2'-(6,7-difluoro-1-(2-methoxyethyl)-1H-benzo[d][1,2,3]triazol-5-yl)-3-fluoro-[1,1'-biphenyl]-4-carbonitrile Step 1

The procedure of steps 1 to 3 in Example 161 was conducted using 2,3-difluoro-N-(2-methoxyethyl)-6-nitroaniline instead of 1-(2,3-difluoro-6-nitro-anilino)-2-methyl-propan-2-ol to give 5-bromo-6,7-difluoro-1-(2-methoxyethyl)benzotriazole.

Step 2

The procedure of steps 1 to 3 in Example 37 was conducted using the 5-bromo-6,7-difluoro-1-(2-methoxyethyl)benzotriazole obtained in step 1 above instead of 1-(4-bromo-3-fluoro-phenyl)-2-methyl-propan-2-ol to give the title compound.

Example 170: Synthesis of (S)-5'-(3-aminopyrrolidine-1-carbonyl)-3-fluoro-2'-(6-fluoro-1-(2-hydroxyethyl)-1H-indol-5-yl)-[1,1'-biphenyl]-4-carbonitrile The procedure of steps 1 to 3 in Example 37 was conducted using 2-(5-bromo-6-fluoro-indol-1-yl)ethanol instead of 1-(4-bromo-3-fluoro-phenyl)-2-methyl-propan-2-ol to give the title compound.

Example 171: Synthesis of 5'-((1R,2R,4S)-rel-2-amino-7-azabicyclo[2.2.1]heptane-7-carbonyl)-3-fluoro-2'-(6-fluoro-1-(2-hydroxy-2-methylpropyl)-1H-indol-5-yl)-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (2.3 g) obtained in step 1 of Example 41 and the 1-(5-bromo-6-fluoro-indol-1-yl)-2-methyl-propan-2-ol (2.02 g) obtained in step 1 of Example 136 were dissolved in 1,4-dioxane (18.1 mL). At room temperature, Pd(dba)$_2$ (250 mg), X-phos (414 mg), and tripotassium phosphate (3.46 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (40.0 mL). At 0° C., 12 N hydrochloric acid (30.0 mL) was added thereto, followed by stirring at room temperature for 2 hours. Then, MTBE was added thereto, the mixture was washed with water and dried over anhydrous sodium sulfate, and the solvent was distilled off to give 3-(4-cyano-3-fluoro-phenyl)-4-[6-fluoro-1-(2-hydroxy-2-methyl-propyl)indol-5-yl]benzoic acid.

Step 2

The 3-(4-cyano-3-fluoro-phenyl)-4-[6-fluoro-1-(2-hydroxy-2-methyl-propyl)indol-5-yl]benzoic acid (8 mg) obtained in step 1 above and the N-((1R,2R,4S)-rel-7-azabicyclo[2.2.1]heptan-2-yl)-2,4-dinitrobenzenesulfonamide-isomer-B hydrochloride (7.47 mg) obtained in step 3 of Example 155 were dissolved in THF (0.30 mL). At room temperature, TEA (0.00748 mL) and HATU (13.6 mg) were added thereto, followed by stirring at 50° C. for 1 hour. The reaction mixture was vacuum-concentrated, and the residue was purified by silica gel column chromatography (mobile phase: hexane/ethyl acetate) to give N-[(1S,3R,4R)-rel-7-[3-(4-cyano-3-fluoro-phenyl)-4-[6-fluoro-1-(2-hydroxy-2-methyl-propyl)indol-5-yl]benzoyl]-7-azabicyclo[2.2.1]heptan-3-yl]-2,4-dinitrobenzenesulfonamide-isomer-B.

Step 3

The N-[(1S,3R,4R)-rel-7-[3-(4-cyano-3-fluoro-phenyl)-4-[6-fluoro-1-(2-hydroxy-2-methyl-propyl)indol-5-yl]benzoyl]-7-azabicyclo[2.2.1]heptan-3-yl]-2,4-dinitrobenzenesulfonamide-isomer-B (13.8 mg) obtained in step 2 above was dissolved in DCM (1.0 mL). At 0° C., mercaptoacetic acid (2.49 µL) and TEA (7.48 µL) were added thereto, followed by stirring at room temperature for 1 hour. Chloroform and 4 N sodium hydroxide were added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 172: Synthesis of (S)-5T-(3-aminopyrrolidine-1-carbonyl)-2'-(6,7-difluoro-1-(2-hydroxy-2-methylpropyl)-1H-indol-5-yl)-3-fluoro-[1,1'-biphenyl]-4-carbonitrile Step 1

5-Bromo-6,7-difluoro-1H-indole (300 mg) was dissolved in DMF (4.31 mL). At room temperature, Cs$_2$CO$_3$ (843 mg) and 2,2-dimethyloxirane (0.230 mL) were added thereto, followed by stirring at 80° C. for 3 hours. The reaction mixture was filtrated, and the solvent was distilled off. Ethyl acetate was added thereto, the mixture was washed sequentially with a saturated aqueous ammonium chloride solution, water, and saturated brine, and dried over anhydrous sodium sulfate, and the solvent was distilled off. The residue was purified by silica gel column chromatography (mobile phase: hexane/ethyl acetate) to give 1-(5-bromo-6,7-difluoro-indol-1-yl)-2-methyl-propan-2-ol.

Step 2

The tert-butyl 3-(4-cyano-3-fluoro-phenyl)-4-(4,4,5,5-tetramethyl-1,3,2-dioxaborolan-2-yl)benzoate (210 mg) obtained in step 1 of Example 41 and the 1-(5-bromo-6,7-difluoro-indol-1-yl)-2-methyl-propan-2-ol (196 mg) obtained in step 1 above were dissolved in 1,4-dioxane (1.65 mL). At room temperature, Pd(dba)$_2$ (22.8 mg), X-phos (37.8 mg), and tripotassium phosphate (316 mg) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (2.63 mL). At 0° C., 12 N hydrochloric acid (2.1 mL) was added thereto, followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-[6,7-difluoro-1-(2-hydroxy-2-methyl-propyl)indol-5-yl]benzoic acid.

Step 3

The 3-(4-cyano-3-fluoro-phenyl)-4-[6,7-difluoro-1-(2-hydroxy-2-methyl-propyl)indol-5-yl]benzoic acid (30 mg) obtained in step 2 above and tert-butyl N-[(3S)-pyrrolidin-3-yl]carbamate (13.2 mg) were dissolved in THF (0.323 mL). At room temperature, TEA (0.027 mL) and HATU (49.1 mg) were added thereto, followed by stirring at 50° C. for 1 hour. The solvent was distilled off under reduced pressure. The residue was purified by silica gel column chromatography (mobile phase: hexane/ethyl acetate) to give tert-butyl N-[(3S)-1-[3-(4-cyano-3-fluoro-phenyl)-4-[6,7-difluoro-1-(2-hydroxy-2-methyl-propyl)indol-5-yl]benzoyl]pyrrolidin-3-yl]carbamate.

Step 4

The tert-butyl N-[(3S)-1-[3-(4-cyano-3-fluoro-phenyl)-4-[6,7-difluoro-1-(2-hydroxy-2-methyl-propyl)indol-5-yl]benzoyl]pyrrolidin-3-yl]carbamate (40 mg) obtained in step 3 above was dissolved in MeOH (0.80 mL). At room temperature, a 4 N hydrochloric acid-1,4-dioxane solution (0.80 mL) was added thereto, followed by stirring at room temperature for 1 hour. Chloroform and a 2 N aqueous sodium hydroxide solution (1.6 mL) were added thereto, the mixture was washed with water and dried over anhydrous sodium sulfate, and the solvent was distilled off. The residue was purified by reversed-phase HPLC (mobile phase: water/acetonitrile) to give the title compound.

Example 173: Synthesis of 5'-(7-amino-2-azabicyclo[2.2.1]heptane-2-carbonyl)-3-fluoro-2'-(6-fluoro-1-(2-hydroxy-2-methylpropyl)-1H-indol-5-yl)-[1,1'-biphenyl]-4-carbonitrile The 3-(4-cyano-3-fluoro-phenyl)-4-[6-fluoro-1-(2-hydroxy-2-methyl-propyl)indol-5-yl]benzoic acid (8 mg) obtained in step 1 of Example 171 was dissolved in THF (0.3 mL). At room temperature, tert-butyl N-(3-azabicyclo[2.2.1]heptan-7-yl)carbamate (3.80 mg), TEA (0.0075 mL), and HATU (13.6 mg) were added thereto, followed by stirring at 50° C. for 3 hours. After the completion of the reaction was confirmed by LCMS, the reaction mixture was concentrated. TFA (0.20 mL) was added to the residue, followed by stirring at room temperature for 5 minutes. After the completion of the reaction was confirmed by LCMS, DMSO (0.8 mL) was added to the reaction mixture, and purification was performed by reversed-phase HPLC (mobile phase: water/acetonitrile) to give the title compound.

Example 174: Synthesis of 5'-(7-amino-2-azabicyclo[2.2.1]heptane-2-carbonyl)-2",3-difluoro-4"-(2-hydroxy-2-methylpropyl)-[1,1':2',1"-terphenyl]-4-carbonitrile Step 1

The 3-(4-cyano-3-fluoro-phenyl)-4-[2-fluoro-4-(2-hydroxy-2-methyl-propyl)phenyl]benzoic acid (100 mg) obtained in step 2 of Example 166 was dissolved in THF (0.982 mL). At room temperature, tert-butyl N-(3-azabicyclo[2.2.1]heptane-7-yl)carbamate (52.1 mg), TEA (0.103 mL), and HATU (187 mg) were added thereto, followed by stirring at 50° C. for 3 hours. The residue was purified by silica gel column chromatography (mobile phase: hexane/ethyl acetate) to give tert-butyl N-[3-[3-(4-cyano-3-fluoro-phenyl)-4-[2-fluoro-4-(2-hydroxy-2-methyl-propyl)phenyl]benzoyl]-3-azabicyclo[2.2.1]heptan-7-yl]carbamate.

Step 2

The tert-butyl N-[3-[3-(4-cyano-3-fluoro-phenyl)-4-[2-fluoro-4-(2-hydroxy-2-methyl-propyl)phenyl]benzoyl]-3-azabicyclo[2.2.1]heptan-7-yl]carbamate (30 mg) obtained in step 1 above was dissolved in MeOH (0.5 mL). At room temperature, 12 N hydrochloric acid (0.5 mL) was added thereto. After the mixture was stirred at room temperature for 0.5 hour, water and a 2 N aqueous sodium hydroxide solution (3.0 mL) were added thereto. The mixture was extracted with chloroform, and the solvent was distilled off. The residue was purified by reversed-phase HPLC (mobile phase: water/acetonitrile) to give the title compound.

Example 175: Synthesis of 5'-((1S,2S,4R)-rel-2-amino-7-azabicyclo[2.2.1]heptane-7-carbonyl)-2'-(6,7-difluoro-1-methyl-1H-benzo[d][1,2,3]triazol-5-yl)-3-fluoro-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (90 mg) obtained in step 1 of Example 41 and 5-bromo-6,7-difluoro-1-methyl-benzotriazole (68.6 mg) were dissolved in 1,4-dioxane (0.71 mL). At room temperature, Pd(dba)$_2$ (9.8 mg), X-phos (16 mg), and tripotassium phosphate (135 mg) were added thereto, followed by stirring at 100° C. overnight. The solvent was distilled off, the residue was purified by silica gel column chromatography (mobile phase: hexane/ethyl acetate), and the solvent was distilled off. The residue was dissolved in TFA (1.0 mL), followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-(6,7-difluoro-1-methyl-benzotriazol-5-yl)benzoic acid.

Step 2

The 3-(4-cyano-3-fluoro-phenyl)-4-(6,7-difluoro-1-methyl-benzotriazol-5-yl)benzoic acid (30 mg) obtained in step 1 above and the N-((1R,2R,4S)-rel-7-azabicyclo[2.2.1]heptan-2-yl)-2,4-dinitrobenzenesulfonamide-isomer-B hydrochloride (30.6 mg) obtained in step 3 of Example 155 were dissolved in THF (0.367 mL). At room temperature, TEA (0.042 mL) and HATU (55.9 mg) were added thereto, followed by stirring at 50° C. for 1 hour. The reaction mixture was vacuum-concentrated, and the residue was purified by silica gel column chromatography (mobile phase: hexane/ethyl acetate) to give N-[(1R,3S,4S)-rel-7-[3-(4-cyano-3-fluoro-phenyl)-4-(6,7-difluoro-1-methyl-benzotriazol-5-yl)benzoyl]-7-azabicyclo[2.2.1]heptan-3-yl]-2,4-dinitrobenzenesulfonamide-isomer-B.

Step 3

The N-[(1R,3S,4S)-rel-7-[3-(4-cyano-3-fluoro-phenyl)-4-(6,7-difluoro-1-methyl-benzotriazol-5-yl)benzoyl]-7-azabicyclo[2.2.1]heptan-3-yl]-2,4-dinitrobenzenesulfonamide-isomer-B (51 mg) obtained in step 2 above was dissolved in DCM (0.70 mL). At 0° C., mercaptoacetic acid (5.8 µL) and TEA (29.1 µL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 176: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (2.3 g) obtained in step 1 of Example 41 and the 1-(5-bromo-6-fluoro-1H-indazol-1-yl)-2-methylpropan-2-ol (2.03 g) obtained in step 1 of Example 142 were dissolved in 1,4-dioxane (18.7 mL). At room temperature, Pd(dba)$_2$ (250 mg), X-phos (414 mg), and tripotassium phosphate (3.46 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (10.0 mL). At 0° C., 12 N hydrochloric acid (10.0 mL) was added thereto, followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-[6-fluoro-1-(2-hydroxy-2-methyl-propyl)indazol-5-yl]benzoic acid.

Step 2

The 3-(4-cyano-3-fluoro-phenyl)-4-[6-fluoro-1-(2-hydroxy-2-methyl-propyl)indazol-5-yl]benzoic acid (30 mg) obtained in step 1 above and the N-((1R,2R,4S)-rel-7-azabicyclo[2.2.1]heptan-2-yl)-2,4-dinitrobenzenesulfonamide-isomer-B hydrochloride (27.9 mg) obtained in step 3 of Example 155 were dissolved in THF (0.34 mL). At room temperature, TEA (0.038 mL) and HATU (51.0 mg) were added thereto, followed by stirring at 50° C. for 1 hour. The reaction mixture was vacuum-concentrated, and the residue was purified by silica gel column chromatography (mobile phase: hexane/ethyl acetate) to give N-[(1S,3R,4R)-rel-7-[3-(4-cyano-3-fluoro-phenyl)-4-[6-fluoro-1-(2-hydroxy-2-methyl-propyl)indazol-5-yl]benzoyl]-7-azabicyclo[2.2.1]heptan-3-yl]-2,4-dinitrobenzenesulfonamide-isomer-B.

Step 3

The N-[(1S,3R,4R)-rel-7-[3-(4-cyano-3-fluoro-phenyl)-4-[6-fluoro-1-(2-hydroxy-2-methyl-propyl)indazol-5-yl]benzoyl]-7-azabicyclo[2.2.1]heptan-3-yl]-2,4-dinitrobenzenesulfonamide-isomer-B (45 mg) obtained in step 2 above was dissolved in DCM (0.58 mL). At 0° C., mercaptoacetic acid (4.9 μL) and TEA (24 μL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 177: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B Step 1

The tert-butyl 3-(4-cyano-3-fluoro-phenyl)-4-(4,4,5,5-tetramethyl-1, 3, 2-dioxaborolan-2-yl)benzoate (3.2 g) obtained in step 1 of Example 41 and the 1-(5-bromo-6,7-difluoro-benzotriazol-1-yl)-2-methyl-propan-2-ol (3.01 g) obtained in step 3 of Example 161 were dissolved in 1,4-dioxane (25.2 mL). At room temperature, Pd(dba)$_2$ (348 mg), X-phos (577 mg), and tripotassium phosphate (4.81 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (15.0 mL). At 0° C., 12 N hydrochloric acid (15.0 mL) was added thereto, followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-[6,7-difluoro-1-(2-hydroxy-2-methyl-propyl)benzotriazol-5-yl]benzoic acid.

Step 2

The 3-(4-cyano-3-fluoro-phenyl)-4-[6,7-difluoro-1-(2-hydroxy-2-methyl-propyl)benzotriazol-5-yl]benzoic acid (30 mg) obtained in step 1 above and the N-((1S,2S,4R)-rel-7-azabicyclo[2.2.1]heptan-2-yl)-2,4-dinitrobenzenesulfonamide-isomer-B hydrochloride (26.8 mg) obtained in step 3 of Example 155 were dissolved in THF (0.33 mL). At room temperature, TEA (0.037 mL) and HATU (48.9 mg) were added thereto, followed by stirring at 50° C. for 1 hour. The reaction mixture was vacuum-concentrated, and the residue was purified by silica gel column chromatography (mobile phase: hexane/ethyl acetate) to give N-[(1S,2S,4R)-rel-7-[3-(4-cyano-3-fluoro-phenyl)-4-[6,7-difluoro-1-(2-hydroxy-2-methyl-propyl)benzotriazol-5-yl]benzoyl]-7-azabicyclo[2.2.1]heptan-3-yl]-2,4-dinitrobenzenesulfonamide-isomer-B.

Step 3

The N-[(1S,2S,4R)-rel-7-[3-(4-cyano-3-fluoro-phenyl)-4-[6,7-difluoro-1-(2-hydroxy-2-methyl-propyl)benzotriazol-5-yl]benzoyl]-7-azabicyclo[2.2.1]heptan-3-yl]-2,4-dinitrobenzenesulfonamide-isomer-B (43 mg) obtained in step 2 above was dissolved in DCM (0.54 mL). At 0° C., mercaptoacetic acid (4.5 μL) and TEA (22.7 IL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 178: Synthesis of 5'-((3-endo)-3-amino-8-azabicyclo[3.2.1]octane-8-carbonyl)-2'-(3-bromo-6-fluoro-1-(2-hydroxy-2-methylpropyl)-1H-indazol-5-yl)-3-fluoro-[1,1'-biphenyl]-4-carbonitrile Step 1

The procedure of steps 1 to 4 in Example 41 was conducted using the 1-(5-bromo-6-fluoro-indazol-1-yl)-2-methyl-propan-2-ol obtained in step 1 of Example 142 instead of 1-(4-bromo-3-fluoro-phenyl)-2-methyl-propan-2-ol to give tert-butyl N-((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate.

Step 2

The tert-butyl N-((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate (10 mg) obtained in step 1 above was dissolved in DMF (0.076 mL). NBS (3.5 mg) was added thereto, followed by stirring at 80° C. overnight. The reaction mixture was diluted with DMSO to 1 mL, and purification was performed by reversed-phase HPLC (mobile phase: water/acetonitrile) to give the title compound.

Example 179: Synthesis of 5'-((3-endo)-3-amino-8-azabicyclo[3.2.1]octane-8-carbonyl)-3-fluoro-2'-(5-fluoro-3-methylbenzo[d]isoxazol-6-yl)-[1,1'-biphenyl]-4-carbonitrile Step 1

3-Bromo-4-fluorophenol (5 g) was dissolved in dichloromethane (114 mL). At 0° C., TEA (5.5 mL) was added thereto, and acetyl chloride (2.8 mL) was added thereto dropwise. The reaction mixture was stirred at 20° C. for 30 minutes and diluted with dichloromethane (100 mL). The resulting product was washed with 0.5 N hydrochloric acid, a saturated aqueous sodium hydrogen carbonate solution, and saturated brine, and the solvent was distilled off to give 3-bromo-4-fluorophenyl acetate.

Step 2

A boron trifluoride-acetic acid complex (53 mL) was added to the 3-bromo-4-fluorophenyl acetate (6.2 g) obtained in step 1 above, followed by stirring at 155° C. for 14 hours. The reaction mixture was cooled to 0° C., and ice was added thereto. The precipitate was collected by filtration, washed with water at 0° C., and dried. The obtained solid was purified by silica gel column chromatography (mobile phase: hexane/ethyl acetate) to give 1-(4-bromo-5-fluoro-2-hydroxyphenyl)ethanone.

Step 3

MeOH (30 mL) was added to the 1-(4-bromo-5-fluoro-2-hydroxyphenyl)ethanone (2.16 g) obtained in step 2 above, hydroxylamine hydrochloride (1.29 g), and sodium acetate (1.14 g), followed by stirring at 60° C. for 1 hour. Ice water was added to the reaction mixture, and the precipitate was collected by filtration, washed with water, and dried. The obtained solid was dissolved in THF (31 mL), and TEA (1.68 mL) and N,N'-carbonyldiimidazole (1.65 g) were added thereto, followed by stirring at 70° C. for 1 hour. The solvent was distilled off, and the residue was purified by silica gel column chromatography (mobile phase: chloroform/ethyl acetate) to give 6-bromo-5-fluoro-3-methylbenzo[d]isoxazol.

Step 4

The procedure of steps 1 to 5 in Example 41 was conducted using the 6-bromo-5-fluoro-3-methylbenzo[d]

isoxazol obtained in step 3 above instead of 1-(4-bromo-3-fluoro-phenyl)-2-methyl-propan-2-ol to give the title compound.

Example 180: Synthesis of (S)-5'-(3-aminopyrrolidine-1-carbonyl)-3-fluoro-2'-(5-fluoro-3-methylbenzo[d]isoxazol-6-yl)-[1,1'-biphenyl]-4-carbonitrile The procedure of steps 1 to 3 in Example 37 was conducted using the 6-bromo-5-fluoro-3-methylbenzo[d]isoxazol obtained in step 3 of Example 179 instead of 1-(4-bromo-3-fluoro-phenyl)-2-methyl-propan-2-ol to give the title compound.

Example 181: Synthesis of 5'-((3-endo)-3-amino-8-azabicyclo[3.2.1]octane-8-carbonyl)-3-fluoro-2'-(6-fluoro-1-(2-hydroxy-2-methylpropyl)-3-methyl-1H-indazol-5-yl)-[1,1'-biphenyl]-4-carbonitrile Step 1
The tert-butyl N-((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate (69 mg) obtained in step 1 of Example 178 was dissolved in DMF (0.53 mL), and NBS (38 mg) was added thereto, followed by stirring at 80° C. overnight. The mixture was cooled to room temperature, and Boc₂O (200 mg) and DMAP (1 mg) were added thereto, followed by stirring at room temperature for 2 hours. Ethyl acetate was added thereto, and the resulting mixture was washed sequentially with water and saturated brine. After the organic layer was dried over anhydrous sodium sulfate, the solvent was distilled off. The solvent was distilled off, and the residue was purified by silica gel column chromatography (mobile phase: hexane/ethyl acetate) to give tert-butyl ((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate.
Step 2
The tert-butyl ((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate (15 mg) obtained in step 1 above, trimethylboroxine (7.7 mg), PdCl₂(dppf)CH₂Cl₂ (1 mg), and cesium carbonate (20 mg) were suspended in 1,4-dioxane, followed by stirring at 125° C. for 30 minutes under microwave irradiation. The solvent was distilled off, and trifluoroacetic acid (0.2 mL) was added to the residue, followed by stirring at room temperature for 10 minutes. The reaction mixture was diluted with DMSO to 1 mL, and purification was performed by reversed-phase HPLC (mobile phase: water/acetonitrile) to give the title compound.

Example 182: Synthesis of 5'-((1R,2S,4S)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile Step 1
tert-Butyl (1S,3S,4R)-rel-3-amino-7-azabicyclo[2.2.1]heptane-7-carboxylate (919 mg) was dissolved in THF (14.4 mL). At 0° C., TEA (1.81 mL) and 2,4-dinitrobenzenesulfonyl chloride (1.73 g) were added thereto, followed by stirring at room temperature overnight. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give tert-butyl (1S,3S,4R)-rel-3-[(2,4-dinitrophenyl)sulfonylamino]-7-azabicyclo[2.2.1]heptane-7-carboxylate.
Step 2
The tert-butyl (1S,3S,4R)-rel-3-[(2,4-dinitrophenyl)sulfonylamino]-7-azabicyclo[2.2.1]heptane-7-carboxylate (100 mg) obtained in step 1 above was dissolved in ethyl acetate (1.00 mL). At room temperature, a 4 N hydrochloric acid-ethyl acetate solution (2.00 mL) was added thereto, followed by stirring at room temperature for 1 hour. The reaction mixture was vacuum-concentrated to give N-[(1S,3S,4R)-rel-7-azabicyclo[2.2.1]heptan-3-yl]-2,4-dinitrobenzenesulfonamide hydrochloride.
Step 3
The 3-(4-cyano-3-fluoro-phenyl)-4-[2-fluoro-4-(2-hydroxy-2-methyl-propyl)phenyl]benzoic acid (30 mg) obtained in step 2 of Example 166 and the N-[(1S,3S,4R)-rel-7-azabicyclo[2.2.1]heptan-3-yl]-2,4-dinitrobenzenesulfonamide hydrochloride (30.7 mg) obtained in step 2 above were dissolved in THF (0.40 mL). At room temperature, TEA (0.0420 mL) and HATU (56.0 mg) were added thereto, followed by stirring at 50° C. for 1 hour. The reaction mixture was vacuum-concentrated, and the residue was purified by silica gel column chromatography (mobile phase: hexane/ethyl acetate) to give N-[(1S,3S,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide.
Step 4
The N-[(1S,3S,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide (55 mg) obtained in step 3 above was dissolved in DCM (0.752 mL). At 0° C., mercaptoacetic acid (6.27 µL) and TEA (31.4 µL) were added thereto, followed by stirring at room temperature for 2 hours. Chloroform was added thereto, the mixture was washed with a 4 N aqueous sodium hydroxide solution, and dried over anhydrous sodium sulfate, and the solvent was distilled off. The residue was purified by reversed-phase HPLC (mobile phase: water/acetonitrile) to give the title compound.

Example 183: Synthesis of 5'-((3-endo)-3-amino-8-azabicyclo[3.2.1]octane-8-carbonyl)-2'-(6,7-difluoro-1-(2-hydroxy-2-methylpropyl)-1H-indol-5-yl)-3-fluoro-[1,1'-biphenyl]-4-carbonitrile Step 1
The 3-(4-cyano-3-fluoro-phenyl)-4-[6,7-difluoro-1-(2-hydroxy-2-methyl-propyl)indol-5-yl]benzoic acid (30 mg) obtained in step 2 of Example 172 and tert-butyl N-[(3-endo)-8-azabicyclo[3.2.1]octan-3-yl]carbamate (16.1 mg) were dissolved in THF (0.323 mL). At room temperature, TEA (0.027 mL) and HATU (49.1 mg) were added thereto, followed by stirring at 50° C. for 1 hour. The solvent was distilled off under reduced pressure. The residue was purified by silica gel column chromatography (mobile phase: hexane/ethyl acetate) to give tert-butyl N-[(3-endo)-8-[3-(4-cyano-3-fluoro-phenyl)-4-[6,7-difluoro-1-(2-hydroxy-2-methyl-propyl)indol-5-yl]benzoyl]-8-azabicyclo[3.2.1]octan-3-yl]carbamate.
Step 2
The tert-butyl N-[(3-endo)-8-[3-(4-cyano-3-fluoro-phenyl)-4-[6,7-difluoro-1-(2-hydroxy-2-methyl-propyl)indol-5-yl]benzoyl]-8-azabicyclo[3.2.1]octan-3-yl]carbamate (42 mg) obtained in step 1 above was dissolved in MeOH (0.84 mL). At room temperature, a 4 N hydrochloric acid-1,4-dioxane solution (0.84 mL) was added thereto, followed by stirring at room temperature for 1 hour. Chloroform and a 2 N aqueous sodium hydroxide solution (1.68 mL) were added thereto, the mixture was washed with water and dried over anhydrous sodium sulfate, and the solvent was distilled off. The residue was purified by reversed-phase HPLC (mobile phase: water/acetonitrile) to give the title compound.

Example 184: Synthesis of 5'-((1R,2S,4S)-rel-2-amino-7-azabicyclo[2.2.1]heptane-7-carbonyl)-3-fluoro-2'-(6-fluoro-1-(2-hydroxy-2-methylpropyl)-1H-indol-5-yl)-[1,1'-biphenyl]-4-carbonitrile The procedure of steps 1 to 3 in Example 171 was conducted using the N-[(1R,2S,4S)-rel-7-azabicyclo[2.2.1]heptan-3-yl]-2,4-dinitrobenzenesulfonamide hydrochloride obtained in step 2 of Example 182 instead of N-((1R,2R,4S)-rel-7-azabicyclo[2.2.1]heptan-2-yl)-2,4-dinitrobenzenesulfonamide-isomer-B hydrochloride to give the title compound.

Example 185: Synthesis of 5'-((1S,2S,4R)-rel-2-amino-7-azabicyclo[2.2.1]heptane-7-carbonyl)-2'-(6,7-difluoro-1-methyl-1H-benzo[d][1,2,3]triazol-5-yl)-3-fluoro-[1,1'-biphenyl]-4-carbonitrile The procedure of steps 3 to 4 in Example 172 was conducted using the 3-(4-cyano-3-fluoro-phenyl)-4-(6,7-difluoro-1-methyl-benzotriazol-5-yl)benzoic acid obtained in step 1 of Example 175 instead of 3-(4-cyano-3-fluoro-phenyl)-4-[6,7-difluoro-1-(2-hydroxy-2-methyl-propyl)indol-5-yl]benzoic acid, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 186: Synthesis of 5'-((3-endo)-3-amino-8-azabicyclo[3.2.1]octane-8-carbonyl)-3-fluoro-2'-(6-fluoro-1-(2-hydroxy-2-methylpropyl)-7-methoxy-1H-indazol-5-yl)-[1,1'-biphenyl]-4-carbonitrile Step 1
5-Bromo-2,3,4-trifluoro-benzaldehyde (480 mg) was dissolved in 1,2-dimethoxyethane (4.8 mL). At room temperature, hydrazine monohydrate (7.68 mL) was added thereto, followed by stirring at 80° C. for 5 hours. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 5-bromo-6,7-difluoro-1H-indazole.
Step 2
The 5-bromo-6,7-difluoro-1H-indazole (97 mg) obtained in step 1 above was dissolved in DMF (1.38 mL). At room temperature, methanol (0.1 mL), cesium carbonate (271 mg), and 2,2-dimethyloxirane (0.074 mL) were added thereto, followed by stirring at 80° C. for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(5-bromo-6-fluoro-7-methoxy-indazol-1-yl)-2-methyl-propan-2-ol.

Step 3
The tert-butyl 3-(4-cyano-3-fluoro-phenyl)-4-(4,4,5,5-tetramethyl-1, 3, 2-dioxaborolan-2-yl)benzoate (45.0 mg) obtained in step 1 of Example 41 and the 1-(5-bromo-6-fluoro-7-methoxy-indazol-1-yl)-2-methyl-propan-2-ol (43.8 mg) obtained in step 2 above were dissolved in 1,4-dioxane (0.50 mL). At room temperature, Pd(dba)$_2$ (4.89 mg), X-phos (8.11 mg), and tripotassium phosphate (67.7 mg) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (0.45 mL). At 0° C., 12 N hydrochloric acid (0.56 mL) was added thereto, followed by stirring at room temperature for 2 hours. MTBE was added thereto, and the mixture was washed with water and dried over anhydrous sodium sulfate. Thereafter, the solvent was distilled off to give 3-(4-cyano-3-fluoro-phenyl)-4-[6-fluoro-1-(2-hydroxy-2-methyl-propyl)-7-methoxy-indazol-5-yl]benzoic acid.
Step 4
The procedure of steps 3 to 4 in Example 172 was conducted using the 3-(4-cyano-3-fluoro-phenyl)-4-[6-fluoro-1-(2-hydroxy-2-methyl-propyl)-7-methoxy-indazol-5-yl]benzoic acid obtained in step 3 above instead of 3-(4-cyano-3-fluoro-phenyl)-4-[6,7-difluoro-1-(2-hydroxy-2-methyl-propyl)indol-5-yl]benzoic acid, and using tert-butyl ((3-endo)-8-azabicyclo[3.2.1]octan-3-yl)carbamate instead of tert-butyl N-[(3S)-pyrrolidin-3-yl]carbamate to give the title compound.

Example 187: Synthesis of (S)-5'-(3-aminopyrrolidine-1-carbonyl)-2'-(6,7-difluoro-1-(2-hydroxy-2-methylpropyl)-1H-indazol-5-yl)-3-fluoro-[1,1'-biphenyl]-4-carbonitrile Step 1
The 5-bromo-6,7-difluoro-1H-indazole (101 mg) obtained in step 1 of Example 186 was dissolved in DMF (1.44 mL). At room temperature, cesium carbonate (283 mg) and 2,2-dimethyloxirane (0.077 mL) were added thereto, followed by stirring at 80° C. overnight. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(5-bromo-6,7-difluoro-indazol-1-yl)-2-methyl-propan-2-ol.
Step 2
The procedure of steps 2 to 4 in Example 172 was conducted using the 1-(5-bromo-6,7-difluoro-indazol-1-yl)-2-methyl-propan-2-ol obtained in step 1 above instead of 1-(5-bromo-6,7-difluoro-indol-1-yl)-2-methyl-propan-2-ol to give the title compound.

Example 188: Synthesis of 5'-((3-endo)-3-amino-8-azabicyclo[3.2.1]octane-8-carbonyl)-2'-(6,7-difluoro-1-(2-hydroxy-2-methylpropyl)-1H-indazol-5-yl)-3-fluoro-[1,1'-biphenyl]-4-carbonitrile The procedure of steps 2 to 4 in Example 172 was conducted using the 1-(5-bromo-6,7-difluoro-indazol-1-yl)-2-methyl-propan-2-ol obtained in step 1 of Example 187 instead of 1-(5-bromo-6,7-difluoro-indol-1-yl)-2-methyl-propan-2-ol, and using tert-butyl ((3-endo)-8-azabicyclo[3.2.1]octan-3-yl)carbamate instead of tert-butyl N-[(3S)-pyrrolidin-3-yl]carbamate to give the title compound.

Example 189: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile The procedure of steps 2 to 4 in Example 172 was conducted using the 1-(5-bromo-6-fluoro-indazol-1-yl)-2-methyl-propan-2-ol obtained in step 1 of Example 142 instead of 1-(5-bromo-6,7-difluoro-indol-1-yl)-2-methyl-propan-2-ol, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 190: Synthesis of (S)-5'-(3-amino-3-methylpyrrolidine-1-carbonyl)-3-fluoro-2'-(6-fluoro-1-(2-hydroxy-2-methylpropyl)-1H-indol-5-yl)-[1,1'-biphenyl]-4-carbonitrile The procedure of steps 2 to 4 in Example 172 was conducted using the 1-(5-bromo-6-fluoro-indol-1-yl)-2-methyl-propan-2-ol obtained in step 1 of Example 136 instead of 1-(5-bromo-6,7-difluoro-indol-1-yl)-2-methyl-propan-2-ol, and using tert-butyl (S)-(3-methylpyrrolidin-3-yl)carbamate instead of tert-butyl N-[(3S)-pyrrolidin-3-yl]carbamate to give the title compound.

Example 191: Synthesis of (S)-5'-(3-amino-3-methylpyrrolidine-1-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile The procedure of steps 3 to 4 in Example 172 was conducted using the 3-(4-cyano-3-fluoro-phenyl)-4-[6,7-difluoro-1-(2-hydroxy-2-methyl-propyl)benzotriazol-5-yl]benzoic acid obtained in step 1 of Example 177 instead of 3-(4-cyano-3-fluoro-phenyl)-4-[6,7-difluoro-1-(2-hydroxy-2-methyl-propyl)indol-5-yl]benzoic acid, and using tert-butyl (S)-(3-methylpyrrolidin-3-yl)carbamate instead of tert-butyl N-[(3S)-pyrrolidin-3-yl]carbamate to give the title compound.

Example 192: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile The procedure of steps 3 to 4 in Example 172 was conducted using the 3-(4-cyano-3-fluoro-phenyl)-4-[6,7-difluoro-1-(2-hydroxy-2-methyl-propyl)benzotriazol-5-yl]benzoic acid obtained in step 1 of Example 177 instead of 3-(4-cyano-3-fluoro-phenyl)-4-[6,7-difluoro-1-(2-hydroxy-2-methyl-propyl)indol-5-yl]benzoic acid, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 193: Synthesis of 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile The procedure of steps 3 to 4 in Example 172 was conducted using the 3-(4-cyano-3-fluoro-phenyl)-4-[2-fluoro-4-(2-hydroxy-2-methyl-propyl)phenyl]benzoic acid obtained in step 2 of Example 166 instead of 3-(4-cyano-3-fluoro-phenyl)-4-[6,7-difluoro-1-(2-hydroxy-2-methyl-propyl)indol-5-yl]benzoic acid, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 194: Synthesis of 5'-((3-endo)-3-amino-8-azabicyclo[3.2.1]octane-8-carbonyl)-3-fluoro-2'-(6-fluoro-1-(3-hydroxy-3-methylbutyl)-1H-indazol-5-yl)-[1,1'-biphenyl]-4-carbonitrile Step 1
5-Bromo-6-fluoro-1H-indazole (200 mg) was dissolved in DMF (3.1 mL). At room temperature, cesium carbonate (606 mg), and 3-hydroxy-3-methyl-butyl ester of 4-methylbenzene sulfonic acid (481 mg) were added thereto, followed by stirring at 90° C. for 16 hours. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 4-(5-bromo-6-fluoro-indazol-1-yl)-2-methyl-butan-2-ol.
Step 2
The procedure of steps 2 to 4 in Example 172 was conducted using the 4-(5-bromo-6-fluoro-indazol-1-yl)-2-methyl-butan-2-ol obtained in step 1 above instead of 1-(5-bromo-6,7-difluoro-indol-1-yl)-2-methyl-propan-2-ol, and using tert-butyl ((3-endo)-8-azabicyclo[3.2.1]octan-3-yl)carbamate instead of tert-butyl N-[(3S)-pyrrolidin-3-yl]carbamate to give the title compound.

Example 195: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-indazol-5-yl)-3-fluoro-[1,1'-biphenyl]-4-carbonitrile The procedure of steps 2 to 4 in Example 172 was conducted using the 1-(5-bromo-6,7-difluoro-indazol-1-yl)-2-methyl-propan-2-ol obtained in step 1 of Example 187 instead of 1-(5-bromo-6,7-difluoro-indol-1-yl)-2-methyl-propan-2-ol, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 196: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-indol-5-yl)-3-fluoro-[1,1'-biphenyl]-4-carbonitrile The procedure of steps 1 to 4 in Example 172 was conducted using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 197: Synthesis of (S)-5'-(3-amino-3-methylpyrrolidine-1-carbonyl)-2'-(6,7-difluoro-1-(2-hydroxy-2-methylpropyl)-1H-indazol-5-yl)-3-fluoro-[1,1'-biphenyl]-4-carbonitrile The procedure of steps 2 to 4 in Example 172 was conducted using the 1-(5-bromo-6,7-difluoro-indazol-1-yl)-2-methyl-propan-2-ol obtained in step 1 of Example 187 instead of 1-(5-bromo-6,7-difluoro-indol-1-yl)-2-methyl-propan-2-ol, and using tert-butyl (S)-(3-methylpyrrolidin-3- yl)carbamate instead of tert-butyl N-[(3S)-pyrrolidin-3-yl]carbamate to give the title compound.

Example 198: Synthesis of (S)-5'-(3-amino-3-methylpyrrolidine-1-carbonyl)-2'-(6,7-difluoro-1-(2-hydroxy-2-methylpropyl)-1H-indol-5-yl)-3-fluoro-[1,1'-biphenyl]-4-carbonitrile The procedure of steps 1 to 4 in Example 172 was conducted using tert-butyl (S)-(3-methylpyrrolidin-3-yl)carbamate instead of tert-butyl N-[(3S)-pyrrolidin-3-yl]carbamate to give the title compound.

Example 199: Synthesis of 3-fluoro-2'-(6-fluoro-1-(2-hydroxy-2-methylpropyl)-1H-indazol-5-yl)-5'-(2,7-diazaspiro[3.4]octane-6-carbonyl)-[1,1'-biphenyl]-4-carbonitrile The procedure of steps 2 to 4 in Example 172 was conducted using the 1-(5-bromo-6-fluoro-indazol-1-yl)-2-methyl-propan-2-ol obtained in step 1 of Example 142 instead of 1-(5-bromo-6,7-difluoro-indol-1-yl)-2-methyl-propan-2-ol, and using tert-butyl 2,7-diazaspiro[3.4]octane-2-carboxylate instead of tert-butyl N-[(3S)-pyrrolidin-3-yl]carbamate to give the title compound.

Example 200: Synthesis of 2'-(6,7-difluoro-1-(2-hydroxy-2-methylpropyl)-1H-indol-5-yl)-3-fluoro-5'-(2,7-diazaspiro[3.4]octane-6-carbonyl)-[1,1'-biphenyl]-4-carbonitrile The procedure of steps 1 to 4 in Example 172 was conducted using tert-butyl 2,7-diazaspiro[3.4]octane-2-carboxylate instead of tert-butyl N-[(3S)-pyrrolidin-3-yl]carbamate to give the title compound.

Example 201: Synthesis of 2'-(6,7-difluoro-1-(2-hydroxy-2-methylpropyl)-1H-indol-5-yl)-3-fluoro-5'-(2,8-diazaspiro[3.5]nonane-2-carbonyl)-[1,1'-biphenyl]-4-carbonitrile The procedure of steps 1 to 4 in Example 172 was conducted using tert-butyl 2,8-diazaspiro[3.5]nonane-6-carboxylate instead of tert-butyl N-[(3S)-pyrrolidin-3-yl]carbamate to give the title compound.

Example 202: Synthesis of 5'-((1S,2S,4R)-rel-2-amino-7-azabicyclo[2.2.1]heptane-7-carbonyl)-3-fluoro-2'-(5-fluoro-3-methylbenzo[d]isoxazol-6-yl)-[1,1'-biphenyl]-4-carbonitrile-isomer-X Step 1
tert-Butyl ((1S,2S,4R)-rel-7-azabicyclo[2.2.1]heptan-2-yl)carbamate hydrochloride (36 mg) was dissolved in DCM (2.89 mL). At room temperature, TEA (40 μL) and benzyl chloroformate (25 μL) were added thereto, followed by stirring at room temperature for 1 hour. The solvent was distilled off, and chloroform and water were added thereto. The mixture was extracted twice with chloroform and washed with water and saturated brine. The solvent was distilled off, and the residue was purified by silica gel column chromatography (mobile phase: hexane/ethyl acetate) to give benzyl (1S,2S,4R)-rel-2-((tert-butoxycarbonyl)amino)-7-azabicyclo[2.2.1]heptane-7-carboxylate.
The benzyl (1S,2S,4R)-rel-2-((tert-butoxycarbonyl)amino)-7-azabicyclo[2.2.1]heptane-7-carboxylate was obtained as a 10 mg/mL ethanol solution, and separation was performed under the following conditions.
The isomer having a shorter retention time was defined as "isomer-X," and the isomer having a longer retention time was defined as "isomer-Y."
Column: Daicel CHIRALPAK IC 2.0×25 cm
Mobile phase: hexane/2-propanol=85/15
Flow rate: 12.5 mL/min
Retention Time of Each Isomer:
benzyl (1S,2S,4R)-rel-2-((tert-butoxycarbonyl)amino)-7-azabicyclo[2.2.1]heptane-7-carboxylate-isomer-X: 16.93 minutes
benzyl (1S,2S,4R)-rel-2-((tert-butoxycarbonyl)amino)-7-azabicyclo[2.2.1]heptane-7-carboxylate-isomer-Y: 23.82 minutes.
Chiral Analysis Conditions:
Column: CHIRALPAK IC 4.6×150 mm
Mobile phase: hexane/2-propanol=85/15
Flow rate: 1.0 mL/min
Retention Time of Each Isomer:
benzyl (1S,2S,4R)-rel-2-((tert-butoxycarbonyl)amino)-7-azabicyclo[2.2.1]heptane-7-carboxylate-isomer-X: 6.972 minutes
benzyl (1S,2S,4R)-rel-2-((tert-butoxycarbonyl)amino)-7-azabicyclo[2.2.1]heptane-7-carboxylate-isomer-Y: 9.895 minutes.
Step 2
The benzyl (1S,2S,4R)-rel-2-((tert-butoxycarbonyl)amino)-7-azabicyclo[2.2.1]heptane-7-carboxylate-isomer-X (93 g) obtained in step 1 above and 10% Pd/C (10 g) were suspended in methanol (1.0 L). The mixture was stirred at room temperature for 5 hours under a hydrogen atmosphere (50 psi). The reaction mixture was filtrated, and the filtrate was concentrated to give tert-butyl ((1S,2S,4R)-rel-7-azabicyclo[2.2.1]heptan-2-yl)carbamate-isomer-X.
Step 3
The procedure of steps 2 to 4 in Example 172 was conducted using the 6-bromo-5-fluoro-3-methylbenzo[d]isoxazol obtained in step 3 of Example 179 instead of 1-(5-bromo-6,7-difluoro-indol-1-yl)-2-methyl-propan-2-ol, and using the tert-butyl ((1S,2S,4R)-rel-7-azabicyclo[2.2.1]heptan-2-yl)carbamate-isomer-X obtained in step 2 above instead of tert-butyl N-[(3S)-pyrrolidin-3-yl]carbamate to give the title compound.

Example 203: Synthesis of 2'-(6,7-difluoro-1-(2-hydroxy-2-methylpropyl)-1H-indol-5-yl)-3-fluoro-5'-(octahydropyrrolo[3,4-c]pyrrole-2-carbonyl)-[1,1'-biphenyl]-4-carbonitrile The procedure of steps 1 to 4 in Example 172 was conducted using tert-butyl hexahydropyrrolo[3,4-c]pyrrole-2(1H)-carboxylate instead of tert-butyl N-[(3S)-pyrrolidin-3-yl]carbamate to give the title compound.

Example 204: Synthesis of (S)-5'-(3-aminopyrrolidine-1-carbonyl)-2'-(1-(2-ethyl-2-hydroxybutyl)-6-fluoro-1H-indazol-5-yl)-3-fluoro-[1,1'-biphenyl]-4-carbonitrile Step 1
5-Bromo-6-fluoro-1H-indazole (300 mg) was dissolved in DMF (4.65 mL). At room temperature, cesium carbonate (90.9 mg) and 2,2-diethyloxirane (0.20 mL) were added thereto, followed by stirring at 90° C. for 16 hours. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 3-[(5-bromo-6-fluoro-indazol-1-yl)methyl]pentan-3-ol.
Step 2
The procedure of steps 2 to 4 in Example 172 was conducted using the 3-[(5-bromo-6-fluoro-indazol-1-yl)methyl]pentan-3-ol obtained in step 1 above instead of 1-(5-bromo-6,7-difluoro-indol-1-yl)-2-methyl-propan-2-ol to give the title compound.

Example 205: Synthesis of 5'-((3-endo)-3-amino-8-azabicyclo[3.2.1]octane-8-carbonyl)-2'-(1-(2-ethyl-2-hydroxybutyl)-6-fluoro-1H-indazol-5-yl)-3-fluoro-[1,1'-biphenyl]-4-carbonitrile The procedure of steps 2 to 4 in Example 172 was conducted using the 3-[(5-bromo-6-fluoro-indazol-1-yl)methyl]pentan-3-ol obtained in step 1 of Example 204 instead of 1-(5-bromo-6,7-difluoro-indol-1-yl)-2-methyl-propan-2-ol, and using tert-butyl ((3-endo)-8-azabicyclo[3.2.1]octan-3-yl)carbamate instead of tert-butyl N-[(3S)-pyrrolidin-3-yl]carbamate to give the title compound.

Example 206: Synthesis of 5'-((1S,2S,4R)-rel-2-amino-7-azabicyclo[2.2.1]heptane-7-carbonyl)-2'-(1-(2-ethyl-2-hydroxybutyl)-6-fluoro-1H-indazol-5-yl)-3-fluoro-[1,1'-biphenyl]-4-carbonitrile-isomer-X The procedure of steps 2 to 4 in Example 172 was conducted using the 3-[(5-bromo-6-fluoro-indazol-1-yl)methyl]pentan-3-01 obtained in step 1 of Example 204 instead of 1-(5-bromo-6,7-difluoro-indol-1-yl)-2-methyl-propan-2-ol, and using the tert-butyl ((1S,2S,4R)-rel-7-azabicyclo[2.2.1]heptan-2-yl)carbamate-isomer-X obtained in step 2 of Example 202 instead of tert-butyl N-[(3S)-pyrrolidin-3-yl]carbamate to give the title compound.

Example 207: Synthesis of 2-(5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)acetic acid-isomer-X Step 1
5-Bromo-6-fluoro-1H-indole (500 mg) was dissolved in DMF (7.79 mL). At room temperature, cesium carbonate (1.67 g) and ethyl 2-chloro acetate (573 mg) were added thereto, followed by stirring at 90° C. for 16 hours. The reaction was terminated with a saturated aqueous ammonium chloride solution. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give ethyl 2-(5-bromo-6-fluoro-indol-1-yl)acetate.
Step 2
The 3-(4-cyano-3-fluoro-phenyl)-4-(4,4,5,5-tetramethyl-1,3,2-dioxaborolan-2-yl)benzoic acid (2 g) obtained in step 2 of Example 41, and the tert-butyl ((1S,2S,4R)-rel-7-azabicyclo[2.2.1]heptan-2-yl)carbamate-isomer-X (1.24 g) obtained in step 2 of Example 202 were dissolved in THF (21.8 mL). At room temperature, TEA (1.52 mL) and HATU (2.28 g) were added thereto, followed by stirring at 50° C. for 1 hour. The reaction mixture was vacuum-concentrated, and the residue was purified by silica gel column chromatography (mobile phase: hexane/ethyl acetate) to give tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X.
Step 3
The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (100 mg) obtained in step 2 above, and the ethyl 2-(5-bromo-6-fluoro-indol-1-yl)acetate (69.5 mg) obtained in step 1 above were suspended in 1,4-dioxane (0.59 mL). At room temperature, Pd(dba)$_2$ (8.2 mg), X-phos (13.6 mg), and tripotassium phosphate (113 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol). The residue was dissolved in MeOH (1.0 mL), and a 5 N aqueous sodium hydroxide solution (1.0 mL) was added thereto, followed by stirring for 1 hour. MTBE was added thereto, and the aqueous layer was extracted. The aqueous layer was acidified with hydrochloric acid, MTBE was added thereto, and the resulting mixture was washed sequentially with water and saturated brine. After the organic layer was dried over anhydrous sodium sulfate, the solvent was distilled off to give 2-(5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indole-1-yl)acetic acid-isomer-X.
Step 4
Acetonitrile (1.0 mL) and a 4 N hydrochloric acid-1,4-dioxane solution (1.0 mL) were added to the 2-(5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indole-1-yl)acetic acid-isomer-X (10 mg) obtained in step 3 above, followed by stirring for 30 minutes. The solvent was distilled off, and the residue was purified by reversed-phase HPLC (mobile phase: water/acetonitrile) to give the title compound.

Example 208: Synthesis of 2-(4'-((1S,2S,4R)-rel-2-amino-7-azabicyclo[2.2.1]heptane-7-carbonyl)-4"-cyano-2,3"-difluoro-[1,1':2',1"-terphenyl]-4-yl)acetic acid-isomer-X The procedure of steps 3 to 4 in Example 207 was conducted using methyl 2-(4-bromo-3-fluorophenyl)acetate instead of ethyl 2-(5-bromo-6-fluoro-indol-1-yl)acetate to give the title compound.

Example 209: Synthesis of 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile-isomer-X Step 1
2-Chloro-1,3-difluoro-4-nitro-benzene (1 g) was dissolved in THF (12.9 mL). TEA (1.08 mL) and 1-amino-2-methyl-propan-2-ol (0.59 mL) were added thereto, followed by stirring at room temperature for 1 hour. Ethyl acetate was added thereto, and the mixture was washed sequentially with water and saturated brine. The organic layer was dried over anhydrous sodium sulfate, and the solvent was distilled off to give 1-(2-chloro-3-fluoro-6-nitro-anilino)-2-methyl-propan-2-ol.

Step 2

The 1-(2-chloro-3-fluoro-6-nitro-anilino)-2-methyl-propan-2-ol (1.3 g) obtained in step 1 above was dissolved in DMF (9.9 mL). At room temperature, NBS (1.1 g) was added thereto, followed by stirring at 90° C. for 1 hour. Ethyl acetate was added thereto, and the mixture was washed sequentially with water and saturated brine, and dried over anhydrous sodium sulfate. Thereafter, the solvent was distilled off. The residue was crystallized from IPE:hexane=1: 1, and washed twice with hexane to give 1-(4-bromo-2-chloro-3-fluoro-6-nitro-anilino)-2-methyl-propan-2-ol.

Step 3

The 1-(4-bromo-2-chloro-3-fluoro-6-nitro-anilino)-2-methyl-propan-2-ol (1.6 g) obtained in step 2 above, NH$_4$Cl (1.6 g), and iron (0.8 g) were suspended in EtOH (7.81 mL) and water (7.81 mL), followed by stirring at 60° C. overnight. MTBE was added thereto, and the mixture was passed through Celite. MTBE was added thereto, and the mixture was washed sequentially with water and saturated brine, and dried over anhydrous sodium sulfate. The solvent was then distilled off to give 1-(6-amino-4-bromo-2-chloro-3-fluoro-anilino)-2-methyl-propan-2-ol.

Step 4

The 1-(6-amino-4-bromo-2-chloro-3-fluoro-anilino)-2-methyl-propan-2-ol (352 mg) obtained in step 3 above was dissolved in water (0.70 mL) and THF (1.76 mL). At 0° C., 12 N hydrochloric acid (1.06 mL) and sodium nitrite (an aqueous solution (0.3 mL) in which 101 mg of sodium nitrite was dissolved) were added thereto dropwise, followed by stirring at room temperature for 1 hour. MTBE was added thereto, and the mixture was washed sequentially with water and saturated brine, and dried over anhydrous sodium sulfate. The solvent was then distilled off. IPE:hexane=1:1 (68 mL) was added to the residue, and the target compound was collected by filtration and washed with IPE:hexane=1:1 to give 1-(5-bromo-7-chloro-6-fluoro-benzotriazol-1-yl)-2-methyl-propan-2-ol.

Step 5

The tert-butyl ((1S,2S,4R)-rel-7-(4'-cyano-3'-fluoro-6-(4, 4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (50 mg) obtained in step 2 of Example 207, and the 1-(5-bromo-7-chloro-6-fluoro-benzotriazol-1-yl)-2-methyl-propan-2-ol (37.4 mg) obtained in step 4 above were suspended in 1,4-dioxane (0.3 mL). At room temperature, Pd(dba)$_2$ (4.1 mg), X-phos (6.8 mg), and tripotassium phosphate (56.7 mg) were added thereto. After nitrogen substitution, the mixture was stirred at 100° C. for 2 hours. Ethyl acetate was added thereto, and the mixture was put on NH-silica gel, and washed with ethyl acetate:methanol=10: 1. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 210: Synthesis of (S)-5'-(3-aminopyrrolidine-1-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was conducted using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 211: Synthesis of 5'-((3-endo)-3-amino-8-azabicyclo[3.2.1]octane-8-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was conducted using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 212: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-indazole-3-carboxylic acid-isomer-X Step 1

The 3-(4-cyano-3-fluoro-phenyl)-4-[6-fluoro-1-(2-hydroxy-2-methyl-propyl)indazol-5-yl]benzoic acid (250 mg) obtained in step 1 of Example 176 was dissolved in THF (2.24 mL). At room temperature, HATU (234 mg), the tert-butyl ((1S,2S,4R)-rel-7-azabicyclo[2.2.1]heptan-2-yl)carbamate-isomer-X (125 mg) obtained in step 2 of Example 202, and TEA (0.156 mL) were added thereto, followed by stirring at 50° C. for 1 hour. The solvent was distilled off under reduced pressure. The residue was purified by silica gel column chromatography (mobile phase: chloroform/methanol) to give tert-butyl ((1S,2S,4R)-rel-7-(4'-cyano-3'-fluoro-6-(6-fluoro-1-(2-hydroxy-2-methylpropyl)-1H-indazol-5-yl)-[1,1'-biphenyl]-3-carbonyl)-7-azabicyclo[2.2.1] heptan-2-yl)carbamate-isomer-X.

Step 2

The tert-butyl ((1S,2S,4R)-rel-7-(4'-cyano-3'-fluoro-6-(6-fluoro-1-(2-hydroxy-2-methylpropyl)-1H-indazol-5-yl)-[1, 1T-biphenyl]-3-carbonyl)-7-azabicyclo[2.2.1]heptan-2-yl) carbamate-isomer-X (289 mg) obtained in step 1 above was dissolved in DMF (4.50 mL). At room temperature, NBS (120 mg) was added thereto, followed by stirring at room temperature for 1 hour. Ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(6-(3-bromo-6-fluoro-1-(2-hydroxy-2-methylpropyl)-1H-indazol-5-yl)-4'-cyano-3'-fluoro-[1,1'-biphenyl]-3-carbonyl)-7-azabicyclo[2.2.1]heptan-2-yl)carbamate-isomer-X.

Step 3

The tert-butyl ((1S,2S,4R)-rel-7-(6-(3-bromo-6-fluoro-1-(2-hydroxy-2-methylpropyl)-1H-indazol-5-yl)-4'-cyano-3'-fluoro-[1,1'-biphenyl]-3-carbonyl)-7-azabicyclo[2.2.1]heptan-2-yl)carbamate-isomer-X (50 mg) obtained in step 2 above and PdCl$_2$(PPh$_3$)$_2$ (2.4 mg) were suspended in 1-methyl-2-pyrrolidinone (0.5 mL). At room temperature, N,N-diethylethanolamine (0.046 mL) was added thereto, and after CO substitution, the mixture was stirred at 125° C. for 1 hour. t-BuOH (0.5 mL) and a 2 N aqueous sodium hydroxide solution (0.25 mL) were added to the reaction mixture, followed by stirring at room temperature for 1 hour. MTBE was added thereto, and the aqueous layer was separated. The aqueous layer was acidified with hydrochloric acid, and extraction was performed with MTBE. After the organic layer was dried over anhydrous sodium sulfate, the solvent was distilled off. Acetonitrile (0.5 mL) and a 4 N hydrochloric acid-1,4-dioxane solution (0.5 mL) were added to the residue, followed by stirring for 10 minutes. The reaction mixture was concentrated, and the residue was purified by reversed-phase HPLC (mobile phase: water/acetonitrile) to give the title compound.

Example 213: Synthesis of 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile Step 1

The 3-(4-cyano-3-fluoro-phenyl)-4-(4,4,5,5-tetramethyl-1,3,2-dioxaborolan-2-yl)benzoic acid (500 mg) obtained in step 2 of Example 41 and tert-butyl ((1S,2S,4R)-rel-7-azabicyclo[2.2.1]heptan-2-yl)carbamate hydrochloride (303.5 mg) were dissolved in THF (5.45 mL). At room temperature, TEA (0.379 mL) and HATU (569.5 mg) were added thereto, followed by stirring at 50° C. for 1 hour. The reaction mixture was vacuum-concentrated, and the residue was purified by silica gel column chromatography (mobile phase: hexane/ethyl acetate) to give tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate.

Step 2

The procedure of steps 1 to 5 in Example 209 was conducted using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 above instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 214: Synthesis of 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X The procedure of steps 1 to 5 in Example 161 was conducted using 3-[(2,3-difluoro-6-nitro-anilino)methyl]pentan-3-ol instead of 1-(2,3-difluoro-6-nitro-anilino)-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X obtained in step 2 of Example 207 instead of tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate to give the title compound.

Example 215: Synthesis of (S)-5'-(3-aminopyrrolidine-1-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile The procedure of steps 1 to 5 in Example 161 was conducted using 3-[(2,3-difluoro-6-nitro-anilino)methyl]pentan-3-ol instead of 1-(2,3-difluoro-6-nitro-anilino)-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate to give the title compound.

Example 216: Synthesis of 5'-((3-endo)-3-amino-8-azabicyclo[3.2.1]octane-8-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile The procedure of steps 1 to 5 in Example 161 was conducted using 3-[(2,3-difluoro-6-nitro-anilino)methyl]pentan-3-ol instead of 1-(2,3-difluoro-6-nitro-anilino)-2-methyl-propan-2-ol to give the title compound.

Example 217: Synthesis of 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile The procedure of steps 1 to 5 in Example 161 was conducted using 3-[(2,3-difluoro-6-nitro-anilino)methyl]pentan-3-ol instead of 1-(2,3-difluoro-6-nitro-anilino)-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate to give the title compound.

Example 218: Synthesis of 5'-((1S,2S,4R)-rel-2-amino-7-azabicyclo[2.2.1]heptane-7-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile-isomer-X The procedure of steps 1 to 5 in Example 209 was conducted using 3-(aminomethyl)pentan-3-ol instead of 1-amino-2-methyl-propan-2-ol to give the title compound.

Example 219: Synthesis of (S)-5'-(3-aminopyrrolidine-1-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile The procedure of steps 1 to 5 in Example 209 was conducted using 3-(aminomethyl)pentan-3-ol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 220: Synthesis of 5'-((3-endo)-3-amino-8-azabicyclo[3.2.1]octane-8-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile The procedure of steps 1 to 5 in Example 209 was conducted using 3-(aminomethyl)pentan-3-ol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 221: Synthesis of 5'-((1S,2S,4R)-rel-2-amino-7-azabicyclo[2.2.1]heptane-7-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile The procedure of steps 1 to 5 in Example 209 was conducted using 3-(aminomethyl)pentan-3-ol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 222: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-indole-3-carboxylic acid-isomer-X Step 1
The 3-(4-cyano-3-fluoro-phenyl)-4-[6-fluoro-1-(2-hydroxy-2-methyl-propyl)indol-5-yl]benzoic acid (250 mg) obtained in step 1 of Example 171 was dissolved in THF (2.24 mL). At room temperature, HATU (234 mg), the tert-butyl ((1S,2S,4R)-rel-7-azabicyclo[2.2.1]heptan-2-yl)carbamate-isomer-X (125 mg) obtained in step 2 of Example 202, and TEA (0.156 mL) were added thereto, followed by stirring at 50° C. for 1 hour. The solvent was distilled off under reduced pressure. The residue was purified by silica gel column chromatography (mobile phase: chloroform/methanol) to give tert-butyl ((1S,2S,4R)-rel-7-(4'-cyano-3'-fluoro-6-(6-fluoro-1-(2-hydroxy-2-methylpropyl)-1H-indol-5-yl)-[1,1'-biphenyl]-3-carbonyl)-7-azabicyclo[2.2.1]heptan-2-yl)carbamate-isomer-X.
Step 2
The tert-butyl ((1S,2S,4R)-rel-7-(4'-cyano-3'-fluoro-6-(6-fluoro-1-(2-hydroxy-2-methylpropyl)-1H-indol-5-yl)-[1,1'-biphenyl]-3-carbonyl)-7-azabicyclo[2.2.1]heptan-2-yl)carbamate-isomer-X (289 mg) obtained in step 1 above was dissolved in DMF (4.50 mL). At room temperature, N-iodosuccinimide (120 mg) was added thereto, followed by stirring at room temperature for 1 hour. Ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(4'-cyano-3'-fluoro-6-(6-fluoro-1-(2-hydroxy-2-methylpropyl)-3-iodo-1H-indol-5-yl)-[1,1'-biphenyl]-3-carbonyl)-7-azabicyclo[2.2.1]heptan-2-yl)carbamate-isomer-X.
Step 3
The tert-butyl ((1S,2S,4R)-rel-7-(4'-cyano-3'-fluoro-6-(6-fluoro-1-(2-hydroxy-2-methylpropyl)-3-iodo-1H-indol-5-yl)-[1,1'-biphenyl]-3-carbonyl)-7-azabicyclo[2.2.1]heptan-2-yl)carbamate-isomer-X (20 mg) obtained in step 2 above and PdCl$_2$(PPh$_3$)$_2$ (0.92 mg) were suspended in 1-methyl-2-pyrrolidinone (0.2 mL). At room temperature, N,N-diethylethanolamine (0.0173 mL) was added thereto, and after CO substitution, the mixture was stirred at 100° C. for 1 hour. t-BuOH (0.2 mL) and a 2 N aqueous sodium hydroxide solution (0.2 mL) were added to the reaction mixture, followed by stirring at room temperature overnight. MTBE was added thereto, and the aqueous layer was separated. The aqueous layer was acidified with hydrochloric acid, and extraction was performed with MTBE. After the organic layer was dried over anhydrous sodium sulfate, the solvent was distilled off. Acetonitrile (0.5 mL) and a 4 N hydrochloric acid-1,4-dioxane solution (0.5 mL) were added to the residue, followed by stirring for 10 minutes. The reaction mixture was concentrated, and the residue was purified by reversed-phase HPLC (mobile phase: water/acetonitrile) to give the title compound.

Example 223: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indazole-3-carboxylic acid-isomer-X Step 1
The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (350 mg) obtained in step 2 of Example 207, and 5-bromo-6-fluoro-1-methyl-indazole (186 mg) were suspended in 1,4-dioxane (2.08 mL). At room temperature, Pd(dba)$_2$ (28.7 mg), X-phos (47.6 mg), and tripotassium phosphate (397 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol) to give tert-butyl ((1S,2S,4R)-rel-7-(4'-cyano-3'-fluoro-6-(6-fluoro-1-methyl-1H-indazol-5-yl)-[1,1'-biphenyl]-3-carbonyl)-7-azabicyclo[2.2.1]heptan-2-yl)carbamate-isomer-X.
Step 2
The procedure of steps 2 to 3 in Example 212 was conducted using the tert-butyl ((1S,2S,4R)-rel-7-(4'-cyano-3'-fluoro-6-(6-fluoro-1-methyl-1H-indazol-5-yl)-[1,1'-biphenyl]-3-carbonyl)-7-azabicyclo[2.2.1]heptan-2-yl)carbamate-isomer-X obtained in step 1 above instead of tert-butyl ((1S,2S,4R)-rel-7-(4'-cyano-3'-fluoro-6-(6-fluoro-1-(2-hydroxy-2-methylpropyl)-1H-indazol-5-yl)-[1,1'-biphenyl]-3-carbonyl)-7-azabicyclo[2.2.1]heptan-2-yl)carbamate-isomer-X to give the title compound.

Example 224: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X Step 1
The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (350 mg) obtained in step 2 of Example 207, and 5-bromo-6-fluoro-1-methyl-indole (185 mg) were suspended in 1,4-dioxane (2.08 mL). At room temperature, Pd(dba)$_2$ (28.7 mg), X-phos (47.6 mg), and tripotassium phosphate (397 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol) to give tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl)carbamate-isomer-X.

Step 2

The tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl)carbamate-isomer-X (209 mg) obtained in step 1 above was dissolved in DMF (3.6 mL). At room temperature, N-iodosuccinimide (121 mg) was added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate-isomer-X.

Step 3

The tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate-isomer-X (211 mg) obtained in step 2 above and $PdCl_2(PPh_3)_2$ (10.5 mg) were suspended in 1-methyl-2-pyrrolidinone (2.11 mL). At room temperature, N,N-diethylethanolamine (0.197 mL) was added thereto, and after CO substitution, the mixture was stirred at 100° C. for 1 hour. t-BuOH (0.2 mL) and a 2 N aqueous sodium hydroxide solution (0.2 mL) were added to the reaction mixture, and the resulting mixture was stirred at room temperature overnight. MTBE was added thereto, and the aqueous layer was separated. The aqueous layer was acidified with hydrochloric acid, and extraction was performed with MTBE. The organic layer was dried over anhydrous sodium sulfate, and the solvent was distilled off to give 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X.

Step 4

Acetonitrile (0.5 mL) and a 4 N hydrochloric acid-1,4-dioxane solution (0.5 mL) were added to the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X (10 mg) obtained in step 3 above, followed by stirring for 10 minutes. The reaction mixture was concentrated, and the residue was purified by reversed-phase HPLC (mobile phase: water/acetonitrile) to give the title compound.

Example 225: Synthesis of 5'-((1S,2S,4R)-rel-2-amino-7-azabicyclo[2.2.1]heptane-7-carbonyl)-2'-(1-(2-ethyl-2-hydroxybutyl)-6-fluoro-1H-indazol-5-yl)-3-fluoro-[1,1'-biphenyl]-4-carbonitrile The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (40 mg) obtained in step 1 of Example 213 and the 3-[(5-bromo-6-fluoro-indazol-1-yl)methyl]pentan-3-ol (29.2 mg) obtained in step 1 of Example 204 were suspended in 1,4-dioxane (0.5 mL). At room temperature, $Pd(dba)_2$ (3.3 mg), X-phos (5.5 mg), and tripotassium phosphate (45.4 mg) were added thereto, followed by stirring at 100° C. for 1 hour. The reaction mixture was filtrated, and the solvent was distilled off. The residue was dissolved in acetonitrile (0.5 mL). At room temperature, a 4 N hydrochloric acid-1,4-dioxane solution (0.5 mL) was added thereto, followed by stirring at room temperature for 5 minutes. The reaction mixture was concentrated, and the residue was purified by reversed-phase HPLC (mobile phase: water/acetonitrile) to give the title compound.

Example 226: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1,3-dihydroisobenzofuran-5-yl)-[1,1'-biphenyl]-4-carbonitrile-isomer-X Step 1

Methyl 5-bromo-4-fluoro-2-iodo-benzoate (2 g) was dissolved in diethyl ether (55.7 mL). At 0° C., a solution of 2.0 M $LiBH_4$ in THF (6.13 mL) and MeOH (0.56 mL) were added thereto, followed by stirring at 0° C. for 1 hour. MTBE was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give (5-bromo-4-fluoro-2-iodo-phenyl)methanol.

Step 2

The (5-bromo-4-fluoro-2-iodo-phenyl) methanol (1.39 g) obtained in step 1 above and 3,4-dihydro-2H-pyran (0.419 mL) were dissolved in DCM (8.4 mL). At room temperature, pyridinium p-toluenesulfonic acid (106 mg) was added thereto, followed by stirring at room temperature overnight. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 2-[(5-bromo-4-fluoro-2-iodo-phenyl)methoxy]tetrahydropyran.

Step 3

The 2-[(5-bromo-4-fluoro-2-iodo-phenyl)methoxy]tetrahydropyran (1.5 g) obtained in step 2 above, $PdCl_2(PPh_3)_2$ (130 mg), and CuI (34 mg) were suspended in THF (18 mL). At room temperature, TEA (18 mL) and 2-methyl-3-butyn-2-ol (0.42 mL) were added thereto, followed by stirring at room temperature for 4 hours. The reaction mixture was filtrated, and the solvent was distilled off. The residue was purified by silica gel column chromatography (mobile phase: hexane/ethyl acetate) to give 4-[4-bromo-5-fluoro-2-(tetrahydropyran-2-yloxymethyl)phenyl]-2-methyl-3-butyn-2-ol.

Step 4

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (150 mg) obtained in step 2 of Example 207, and the 4-[4-bromo-5-fluoro-2-(tetrahydropyran-2-yloxymethyl)phenyl]-2-methyl-3-butyn-2-ol (129 mg) obtained in step 3 above were suspended in 1,4-dioxane (0.89 mL). At room temperature, $Pd(dba)_2$ (12.3 mg) and X-phos (20.4 mg) were added thereto, followed by stirring at 100° C. for 1 hour. The reaction mixture was filtrated, and the solvent was distilled off. The residue was purified by silica gel column chromatography (mobile phase: hexane/ethyl acetate). The residue was dissolved in THF (0.92 mL) and water (0.46 mL). At room temperature, p-toluenesulfonic acid monohydrate (6.9 mg) was added thereto, followed by stirring at 70° C. for 1 hour. Ethyl acetate was added thereto, and the mixture was washed sequentially with water and saturated brine, and dried over anhydrous sodium sulfate. Then, the solvent was distilled off. The residue was purified by silica gel column chromatography (mobile phase: hexane/ethyl acetate) to give tert-butyl ((1S,2S,4R)-rel-7-(4"-cyano-2,3"-difluoro-4-(3-hydroxy-3-methyl-1-butyn-1-yl)-5-(hydroxymethyl)-[1,1':2',1"-terphenyl]-4'-carbonyl)-7-azabicyclo[2.2.1]heptan-2-yl)carbamate-isomer-X.

Step 5

The tert-butyl ((1S,2S,4R)-rel-7-(4"-cyano-2,3"-difluoro-4-(3-hydroxy-3-methyl-1-butyn-1-yl)-5-(hydroxymethyl)-[1,1':2',1"-terphenyl]-4'-carbonyl)-7-azabicyclo[2.2.1]heptan-2-yl)carbamate-isomer-X (30 mg) obtained in step 4 above was dissolved in 1,4-dioxane (0.24 mL). At room temperature, a solution of 1.0 M TBAF in THF (0.14 mL) was added thereto, followed by stirring at 100° C. for 1 hour. EtOH (0.12 mL) and 10% Pd/C (30 mg) were added to the reaction mixture, and after hydrogen substitution, the resulting mixture was stirred at 70° C. for 30 minutes. The reaction mixture was filtrated, and the filtrate was concentrated. The residue was dissolved in THF. At room temperature, TEA (0.013 mL), DMAP (1.1 mg), and Boc₂O (20.4 mg) were added thereto, followed by stirring at 70° C. for 1 hour. Ethyl acetate was added thereto, the mixture was washed 5 times with phosphoric acid at a concentration of about 0.5 mol/L, washed with saturated brine, and dried over anhydrous sodium sulfate. Thereafter, the solvent was distilled off. The residue was dissolved in acetonitrile (0.5 mL). At room temperature, a 4 N hydrochloric acid-1,4-dioxane solution (0.5 mL) was added thereto, followed by stirring at room temperature for 5 minutes. After the completion of the reaction was confirmed by LCMS, the solvent was distilled off. The residue was purified by reversed-phase HPLC (mobile phase: water/acetonitrile) to give the title compound.

Example 227: Synthesis of 5'-((S)-3-aminopyrrolidine-1-carbonyl)-3-fluoro-2'-(6-fluoro-1-(2-hydroxy-2-methylpropyl)-1,3-dihydroisobenzofuran-5-yl)-[1,1'-biphenyl]-4-carbonitrile Step 1

The tert-butyl 3-(4-cyano-3-fluoro-phenyl)-4-(4,4,5,5-tetramethyl-1,3,2-dioxaborolan-2-yl)benzoate (400 mg) obtained in step 1 of Example 41, and the 4-[4-bromo-5-fluoro-2-(tetrahydropyran-2-yloxymethyl)phenyl]-2-methyl-3-butyn-2-ol (456 mg) obtained in step 3 of Example 226 were suspended in 1,4-dioxane (3.15 mL). At room temperature, Pd(dba)₂ (43.5 mg), X-phos (144 mg), and tripotassium phosphate (601 mg) were added thereto, followed by stirring at 100° C. for 1 hour. The reaction mixture was filtrated, and the solvent was distilled off. The residue was purified by silica gel column chromatography (mobile phase: chloroform/methanol). The residue was dissolved in THF (1.62 mL). At room temperature, water (0.81 mL) and p-toluenesulfonic acid monohydrate (12.3 mg) were added thereto, followed by stirring at 70° C. for 1 hour. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give tert-butyl 3-(4-cyano-3-fluoro-phenyl)-4-[2-fluoro-5-(hydroxymethyl)-4-(3-hydroxy-3-methyl-1-butenyl)phenyl]benzoate.

Step 2

The tert-butyl 3-(4-cyano-3-fluoro-phenyl)-4-[2-fluoro-5-(hydroxymethyl)-4-(3-hydroxy-3-methyl-1-butenyl)phenyl]benzoate (90 mg) obtained in step 1 above was dissolved in 1,4-dioxane (0.9 mL). At room temperature, a solution of 1.0 M TBAF in THF (0.54 mL) was added thereto, followed by stirring at 100° C. for 2 hours. EtOH (0.30 mL) and 10% Pd/C (90 mg) were added to the reaction mixture, and after hydrogen substitution, stirring was performed at 70° C. overnight. The reaction mixture was filtrated, and the solvent was distilled off. The residue was purified by silica gel column chromatography (mobile phase: hexane/ethyl acetate). The residue was dissolved in THF (1.0 mL). At room temperature, 12 N hydrochloric acid (0.5 mL) was added thereto, followed by stirring at room temperature for 1.5 hours. MTBE was added thereto, and extraction was performed twice with a 2 N aqueous sodium hydroxide solution. The aqueous layer was acidified with 2 N hydrochloric acid, and extraction was performed twice with MTBE. The organic layer was sequentially washed with saturated brine, and dried over anhydrous sodium sulfate, and the solvent was distilled off to give 3-(4-cyano-3-fluoro-phenyl)-4-[6-fluoro-1-(2-hydroxy-2-methyl-propyl)-1,3-dihydroisobenzofuran-5-yl]benzoic acid.

Step 3

The 3-(4-cyano-3-fluoro-phenyl)-4-[6-fluoro-1-(2-hydroxy-2-methyl-propyl)-1,3-dihydroisobenzofuran-5-yl]benzoic acid (10 mg) obtained in step 2 above was dissolved in THF (0.5 mL). At room temperature, HATU (9.31 mg), tert-butyl N-[(3S)-pyrrolidin-3-yl]carbamate (43.5 mg), and TEA (6.2 µL) were added thereto, followed by stirring at 50° C. for 1 hour. The solvent was distilled off, and MeOH (0.5 mL) and a 4 N hydrochloric acid-1,4-dioxane solution (0.5 mL) were added thereto, followed by stirring at room temperature for 30 minutes. The solvent was distilled off, and the residue was purified by reversed-phase HPLC (mobile phase: water/acetonitrile) to give the title compound.

Example 228: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile-isomer-X The procedure of steps 1 to 5 in Example 209 was conducted using 1,3-difluoro-2-methyl-4-nitro-benzene instead of 2-chloro-1,3-difluoro-4-nitro-benzene to give the title compound.

Example 229: Synthesis of (S)-5'-(3-aminopyrrolidine-1-carbonyl)-3-fluoro-2'-(5-fluoro-3-(2-hydroxy-2-methylpropyl)benzo[d]isoxazol-6-yl)-[1,1'-biphenyl]-4-carbonitrile Step 1

The 1-(4-bromo-5-fluoro-2-hydroxyphenyl)ethanone (150 mg) obtained in step 2 of Example 179 was dissolved in THF (3.2 mL). At −25° C., lithium diisopropylamide (1.0 M, a THF solution) (3.2 mL) was added thereto, followed by stirring at −25° C. for 1 hour. The mixture was cooled to −40° C., and acetone (0.118 mL) was added thereto, followed by stirring at −40° C. for 1 hour. After a phosphoric acid aqueous solution was added thereto, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(4-bromo-5-fluoro-2-hydroxy-phenyl)-3-hydroxy-3-methyl-butan-1-one.

Step 2

The 1-(4-bromo-5-fluoro-2-hydroxy-phenyl)-3-hydroxy-3-methyl-butan-1-one (60 mg) obtained in step 1 above, hydroxylamine hydrochloride (28.6 mg), and sodium acetate (25.4 mg) were dissolved in methanol (0.69 mL), followed by stirring at 60° C. overnight. MTBE was added thereto, and the mixture was washed sequentially with water and saturated brine. After the organic layer was dried over anhydrous sodium sulfate, the solvent was distilled off. The residue was dissolved in THF (0.69 mL), and N,N'-carbonyldiimidazole (36.8 mg) and TEA (0.037 mL) were added thereto, followed by stirring at 70° C. for 1 hour. The solvent was distilled off, and the residue was purified by silica gel column chromatography (mobile phase: hexane/ethyl acetate) to give 1-(6-bromo-5-fluoro-1,2-benzooxazol-3-yl)-2-methyl-propan-2-ol.

Step 3

The procedure of steps 1 to 3 in Example 37 was conducted using the 1-(6-bromo-5-fluoro-1,2-benzooxazol-3-yl)-2-methyl-propan-2-ol obtained in step 2 above instead of 1-(4-bromo-3-fluoro-phenyl)-2-methyl-propan-2-ol to give the title compound.

Example 230: Synthesis of 2-(5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)acetamide Step 1

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (100 mg) obtained in step 1 of Example 213, and the ethyl 2-(5-bromo-6-fluoro-indol-1-yl)acetate (69.5 mg) obtained in step 1 of Example 207 were suspended in 1,4-dioxane (0.59 mL). At room temperature, Pd(dba)$_2$ (8.2 mg), X-phos (13.6 mg), and tripotassium phosphate (113 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol). The residue was dissolved in MeOH (1.0 mL), and a 5 N aqueous sodium hydroxide solution (1.0 mL) was added thereto, followed by stirring for 1 hour. MTBE was added thereto, and the aqueous layer was extracted. The aqueous layer was acidified with hydrochloric acid, MTBE was added thereto, and the mixture was washed sequentially with water and saturated brine. The organic layer was dried over anhydrous sodium sulfate, and the solvent was distilled off to give 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indol-1-yl)acetic acid.

Step 2

The 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indol-1-yl)acetic acid (10 mg) obtained in step 1 above was dissolved in THF (0.32 mL). Then, N,N'-carbonyldiimidazole (5.2 mg) was added thereto, and the mixture was stirred at room temperature for 20 minutes. Twenty-eight percent aqueous ammonia (0.06 mL) was added thereto, and the mixture was stirred at room temperature for 20 minutes. The solvent was distilled off, and acetonitrile (0.2 mL) and a 4 N hydrochloric acid-1,4-dioxane solution (0.2 mL) were added to the residue, followed by stirring for 30 minutes. The solvent was distilled off, and the residue was purified by reversed-phase HPLC (mobile phase: water/acetonitrile) to give the title compound.

Example 231: Synthesis of 2-(5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)-N-methylacetamide The 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indol-1-yl)acetic acid (10 mg) obtained in step 1 of Example 230 was dissolved in THF (0.064 mL). At room temperature, HATU (6.7 mg), methylamine hydrochloride (2.2 mg), and TEA (6.7 µL) were added thereto, followed by stirring at 50° C. for 1 hour. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 232: Synthesis of 2-(5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)-N,N-dimethylacetamide The procedure of Example 231 was conducted using dimethylamine hydrochloride instead of methylamine hydrochloride to give the title compound.

Example 233: Synthesis of 2-(4'-((1S,2S,4R)-rel-2-amino-7-azabicyclo[2.2.1]heptane-7-carbonyl)-4''-cyano-2,3''-difluoro-[1,1':2',1''-terphenyl]-4-yl)acetamide Step 1

2-(4-Bromo-3-fluoro-phenyl)acetic acid (600 mg) was dissolved in THF (10.3 mL). At room temperature, HATU (1.08 g), NH$_4$Cl (275.4 mg), and TEA (1.08 mL) were added thereto, followed by stirring at 50° C. for 1 hour. The solvent was distilled off, and the residue was purified by silica gel column chromatography (mobile phase: chloroform/methanol) to give 2-(4-bromo-3-fluoro-phenyl) acetamide.

Step 2

The procedure of Example 225 was conducted using the 2-(4-bromo-3-fluoro-phenyl)acetamide obtained in step 1 above instead of 3-[(5-bromo-6-fluoro-indazol-1-yl)methyl]pentan-3-ol to give the title compound.

Example 234: Synthesis of 2-(4'-((1S,2S,4R)-rel-2-amino-7-azabicyclo[2.2.1]heptane-7-carbonyl)-4''-cyano-2,3''-difluoro-[1,1':2',1''-terphenyl]-4-yl)-N-methylacetamide Step 1

2-(4-Bromo-3-fluoro-phenyl)acetic acid (600 mg) was dissolved in THF (10.3 mL). At room temperature, HATU (1.08 g), methylamine (ca. 9.8 mol/L in MeOH) (0.525 mL), and TEA (1.08 mL) were added thereto, followed by stirring at 50° C. for 1 hour. The solvent was distilled off, and the residue was purified by silica gel column chromatography (mobile phase: chloroform/methanol) to give 2-(4-bromo-3-fluoro-phenyl)-N-methyl-acetamide.
Step 2

The procedure of Example 225 was conducted using the 2-(4-bromo-3-fluoro-phenyl)-N-methyl-acetamide obtained in step 1 above instead of 3-[(5-bromo-6-fluoro-indazol-1-yl)methyl]pentan-3-ol to give the title compound.

Example 235: Synthesis of 2-(4'-((1S,2S,4R)-rel-2-amino-7-azabicyclo[2.2.1]heptane-7-carbonyl)-4''-cyano-2,3''-difluoro-[1,1':2',1''-terphenyl]-4-yl)-N,N-dimethylacetamide Step 1

2-(4-Bromo-3-fluoro-phenyl)acetic acid (600 mg) was dissolved in THF (10.3 mL). At room temperature, HATU (1.08 g), dimethylamine hydrochloride (419.9 mg), and TEA (1.08 mL) were added thereto, followed by stirring at 50° C. for 1 hour. The solvent was distilled off, and the residue was purified by silica gel column chromatography (mobile phase: chloroform/methanol) to give 2-(4-bromo-3-fluoro-phenyl)-N,N-dimethyl-acetamide.
Step 2

The procedure of Example 225 was conducted using the 2-(4-bromo-3-fluoro-phenyl)-N,N-dimethyl-acetamide obtained in step 1 above instead of 3-[(5-bromo-6-fluoro-indazol-1-yl)methyl]pentan-3-ol to give the title compound.

Example 236: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxyamide-isomer-X The 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X (10 mg) obtained in step 3 of Example 224 was dissolved in THF (0.32 mL). Then, N,N'-carbonyldiimidazole (5.2 mg) was added thereto, and the mixture was stirred at room temperature for 20 minutes. Twenty-eight percent aqueous ammonia (0.1 mL) was added thereto, and the mixture was stirred at room temperature for 20 minutes. The solvent was distilled off, and acetonitrile (0.2 mL) and a 4 N hydrochloric acid-1,4-dioxane solution (0.2 mL) were added to the residue, followed by stirring for 30 minutes. The solvent was distilled off, and the residue was purified by reversed-phase HPLC (mobile phase: water/acetonitrile) to give the title compound.

Example 237: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,1-dimethyl-1H-indole-3-carboxyamide-isomer-X The 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X (10 mg) obtained in step 3 of Example 224 was dissolved in THF (0.064 mL). At room temperature, HATU (6.7 mg), methylamine hydrochloride (2.2 mg) and TEA (6.7 μL) were added thereto, followed by stirring at 50° C. for 1 hour. The solvent was distilled off, and acetonitrile (0.5 mL) and a 4 N hydrochloric acid-1,4-dioxane solution (0.5 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 238: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,N,1-trimethyl-1H-indole-3-carboxyamide-isomer-X The procedure of Example 237 was conducted using dimethylamine hydrochloride instead of methylamine hydrochloride to give the title compound.

Example 239: Synthesis of (S)-5'-(3-aminopyrrolidine-1-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile The procedure of steps 1 to 5 of Example 209 was conducted using 1,3-difluoro-2-methyl-4-nitro-benzene instead of 2-chloro-1,3-difluoro-4-nitro-benzene, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 240: Synthesis of 5'-((3-endo)-3-amino-8-azabicyclo[3.2.1]octane-8-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile The procedure of steps 1 to 5 in Example 209 was conducted using 1,3-difluoro-2-methyl-4-nitro-benzene instead of 2-chloro-1,3-difluoro-4-nitro-benzene, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 241: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile The procedure of steps 1 to 5 in Example 209 was conducted using 1,3-difluoro-2-methyl-4-nitro-benzene instead of 2-chloro-1,3-difluoro-4-nitro-benzene, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 242: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid Step 1

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (200 mg) obtained in step 1 of Example 213 and 5-bromo-6-fluoro-1-methyl-indole (105.6 mg) were suspended in 1,4-dioxane (1.19 mL). At room temperature, Pd(dba)$_2$ (16.4 mg), X-phos (27.2 mg), and tripotassium phosphate (226.9 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol) to give tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl)carbamate.

Step 2

The tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl)carbamate (209 mg) obtained in step 1 above was dissolved in DMF (3.6 mL). At room temperature, N-iodosuccinimide (121 mg) was added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate.

Step 3

The tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate (211 mg) obtained in step 2 above and PdCl$_2$(PPh$_3$)$_2$ (10.5 mg) were suspended in 1-methyl-2-pyrrolidinone (2.11 mL). At room temperature, N,N-diethylethanolamine (0.197 mL) was added thereto, and after CO substitution, the mixture was stirred at 100° C. for 1 hour. t-BuOH (0.2 mL) and a 2 N aqueous sodium hydroxide solution (0.2 mL) were added to the reaction mixture, and the resulting mixture was stirred at room temperature overnight. MTBE was added thereto, and the aqueous layer was separated. The aqueous layer was acidified with hydrochloric acid, and extraction was performed with MTBE. The organic layer was dried over anhydrous sodium sulfate, and the solvent was distilled off to give 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid.

Step 4

Acetonitrile (0.5 mL) and a 4 N hydrochloric acid-1,4-dioxane solution (0.5 mL) were added to the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid (10 mg) obtained in step 3 above, followed by stirring for 10 minutes. The reaction mixture was concentrated, and the residue was purified by reversed-phase HPLC (mobile phase: water/acetonitrile) to give the title compound.

Example 243: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,1-dimethyl-1H-indole-3-carboxamide The procedure of Example 237 was conducted using the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid obtained in step 3 of Example 242 instead of 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X to give the title compound.

Example 244: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,N,1-trimethyl-1H-indole-3-carboxamide The procedure of Example 237 was conducted using the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid obtained in step 3 of Example 242 instead of 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X, and using dimethylamine hydrochloride instead of methylamine hydrochloride to give the title compound.

Example 245: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxamide The procedure of Example 236 was conducted using the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid obtained in step 3 of Example 242 instead of 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X to give the title compound.

Example 246: Synthesis of 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile-isomer-X The procedure of steps 1 to 5 in Example 209 was conducted using 2-(difluoromethyl)-1,3-difluoro-4-nitro-benzene instead of 2-chloro-1,3-difluoro-4-nitro-benzene to give the title compound.

Example 247: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile-isomer-X The procedure of steps 1 to 5 in Example 209 was conducted using 2,6-difluoro-3-nitro-benzonitrile instead of 2-chloro-1,3-difluoro-4-nitro-benzene, and using THF instead of EtOH to give the title compound.

Example 248: Synthesis of (S)-5'-(3-aminopyrrolidine-1-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was conducted using 2-(difluoromethyl)-1,3-difluoro-4-nitro-benzene instead of 2-chloro-1,3-difluoro-4-nitro-benzene, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 249: Synthesis of (S)-5-(5-(3-aminopyrrolidine-1-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile The procedure of steps 1 to 5 in Example 209 was conducted using 2,6-difluoro-3-nitro-benzonitrile instead of 2-chloro-1,3-difluoro-4-nitro-benzene, using THF instead of EtOH, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 250: Synthesis of 5'-((3-endo)-3-amino-8-azabicyclo[3.2.1]octane-8-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was conducted using 2-(difluoromethyl)-1,3-difluoro-4-nitro-benzene instead of 2-chloro-1,3-difluoro-4-nitro-benzene, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 251: Synthesis of 5-(5-((3-endo)-3-amino-8-azabicyclo[3.2.1]octane-8-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile The procedure of steps 1 to 5 in Example 209 was conducted using 2,6-difluoro-3-nitro-benzonitrile instead of 2-chloro-1,3-difluoro-4-nitro-benzene, using THF instead of EtOH, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 252: Synthesis of 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was conducted using 2-(difluoromethyl)-1,3-difluoro-4-nitro-benzene instead of 2-chloro-1,3-difluoro-4-nitro-benzene, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 253: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile The procedure of steps 1 to 5 in Example 209 was conducted using 2,6-difluoro-3-nitro-benzonitrile instead of 2-chloro-1,3-difluoro-4-nitro-benzene, using THF instead of EtOH, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 254: Synthesis of 5'-((1S,2S,4R)-rel-2-amino-7-azabicyclo[2.2.1]heptane-7-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile-isomer-X The procedure of steps 1 to 5 in Example 209 was conducted using 1,2,3-trifluoro-4-nitro-benzene instead of 2-chloro-1,3-difluoro-4-nitro-benzene, and using 1-(aminomethyl)cyclobutanol instead of 1-amino-2-methyl-propan-2-ol to give the title compound.

Example 255: Synthesis of (S)-5'-(3-aminopyrrolidine-1-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 1,2,3-trifluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan- 2-yl)-[1,1'-biphenyl]-3-carbonyl)-7-azabicyclo[2.2.1]heptan-2-yl)carbamate-isomer-X to give the title compound.

Example 256: Synthesis of 5'-((3-endo)-3-amino-8-azabicyclo[3.2.1]octane-8-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 1,2,3-trifluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 257: Synthesis of 5'-((1S,2S,4R)-rel-2-amino-7-azabicyclo[2.2.1]heptane-7-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile-isomer-X The procedure of steps 1 to 5 in Example 209 was conducted using 1-(aminomethyl)cyclobutanol instead of 1-amino-2-methyl-propan-2-ol to give the title compound.

Example 258: Synthesis of (S)-5'-(3-aminopyrrolidine-1-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 259: Synthesis of 5'-((3-endo)-3-amino-8-azabicyclo[3.2.1]octane-8-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 260: Synthesis of 5'-((1S,2S,4R)-rel-2-amino-7-azabicyclo[2.2.1]heptane-7-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile-isomer-X The procedure of steps 1 to 5 in Example 209 was conducted using 2-(difluoromethyl)-1,3-difluoro-4-nitro-benzene instead of 2-chloro-1,3-difluoro-4-nitro-benzene, and using 1-(aminomethyl)cyclobutanol instead of 1-amino-2-methyl-propan-2-ol to give the title compound.

Example 261: Synthesis of (S)-5'-(3-aminopyrrolidine-1-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 2-(difluoromethyl)-1,3-difluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 262: Synthesis of 5'-((3-endo)-3-amino-8-azabicyclo[3.2.1]octane-8-carbonyl)-2'-(7-(difluoromethyl)-6-fluoro-1-((l-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 2-(difluoromethyl)-1,3-difluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 263: Synthesis of 5'-((1S,2S,4R)-rel-2-amino-7-azabicyclo[2.2.1]heptane-7-carbonyl)-2'-(7-(difluoromethyl)-6-fluoro-1-((l-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 2-(difluoromethyl)-1,3-difluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo [2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,

Example 264: Synthesis of 5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile-isomer-X The procedure of steps 1 to 5 in Example 209 was conducted using 2,6-difluoro-3-nitro-benzonitrile instead of 2-chloro-1,3-difluoro-4-nitro-benzene, and using 1-(aminomethyl)cyclobutanol instead of 1-amino-2-methyl-propan-2-ol to give the title compound.

Example 265: Synthesis of (S)-5-(5-(3-aminopyrrolidine-1-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile The procedure of steps 1 to 5 in Example 209 was conducted using 2,6-difluoro-3-nitro-benzonitrile instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 266: Synthesis of 5-(5-((3-endo)-3-amino-8-azabicyclo[3.2.1]octane-8-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile The procedure of steps 1 to 5 in Example 209 was conducted using 2,6-difluoro-3-nitro-benzonitrile instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 267: Synthesis of 5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile The procedure of steps 1 to 5 in Example 209 was conducted using 2,6-difluoro-3-nitro-benzonitrile instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 268: Synthesis of 5'-((1S,2S,4R)-rel-2-amino-7-azabicyclo[2.2.1]heptane-7-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 1,2,3-trifluoro-4-nitro-benzene instead of 2-chloro-1, 3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 269: Synthesis of 5'-((1S,2S,4R)-rel-2-amino-7-azabicyclo[2.2.1]heptane-7-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was conducted using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 270: Synthesis of 5'-((1S,2S,4R)-rel-2-amino-7-azabicyclo[2.2.1]heptane-7-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile-isomer-X The procedure of steps 1 to 5 in Example 209 was conducted using 1,3-difluoro-2-methyl-4-nitro-benzene instead of 2-chloro-1,3-difluoro-4-nitro-benzene, and using 1-(aminomethyl)cyclobutanol instead of 1-amino-2-methyl-propan-2-ol to give the title compound.

Example 271: Synthesis of (S)-5'-(3-aminopyrrolidine-1-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile The procedure of steps 1 to 5 in Example 209 was conducted using 1,3-difluoro-2-methyl-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan- 2-yl)-[1,1'-biphenyl]-3-carbonyl)-7-azabicyclo[2.2.1]heptan-2-yl)carbamate-isomer-X to give the title compound.

Example 272: Synthesis of 5'-((3-endo)-3-amino-8-azabicyclo[3.2.1]octane-8-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile The procedure of steps 1 to 5 in Example 209 was conducted using 1,3-difluoro-2-methyl-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1v-biphenyl]-3-carbonyl)-7-azabicyclo[2.2.1]heptan-2-yl)carbamate-isomer-X to give the title compound.

Example 273: Synthesis of 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X Step 1

2-Bromo-1,3-difluoro-4-nitro-benzene (3 g) was dissolved in THF (31.5 mL). TEA (2.6 mL) and 1-amino-2-methyl-propan-2-ol (1.4 mL) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(2-bromo-3-fluoro-6-nitro-anilino)-2-methyl-propan-2-ol.

Step 2

The 1-(2-bromo-3-fluoro-6-nitro-anilino)-2-methyl-propan-2-ol (1.03 g) obtained in step 1 above was dissolved in acetic acid (6.7 mL). At room temperature, N-iodosuccinimide (981 mg) was added thereto, followed by stirring at 50° C. for 3 hours. MTBE and water were added thereto, and extraction was performed twice with MTBE. The combined organic layers were dried over anhydrous sodium sulfate, and the solvent was distilled off. The residue was purified by silica gel column chromatography (mobile phase: hexane/ethyl acetate) to give 1-(2-bromo-3-fluoro-4-iodo-6-nitro-anilino)-2-methyl-propan-2-ol.

Step 3

The 1-(2-bromo-3-fluoro-4-iodo-6-nitro-anilino)-2-methyl-propan-2-ol (1.33 g) obtained in step 2 above and iron (1.33 g) were dissolved in THF (10.2 mL) and a 2 N hydrochloric acid (10.2 mL), followed by stirring at 60° C. for 1 hour. MTBE was added thereto, and the mixture was passed through Celite. MTBE was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(6-amino-2-bromo-3-fluoro-4-iodo-anilino)-2-methyl-propan-2-ol.

Step 4

The 1-(6-amino-2-bromo-3-fluoro-4-iodo-anilino)-2-methyl-propan-2-ol (940 mg) obtained in step 3 above was dissolved in water (1.88 mL) and THF (4.7 mL). At 0° C., 12 N hydrochloric acid (2.82 mL) and an aqueous sodium nitrite solution (an aqueous solution obtained by dissolving 209 mg of sodium nitrite in 0.63 mL of water) were added thereto dropwise, followed by stirring at room temperature for 1 hour. MTBE was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(7-bromo-6-fluoro-5-iodo-benzotriazol-1-yl)-2-methyl-propan-2-ol.

Step 5

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (50 mg) obtained in step 2 of Example 207 and the 1-(7-bromo-6-fluoro-5-iodo-benzotriazol-1-yl)-2-methyl-propan-2-ol (47.9 mg) obtained in step 4 above were dissolved in 1,4-dioxane (0.3 mL). At room temperature, $Pd(dba)_2$ (4.1 mg), X-phos (6.8 mg), and tripotassium phosphate (56.7 mg) were added thereto. After nitrogen substitution, the mixture was stirred at 90° C. overnight. Ethyl acetate was added thereto, and the mixture was put on NH-silica gel, and washed with ethyl acetate:methanol=10:1. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 274: Synthesis of (S)-5'-(3-aminopyrrolidine-1-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 273 was conducted using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 275: Synthesis of 5'-((3-endo)-3-amino-8-azabicyclo[3.2.1]octane-8-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 273 was conducted using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 276: Synthesis of 5'-((1S,2S,4R)-rel-2-amino-7-azabicyclo[2.2.1]heptane-7-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile The procedure of steps 1 to 5 in Example 209 was conducted using 1,3-difluoro-2-methyl-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 277: Synthesis of 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 273 was conducted using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 278: Synthesis of 5'-((1R,2R,4S)-rel-2-amino-7-azabicyclo[2.2.1]heptane-7-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile Step 1

The 1-(2-bromo-3-fluoro-6-nitro-anilino)-2-methyl-propan-2-ol (975 mg) obtained in step 1 of Example 273 was dissolved in 1,4-dioxane (10.6 mL). At room temperature, dichlorobis(tricyclohexylphosphine)palladium(II) (234 mg), cyclopropyl boronic acid (464 mg), and tripotassium phosphate (2.02 g) were added thereto, followed by stirring at 10° C. overnight. The solvent was distilled off, and the residue was purified by silica gel column chromatography (mobile phase: hexane/ethyl acetate) to give 1-((2-cyclopropyl-3-fluoro-6-nitrophenyl)amino)-2-methylpropan-2-ol.
Step 2

The 1-((2-cyclopropyl-3-fluoro-6-nitrophenyl)amino)-2-methylpropan-2-ol (204 mg) obtained in step 1 above was dissolved in acetonitrile (1.5 mL). At room temperature, NBS (196 mg) was added thereto, followed by stirring at 50° C. for 1 hour. The solvent was distilled off, and the residue was purified by silica gel column chromatography (mobile phase: hexane/ethyl acetate) to give 1-((4-bromo-2-cyclopropyl-3-fluoro-6-nitrophenyl)amino)-2-methylpropan-2-ol.
Step 3

The 1-((4-bromo-2-cyclopropyl-3-fluoro-6-nitrophenyl)amino)-2-methylpropan-2-ol (250 mg) obtained in step 2 above and iron (250 mg) were dissolved in THF (2.4 mL) and a 2 N hydrochloric acid (2.4 mL), followed by stirring at 60° C. for 1 hour. Ethyl acetate was added thereto, and the mixture was passed through Celite. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-((6-amino-4-bromo-2-cyclopropyl-3-fluorophenyl)amino)-2-methylpropan-2-ol.
Step 4

The 1-((6-amino-4-bromo-2-cyclopropyl-3-fluorophenyl)amino)-2-methylpropan-2-ol (192 mg) obtained in step 3 above was dissolved in THF (2.0 mL) and a 2 N hydrochloric acid (2.0 mL). An aqueous sodium nitrite solution (an aqueous solution obtained by dissolving 54 mg of sodium nitrite in 0.16 mL of water) was added thereto dropwise, followed by stirring at room temperature for 1 hour. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(5-bromo-7-cyclopropyl-6-fluoro-1H-benzo[d][1,2,3]triazol-1-yl)-2-methylpropan-2-ol.
Step 5

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (15 mg) obtained in step 1 of Example 213, and the 1-(5-bromo-7-cyclopropyl-6-fluoro-1H-benzo[d][1,2,3]triazol-1-yl)-2-methylpropan-2-ol (10.5 mg) obtained in step 4 above were dissolved in 1,4-dioxane (0.2 mL). Pd(dba)$_2$ (1.2 mg), X-phos (2.0 mg), and tripotassium phosphate (17 mg) were added thereto. After nitrogen substitution, the mixture was stirred at 100° C. overnight. Ethyl acetate was added thereto, and the mixture was put on NH-silica gel, and washed with ethyl acetate:methanol=10:1. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 279: Synthesis of 5'-((1R,2R,4S)-rel-2-amino-7-azabicyclo[2.2.1]heptane-7-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile-isomer-X The procedure of steps 1 to 5 in Example 278 was conducted using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X obtained in step 2 of Example 207 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate to give the title compound.

Example 280: Synthesis of (S)-5'-(3-aminopyrrolidine-1-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 278 was conducted using the tert-butyl N-[(3S)-1-[3-(4-cyano-3-fluoro-phenyl)-4-(4,4,5,5-tetramethyl-1,3,2-dioxaborolan- 2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate to give the title compound.

Example 281: Synthesis of 5'-((3-endo)-3-amino-8-azabicyclo[3.2.1]octane-8-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 278 was conducted using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate to give the title compound.

Example 282: Synthesis of (S)-5'-((3-aminopyrrolidin-1-yl)methyl)-4''-methyl-[1,1':2',1''-terphenyl]-4-carbonitrile Step 1
3-Bromo-4-chloro-benzaldehyde (100 mg) and tert-butyl N-[(3S)-pyrrolidin-3-yl]carbamate (93.4 mg) were dissolved in MeOH (1.0 mL). At 0° C., acetic acid (0.1 mL) and borane-2-picoline complex (146 mg) were added thereto, followed by stirring at room temperature overnight. Ethyl acetate was added thereto, and the resulting mixture was washed sequentially with water and saturated brine, and dried over anhydrous sodium sulfate. The solvent was then distilled off. The residue was purified by silica gel column chromatography (mobile phase: hexane/ethyl acetate) to give tert-butyl N-[(3S)-1-[(3-bromo-4-chloro-phenyl)methyl]pyrrolidin-3-yl]carbamate.
Step 2
The tert-butyl N-[(3S)-1-[(3-bromo-4-chloro-phenyl)methyl]pyrrolidin-3-yl]carbamate (60 mg) obtained in step 1 above and (4-cyanophenyl)boronic acid (24.9 mg) were dissolved in 1,4-dioxane (0.77 mL). At room temperature, $PdCl_2(dppf)CH_2Cl_2$ (3.4 mg) and tripotassium phosphate (97.9 mg) were added thereto, followed by stirring at 125° C. for 45 minutes. The reaction mixture was filtrated, and the solvent was distilled off. The residue was purified by silica gel column chromatography (mobile phase: hexane/ethyl acetate) to give tert-butyl N-[(3S)-1-[[4-chloro-3-(4-cyanophenyl)phenyl]methyl]pyrrolidin-3-yl]carbamate.
Step 3
The tert-butyl N-[(3S)-1-[[4-chloro-3-(4-cyanophenyl)phenyl]methyl]pyrrolidin-3-yl]carbamate (20 mg) obtained in step 2 above, p-tolylboronic acid (13.2 mg), $Pd_2(dba)_3$ (2.23 mg), tripotassium phosphate (20.6 mg), and a solution of 1 M $PCy_3$ in THF (0.1 mL) were suspended in 1,4-dioxane (0.5 mL), followed by stirring at 160° C. for 45 minutes. The reaction mixture was filtered through NH-silica gel, and the solvent of the filtrate was distilled off. The residue was purified by silica gel column chromatography (mobile phase: hexane/ethyl acetate) to give tert-butyl N-[(3S)-1-[[3-(4-cyanophenyl)-4-(p-tolyl)phenyl]methyl]pyrrolidin-3-yl]carbamate.
Step 4
The tert-butyl N-[(3S)-1-[[3-(4-cyanophenyl)-4-(p-tolyl)phenyl]methyl]pyrrolidin-3-yl]carbamate (10 mg) obtained in step 3 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 283: Synthesis of 5'-(((1S,2S,4R)-rel-2-amino-7-azabicyclo[2.2.1]heptan-7-yl)methyl)-2'',3-difluoro-4''-methyl-[1,1':2',1''-terphenyl]-4-carbonitrile-isomer-X Step 1
3-Bromo-4-chloro-benzaldehyde (1.1 g) was dissolved in 1,4-dioxane (13 mL). At room temperature, (4-cyano-3-fluoro-phenyl)boronic acid (870 mg), $PdCl_2(dppf)CH_2Cl_2$ (110 mg), and a 2 M aqueous sodium carbonate solution (6.3 mL) were added thereto, followed by stirring at 90° C. for 5 hours. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 4-(2-chloro-5-formyl-phenyl)-2-fluoro-benzonitrile.
Step 2
The 4-(2-chloro-5-formyl-phenyl)-2-fluoro-benzonitrile (505 mg) obtained in step 1 above was dissolved in 1,4-dioxane (19.45 mL). At room temperature, (2-fluoro-4-methyl-phenyl)boronic acid (599 mg), $Pd_2dba_3$ (89 mg), a solution of 1 M $PCy_3$ in THF (0.1 mL), and tripotassium phosphate (1.24 g) were added thereto, and the mixture was stirred in a microwave reactor at 160° C. for 1 hour. The solvent was distilled off, and the residue was purified by silica gel column chromatography (mobile phase: hexane/ethyl acetate) to give 2-fluoro-4-[2-(2-fluoro-4-methyl-phenyl)-5-formyl-phenyl]benzonitrile.
Step 3
The 2-fluoro-4-[2-(2-fluoro-4-methyl-phenyl)-5-formyl-phenyl]benzonitrile (10 mg) obtained in step 2 above was dissolved in DCM (0.6 mL). At room temperature, the tert-butyl ((1S,2S,4R)-rel-7-azabicyclo[2.2.1]heptan-2-yl)carbamate-isomer-X (9.55 mg) synthesized in step 2 of Example 202 and sodium triacetoxyborohydride (25.4 mg) were added thereto, followed by stirring at room temperature for 1 hour. The solvent was distilled off, chloroform was added thereto, and the insoluble matter was filtered off. The solvent was distilled off, and acetonitrile (0.2 mL) and 4 N hydrochloric acid-1,4-dioxane solution (0.2 mL) were added thereto, followed by stirring for 10 minutes. DMSO (0.6 mL) was added thereto, and purification was performed by reversed-phase HPLC (mobile phase: water/acetonitrile) to give the title compound.

Example 284: Synthesis of (S)-5'-((3-amino-3-methylpyrrolidin-1-yl)methyl)-2'',3-difluoro-4''-methyl-[1,1':2',1''-terphenyl]-4-carbonitrile The procedure of step 3 in Example 283 was conducted using tert-butyl (S)-(3-methylpyrrolidin-3-yl)carbamate instead of tert-butyl ((1S,2S,4R)-rel-7-azabicyclo[2.2.1]heptan-2-yl)carbamate-isomer-X to give the title compound.

Example 285: Synthesis of 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X dihydrochloride Step 1

3-Bromo-4-chlorobenzoic acid (19 g) was dissolved in DMF (160 mL). At 25° C., DMAP (20 g) and WSC HCl (31 g) were added thereto, followed by the addition of t-BuOH (38 mL). The resulting mixture was stirred at room temperature overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl 3-bromo-4-chloro-benzoate.

Step 2

The tert-butyl 3-bromo-4-chloro-benzoate (1.00 g) obtained in step 1 above was dissolved in 1,4-dioxane (8.6 mL). At room temperature, (4-cyano-3-fluoro-phenyl)boronic acid (509 mg), Pd(PPh$_3$)$_4$ (119 mg), and a 2 M aqueous sodium carbonate solution (4.3 mL) were added thereto, and the reaction mixture was stirred in a microwave reactor at 120° C. for 30 minutes. The reaction mixture was filtrated, and the solvent was distilled off. The residue was purified by silica gel column chromatography (mobile phase: hexane/ethyl acetate) to give tert-butyl 4-chloro-3-(4-cyano-3-fluoro-phenyl)benzoate.

Step 3

The tert-butyl 4-chloro-3-(4-cyano-3-fluoro-phenyl)benzoate (300 mg) obtained in step 2 above was dissolved in 1,4-dioxane (5 mL). At room temperature, Pd(OAc)$_2$ (40 mg), KOAc (300 mg), bispinacolatodiboron (500 mg), and Silica-SMAP (50 mg) were added thereto, followed by stirring at 100° C. for 26 hours. The reaction mixture was filtrated, and the solvent was distilled off. The residue was purified by silica gel column chromatography (mobile phase: hexane/ethyl acetate) to give tert-butyl 3-(4-cyano-3-fluoro-phenyl)-4-(4,4,5,5-tetramethyl-1,3,2-dioxaborolan-2-yl)benzoate.

Step 4

1,2,3-Trifluoro-4-nitro-benzene (500 mg), 1-amino-2-methyl-propan-2-ol (302 mg), and triethylamine (0.590 mL) were dissolved in THF (5.65 mL), followed by stirring at 45° C. for 5 hours. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(2,3-difluoro-6-nitro-anilino)-2-methyl-propan-2-ol.

Step 5

The 1-(2,3-difluoro-6-nitro-anilino)-2-methyl-propan-2-ol (74.1 g) obtained in step 4 above was dissolved in DMF (602 mL). At room temperature, NBS (64.3 g) was added thereto, followed by stirring at 90° C. for 1 hour. Ethyl acetate was added thereto, and the mixture was washed 3 times with water. Subsequently, washing was performed with saturated brine, drying was performed over anhydrous sodium sulfate, and the solvent was then distilled off. The residue was crystallized from IPE:hexane=1:1, and the crystals were washed twice with hexane. The obtained crystals were dried to give 1-(4-bromo-2,3-difluoro-6-nitro-anilino)-2-methyl-propan-2-ol.

Step 6

The 1-(4-bromo-2,3-difluoro-6-nitro-anilino)-2-methyl-propan-2-ol (82.2 g) obtained in step 5 above, ammonium chloride (82.2 g), and iron powder (41.1 g) were suspended in EtOH (421 mL) and water (421 mL), followed by stirring at 60° C. overnight. MTBE was added thereto, and the mixture was passed through Celite. MTBE was added thereto, and the mixture was washed sequentially with water and saturated brine, and dried over anhydrous sodium sulfate. The solvent was then distilled off to give 1-(6-amino-4-bromo-2,3-difluoro-anilino)-2-methyl-propan-2-ol.

Step 7

The 1-(6-amino-4-bromo-2,3-difluoro-anilino)-2-methyl-propan-2-ol (68.1 g) obtained in step 6 above was dissolved in water (136 mL) and THF (341 mL). At 0° C., 12 N hydrochloric acid (204 mL) and sodium nitrite (an aqueous solution (60 mL) in which 20.7 g of sodium nitrite was dissolved) were added thereto dropwise over 3 minutes, followed by stirring at room temperature for 1 hour. MTBE was added thereto, and the mixture was washed sequentially with water and saturated brine, and dried over anhydrous sodium sulfate. The solvent was then distilled off. IPE:hexane=1:1 (68 mL) was added to the residue, and the generated solid was collected by filtration and washed with IPE:hexane=1:1. The obtained solid was dried to give 1-(5-bromo-6,7-difluoro-benzotriazol-1-yl)-2-methyl-propan-2-ol.

Step 8

The tert-butyl 3-(4-cyano-3-fluoro-phenyl)-4-(4,4,5,5-tetramethyl-1,3,2-dioxaborolan-2-yl)benzoate (3.2 g) obtained in step 3 above and the 1-(5-bromo-6,7-difluoro-benzotriazol-1-yl)-2-methyl-propan-2-ol (3.01 g) obtained in step 7 above were dissolved in 1,4-dioxane (25.2 mL). At room temperature, Pd(dba)$_2$ (348 mg), X-Phos (577 mg), and tripotassium phosphate (4.81 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (15.0 mL). At 0° C., 12 N hydrochloric acid (15.0 mL) was added thereto, followed by stirring at room temperature for 2 hours. MTBE was added thereto, the mixture was washed with water, and dried over anhydrous sodium sulfate, and the solvent was distilled off to give 3-(4-cyano-3-fluoro-phenyl)-4-[6,7-difluoro-1-(2-hydroxy-2-methyl-propyl)benzotriazol-5-yl]benzoic acid.

Step 9

The 3-(4-cyano-3-fluoro-phenyl)-4-[6,7-difluoro-1-(2-hydroxy-2-methyl-propyl)benzotriazol-5-yl]benzoic acid (120 mg) obtained in step 8 above was dissolved in THF (1.29 mL). At room temperature, WSC HCl (98.6 mg) and HOBt (78.8 mg) were added thereto, followed by stirring at room temperature for 20 minutes. Sodium borohydride (19.5 mg) was added thereto, followed by stirring for 1 hour. The solvent was distilled off under reduced pressure. The residue was purified by silica gel column chromatography (mobile phase: chloroform/methanol) to give 4-[2-[6,7-difluoro-1-(2-hydroxy-2-methyl-propyl)benzotriazol-5-yl]-5-(hydroxymethyl)phenyl]-2-fluoro-benzonitrile.

Step 10

The 4-[2-[6,7-difluoro-1-(2-hydroxy-2-methyl-propyl)benzotriazol-5-yl]-5-(hydroxymethyl)phenyl]-2-fluoro-benzonitrile (100 mg) obtained in step 9 above was dissolved in DCM (2.21 mL). At room temperature, Dess-Martin periodinane (103 mg) was added thereto, followed by stirring at room temperature overnight. The reaction mixture was vacuum-concentrated, and the residue was purified by silica gel column chromatography (mobile phase: hexane/ethyl acetate) to give 4-[2-[6,7-difluoro-1-(2-hydroxy-2-methyl-propyl)benzotriazol-5-yl]-5-formyl-phenyl]-2-fluoro-benzonitrile.
Step 11

The 4-[2-[6,7-difluoro-1-(2-hydroxy-2-methyl-propyl)benzotriazol-5-yl]-5-formyl-phenyl]-2-fluoro-benzonitrile (50 mg) obtained in step 10 above was dissolved in DCM (1.11 mL). At room temperature, the tert-butyl ((1S,2S,4R)-rel-7-azabicyclo[2.2.1]heptan-2-yl)carbamate-isomer-X (47.1 mg) synthesized in step 2 of Example 202 was added thereto, followed by stirring at room temperature for 30 minutes. At room temperature, sodium triacetoxyborohydride (94.1 mg) was added thereto, followed by stirring at room temperature overnight. After the addition of chloroform, the insoluble matter was filtered off, and the solvent was distilled off. The residue was purified by silica gel column chromatography (NH-silica gel, mobile phase: hexane/ethyl acetate), and the solvent was distilled off. The residue was dissolved in MeOH (1.0 mL), and a 4 N hydrochloric acid-1,4-dioxane solution (1.0 mL) was added thereto, followed by stirring for 30 minutes. The solvent was removed from the reaction mixture to give the title compound.

Example 286: Synthesis of 5'-(((1S,2S,4R)-rel-2-amino-7-azabicyclo[2.2.1]heptan-7-yl)methyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile-isomer-X dihydrochloride The procedure of steps 4 to 11 in Example 285 was conducted using 2-chloro-1,3-difluoro-4-nitro-benzene instead of 1,2,3-trifluoro-4-nitro-benzene, and using 1-(aminomethyl)cyclobutanol instead of 1-amino-2-methyl-propan-2-ol to give the title compound.

Example 287: Synthesis of 5'-(((1S,2S,4R)-rel-2-amino-7-azabicyclo[2.2.1]heptan-7-yl)methyl)-3-fluoro-2'-(6-fluoro-1-(2-hydroxy-2-methylpropyl)-1H-indazol-5-yl)-[1,1'-biphenyl]-4-carbonitrile-isomer-X dihydrochloride Step 1

5-Bromo-6-fluoro-1H-indazole (94 mg) was dissolved in DMF (1.5 ml). At room temperature, cesium carbonate (285 mg) and 2,2-dimethyloxirane (0.078 mL) were added thereto, followed by stirring at 90° C. for 16 hours. The reaction was quenched with a saturated aqueous ammonium chloride solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indazol-1-yl)-2-methyl-propan-2-ol.
Step 2

The procedure of steps 8 to 11 in Example 285 was conducted using the 1-(5-bromo-6-fluoro-indazol-1-yl)-2-methyl-propan-2-ol obtained in step 1 above instead of 1-(5-bromo-6,7-difluoro-benzotriazol-1-yl)-2-methyl-propan-2-ol to give the title compound.

Example 288: Synthesis of 5'-(((1S,2S,4R)-rel-2-amino-7-azabicyclo[2.2.1]heptan-7-yl)methyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile-isomer-X dihydrochloride The procedure of steps 4 to 11 in Example 285 was conducted using 2-chloro-1,3-difluoro-4-nitro-benzene instead of 1,2,3-trifluoro-4-nitro-benzene, and using 3-(aminomethyl)pentan-3-ol instead of 1-amino-2-methyl-propan-2-ol to give the title compound.

Example 289: Synthesis of 5'-(((1S,2S,4R)-rel-2-amino-7-azabicyclo[2.2.1]heptan-7-yl)methyl)-3-fluoro-2'-(6-fluoro-1-(2-hydroxy-2-methylpropyl)-1H-indol-5-yl)-[1,1'-biphenyl]-4-carbonitrile-isomer-X dihydrochloride Step 1

5-Bromo-6-fluoro-1H-indole (50 mg) was dissolved in DMF (0.78 mL). At room temperature, cesium carbonate (151 mg) and 2,2-dimethyloxirane (42 μL) were added thereto, followed by stirring at 90° C. for 16 hours. The reaction was quenched with a saturated aqueous ammonium chloride solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indol-1-yl)-2-methyl-propan-2-ol.
Step 2

The procedure of steps 8 to 11 in Example 285 was conducted using the 1-(5-bromo-6-fluoro-indol-1-yl)-2-methyl-propan-2-ol obtained in step 1 above instead of 1-(5-bromo-6,7-difluoro-benzotriazol-1-yl)-2-methyl-propan-2-ol to give the title compound.

Example 290: Synthesis of 5'-(((1S,2S,4R)-rel-2-amino-7-azabicyclo[2.2.1]heptan-7-yl)methyl)-2",3-difluoro-4"-(2-hydroxy-2-methylpropyl)-[1,1':2',1"-terphenyl]-4-carbonitrile-isomer-x dihydrochloride Step 1

Methyl 2-(4-bromo-3-fluoro-phenyl)acetate (500 mg) was dissolved in THF (2.2 mL). At −30° C., a solution of 3 M MeMgBr in diethyl ether (5.40 mL) was added thereto dropwise, followed by stirring at room temperature overnight. The reaction mixture was introduced into an aqueous ammonium chloride solution, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(4-bromo-3-fluoro-phenyl)-2-methyl-propan-2-ol.
Step 2

The procedure of steps 8 to 11 in Example 285 was conducted using the 1-(4-bromo-3-fluoro-phenyl)-2-methyl-propan-2-ol obtained in step 1 above instead of 1-(5-bromo-6,7-difluoro-benzotriazol-1-yl)-2-methyl-propan-2-ol to give the title compound.

Example 291: Synthesis of (S)-5'-((3-aminopyrrolidin-1-yl)methyl)-2",3-difluoro-4"-(2-hydroxy-2-methylpropyl)-[1,1':2',1"-terphenyl]-4-carbonitrile dihydrochloride The procedure of steps 8 to 11 in Example 285 was conducted using the 1-(4-bromo-3-fluoro-phenyl)-2-methyl-propan-2-ol obtained in step 1 of Example 290 instead of 1-(5-bromo-6,7-difluoro-benzotriazol-1-yl)-2-methyl-propan-2-ol, and using tert-butyl N-[(3S)-pyrrolidin-3-yl]carbamate instead of tert-butyl ((1S,2S,4R)-rel-7-azabicyclo[2.2.1]heptan-2-yl)carbamate-isomer-X to give the title compound.

Example 292: Synthesis of 5'-(1-((1S,2S,4R)-rel-2-amino-7-azabicyclo[2.2.1]heptan-7-yl)ethyl)-2",3-difluoro-4"-methyl-[1,1':2',1"-terphenyl]-4-carbonitrile-isomer-X dihydrochloride Step 1

1-(3-Bromo-4-chloro-phenyl)ethanone (2.00 g) was dissolved in 1,4-dioxane (14.3 mL). At room temperature, (4-cyano-3-fluoro-phenyl)boronic acid (1.55 g), PdCl$_2$(dppf)CH$_2$Cl$_2$ (188 mg), and a 2 M aqueous sodium carbonate solution (10.7 mL) were added thereto, followed by stirring at 90° C. overnight. Ethyl acetate was added thereto, and the resulting mixture was washed sequentially with water and saturated brine. After the organic layer was dried over anhydrous sodium sulfate, the solvent was distilled off. Diethyl ether was added thereto, and the precipitate was collected by filtration to give 4-(5-acetyl-2-chloro-phenyl)-2-fluoro-benzonitrile.

Step 2

The 4-(5-acetyl-2-chloro-phenyl)-2-fluoro-benzonitrile (200 mg) obtained in step 1 above and the tert-butyl ((1S,2S,4R)-rel-7-azabicyclo[2.2.1]heptan-2-yl)carbamate-isomer-X (160 mg) synthesized in step 2 of Example 202 were suspended in titanium isopropoxide (1.0 mL), followed by stirring for 3 days. EtOH (5 mL) and sodium borohydride (138 mg) were added thereto, followed by stirring for 1 hour. The mixture was diluted with THF, Celite was added thereto, filtration was performed through a Celite bed, and the solvent was distilled off. The residue was purified by silica gel column chromatography (NH silica, mobile phase: hexane/ethyl acetate) to give tert-butyl N-[(1S,3R,4R)-7-[1-[4-chloro-3-(4-cyano-3-fluoro-phenyl)phenyl]ethyl]-7-azabicyclo[2.2.1]heptan-3-yl]carbamate.

Step 3

The tert-butyl N-[(1S,3R,4R)-7-[1-[4-chloro-3-(4-cyano-3-fluoro-phenyl)phenyl]ethyl]-7-azabicyclo[2.2.1]heptan-3-yl]carbamate (20 mg) obtained in step 2 above was dissolved in DMF (0.50 mL). At room temperature, (2-fluoro-4-methyl-phenyl)boronic acid (19.7 mg), S-Phos (1.75 mg), Pd(dba)$_2$ (1.22 mg), and tripotassium phosphate (27.1 mg) were added thereto, and the mixture was stirred in a microwave reactor at 160° C. for 45 minutes. MTBE was added thereto, and the mixture was washed 3 times with water. Subsequently, washing was performed with saturated brine, drying was performed over anhydrous sodium sulfate, and the solvent was then distilled off. The residue was purified by reversed-phase HPLC (mobile phase: water/acetonitrile), and the target fractions were combined, neutralized with an aqueous sodium hydrogen carbonate solution, and extracted twice with chloroform. The solvent was distilled off, the residue was dissolved in MeOH (1.0 mL), and a 4 N hydrochloric acid-1,4-dioxane solution (1.0 mL) was added thereto, followed by stirring for 30 minutes. The solvent was removed from the reaction mixture to give the title compound.

Example 293: Synthesis of 5'-(((1S,2S,4R)-rel-2-amino-7-azabicyclo[2.2.1]heptan-7-yl)methyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X dihydrochloride The procedure of steps 4 to 11 in Example 285 was conducted using 3-(aminomethyl)pentan-3-ol instead of 1-amino-2-methyl-propan-2-ol to give the title compound.

Example 294: Synthesis of 5'-((1S,2S,4R)-rel-2-amino-7-azabicyclo[2.2.1]heptan-7-yl)methyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X dihydrochloride Step 1

2-Bromo-1,3-difluoro-4-nitro-benzene (3.00 g) was dissolved in THF (31.5 mL). TEA (2.63 mL) and 1-amino-2-methyl-propan-2-ol (1.40 mL) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(2-bromo-3-fluoro-6-nitro-anilino)-2-methyl-propan-2-ol.

Step 2

The 1-(2-bromo-3-fluoro-6-nitro-anilino)-2-methyl-propan-2-ol (1.03 g) obtained in step 1 above was dissolved in acetic acid (6.7 mL). At room temperature, N-iodosuccinimide (981 mg) was added thereto, followed by stirring at 50° C. for 3 hours. MTBE and water were added thereto, and the mixture was extracted twice with MTBE. After the combined organic layers were dried over anhydrous sodium sulfate, the solvent was distilled off. The residue was purified by silica gel column chromatography (mobile phase: hexane/ethyl acetate) to give 1-(2-bromo-3-fluoro-4-iodo-6-nitro-anilino)-2-methyl-propan-2-ol.

Step 3

The 1-(2-bromo-3-fluoro-4-iodo-6-nitro-anilino)-2-methyl-propan-2-ol (1.33 g) obtained in step 2 above and iron powder (1.33 g) were suspended in THF (10.2 mL) and a 2 N hydrochloric acid (10.2 mL), followed by stirring at 60° C. for 1 hour. MTBE was added thereto, and the mixture was passed through Celite. MTBE was added thereto, and the mixture was washed sequentially with water and saturated brine, and dried over anhydrous sodium sulfate. The solvent was then distilled off. The residue was purified by silica gel column chromatography (mobile phase: hexane/ethyl acetate) to give 1-(6-amino-2-bromo-3-fluoro-4-iodo-anilino)-2-methyl-propan-2-ol.

Step 4

The 1-(6-amino-2-bromo-3-fluoro-4-iodo-anilino)-2-methyl-propan-2-ol (940 mg) obtained in step 3 above was dissolved in water (1.88 mL) and THF (4.7 mL). At 0° C., 12 N hydrochloric acid (2.82 mL) and an aqueous sodium nitrite solution (an aqueous solution obtained by dissolving 209 mg of sodium nitrite in 0.63 mL of water) were added thereto, followed by stirring at room temperature for 1 hour. MTBE was added thereto, and the mixture was washed sequentially with water and saturated brine, and dried over anhydrous sodium sulfate. The solvent was then distilled off. The residue was purified by silica gel column chromatography (mobile phase: hexane/ethyl acetate) to give 1-(7-bromo-6-fluoro-5-iodo-benzotriazol-1-yl)-2-methyl-propan-2-ol.

Step 5

The tert-butyl 3-(4-cyano-3-fluoro-phenyl)-4-(4,4,5,5-tetramethyl-1,3,2-dioxaborolan-2-yl)benzoate (3 g) obtained in step 3 of Example 285 and the 1-(7-bromo-6-fluoro-5-iodo-benzotriazol-1-yl)-2-methyl-propan-2-ol (3.228 g) obtained in step 5 above were dissolved in 1,4-dioxane (23.6 mL). At room temperature, PdCl$_2$(PPh$_3$)$_2$ (398 mg) and tripotassium phosphate (4.513 g) were added thereto. After nitrogen substitution and degassing, the mixture was stirred at 100° C. overnight. The reaction mixture was passed through Celite, and the solvent was distilled off. The residue was purified by silica gel column chromatography (mobile phase: hexane/ethyl acetate), and the solvent was distilled off. THF (45.0 mL) and 12 N hydrochloric acid (45.0 mL) were added to the residue, followed by stirring at room temperature for 2 hours. MTBE and water were added thereto for partition. After the organic layer was washed with saturated brine and dried over anhydrous sodium sulfate, the solvent was distilled off. The residue was crystallized from diethyl ether/hexane to give 4-[7-bromo-6-fluoro-1-(2-hydroxy-2-methyl-propyl)benzotriazol-5-yl]-3-(4-cyano-3-fluoro-phenyl)benzoic acid.

Step 6

The 4-[7-bromo-6-fluoro-1-(2-hydroxy-2-methyl-propyl)benzotriazol-5-yl]-3-(4-cyano-3-fluoro-phenyl)benzoic acid (88.0 mg) obtained in step 5 above was dissolved in THF (0.834 mL). At room temperature, WSC HCl (64.0 mg) and HOBt (51.1 mg) were added thereto, followed by stirring at room temperature for 20 minutes. Sodium borohydride (18.9 mg) was added thereto, followed by stirring for 1 hour. The solvent was distilled off under reduced pressure. The residue was purified by silica gel column chromatography (mobile phase: hexane/ethyl acetate) to give 4-[2-[7-bromo-6-fluoro-1-(2-hydroxy-2-methyl-propyl)benzotriazol-5-yl]-5-(hydroxymethyl)phenyl]-2-fluoro-benzonitrile.

Step 7

The 4-[2-[7-bromo-6-fluoro-1-(2-hydroxy-2-methyl-propyl)benzotriazol-5-yl]-5-(hydroxymethyl)phenyl]-2-fluoro-benzonitrile (43.5 mg) obtained in step 6 above was dissolved in DCM (0.847 mL). At room temperature, Dess-Martin periodinane (39.5 mg) was added thereto, followed by stirring at room temperature overnight. The reaction mixture was vacuum-concentrated, and the residue was purified by silica gel column chromatography (mobile phase: hexane/ethyl acetate) to give 4-[2-[7-bromo-6-fluoro-1-(2-hydroxy-2-methyl-propyl)benzotriazol-5-yl]-5-formyl-phenyl]-2-fluoro-benzonitrile.

Step 8

The 4-[2-[7-bromo-6-fluoro-1-(2-hydroxy-2-methyl-propyl)benzotriazol-5-yl]-5-formyl-phenyl]-2-fluoro-benzonitrile (37.2 mg) obtained in step 7 above was dissolved in DCM (1.00 mL). At room temperature, the tert-butyl ((1S,2S,4R)-rel-7-azabicyclo[2.2.1]heptan-2-yl)carbamate-isomer-X (30.9 mg) synthesized in step 2 of Example 202 was added thereto, followed by stirring at room temperature for 30 minutes. At room temperature, sodium triacetoxyborohydride (27.8 mg) was added thereto, followed by stirring at room temperature overnight. After the addition of chloroform, the insoluble matter was filtered off, and the solvent was distilled off. The residue was purified by silica gel column chromatography (NH-silica gel, mobile phase: hexane/ethyl acetate), and the solvent was distilled off. The residue was dissolved in MeOH (1.0 mL), and a 4 N hydrochloric acid-1,4-dioxane solution (1.0 mL) was added thereto, followed by stirring for 30 minutes. The solvent was removed from the reaction mixture to give the title compound.

Example 295: Synthesis of 5'-(((1S,2S,4R)-rel-2-amino-7-azabicyclo[2.2.1]heptan-7-yl)methyl)-2'-(7-bromo-1-(2-ethyl-2-hydroxybutyl)-6-fluoro-1H-benzo[d][1,2,3]triazol-5-yl)-3-fluoro-[1,1'-biphenyl]-4-carbonitrile-isomer-X dihydrochloride The procedure of steps 1 to 8 in Example 294 was conducted using 3-(aminomethyl)pentan-3-ol instead of 1-amino-2-methyl-propan-2-ol to give the title compound.

The following are lists of the compounds of Examples 1 to 295.

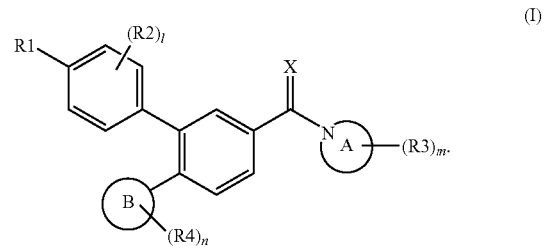

(I)

In the following tables, if the structure:

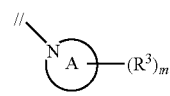

is shown as:

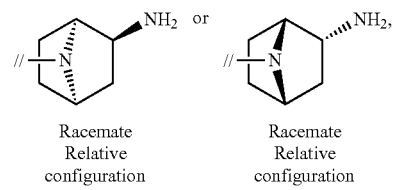

Racemate
Relative
configuration

Racemate
Relative
configuration then the compound represents a mixture of compounds having the structure:

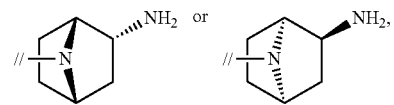

if the structure is shown as:

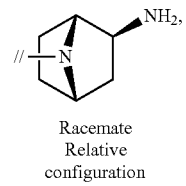

Racemate
Relative
configuration then the compound represents a mixture of compounds having the structure:

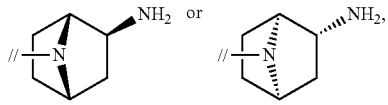

and if the structure is shown as:

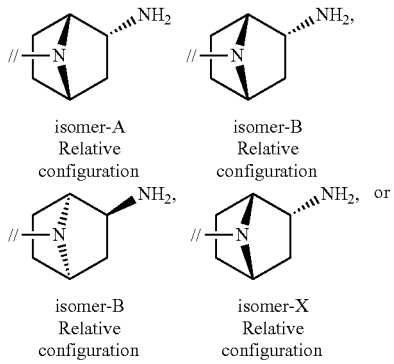

isomer-A
Relative configuration isomer-B
Relative configuration isomer-B
Relative configuration isomer-X
Relative configuration

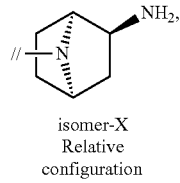

isomer-X
Relative configuration then the compound has one of the following structures:

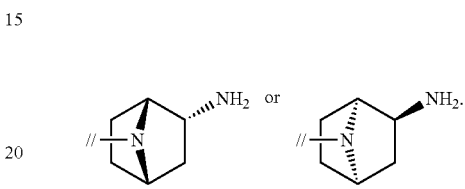

The term "salt form" indicates a salt form. The term "free" indicates a free form.

TABLE 1

| Ex. No. | R¹—⟨⟩—(R²)ₗ | ⟨N-A⟩—(R³)ₘ | ⟨B⟩—(R⁴)ₙ | R5 R6 | salt form | MS m/z (M + 1) | NMR |
|---|---|---|---|---|---|---|---|
| 1 | 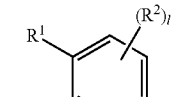 | 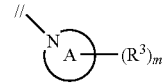 | 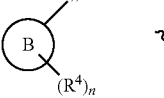 | 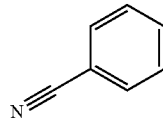 | free | 382.4 | 1H-NMR (DMSO-D6) δ: 7.74 (2H, d, J = 8.1 Hz), 7.66-7.61 (1H, m), 7.53 (1H, d, J = 8.4 Hz), 7.49 (1H, d, J = 8.1 Hz), 7.33 (2H, d, J = 6.1 Hz), 7.09 (2H, d, J = 8.1 Hz), 7.01 (2H, d, J = 7.7 Hz), 3.70-3.40 (4H, m), 3.24-3.13 (1H, m), 2.27 (3H, s), 2.03-1.90 (1H, m), 1.70-1.59 (1H, m). |
| 2 | 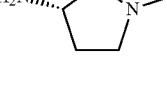 | 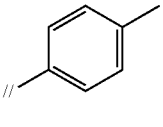 |  | 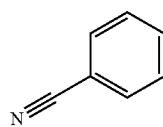 | free | 398.2 | 1H-NMR (DMSO-D6) δ: 7.74 (2H, d, J = 8.2 Hz), 7.52-7.49 (1H, m), 7.45-7.41 (2H, m), 7.32 (2H, dd, J = 8.4, 2.3 Hz), 7.09 (2H, d, J = 8.2 Hz), 7.01 (2H, d, J = 8.2 Hz), 3.99-3.51 (4H, m), 2.27 (3H, s), 2.15-2.01 (1H, m), 1.83-1.70 (1H, m), 1.31-1.19 (1H, m). |
| 3 | 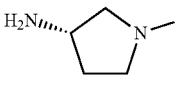 | 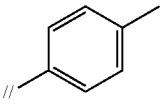 |  | 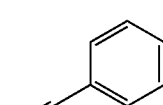 | free | 396.4 | 1H-NMR (DMSO-D6) δ: 7.74 (2H, d, J = 8.1 Hz), 7.49 (2H, s), 7.38 (1H, s), 7.33 (2H, d, J = 8.1 Hz), 7.09 (2H, d, J = 8.1 Hz), 7.01 (2H, d, J = 8.1 Hz), 4.38-4.23 (1H, m), 3.73-3.61 (1H, m), 3.16-3.05 (1H, m), 3.01-2.89 (1H, m), 2.87-2.79 (1H, m), 2.27 (3H, s), 1.87-1.64 (4H, m). |

TABLE 1-continued

| Ex. No. | R¹─⟨⟩─(R²)ₗ | ⟨N-A⟩-(R³)ₘ | ⟨B⟩-(R⁴)ₙ | R5,R6 | salt form | MS m/z (M + 1) | NMR |
|---|---|---|---|---|---|---|---|
| 4 | 4-CN-phenyl | 2,7-diazaspiro[3.5]nonane (HN-piperidine/azetidine spiro) | 4-methylphenyl | C=O | free | 422.5 | 1H-NMR (DMSO-D6) δ: 7.76 (3H, d, J = 8.2 Hz), 7.63 (1H, s), 7.53 (1H, d, J = 7.6 Hz), 7.32 (2H, d, J = 8.2 Hz), 7.10 (2H, d, J = 7.6 Hz), 7.00 (2H, d, J = 7.6 Hz), 4.24 (1H, d, J = 8.9 Hz), 4.12 (1H, d, J = 8.9 Hz), 3.95 (1H, d, J = 9.5 Hz), 3.78 (1H, d, J = 10.2 Hz), 3.51 (2H, s), 2.95 (2H, s), 2.27 (3H, s), 1.86-1.80 (2H, m), 1.71-1.60 (2H, m). |
| 5 | 4-CN-phenyl | 2,6-diazaspiro[3.4]octane | 4-methylphenyl | C=O | free | 408.5 | 1H-NMR (DMSO-D6) δ: 7.76 (2H, d, J = 8.2 Hz), 7.67-7.61 (1H, m), 7.58-7.47 (2H, m), 7.35-7.29 (2H, m), 7.14-7.07 (2H, m), 7.00 (2H, d, J = 8.2 Hz), 4.12-4.03 (1H, m), 3.96-3.84 (2H, m), 3.76-3.71 (2H, m), 3.59-3.47 (3H, m), 2.26 (3H, s), 2.19-2.11 (2H, m). |
| 6 | 4-CN-phenyl | 2,7-diazaspiro[4.4]nonane | 4-methylphenyl | C=O | free | 422.2 | 1H-NMR (DMSO-D6) δ: 7.76 (2H, t, J = 4.3 Hz), 7.65 (1H, dd, J = 7.9, 1.8 Hz), 7.56 (1H, dd, J = 18.9, 1.5 Hz), 7.50 (1H, d, J = 7.9 Hz), 7.34 (2H, d, J = 8.2 Hz), 7.11 (2H, d, J = 7.6 Hz), 7.01 (2H, dd, J = 8.2, 2.4 Hz), 3.61-3.47 (4H, m), 2.95 (4H, t, J = 1.7 Hz), 2.28 (3H, s), 1.92-1.72 (4H, m). |
| 7 | 4-CN-phenyl | 8-azabicyclo[3.2.1]octan-3-amine | 4-methylphenyl | C=O | free | 422.3 | 1H-NMR (DMSO-D6) δ: 7.73 (2H, d, J = 8.4 Hz), 7.56 (1H, d, J = 7.7 Hz), 7.50 (1H, d, J = 7.7 Hz), 7.44 (1H, s), 7.32 (2H, d, J = 8.4 Hz), 7.08 (2H, d, J = 8.1 Hz), 6.99 (2H, d, J = 7.7 Hz), 4.65-4.57 (1H, m), 4.19-4.11 (1H, m), 3.47-3.35 (2H, m), 2.26 (2H, s), 2.04-1.44 (8H, m). |
| 8 | 4-CN-phenyl | 3-amino-3-methylpyrrolidine | 4-methylphenyl | C=O | free | 396.1 | 1H-NMR (DMSO-D6) δ: 7.76 (2H, d, J = 8.2 Hz), 7.69-7.61 (1H, m), 7.51 (2H, d, J = 7.9 Hz), 7.33-7.32 (2H, m), 7.10 (2H, d, J = 7.9 Hz), 7.01 (2H, d, J = 7.0 Hz), 3.81-3.40 (4H, m), 2.27 (3H, s), 2.03-1.90 (2H, m), 1.44-1.22 (3H, m). |

TABLE 2

| | | | | | | | |
|---|---|---|---|---|---|---|---|
| 9 | 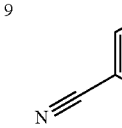 | 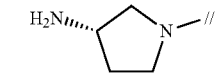 | 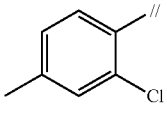 |  | free | 416.0 418.0 | 1H-NMR (DMSO-D6) δ: 7.74 (2H, d, J = 8.2 Hz), 7.67-7.59 (2H, m), 7.44 (1H, d, J = 7.9 Hz), 7.34-7.23 (3H, m), 7.16-7.10 (2H, m), 3.95-3.45 (5H, m), 2.29 (3H, s), 2.28-2.19 (1H, m), 2.06-1.96 (1H, m). |
| 10 | 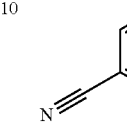 |  | 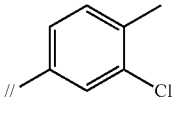 |  | free | 416.2 418.1 | 1H-NMR (DMSO-D6) δ: 7.72 (2H, d, J = 8.2 Hz), 7.62-7.57 (1H, m), 7.50 (2H, d, J = 8.2 Hz), 7.28 (2H, d, J = 7.6 Hz), 7.17 (2H, d, J = 9.5 Hz), 6.85 (1H, d, J = 7.0 Hz), 3.82-3.52 (5H, m), 2.22 (3H, s), 2.19-2.12 (1H, m), 1.95-1.87 (1H, m). |
| 11 | 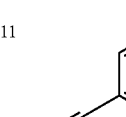 |  | 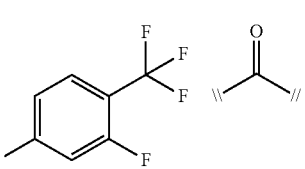 |  | free | 454.2 | 1H-NMR (DMSO-D6) δ: 7.74 (2H, d, J = 8.2 Hz), 7.66-7.52 (4H, m), 7.35-7.26 (3H, m), 7.01 (1H, d, J = 8.2 Hz), 3.86-3.47 (5H, m), 2.23-2.10 (1H, m), 1.98-1.87 (1H, m). |
| 12 | 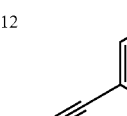 | 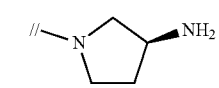 | 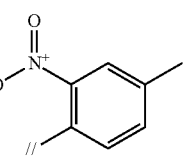 |  | free | 427.2 | 1H-NMR (DMSO-D6) δ: 7.80 (2H, d, J = 8.2 Hz), 7.76 (1H, s), 7.73-7.67 (1H, m), 7.66-7.58 (2H, m), 7.43-7.35 (3H, m), 7.31 (1H, d, J = 7.6 Hz), 4.13-4.07 (1H, m), 3.92-3.67 (2H, m), 3.64-3.49 (2H, m), 3.16 (3H, s), 2.28-2.15 (1H, m), 2.02-1.91 (1H, m). |
| 13 | 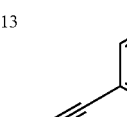 |  | 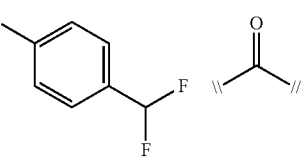 |  | free | 418.2 | 1H-NMR (DMSO-D6) δ: 7.70 (2H, d, J = 8.2 Hz), 7.65-7.59 (1H, m), 7.52 (2H, d, J = 8.2 Hz), 7.43 (2H, d, J = 8.2 Hz), 7.27 (2H, d, J = 7.0 Hz), 7.20 (2H, d, J = 8.2 Hz), 3.87-3.48 (5H, m), 3.14-3.06 (1H, m), 2.22-2.10 (1H, m), 1.99-1.86 (1H, m). |
| 14 | 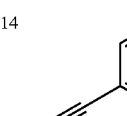 |  | 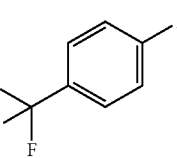 |  | free | 436.2 | 1H-NMR (DMSO-D6) δ: 7.71 (2H, d, J = 8.2 Hz), 7.65-7.58 (3H, m), 7.54 (2H, d, J = 7.6 Hz), 7.33-7.24 (4H, m), 3.83-3.53 (5H, m), 2.23-2.11 (1H, m), 1.98-1.89 (1H, m). |
| 15 | 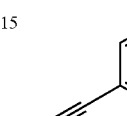 |  | 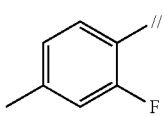 |  | free | 400.2 | 1H-NMR (DMSO-D6) δ: 7.68 (2H, d, J = 8.2 Hz), 7.63-7.56 (1H, m), 7.56-7.49 (1H, m), 7.44 (1H, d, J = 8.2 Hz), 7.24 (2H, d, J = 7.6 Hz), 7.10 (1H, t, J = 7.9 Hz), 6.95 (1H, d, J = 7.6 Hz), 6.85 (1H, d, J = 10.8 Hz), 3.83-3.53 (5H, m), 2.22 (3H, s), 2.19-2.10 (1H, m), 1.98-1.88 (1H, m). |
| 16 | 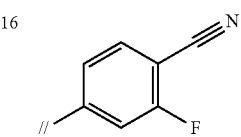 |  | 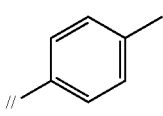 |  | free | 400.1 | 1H-NMR (DMSO-D6) δ: 7.75 (1H, t, J = 7.6 Hz), 7.60 (1H, d, J = 7.6 Hz), 7.47 (1H, d, J = 7.6 Hz), 7.33-7.24 (1H, m), 7.07-6.95 (6H, m), 4.02-3.52 (5H, m), 2.22 (3H, s), |

TABLE 2-continued
| | | | | | | | |
|---|---|---|---|---|---|---|---|
| | | | | | | | 2.18-2.11 (1H, m), 1.98-1.87 (1H, m). |
| 17 | 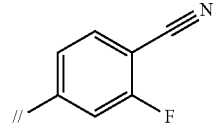 |  | 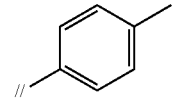 |  | free | 440.2 | 1H-NMR (DMSO-D6) δ: 7.80 (1H, t, J = 7.5 Hz), 7.61-7.58 (1H, m), 7.52-7.49 (2H, m), 7.38 (1H, dd, J = 10.5, 1.4 Hz), 7.12 (2H, d, J = 7.9 Hz), 7.11-7.09 (1H, m), 7.04 (2H, d, J = 7.9 Hz), 4.63-4.57 (1H, m), 4.14-4.06 (1H, m), 2.28 (3H, s), 2.24-2.02 (2H, m), 2.00-1.89 (1H, m), 1.84-1.51 (3H, m), 1.34-1.14 (3H, m). |
| 18 | 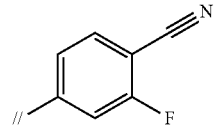 |  | 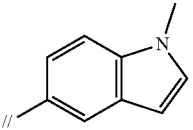 |  | free | 479.2 | 1H-NMR (DMSO-D6) δ: 7.76 (1H, t, J = 7.5 Hz), 7.62-7.56 (2H, m), 7.51-7.50 (1H, m), 7.44-7.42 (1H, m), 7.41-7.37 (1H, m), 7.35-7.31 (2H, m), 7.11 (1H, d, J = 8.2 Hz), 6.83 (1H, d, J = 8.2 Hz), 6.40 (1H, d, J = 3.1 Hz), 4.65-4.58 (1H, m), 4.22-4.10 (1H, m), 3.77 (3H, s), 3.74-3.72 (1H, m), 2.04-1.19 (8H, m). |

| | | | | | | NMR |
|---|---|---|---|---|---|---|
| 19 | F-C≡N-F benzonitrile | N-methylpyrrolidin-3-amine | p-tolyl | acetyl | free | 418.1 | 1H-NMR (DMSO-D6) δ: 7.71-7.68 (1H, m), 7.62 (1H, s), 7.55 (1H, d, J = 7.9 Hz), 7.24-7.13 (4H, m), 7.06 (2H, d, J = 7.9 Hz), 3.90-3.53 (4H, m), 3.49-3.41 (1H, m), 2.30 (3H, s), 2.25-2.16 (1H, m), 1.99-1.93 (1H, m). |
| 20 | 2-fluoro-4-substituted benzonitrile | N-methylpyrrolidin-3-amine | 3-fluoro-4-(2-methoxyethyl)phenyl | acetyl | free | 462.1 | 1H-NMR (DMSO-D6) δ: 7.80 (1H, t, J = 7.5 Hz), 7.70-7.66 (1H, m), 7.62 (1H, dd, J = 6.6, 1.5 Hz), 7.51 (1H, d, J = 7.7 Hz), 7.33 (1H, d, J = 10.6 Hz), 7.24 (1H, t, J = 7.9 Hz), 7.13-7.08 (2H, m), 7.00 (1H, d, J = 10.3 Hz), 3.68-3.56 (2H, m), 3.55-3.40 (4H, m), 3.23 (3H, s), 3.22-3.11 (1H, m), 2.81 (2H, t, J = 6.6 Hz), 2.03-1.88 (1H, m), 1.69-1.57 (1H, m). |
| 21 | 2-fluoro-4-substituted benzonitrile | tropane-3-amine | 3-fluoro-4-methylphenyl | acetyl | free | 458.2 | 1H-NMR (DMSO-D6) δ: 7.81 (1H, t, J = 7.6 Hz), 7.61 (1H, d, J = 1.5 Hz), 7.50 (1H, d, J = 7.6 Hz), 7.37 (1H, d, J = 9.2 Hz), 7.21 (1H, t, J = 7.9 Hz), 7.11 (1H, dd, J = 8.2 Hz), 7.05 (1H, d, J = 8.2 Hz), 6.95 (1H, d, J = 11.3 Hz), 4.63-4.57 (1H, m), 4.12-4.05 (1H, m), 2.31 (3H, s), 2.25-2.02 (3H, m), 2.00-1.69 (3H, m), 1.65-1.50 (2H, m), 1.47-1.34 (1H, m). |
| 22 | 2-fluoro-4-substituted benzonitrile | tropane-3-amine | 3-fluoro-4-(2-methoxyethyl)phenyl | acetyl | free | 502.2 | 1H-NMR (DMSO-D6) δ: 7.81 (1H, t, J = 7.5 Hz), 7.62 (1H, dd, J = 7.8, 1.7 Hz), 7.56-7.52 (2H, m), 7.35 (1H, dd, J = 10.5, 1.4 Hz), 7.24 (1H, t, J = 7.9 Hz), 7.13-7.09 (2H, m), 7.02-6.99 (1H, m), 4.62 (1H, s), 4.10 (1H, s), 3.53 (2H, t, J = 6.7 Hz), 3.40-3.34 (1H, m), 3.23 (3H, s), 2.81 (2H, t, J = 6.7 Hz), 2.33-1.90 (6H, m), 1.70-1.55 (2H, m). |
| 23 | 2-fluoro-4-substituted benzonitrile | tropane-3-amine | 5-fluoro-1-methylindol-6-yl | acetyl | free | 497.2 | 1H-NMR (DMSO-D6) δ: 7.76 (1H, t, J = 7.6 Hz), 7.62 (1H, dd, J = 7.8, 1.7 Hz), 7.57-7.50 (3H, m), 7.39-7.34 (2H, m), 7.22 (1H, d, J = 11.3 Hz), 7.13-7.09 (1H, m), 6.46-6.43 (1H, m), 4.63 (1H, s), 3.74 (3H, s), 4.15 (1H, s), 3.19-3.13 (1H, m), 2.05-1.78 (4H, m), 1.77-1.67 (2H, m), 1.65-1.56 (1H, m), 1.48-1.39 (1H, m). |

TABLE 3-continued

| | | | | | |
|---|---|---|---|---|---|
| 24 | (2-fluoro-4-iodo benzonitrile) | (8-methyl-8-azabicyclo[3.2.1]octan-3-amine) | (6-fluoro-1-methyl-1H-indazol-5-yl) | acetyl | free | 498.2 | 1H-NMR (DMSO-D6) δ: 8.09 (1H, d, J = 0.9 Hz), 7.81-7.75 (2H, m), 7.65 (1H, dd, J = 7.8, 1.7 Hz), 7.60-7.55 (2H, m), 7.46 (1H, d, J = 10.7 Hz), 7.41 (1H, dd, J = 10.5, 1.4 Hz), 7.11 (1H, dd, J = 7.9, 1.5 Hz), 4.64 (1H, s), 4.14 (1H, s), 3.99 (3H, s), 3.36-3.30 (1H, m), 2.06-1.44 (8H, m). |
| 25 | (2-fluoro-4-iodo benzonitrile) | (3-methylpyrrolidin-3-amine) | (4-fluoro-3-(2-methoxyethyl)phenyl) | acetyl | free | 476.1 | 1H-NMR (DMSO-D6) δ: 7.85-7.80 (1H, m), 7.74-7.59 (2H, m), 7.55 (1H, d, J = 7.9 Hz), 7.35-7.29 (1H, m), 7.26-7.21 (1H, m), 7.11 (2H, d, J = 7.9 Hz), 7.01 (1H, d, J = 11.0 Hz), 3.79-3.44 (6H, m), 3.23 (3H, s), 2.85-2.79 (2H, m), 2.10-1.98 (2H, m), 1.47-1.27 (3H, m). |

TABLE 4

| | | | | | NMR |
|---|---|---|---|---|---|
| 26 | (4-cyano-3-fluorophenyl) | (tropane-NH2, exo) | (3-fluoro-4-(2-methoxyethyl)phenyl) | acyl | free | 502.1 | 1H-NMR (DMSO-D6) δ: 7.82 (1H, t, J = 7.5 Hz), 7.63 (1H, d, J = 7.9 Hz), 7.57-7.52 (2H, m), 7.34 (1H, t, J = 9.8 Hz), 7.24 (1H, d, J = 7.9 Hz), 7.15-7.09 (2H, m), 7.01 (1H, s), 4.63 (1H, d, J = 11.3 Hz), 4.13 (1H, s), 3.53 (2H, t, J = 5.6 Hz), 3.42-3.36 (1H, m), 3.23 (3H, s), 2.81 (2H, t, J = 6.6 Hz), 2.09-1.45 (8H, m). |
| 27 | | | | | free | 488.2 | 1H-NMR (DMSO-D6) δ: 7.83-7.78 (1H, m), 7.71-7.48 (3H, m), 7.39-7.31 (1H, m), 7.27-7.21 (1H, m), 7.15-7.08 (2H, m), 7.03-6.98 (1H, m), 4.77-4.47 (1H, m), 4.29-3.95 (1H, m), 3.66-3.38 (4H, m), 3.23 (3H, d, J = 0.9 Hz), 2.99-2.88 (1H, m), 2.81 (2H, t, J = 6.5 Hz), 2.72-2.55 (1H, m), 2.01-1.43 (4H, m). |
| 28 | | | | | free | 516.3 | 1H-NMR (DMSO-D6) δ: 7.80 (1H, t, J = 7.5 Hz), 7.64-7.61 (1H, m), 7.57-7.52 (2H, m), 7.29-7.26 (1H, m), 7.21 (1H, t, J = 7.9 Hz), 7.15 (1H, dd, J = 8.2, 1.2 Hz), 7.07 (1H, dd, J = 7.9, 0.9 Hz), 6.95 (1H, d, J = 11.3 Hz), 4.61 (1H, s), 4.40 (1H, s), 4.09 (1H, s), 3.19-3.11 (1H, m), 2.65 (2H, s), 2.11-1.59 (6H, m), 1.58-1.48 (1H, m), 1.41-1.33 (1H, m), 1.04 (6H, s). |
| 29 | | | | | free | 398.6 | 1H-NMR (DMSO-D6) δ: 7.74 (2H, d, J = 8.5 Hz), 7.67-7.63 (1H, m), 7.54 (1H, dd, J = 10.5, 1.7 Hz), 7.50 (1H, d, J = 7.9 Hz), 7.34 (2H, d, J = 8.2 Hz), 7.22 (2H, d, J = 8.2 Hz), 7.08 (2H, d, J = 8.2 Hz), 6.19 (1H, t, J = 5.6 Hz), 4.47 (2H, d, J = 5.8 Hz), 3.71-3.50 (2H, m), 3.27-3.13 (2H, m), 2.55-2.53 (1H, m), 2.04-1.90 (1H, m), 1.70-1.61 (1H, m). |
| 30 | | | | | free | 426.2 | 1H-NMR (DMSO-D6) δ: 7.73 (2H, d, J = 8.5 Hz), 7.66-7.62 (1H, m), 7.55-7.49 (2H, m), 7.32 (2H, d, J = 7.3 Hz), 7.15 (2H, d, J = 8.2 Hz), 7.03 (2H, d, J = 8.2 Hz), 3.68-3.46 (6H, m), 3.22 (3H, s), 3.20-3.12 (1H, m), 2.77 (2H, t, J = 6.9 Hz), 2.02-1.87 (2H, m), 1.69-1.57 (1H, m). |

TABLE 4-continued

| | | | | | | |
|---|---|---|---|---|---|---|
| 31 | 4-cyanophenyl | (3S)-3-aminopyrrolidinyl | 4-(2-hydroxyethyl)phenyl | C=O | free | 412.1 | 1H-NMR (DMSO-D6) δ: 7.74 (2H, d, J = 8.5 Hz), 7.66-7.62 (1H, m), 7.55-7.49 (2H, m), 7.35-7.32 (2H, m), 7.13 (2H, d, J = 7.9 Hz), 7.03 (2H, d, J = 8.2 Hz), 4.53 (1H, t, J = 5.2 Hz), 3.62-3.56 (2H, m), 3.30-3.14 (4H, m), 2.73-2.66 (2H, m), 2.55-2.53 (1H, m), 2.03-1.90 (1H, m), 1.67-1.59 (1H, m). |
| 32 | 4-cyanophenyl | (3S)-3-aminopyrrolidinyl | 4-(3-hydroxypropyl)phenyl | C=O | free | 426.2 | 1H-NMR (DMSO-D6) δ: 7.49-7.38 (2H, m), 7.39-7.30 (1H, m), 7.27-7.14 (2H, m), 7.10-6.98 (2H, m), 6.90-6.67 (4H, m), 4.26-4.08 (1H, m), 3.47-3.11 (5H, m), 2.93-2.75 (2H, m), 2.38-2.14 (2H, m), 1.78-1.44 (2H, m). |
| 33 | 4-cyanophenyl | 3-amino-1-methylpyrrolidinyl | 4-(1-(hydroxymethyl)cyclopropyl)phenyl | C=O | free | 438.2 | 1H-NMR (DMSO-D6) δ: 7.68 (2H, d, J = 8.2 Hz), 7.63-7.53 (1H, m), 7.46 (2H, t, J = 8.2 Hz), 7.26 (2H, d, J = 7.0 Hz), 7.12 (2H, d, J = 7.6 Hz), 6.95 (2H, d, J = 8.2 Hz), 4.65 (1H, s), 3.92-3.60 (5H, m), 3.09 (2H, s), 2.24-2.08 (1H, m), 2.01-1.86 (1H, m), 0.77 (2H, s), 0.65 (2H, s). |

TABLE 5

| | | | | | NMR |
|---|---|---|---|---|---|
| 34 | (4-cyanophenyl) | (3-aminopyrrolidin-1-yl) | 4-(2-hydroxy-2-methylpropyl)phenyl | acyl | free | 440.2 | 1H-NMR (DMSO-D6) δ: 7.63 (2H, d, J = 7.0 Hz), 7.56 (1H, t, J = 5.7 Hz), 7.46 (2H, t, J = 10.2 Hz), 7.24 (2H, d, J = 7.6 Hz), 7.04 (2H, d, J = 7.6 Hz), 6.93 (2H, d, J = 7.0 Hz), 4.28 (1H, s), 3.64-3.48 (5H, m), 2.55 (2H, s), 1.98-1.87 (1H, m), 1.65-1.54 (1H, m), 0.96 (6H, s). |
| 35 | (4-cyanophenyl) | (3-aminopyrrolidin-1-yl) | 1-(4-methylphenoxy)-2-hydroxypropyl | acyl | free | 442.2 | 1H-NMR (DMSO-D6) δ: 7.78 (2H, d, J = 8.5 Hz), 7.67-7.61 (1H, m), 7.57-7.51 (2H, m), 7.35-7.30 (2H, m), 7.03 (2H, d, J = 8.5 Hz), 6.85 (2H, d, J = 8.5 Hz), 3.96-3.87 (1H, m), 3.85-3.68 (4H, m), 3.66-3.46 (2H, m), 3.27-3.21 (1H, m), 2.59-2.51 (1H, m), 2.29-2.17 (1H, m), 2.04-1.94 (1H, m), 1.13 (3H, d, J = 6.4 Hz). |
| 36 | (4-cyano-2-fluorophenyl) | (3-aminopyrrolidin-1-yl) | 3-fluoro-4-methylphenyl | acyl | free | 418.1 | 1H-NMR (DMSO-D6) δ: 7.85-7.81 (1H, m), 7.71-7.67 (1H, m), 7.63 (1H, s), 7.54 (1H, d, J = 7.6 Hz), 7.38-7.32 (1H, m), 7.24-7.18 (1H, m), 7.10 (1H, d, J = 7.6 Hz), 7.06 (1H, d, J = 8.2 Hz), 6.96 (1H, d, J = 11.4 Hz), 4.12-4.07 (1H, m), 3.92-3.53 (4H, m), 2.31 (3H, s), 2.26-2.17 (1H, m), 2.02-1.91 (1H, m). |
| 37 | (4-cyano-2-fluorophenyl) | (3-aminopyrrolidin-1-yl) | 4-(2-hydroxy-2-methylpropyl)-3-fluorophenyl | acyl | free | 476.1 | 1H-NMR (DMSO-D6) δ: 7.79 (1H, t, J = 7.5 Hz), 7.70-7.67 (1H, m), 7.63 (1H, dd, J = 6.6, 1.5 Hz), 7.52 (1H, d, J = 8.1 Hz), 7.27 (1H, d, J = 10.3 Hz), 7.21 (1H, t, J = 7.9 Hz), 7.14 (1H, dd, J = 8.1, 1.5 Hz), 7.06 (1H, d, J = 7.7 Hz), 6.95 (1H, d, J = 11.4 Hz), 4.39 (1H, s), 3.68-3.55 (2H, m), 3.54-3.41 (2H, m), 3.21-3.12 (1H, m), 2.65 (2H, s), 2.03-1.88 (1H, m), 1.70-1.59 (1H, m), 1.04 (6H, s). |
| 38 | (4-cyano-2-fluorophenyl) | (1-oxa-8-azaspiro[5.3]nonan-8-yl) | 4-(2-methoxyethyl)-2,3-difluorophenyl | acyl | free | 504.2 | 1H-NMR (CDCl3) δ: 7.76-7.69 (2H, m), 7.49-7.43 (2H, m), 7.09-6.96 (4H, m), 6.83 (1H, dd, J = 10.6, 0.9 Hz), 4.23 (2H, dd, J = 23.5, 9.2 Hz), 4.10 (2H, s), 3.75-3.64 (2H, m), 3.60 (2H, t, J = 6.6 Hz), 3.35 (3H, s), 3.00 (2H, s), 2.90-2.80 (4H, m). |

TABLE 5-continued
| | | | | | |
|---|---|---|---|---|---|
| 39 | 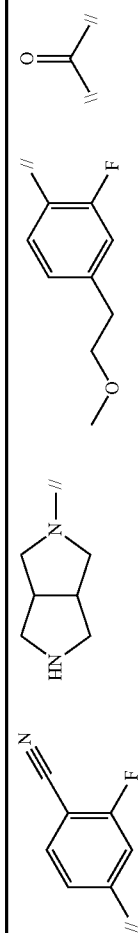 |  | | free | 488.1 | 1H-NMR (DMSO-D6) δ: 7.80 (1H, t, J = 7.6 Hz), 7.65 (1H, d, J = 7.0 Hz), 7.57 (1H, d, J = 10.8 Hz), 7.51 (1H, d, J = 7.6 Hz), 7.33 (1H, d, J = 10.2 Hz), 7.23 (1H, t, J = 7.9 Hz), 7.14-7.06 (2H, m), 7.00 (1H, d, J = 11.4 Hz), 3.86-3.64 (2H, m), 3.58-3.47 (4H, m), 3.23 (3H, s), 3.03-2.86 (2H, m), 2.81 (2H, t, J = 6.7 Hz), 2.77-2.55 (4H, m). |
| 40 | 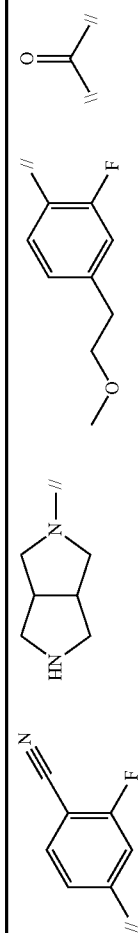 |  | | free | 458.3 | 1H-NMR (DMSO-D6) δ: 7.82-7.77 (1H, m), 7.69-7.64 (1H, m), 7.60 (1H, d, J = 8.9 Hz), 7.54 (1H, d, J = 7.6 Hz), 7.27 (1H, d, J = 10.8 Hz), 7.15 (3H, d, J = 7.0 Hz), 7.03 (2H, d, J = 7.0 Hz), 3.74-3.53 (4H, m), 3.52-3.49 (1H, m), 3.22-3.13 (1H, m), 2.63 (2H, s), 2.07-1.97 (1H, m), 1.76-1.67 (1H, m), 1.03 (6H, s). |

TABLE 6

| | | | | | NMR |
|---|---|---|---|---|---|
| 41 | (4-cyano-3-fluorophenyl) | (8-azabicyclo amine) | (3-fluoro-4-(2-hydroxy-2-methylpropyl)phenyl) | free | 516.2 | 1H-NMR (DMSO-D6) δ: 7.80 (1H, t, J = 7.6 Hz), 7.61 (1H, dd, J = 7.8, 1.7 Hz), 7.53 (2H, dd, J = 10.8, 4.7 Hz), 7.29 (1H, dd, J = 10.7, 1.2 Hz), 7.22 (1H, t, J = 7.9 Hz), 7.15 (1H, dd, J = 7.9, 1.5 Hz), 7.07 (1H, dd, J = 7.9, 1.2 Hz), 6.96 (1H, d, J = 11.3 Hz), 4.57 (1H, br s), 4.40 (1H, s), 4.05 (1H, br s), 2.65 (2H, s), 2.35-2.21 (2H, m), 2.12-2.03 (1H, m), 1.99-1.81 (3H, m), 1.61-1.47 (3H, m), 1.06 (6H, d, J = 14.6 Hz). |
| 42 | (4-cyanophenyl) | (N-methylpyrrolidin-3-amine) | (4-methylphenyl) | free | 396.3 | 1H-NMR (DMSO-D6) δ: 7.71 (2H, d, J = 7.7 Hz), 7.61 (1H, dd, J = 7.7, 1.5 Hz), 7.50 (1H, s), 7.46 (1H, dd, J = 8.1, 2.6 Hz), 7.30 (2H, d, J = 8.4 Hz), 7.07 (2H, d, J = 8.1 Hz), 6.98 (2H, d, J = 7.7 Hz), 3.63-3.44 (3H, m), 3.25-3.07 (2H, m), 2.27-2.16 (6H, m), 1.94-1.85 (1H, m), 1.75-1.68 (1H, m). |
| 43 | (4-cyanophenyl) | (1-methylpyrrolidin-3-amine) | (4-(benzyloxy)phenyl) | free | 474.5 | 1H-NMR (DMSO-D6) δ: 7.75 (2H, d, J = 7.6 Hz), 7.67-7.61 (1H, m), 7.56-7.50 (2H, m), 7.45-7.30 (7H, m), 7.04 (2H, d, J = 7.6 Hz), 6.93 (2H, d, J = 7.6 Hz), 5.07 (2H, s), 4.17-4.07 (1H, m), 3.91-3.52 (4H, m), 2.26-2.15 (1H, m), 2.00-1.90 (1H, m). |
| 44 | (4-cyanophenyl) | (1-methylpyrrolidin-3-amine) | (1-phenylcarbamoyl-1-(4-methylphenyl)cyclopropyl) | free | 527.2 | 1H-NMR (DMSO-D6) δ: 8.96 (1H, s), 7.74 (2H, dd, J = 6.7, 1.8 Hz), 7.67-7.64 (1H, m), 7.54 (4H, tt, J = 12.7, 4.8 Hz), 7.37 (2H, dd, J = 8.2, 1.5 Hz), 7.32-7.28 (4H, m), 7.13 (2H, d, J = 8.2 Hz), 7.07-7.04 (1H, m), 3.68-3.43 (5H, m), 1.99 (1H, d, J = 6.1 Hz), 1.66 (1H, dd, J = 7.0, 2.2 Hz), 1.44 (2H, dd, J = 6.7, 4.3 Hz), 1.12 (2H, dd, J = 6.9, 4.4 Hz). |
| 45 | (4-cyanophenyl) | (pyrrolidin-3-amine) | (2-(4-methylphenyl)ethyl acetate) | free | 454.5 | 1H-NMR (DMSO-D6) δ: 7.73 (2H, d, J = 8.2 Hz), 7.67-7.62 (1H, m), 7.56-7.50 (2H, m), 7.32 (2H, d, J = 5.7 Hz), 7.16 (2H, d, J = 8.2 Hz), 7.05 (2H, d, J = 8.2 Hz), 4.19 (2H, t, J = 6.9 Hz), 3.72-3.43 (4H, m), 2.86 (2H, t, J = 6.9 Hz), 3.22-3.13 (1H, m), 2.06-1.88 (4H, m), 1.69-1.58 (1H, m). |

TABLE 6-continued

| 46 | [4-cyanophenyl] | [(3S)-1-methylpyrrolidin-3-yl]amino | 4-(2-hydroxyethyl)phenyl C(=O) | free | 426.5 | 1H-NMR (DMSO-D6) δ: 7.74 (2H, d, J = 8.2 Hz), 7.64 (1H, d, J = 8.2 Hz), 7.53 (1H, s), 7.49 (1H, d, J = 8.2 Hz), 7.33 (2H, d, J = 8.2 Hz), 7.13 (2H, d, J = 8.2 Hz), 7.03 (2H, d, J = 7.6 Hz), 3.71-3.45 (7H, m), 3.26-3.12 (1H, m), 2.69 (2H, t, J = 6.7 Hz), 2.34-2.19 (3H, m), 2.06-1.90 (1H, m), 1.83-1.72 (1H, m). |
|----|---|---|---|---|---|---|
| 47 | [4-cyanophenyl] | [(3S)-1-methylpyrrolidin-3-yl]amino | 4-(2-methoxyethyl)phenyl C(=O) | free | 440.5 | 1H-NMR (DMSO-D6) δ: 7.73 (2H, d, J = 8.2 Hz), 7.64 (1H, d, J = 8.9 Hz), 7.56-7.47 (2H, m), 7.33 (2H, d, J = 8.2 Hz), 7.15 (2H, d, J = 7.6 Hz), 7.03 (2H, d, J = 7.6 Hz), 3.69-3.38 (6H, m), 3.26-3.08 (4H, m), 2.78 (2H, t, J = 6.7 Hz), 2.32-2.19 (3H, m), 2.04-1.87 (1H, m), 1.81-1.69 (1H, m). |

TABLE 7

| | | | | | |
|---|---|---|---|---|---|
| 48 | (4-cyanophenyl) | (3-dimethylamino-pyrrolidinyl) | 4-(1-hydroxymethyl-cyclopropyl)phenyl | acetyl | free | 466.2 | 1H-NMR (DMSO-D6) δ: 7.57 (2H, d, J = 7.6 Hz), 7.57 (1H, t, J = 8.6 Hz), 7.43 (2H, dd, J = 19.4, 4.8 Hz), 7.27 (2H, d, J = 8.2 Hz), 7.11 (2H, d, J = 8.2 Hz), 6.95 (2H, d, J = 5.7 Hz), 4.65-4.53 (1H, m), 3.68-3.38 (5H, m), 3.17-3.08 (1H, m), 2.71-2.58 (1H, m), 2.11 (3H, s), 2.04 (3H, s), 1.99-1.91 (1H, m), 1.74-1.58 (1H, m), 0.76 (2H, s), 0.65 (2H, s). |
| 49 | | 3-aminopyrrolidinyl | 3-fluoro-4-methylphenyl | acetyl | free | 400.2 | 1H-NMR (DMSO-D6) δ: 7.71 (2H, d, J = 8.2 Hz), 7.62-7.56 (1H, m), 7.49 (2H, d, J = 8.2 Hz), 7.28 (2H, d, J = 7.0 Hz), 7.11 (1H, t, J = 7.9 Hz), 6.87 (1H, d, J = 10.8 Hz), 6.73 (1H, d, J = 7.6 Hz), 3.86-3.47 (5H, m), 2.21-2.09 (4H, m), 2.00-1.86 (1H, m). |
| 50 | | 3-aminopyrrolidinyl | 4-chlorophenyl | acetyl | free | 402.1 / 404.1 | 1H-NMR (DMSO-D6) δ: 7.71 (2H, d, J = 8.2 Hz), 7.64-7.56 (1H, m), 7.54-7.40 (2H, m), 7.33-7.22 (4H, m), 7.07 (2H, d, J = 8.2 Hz), 4.04-3.50 (5H, m), 2.20-2.04 (1H, m), 1.96-1.82 (1H, m). |
| 51 | | 3-aminopyrrolidinyl | 4-bromophenyl | acetyl | free | 446.0 / 448.0 | 1H-NMR (DMSO-D6) δ: 7.71 (2H, d, J = 8.2 Hz), 7.65-7.57 (1H, m), 7.55-7.46 (2H, m), 7.43 (2H, d, J = 8.2 Hz), 7.27 (2H, d, J = 7.0 Hz), 7.01 (2H, d, J = 8.2 Hz), 3.78-3.50 (5H, m), 2.17-2.06 (1H, m), 1.92-1.82 (1H, m). |
| 52 | | diazabicyclic | 4-methylphenyl | acetyl | free | 394.5 | 1H-NMR (DMSO-D6) δ: 7.75 (2H, d, J = 8.2 Hz), 7.67-7.50 (3H, m), 7.33 (2H, t, J = 8.6 Hz), 7.10 (2H, d, J = 7.6 Hz), 7.01 (2H, d, J = 7.6 Hz), 4.79-4.75 (1H, m), 4.51-4.47 (1H, m), 4.06 (1H, d, J = 18.4 Hz), 3.73-3.52 (2H, m), 3.15-3.02 (1H, m), 2.27 (3H, s), 2.04-1.91 (1H, m), 1.82-1.66 (1H, m). |
| 53 | | 3-aminopyrrolidinyl N-methyl | 4-(2-aminoethyl)phenyl | acetyl | free | 411.1 | 1H-NMR (DMSO-D6) δ: 7.74 (2H, dd, J = 6.6, 2.0 Hz), 7.65 (1H, s), 7.54-7.50 (2H, m), 7.34-7.33 (2H, m), 7.14 (2H, d, J = 8.2 Hz), 7.06 (2H, ddd, J = 14.0, 4.3, 2.5 Hz), 3.59 (5H, s), 2.85 (2H, s), 2.69-2.67 (2H, m), 1.70-1.60 (1H, m), 1.24 (1H, s). |

TABLE 7-continued

| | | | | | |
|---|---|---|---|---|---|
| 54 | ![structure with NH2 pyrrolidine and benzonitrile] | ![4-iodophenyl with C=O] | free | 494 | 1H-NMR (DMSO-D6) δ: 7.71 (2H, d, J = 8.2 Hz), 7.63-7.56 (3H, m), 7.53-7.45 (2H, m), 7.26 (2H, d, J = 7.6 Hz), 6.86 (2H, d, J = 8.2 Hz), 3.87-3.47 (5H, m), 2.23-2.08 (1H, m), 1.98-1.86 (1H, m). |
| 55 | ![structure with NH2 pyrrolidine and benzonitrile] | ![4-methylphenyl-CH2CH2-NHC(O)-] | free | 453.2 | 1H-NMR (DMSO-D6) δ: 7.85-7.79 (1H, m), 7.68 (2H, d, J = 8.2 Hz), 7.61-7.55 (1H, m), 7.52-7.44 (2H, m), 7.27-7.22 (2H, m), 7.06 (2H, d, J = 7.6 Hz), 6.97 (2H, d, J = 7.6 Hz), 3.83-3.52 (5H, m), 3.17-3.12 (2H, m), 2.60 (2H, t, J = 7.3 Hz), 2.22-2.10 (1H, m), 1.98-1.86 (1H, m), 1.69 (3H, s). |
| 56 | ![structure with NH2 pyrrolidine and benzonitrile] | ![4-methylphenyl-propyl-C(O)-] | free | 410.2 | 1H-NMR (DMSO-D6) δ: 7.67 (2H, d, J = 8.2 Hz), 7.63-7.55 (1H, m), 7.54-7.45 (2H, m), 7.25 (2H, d, J = 8.2 Hz), 7.04 (2H, d, J = 8.2 Hz), 6.95 (2H, d, J = 7.6 Hz), 3.88-3.48 (5H, m), 2.48-2.44 (2H, m), 2.22-2.08 (1H, m), 1.97-1.86 (1H, m), 1.49 (2H, dd, J = 14.9, 7.3 Hz), 0.80 (3H, t, J = 7.3 Hz). |

TABLE 8

| # | R1 | R2 | R3 | R4 | MS | 1H-NMR |
|---|---|---|---|---|---|---|
| 57 | 4-cyanophenyl | (3-aminopyrrolidin-1-yl) | 2-naphthyl | acetyl | free | 418.2 | 1H-NMR (DMSO-D6) δ: 7.83-7.76 (3H, m), 7.73-7.61 (5H, m), 7.59-7.53 (1H, m), 7.49-7.41 (2H, m), 7.29 (2H, d, J = 7.6 Hz), 7.03 (1H, d, J = 8.9 Hz), 4.03-3.55 (5H, m), 2.24-2.12 (1H, m), 1.98-1.88 (1H, m). |
| 58 | 4-cyanophenyl | (3-methylaminopyrrolidin-1-yl) | 4-(1-hydroxymethylcyclopropyl)phenyl | acetyl | free | 452.1 | 1H-NMR (DMSO-D6) δ: 7.74 (2H, d, J = 8.2 Hz), 7.63 (1H, m), 7.53-7.51 (1H, m), 7.49 (1H, d, J = 7.9 Hz), 7.34 (2H, d, J = 8.5 Hz), 7.19 (2H, d, J = 8.2 Hz), 7.03 (2H, d, J = 8.2 Hz), 4.67 (1H, t, J = 5.5 Hz), 3.71-3.47 (6H, m), 3.27-3.16 (1H, m), 2.35-2.21 (3H, m), 2.03-1.94 (1H, m), 1.81-1.72 (1H, m), 0.85-0.82 (2H, m), 0.74-0.70 (2H, m). |
| 59 | 4-cyanophenyl | (3-aminopyrrolidin-1-yl) | 4-(1-hydroxymethylcyclopropyl)phenyl | acetyl | free | 438.1 | 1H-NMR (DMSO-D6) δ: 7.76-7.62 (3H, m), 7.58-7.50 (2H, m), 7.36-7.26 (2H, m), 7.14-7.02 (4H, m), 5.34-5.31 (1H, m), 3.89-3.58 (6H, m), 3.23-3.13 (1H, m), 2.05-1.95 (1H, m), 1.74-1.66 (1H, m), 0.94-0.84 (4H, m). |
| 60 | 4-cyanophenyl | (3-aminopyrrolidin-1-yl) | 4-(2-methylprop-1-enyl)phenyl | acetyl | free | 422.1 | 1H-NMR (DMSO-D6) δ: 7.67 (2H, d, J = 7.6 Hz), 7.62-7.55 (1H, m), 7.51-7.43 (2H, m), 7.26 (2H, d, J = 7.6 Hz), 7.03 (4H, dd, J = 28.6, 7.6 Hz), 6.15 (1H, s), 3.68-3.48 (5H, m), 2.01-1.89 (1H, m), 1.79 (3H, s), 1.74 (3H, s), 1.67-1.59 (1H, m). |
| 61 | 4-cyanophenyl | (3-aminopyrrolidin-1-yl) | 4-(3-hydroxy-3-methylbutyl)phenyl | acetyl | free | 454.3 | 1H-NMR (DMSO-D6) δ: 7.74 (2H, d, J = 7.0 Hz), 7.67-7.61 (1H, m), 7.57-7.49 (2H, m), 7.33 (2H, d, J = 7.6 Hz), 7.11 (2H, d, J = 7.6 Hz), 7.02 (2H, d, J = 7.0 Hz), 3.82-3.56 (4H, m), 3.53-3.47 (1H, m), 3.21-3.13 (1H, m), 2.62-2.55 (2H, m), 2.13-2.03 (1H, m), 1.86-1.75 (1H, m), 1.64-1.57 (2H, m), 1.12 (6H, s). |

| | | | | | | NMR |
|---|---|---|---|---|---|---|
| 62 | [4-cyanophenyl] | [(3S)-3-aminopyrrolidine] | [4-(2-(1-hydroxycyclopropyl)ethyl)phenyl] | acryloyl | free | 452.2 | 1H-NMR (DMSO-D6) δ: 7.74 (2H, d, J = 8.2 Hz), 7.68-7.62 (1H, m), 7.58-7.51 (2H, m), 7.32 (2H, d, J = 7.0 Hz), 7.12 (2H, d, J = 7.6 Hz), 7.02 (2H, d, J = 7.0 Hz), 4.15-4.08 (1H, m), 3.94-3.55 (4H, m), 3.53-3.48 (2H, m), 3.19-3.14 (1H, m), 2.77-2.69 (2H, m), 2.41-2.39 (2H, m), 2.31-2.17 (1H, m), 2.02-1.94 (1H, m), 0.91-0.89 (2H, m). |
| 63 | [2-fluoro-4-cyanophenyl] | [(3R)-3-aminopyrrolidine] | [4-(2-hydroxyethyl)phenyl] | acryloyl | free | 430.3 | 1H NMR (DMSO-D6) δ: 8.30 (1H, s), 7.80 (1H, t, J = 7.0 Hz), 7.69-7.64 (1H, m), 7.58 (1H, d, J = 7.6 Hz), 7.51 (1H, d, J = 8.2 Hz), 7.35 (1H, d, J = 11.4 Hz), 7.16 (2H, d, J = 7.6 Hz), 7.11 (1H, d, J = 8.2 Hz), 7.05 (2H, d, J = 7.0 Hz), 3.69-3.52 (6H, m), 3.24-3.17 (1H, m), 2.71 (2H, t, J = 6.3 Hz), 2.04-1.93 (1H, m), 1.73-1.63 (1H, m). |
| 64 | [4-cyanophenyl] | [(3S)-3-aminopyrrolidine] | [3-fluoro-4-(2-hydroxy-2-methylpropyl)phenyl] | acryloyl | free | 458.2 | 1H-NMR (DMSO-D6) δ: 7.73-7.63 (3H, m), 7.59 (1H, d, J = 10.8 Hz), 7.51 (1H, d, J = 8.2 Hz), 7.31 (2H, d, J = 7.6 Hz), 7.20-7.14 (1H, m), 7.03 (1H, d, J = 7.5 Hz), 6.92 (1H, d, J = 11.4 Hz), 3.70-3.54 (4H, m), 3.52-3.49 (1H, m), 3.24-3.20 (1H, m), 2.64 (2H, s), 2.08-1.96 (1H, m), 1.76-1.66 (1H, m), 1.04 (6H, s). |

TABLE 9

| | | | | | | |
|---|---|---|---|---|---|---|
| 65 | 2-fluoro-4-cyanophenyl | (3-aminopyrrolidin-1-yl) | 4-(3-hydroxy-3-methylbutyl)phenyl | acyl | free | 472.2 | 1H-NMR (DMSO-D6) δ: 7.80 (1H, t, J = 7.3 Hz), 7.69-7.64 (1H, m), 7.59 (1H, d, J = 8.2 Hz), 7.52 (1H, d, J = 8.2 Hz), 7.33 (1H, m), 7.04 (2H, d, J = 7.6 Hz), 7.15-7.09 (3H, m), 3.70-3.57 (1H, m), 3.54-3.49 (1H, m), 3.24-3.17 (1H, m), 2.63-2.57 (2H, m), 2.07-1.93 (1H, m), 1.77-1.64 (1H, m), 1.64-1.58 (2H, m), 1.12 (6H, s). |
| 66 | 4-cyanophenyl | (3-aminopyrrolidin-1-yl) | 4-(1-(methoxymethyl)cyclopropyl)phenyl | acyl | free | 452.2 | 1H-NMR (DMSO-D6) δ: 7.74 (2H, d, J = 7.6 Hz), 7.67-7.61 (1H, m), 7.56-7.49 (2H, m), 7.33 (2H, d, J = 8.2 Hz), 7.17 (2H, d, J = 7.0 Hz), 7.03 (2H, d, J = 7.0 Hz), 3.82-3.52 (5H, m), 3.51 (2H, s), 3.21 (3H, s), 2.15-2.01 (1H, m), 1.89-1.75 (1H, m), 0.89-0.78 (4H, m). |
| 67 | 4-cyanophenyl | (3-aminopyrrolidin-1-yl) | 3-fluoro-4-(hydroxymethyl)cyclopropyl)phenyl | acyl | free | 456.2 | 1H NMR (DMSO-D6) δ: 7.73 (2H, d, J = 6.3 Hz), 7.67-7.61 (1H, m), 7.57-7.48 (2H, m), 7.39-7.24 (4H, m), 7.02 (1H, d, J = 7.6 Hz), 3.73-3.53 (4H, m), 3.51 (1H, s), 3.19-3.10 (1H, m), 2.54 (2H, s), 1.72-1.58 (1H, m), 1.48-1.35 (1H, m), 0.83-0.42 (4H, m). |
| 68 | 4-cyanophenyl | (3-aminopyrrolidin-1-yl) | 4-(1-hydroxycyclopropyl)phenyl | acyl | free | 464.2 | 1H-NMR (DMSO-D6) δ: 7.74 (2H, d, J = 8.5 Hz), 7.67-7.61 (1H, m), 7.57-7.48 (2H, m), 7.39-7.33 (3H, m), 7.28 (2H, d, J = 8.2 Hz), 7.02 (1H, d, J = 8.2 Hz), 5.16 (1H, s), 3.78-3.54 (4H, m), 3.21-3.13 (1H, m), 2.04-1.95 (1H, m), 1.67-1.58 (1H, m), 0.82-0.70 (4H, m), 0.57-0.42 (4H, m). |
| 69 | 2-fluoro-4-cyanophenyl | (3-aminopyrrolidin-1-yl) | 4-(2-methoxyethyl)phenyl | acyl | free | 444.1 | 1H-NMR (DMSO-D6) δ: 7.81 (1H, s), 7.72-7.47 (3H, m), 7.37-7.31 (1H, m), 7.18 (2H, d, J = 7.6 Hz), 7.13-7.01 (3H, m), 4.29-4.11 (1H, m), 3.88-3.56 (4H, m), 3.52 (2H, t, J = 5.7 Hz), 3.22 (3H, s), 2.79 (2H, t, J = 6.4 Hz), 2.23-2.03 (1H, m), 1.54-1.34 (1H, m). |

TABLE 9-continued

| # | Ar1 | Ar2 | R | Salt | MS | 1H-NMR |
|---|---|---|---|---|---|---|
| 70 | 4-cyanophenyl | (3S)-3-aminopyrrolidin-1-yl | 3-fluoro-4-(2-hydroxyethyl)phenyl | C(=O) | free | 430 | 1H-NMR (DMSO-D6) δ: 7.74 (2H, d, J = 8.2 Hz), 7.69-7.63 (1H, m), 7.58 (1H, d, J = 12.5 Hz), 7.49 (1H, d, J = 7.9 Hz), 7.32 (2H, d, J = 7.6 Hz), 7.19 (1H, t, J = 7.9 Hz), 7.06 (1H, d, J = 7.6 Hz), 6.96 (1H, d, J = 11.0 Hz), 4.70-4.64 (1H, m), 3.72-3.46 (6H, m), 3.26-3.18 (1H, m), 2.74-2.68 (2H, m), 2.08-1.98 (1H, m), 1.78-1.68 (1H, m). |
| 71 | 4-cyanophenyl | (3R)-3-aminopyrrolidin-1-yl | 3-fluoro-4-(2-methoxyethyl)phenyl | C(=O) | free | 444.1 | 1H-NMR (DMSO-d6) δ: 7.73 (2H, d, J = 6.7 Hz), 7.67-7.64 (1H, m), 7.57 (1H, dd, J = 10.8, 1.4 Hz), 7.50 (1H, d, J = 7.9 Hz), 7.31 (2H, d, J = 7.6 Hz), 7.20 (1H, t, J = 7.8 Hz), 7.07 (1H, dd, J = 7.9, 1.2 Hz), 6.97 (1H, d, J = 11.3 Hz), 3.6S-3.45 (6H, m), 3.23 (3H, s), 3.21-3.15 (1H, m), 2.80 (2H, t, J = 6.6 Hz), 2.04-1.93 (1H, m), 1.72-1.62 (1H, m). |
| 72 | 4-cyanophenyl | (3S)-3-aminopyrrolidin-1-yl | 4-(1-hydroxy-2-methylpropan-2-yl)phenyl | C(=O) | free | 440.1 | 1H-NMR (DMSO-D6) δ: 7.74 (2H, d, J = 8.2 Hz), 7.64 (1H, t, J = 7.3 Hz), 7.55-7.49 (2H, m), 7.34 (2H, d, J = 7.0 Hz), 7.28 (2H, d, J = 8.2 Hz), 7.05 (2H, d, J = 8.2 Hz), 4.69-4.65 (1H, m), 3.70-3.37 (6H, m), 3.25-3.18 (1H, m), 2.08-1.95 (1H, m), 1.76-1.68 (1H, m), 1.19 (6H, s). |

TABLE 10

| | | | | | |
|---|---|---|---|---|---|
| 73 | (4-cyanophenyl) | (1-methylpyrrolidin-3-yl)amine | 4-iodophenethyl with F | acetyl | free | 414.1 | 1H-NMR (DMSO-D6) δ: 7.75 (2H, d, J = 7.9 Hz), 7.65 (1H, t, J = 7.6 Hz), 7.58-7.49 (2H, m), 7.33 (2H, d, J = 7.3 Hz), 7.19 (2H, d, J = 7.9 Hz), 7.07 (2H, d, J = 7.6 Hz), 4.63 (2H, dt, J = 47.2, 6.2 Hz), 3.72-3.47 (4H, m), 3.27-3.21 (1H, m), 2.95 (2H, dt, J = 25.2, 6.2 Hz), 2.10-1.99 (1H, m), 1.81-1.71 (1H, m). |
| 74 | | | | acetyl | free | 488.1 | 1H-NMR (DMSO-D6) δ: 7.84-7.78 (1H, m), 7.71-7.62 (2H, m), 7.56-7.51 (1H, m), 7.36-7.30 (1H, m), 7.25-7.21 (1H, m), 7.13-7.09 (2H, m), 7.03-6.98 (1H, m), 4.09-3.49 (10H, m), 3.22 (3H, s), 2.84-2.78 (2H, m), 2.19-2.10 (2H, m). |
| 75 | | | | acetyl | free | 502.1 | 1H-NMR (DMSO-D6) δ: 7.84-7.79 (2H, m), 7.73-7.70 (1H, m), 7.57-7.52 (1H, m), 7.32 (1H, d, J = 10.4 Hz), 7.25-7.20 (1H, m), 7.11 (2H, d, J = 7.3 Hz), 7.00 (1H, d, J = 11.0 Hz), 4.19 (1H, d, J = 8.2 Hz), 4.10 (1H, d, J = 8.2 Hz), 3.90 (1H, d, J = 9.8 Hz), 3.75 (1H, d, J = 10.1 Hz), 3.55-3.50 (2H, m), 3.25-3.07 (7H, m), 2.88-2.78 (2H, m), 1.86-1.73 (2H, m), 1.67-1.52 (2H, m). |
| 76 | | | | acetyl | free | 502.1 | 1H-NMR (DMSO-D6) δ: 7.82-7.77 (1H, m), 7.72-7.62 (2H, m), 7.57-7.51 (1H, m), 7.29-7.25 (1H, m), 7.22-7.18 (1H, m), 7.16-7.11 (1H, m), 7.09-7.05 (1H, m), 6.98-6.92 (1H, m), 4.40 (1H, s), 3.90-3.44 (6H, m), 2.67-2.64 (2H, m), 2.18-2.06 (2H, m), 2.04-1.90 (2H, m), 1.04 (6H, s). |
| 77 | | | | acetyl | free | 516.1 | 1H-NMR (DMSO-D6) δ: 7.84-7.71 (3H, m), 7.57-7.54 (1H, m), 7.29-7.24 (1H, m), 7.21-7.17 (1H, m), 7.15-7.11 (1H, m), 7.08-7.05 (1H, m), 6.97-6.93 (1H, m), 4.39 (1H, s), 4.14-4.02 (2H, m), 3.85-3.68 (2H, m), 2.95-2.84 (2H, m), 2.71-2.62 (4H, m), 1.78-1.68 (2H, m), 1.52-1.42 (2H, m), 1.04 (6H, s). |

TABLE 10-continued

| # | | | | | | NMR |
|---|---|---|---|---|---|---|
| 78 | (cyanofluorophenyl) | (diazaspiro[4.5]decane) | (methoxyethyl-fluorophenyl) | C(=O) | 516.2 free | 1H-NMR (CD3OD) δ: 7.64-7.55 (4H, m), 7.22-7.08 (4H, m), 6.92 (1H, d, J = 11.0 Hz), 4.01-3.88 (1H, m), 3.77-3.71 (2H, m), 3.67 (3H, s), 3.63-3.58 (3H, m), 3.47-3.40 (2H, m), 3.23-3.15 (2H, m), 2.87 (2H, t, J = 6.6 Hz), 2.09-2.01 (2H, m), 1.83-1.65 (4H, m). |
| 79 | (cyanofluorophenyl) | (azaspiro) | (methoxyethyl-fluorophenyl) | C(=O) | 502.1 free | 1H-NMR (DMSO-D6) δ: 7.83-7.00 (9H, m), 3.82 (12H, tt, J = 147.2, 54.5 Hz), 3.24 (3H, d, J = 5.5 Hz), 2.82 (2H, t, J = 6.4 Hz), 1.76 (1H, s), 1.48 (1H, s). |
| 80 | (cyanofluorophenyl) | (diazepane) | (methoxyethyl-fluorophenyl) | C(=O) | 476.2 free | 1H-NMR (CD3OD) δ: 7.65-7.54 (4H, m), 7.13 (4H, ddd, J = 29.3, 15.0, 6.6 Hz), 6.90 (1H, d, J = 11.4 Hz), 4.02-3.97 (1H, m), 3.90-3.82 (1H, m), 3.74-3.67 (2H, m), 3.59 (2H, t, J = 6.4 Hz), 3.49-3.43 (2H, m), 3.39-3.35 (2H, m), 3.31 (3H, s), 2.85 (2H, t, J = 6.6 Hz), 2.24-2.05 (2H, m). |
| 81 | (cyanofluorophenyl) | (azaspiro) | (difluorophenyl) | C(=O) | 488.2 free | 1H-NMR (DMSO-D6) δ: 7.83-7.79 (1H, m), 7.72-7.60 (2H, m), 7.55-7.51 (1H, m), 7.36-7.30 (1H, m), 7.27-7.21 (1H, m), 7.15-7.08 (2H, m), 7.03-6.98 (1H, m), 3.86-3.38 (10H, m), 3.23 (3H, s), 2.85-2.79 (2H, m), 2.38-2.02 (2H, m). |

TABLE 11

| | | | | | |
|---|---|---|---|---|---|
| 82 | benzonitrile-F | diazabicyclic-HN | F-phenyl-OMe | acetyl | free | 474.1 | 1H-NMR (DMSO-D6) δ: 7.82 (1H, t, J = 7.3 Hz), 7.74-7.60 (2H, m), 7.56 (1H, d, J = 7.9 Hz), 7.39-7.30 (1H, m), 7.24 (1H, t, J = 7.6 Hz), 7.14-7.09 (2H, m), 7.01 (1H, d, J = 11.0 Hz), 4.57 (1H, s), 4.27 (1H, s), 3.79-3.72 (1H, m), 3.66-3.61 (1H, m), 3.57-3.51 (2H, m), 3.46-3.40 (1H, m), 3.22 (3H, s), 3.21-3.17 (1H, m), 2.84-2.79 (2H, m), 2.14-2.05 (1H, m), 1.90-1.73 (1H, m). |
| 83 | | | | | free | 502.1 | 1H-NMR (DMSO-D6) δ: 7.81 (1H, t, J = 7.6 Hz), 7.59-7.51 (3H, m), 7.33 (1H, dd, J = 10.7, 1.2 Hz), 7.24 (1H, t, J = 7.9 Hz), 7.11 (2H, d, J = 8.2 Hz), 7.00 (1H, d, J = 10.4 Hz), 3.79-3.57 (6H, m), 3.53 (2H, t, J = 6.7 Hz), 3.23 (3H, s), 2.81 (2H, t, J = 6.7 Hz), 2.25-2.17 (2H, m), 2.01-1.81 (4H, m). |
| 84 | | | | | free | 502.2 | 1H-NMR (DMSO-D6) δ: 7.84-7.79 (2H, m), 7.72 (1H, s), 7.54 (1H, d, J = 7.9 Hz), 7.33 (1H, d, J = 10.4 Hz), 7.22 (1H, t, J = 7.9 Hz), 7.14-7.09 (2H, m), 7.00 (1H, d, J = 11.3 Hz), 4.15 (2H, s), 3.83 (2H, s), 3.53 (2H, t, J = 6.6 Hz), 3.22 (3H, s), 2.97-2.85 (4H, m), 2.81 (2H, t, J = 6.6 Hz), 1.89-1.63 (4H, m). |
| 85 | | | | | free | 474.2 | 1H-NMR (DMSO-D6) δ: 7.81 (1H, t, J = 7.6 Hz), 7.71-7.62 (2H, m), 7.59-7.51 (1H, m), 7.38-7.30 (1H, m), 7.27-7.22 (1H, m), 7.15-7.08 (2H, m), 7.03-6.98 (1H, m), 4.72 (1H, s), 4.39 (1H, s), 3.86-3.61 (2H, m), 3.56-3.49 (2H, m), 3.22 (3H, s), 3.10-2.93 (2H, m), 2.84-2.79 (2H, m), 1.91-1.60 (2H, m). |
| 86 | | | | | free | 488.2 | 1H-NMR (DMSO-D6) δ: 7.81 (1H, t, J = 7.5 Hz), 7.74-7.53 (3H, m), 7.38-7.31 (1H, m), 7.24 (1H, t, J = 7.9 Hz), 7.14-7.09 (2H, m), 7.01 (1H, d, J = 11.0 Hz), 4.76 (1H, s), 4.44 (1H, s), 4.02-3.85 (1H, m), 3.72-3.57 (1H, m), 3.53 (2H, t, J = 6.7 Hz), 3.22 (3H, s), 3.12-2.97 (2H, m), 2.81 (2H, t, J = 6.7 Hz), 2.63 (3H, s), 2.18-1.91 (2H, m). |

TABLE 11-continued

| | | | | | | |
|---|---|---|---|---|---|---|
| 87 | (2-fluoro-4-cyanophenyl) | (N-methyl diazabicyclic) | (3-fluoro-4-(2-methoxyethyl)phenyl) | acryloyl | free | 488.1 | 1H-NMR (DMSO-D6) δ: 7.81 (1H, t, J = 7.5 Hz), 7.75-7.51 (3H, m), 7.34 (1H, t, J = 10.5 Hz), 7.24 (1H, t, J = 7.9 Hz), 7.14-7.08 (2H, m), 7.01 (1H, d, J = 11.3 Hz), 4.72 (1H, s), 4.39 (1H, s), 3.89-3.59 (2H, m), 3.53 (2H, t, J = 6.6 Hz), 3.22 (3H, s), 3.08-2.90 (2H, m), 2.81 (2H, t, J = 6.7 Hz), 2.54 (3H, s), 2.16-1.84 (2H, m). |
| 88 | (2-fluoro-4-cyanophenyl) | (diazabicyclic NH) | (3-fluoro-4-(2-methoxyethyl)phenyl) | acryloyl | free | 488.1 | 1H-NMR (DMSO-D6) δ: 7.80-7.75 (1H, m), 7.55-7.49 (2H, m), 7.47 (1H, d, J = 1.5 Hz), 7.28 (1H, dd, J = 10.5, 1.4 Hz), 7.22 (1H, t, J = 7.9 Hz), 7.10 (2H, dt, J = 10.5, 3.8 Hz), 6.97 (1H, d, J = 11.3 Hz), 4.31-4.21 (1H, m), 3.54-3.29 (6H, m), 3.21 (3H, s), 3.00-2.93 (1H, m), 2.79 (2H, t, J = 6.6 Hz), 1.76-1.48 (4H, m). |
| 89 | (2-fluoro-4-cyanophenyl) | (3-aminopyrrolidinyl) | (benzothiazolyl) | acryloyl | free | 443.1 | 1H-NMR (DMSO-D6) δ: 9.34 (1H, s), 7.89 (1H, s), 7.73-7.58 (5H, m), 7.42-7.33 (1H, m), 7.11 (1H, d, J = 8.2 Hz), 7.07-7.01 (1H, m), 3.85-3.50 (5H, m), 2.20-2.07 (1H, m), 1.97-1.82 (1H, m). |

TABLE 12

| | | | | | |
|---|---|---|---|---|---|
| 90 | (2-fluoro-4-ethynylphenyl)benzonitrile | (3S)-pyrrolidin-3-amine | 1-methyl-pyrazolo[3,4-b]pyridine | C=O | free | 441.2 | 1H-NMR (DMSO-D6) δ: 8.19 (1H, d, J = 1.9 Hz), 8.08 (1H, s), 8.04 (1H, d, J = 1.9 Hz), 7.72 (1H, t, J = 7.6 Hz), 7.68-7.65 (1H, m), 7.61 (2H, d, J = 8.2 Hz), 7.44-7.37 (1H, m), 7.07-6.99 (1H, m), 3.97 (3H, s), 3.86-3.42 (5H, m), 2.23-2.09 (1H, m), 1.99-1.86 (1H, m). |
| 91 | | | 1-methyl-benzimidazole | C=O | free | 440.2 | 1H-NMR (DMSO-D6) δ: 8.23 (1H, s), 7.69 (1H, t, J = 7.6 Hz), 7.66-7.60 (1H, m), 7.54 (2H, d, J = 7.6 Hz), 7.43 (2H, d, J = 6.3 Hz), 7.35-7.28 (1H, m), 7.06-7.00 (1H, m), 6.98-6.91 (1H, m), 3.86-3.53 (8H, m), 2.22-2.10 (1H, m), 1.99-1.89 (1H, m). |
| 92 | | | 1-methyl-indazole | C=O | free | 440.2 | 1H-NMR (DMSO-D6) δ: 7.75-7.71 (1H, m), 7.70-7.66 (1H, m), 7.64 (1H, s), 7.62-7.58 (2H, m), 7.50 (1H, d, J = 8.9 Hz), 7.37-7.32 (2H, m), 7.08 (1H, d, J = 7.9 Hz), 7.04 (1H, d, J = 8.5 Hz), 4.41-4.12 (4H, m), 3.32-3.24 (1H, m), 3.16 (3H, s), 2.21-2.10 (1H, m), 1.82-1.59 (1H, m). |
| 93 | | | 2-methyl-indazole | C=O | free | 440.2 | 1H-NMR (DMSO-D6) δ: 8.30 (1H, s), 7.75 (1H, t, J = 7.5 Hz), 7.69-7.64 (1H, m), 7.62-7.58 (2H, m), 7.55 (1H, s), 7.44 (1H, d, J = 9.2 Hz), 7.40-7.33 (1H, m), 7.08 (1H, d, J = 8.4 Hz), 6.86 (1H, d, J = 9.2 Hz), 4.13 (3H, s), 3.91-3.40 (4H, m), 3.19-3.09 (1H, m), 2.27-2.17 (1H, m), 2.06-1.93 (1H, m). |
| 94 | | | 4-fluoro-3-(2-methoxyethyl)phenyl | C=S | free | 478.2 | 1H-NMR (DMSO-D6) δ: 7.80 (1H, t, J = 7.5 Hz), 7.57-7.54 (1H, m), 7.51-7.49 (1H, m), 7.47 (1H, d, J = 7.9 Hz), 7.31 (1H, ddd, J = 10.6, 5.3, 1.4 Hz), 7.24 (1H, td, J = 7.9, 2.4 Hz), 7.10 (2H, d, J = 7.6 Hz), 7.00 (1H, d, J = 11.3 Hz), 4.00-3.56 (4H, m), 3.53 (2H, t, J = 6.7 Hz), 3.32-3.27 (1H, m), 3.23 (3H, s), 2.81 (2H, t, J = 6.6 Hz), 2.18-2.04 (1H, m), 1.85-1.74 (1H, m). |

TABLE 12-continued

| | | | | | |
|---|---|---|---|---|---|
| 95 | 4-cyano-2-fluorophenyl | 3-aminopyrrolidine | 6-fluoro-benzimidazole | acetyl | free | 458.2 | 1H-NMR (DMSO-D6) δ: 8.34 (1H, s), 7.78 (1H, t, J = 7.5 Hz), 7.71 (1H, t, J = 6.4 Hz), 7.67-7.63 (2H, m), 7.60 (1H, d, J = 7.9 Hz), 7.47-7.35 (2H, m), 7.11 (1H, d, J = 7.9 Hz), 3.81 (3H, s), 3.78-3.60 (5H, m), 2.31-2.19 (1H, m), 2.07-1.96 (1H, m). |
| 96 | | | | | free | 459.2 | 1H-NMR (DMSO-D6) δ: 7.95-8.15 (2H, m), 7.60-7.79 (4H, m), 7.37-7.46 (1H, m), 7.07-7.13 (1H, m), 4.24 (3H, s), 4.09-3.49 (5H, m), 1.95-2.20 (2H, m). |
| 97 | | | | | free | 426.3 | 1H-NMR (DMSO-D6) δ: 8.30 (1H, d, J = 9.9 Hz), 7.75 (2H, d, J = 8.1 Hz), 7.57 (1H, d, J = 8.1 Hz), 7.52 (1H, d, J = 7.7 Hz), 7.46 (1H, s), 7.32 (2H, d, J = 8.1 Hz), 7.16-7.09 (3H, m), 4.64-4.52 (1H, m), 4.19-4.07 (1H, m), 3.45-3.37 (1H, m), 2.11-1.40 (8H, m). |
| 98 | | | | | free | 442.2 444.2 | 1H-NMR (DMSO-D6) δ: 8.30 (1H, d, J = 8.4 Hz), 7.76 (2H, d, J = 8.4 Hz), 7.58 (1H, d, J = 7.7 Hz), 7.53 (1H, d, J = 8.1 Hz), 7.46 (1H, s), 7.35-7.32 (3H, m), 7.13 (2H, d, J = 8.4 Hz), 4.65-4.58 (1H, m), 4.16-4.08 (1H, m), 3.44-3.38 (1H, m), 2.04-1.47 (8H, m). |

TABLE 13

| # | | | | | | NMR |
|---|---|---|---|---|---|---|
| 99 | | | | | free | 402.2 | 1H-NMR (DMSO-D6) δ: 8.36 (2H, d, J = 6.7 Hz), 7.90 (1H, t, J = 7.8 Hz), 7.81 (1H, d, J = 13.1 Hz), 7.75 (1H, dd, J = 7.9, 1.8 Hz), 7.64 (2H, d, J = 7.6 Hz), 7.33 (2H, d, J = 6.4 Hz) 7.26 (2H, d, J = 6.4 Hz), 3.95-3.72 (4H, m), 3.51-3.45 (1H, m), 2.50 (3H, s), 2.31-2.21 (1H, m), 2.02-1.93 (1H, m). |
| 100 | | | | | free | 430.3 | 1H-NMR (DMSO-D6) δ: 7.94-7.86 (3H, m), 7.73-7.65 (1H, m), 7.62-7.54 (2H, m), 7.50-7.43 (1H, m), 7.29-7.22 (1H, m), 7.19-7.14 (1H, m), 3.93-3.57 (5H, m), 3.03 (6H, s), 2.30-2.18 (1H, m), 2.06-1.94 (1H, m). |
| 101 | | | | | free | 441.2 | 1H-NMR (DMSO-D6) δ: 7.93-7.88 (2H, m), 7.76-7.62 (4H, m), 7.41 (1H, t, J = 9.5 Hz), 7.19 (1H, d, J = 8.8 Hz), 7.10-7.05 (1H, m), 4.28 (3H, s), 3.72-3.41 (5H, m), 2.27-2.18 (1H, m), 2.05-1.95 (1H, m). |
| 102 | | | | | free | 476.2 | 1H-NMR (DMSO-D6) δ: 8.27 (1H, s), 7.80 (1H, t, J = 7.6 Hz), 7.73 (1H, t, J = 5.5 Hz), 7.67 (1H, s), 7.63 (1H, d, J = 7.9 Hz), 7.48-7.40 (2H, m), 7.16-7.10 (1H, m), 3.98 (3H, s), 3.92-3.44 (5H, m), 2.31-2.20 (1H, m), 2.07-1.96 (1H, m). |
| 103 | | | | | free | 454.2 | 1H-NMR (DMSO-D6) δ: 7.79-7.73 (1H, m), 7.70-7.65 (1H, m), 7.63-7.55 (2H, m), 7.39 (1H, d, J = 8.2 Hz), 7.32 (1H, d, J = 1.2 Hz), 7.12-7.07 (1H, m), 6.96-6.91 (1H, m), 3.72 (3H, t, J = 6.7 Hz), 3.67-3.48 (5H, m), 2.54 (3H, s), 1.99 (1H, dd, J = 9.0, 3.8 Hz), 1.67-1.62 (1H, m). |
| 104 | | | | | free | 476.2 | 1H-NMR (DMSO-D6) δ: 7.91-7.86 (3H, m), 7.81-7.65 (4H, m), 7.57 (1H, d, J = 1.5 Hz), 7.53 (2H, td, J = 6.6, 3.4 Hz), 7.46 (1H, dd, J = 10.4, 1.2 Hz), 7.16-7.12 (2H, m), 4.65 (1H, s), 4.19 (1H, s), 3.51-3.43 (1H, m), 2.11-1.49 (8H, m). |

TABLE 13-continued

| 105 | | | | free | 495.2 | 1H-NMR (DMSO-D6) δ: 8.93 (1H, d, J = 2.1 Hz), 8.44 (1H, d, J = 8.9 Hz), 7.81 (1H, d, J = 8.5 Hz), 7.78-7.61 (5H, m), 7.50-7.43 (2H, m), 7.13 (1H, d, J = 6.7 Hz), 4.65 (1H, s), 4.18 (1H, s), 3.49-3.40 (1H, m), 2.09-1.17 (8H, m). |
|---|---|---|---|---|---|---|
| 106 | | | | free | 497.3 | 1H-NMR (DMSO-D6) δ: 7.85 (1H, t, J = 7.6 Hz), 7.59-7.38 (4H, m), 7.16 (1H, dd, J = 7.9, 0.9 Hz), 6.58 (1H, d, J = 8.2 Hz), 6.52 (1H, d, J = 1.8 Hz), 6.48 (1H, dd, J = 8.2, 1.8 Hz), 4.61 (1H, s), 4.22-4.13 (3H, m), 3.45-3.40 (1H, m), 3.26-3.22 (2H, m), 2.81 (3H, s), 2.06-1.15 (8H, m). |
| 107 | | | | free | 477.3 | 1H-NMR (DMSO-D6) δ: 8.92 (1H, dd, J = 4.3, 1.8 Hz), 8.39-8.35 (1H, m), 7.95-7.88 (2H, m), 7.80-7.73 (2H, m), 7.69 (1H, dd, J = 7.8, 1.7 Hz), 7.59-7.55 (2H, m), 7.50 (1H, dd, J = 10.4, 1.5 Hz), 7.30 (1H, dd, J = 8.4, 1.7 Hz), 7.15 (1H, dd, J = 8.2, 1.5 Hz), 4.68 (1H, s), 4.25 (1H, s), 3.69-3.57 (1H, m), 2.14-1.56 (8H, m). |

TABLE 14

| | | | | | |
|---|---|---|---|---|---|
| 108 | (3-cyano-2-fluorophenyl) | (8-azabicyclo NH2) | (6-fluoro-1-methylbenzimidazole) | acetyl | free | 498.2 | 1H-NMR (DMSO-D6) δ: 8.23 (1H, s), 7.77 (1H, t, J = 7.5 Hz), 7.65-7.62 (2H, m), 7.59 (1H, d, J = 7.9 Hz), 7.55 (1H, d, J = 1.5 Hz), 7.43-7.38 (2H, m), 7.12 (1H, dd, J = 7.9, 1.5 Hz), 4.65 (1H, s), 4.18 (1H, s), 3.80 (3H, s), 3.39-3.35 (1H, m), 2.11-1.66 (7H, m), 1.58-1.44 (1H, m). |
| 109 | | | | | free | 499.3 | 1H-NMR (DMSO-D6) δ: 8.14 (1H, d, J = 6.4 Hz), 7.77 (1H, t, J = 7.5 Hz), 7.72-7.63 (3H, m), 7.58 (1H, d, J = 1.5 Hz), 7.46 (1H, d, J = 10.4 Hz), 7.14 (1H, dd, J = 8.1, 1.4 Hz), 4.65 (1H, s), 4.26 (3H, s), 4.16 (1H, s), 3.37-3.33 (1H, m), 2.12-1.46 (8H, m). |
| 110 | | | | | free | 498.2 | 1H-NMR (DMSO-D6) δ: 8.11 (1H, s), 7.76 (1H, t, J = 7.5 Hz), 7.65 (1H, dd, J = 7.9, 1.8 Hz), 7.61 (1H, d, J = 7.9 Hz), 7.58 (1H, d, J = 1.5 Hz), 7.50 (1H, d, J = 8.5 Hz), 7.42 (1H, dd, J = 10.5, 1.4 Hz), 7.25 (1H, dd, J = 8.5, 7.0 Hz), 7.10 (1H, dd, J = 7.9, 1.5 Hz), 4.64 (1H, s), 4.16 (1H, s), 4.06 (3H, s), 3.42-3.36 (1H, m), 2.08-1.44 (8H, m). |
| 111 | | | | | free | 462.2 | 1H-NMR (DMSO-D6) δ: 8.32 (1H, s), 7.74 (2H, d, J = 8.5 Hz), 7.63 (2H, t, J = 5.5 Hz), 7.56 (1H, s), 7.50 (1H, s), 7.45 (1H, d, J = 8.9 Hz), 7.37 (2H, d, J = 8.5 Hz), 6.88 (1H, dd, J = 8.9, 1.8 Hz), 4.72-4.65 (1H, m), 4.32-4.22 (1H, m), 4.15 (3H, s), 2.12-1.54 (9H, m). |
| 112 | | | | | free | 544.2 | 1H-NMR (DMSO-D6) δ: 7.82 (1H, t, J = 7.5 Hz), 7.64 (1H, dd, J = 7.8, 1.7 Hz), 7.56-7.53 (2H, m), 7.35 (1H, d, J = 10.7 Hz), 7.25 (1H, t, J = 7.9 Hz), 7.15-7.10 (2H, m), 7.01 (1H, d, J = 11.9 Hz), 4.67-4.61 (1H, m), 4.17-4.10 (1H, m), 3.54 (2H, t, J = 6.7 Hz), 3.47-3.45 (1H, m), 3.23 (3H, s), 3.02-2.94 (1H, m), 2.82 (2H, t, J = 6.7 Hz), 2.04-1.31 (8H, m), 1.01 (6H, d, J = 6.1 Hz). |

TABLE 14-continued
| | | | | | |
|---|---|---|---|---|---|
| 113 | 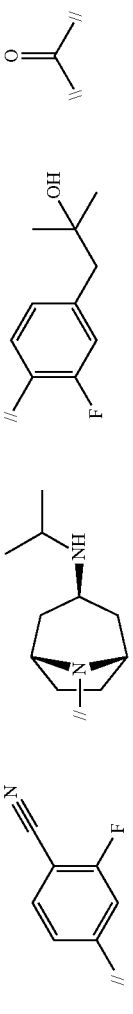 | 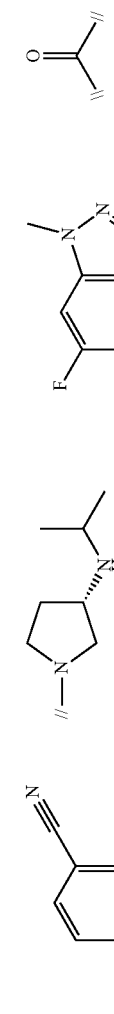 | 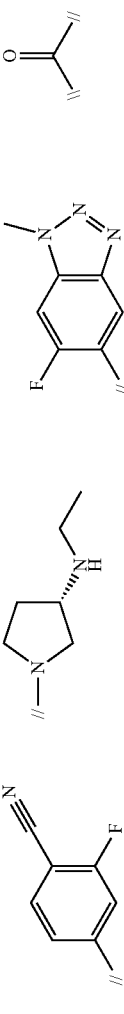 | free | 558.2 | 1H-NMR (DMSO-D6) δ: 7.81 (1H, t, J = 7.5 Hz), 7.64 (1H, dd, J = 7.8, 1.7 Hz), 7.58-7.54 (2H, m), 7.29 (1H, d, J = 9.2 Hz), 7.22 (1H, t, J = 7.8 Hz), 7.16 (1H, dd, J = 8.1, 1.4 Hz), 7.07 (1H, d, J = 7.9 Hz), 6.96 (1H, d, J = 11.3 Hz), 4.66-4.61 (1H, m), 4.42-4.38 (1H, m), 4.16-4.10 (1H, m), 3.48-3.43 (1H, m), 3.02-2.93 (1H, m), 2.68-2.65 (2H, m), 2.06-1.32 (8H, m), 1.04 (6H, s), 1.00 (6H, d, J = 5.8 Hz). |
| 114 | | | | free | 487.2 | 1H-NMR (DMSO-D6) δ: 7.82-7.63 (6H, m), 7.49-7.40 (1H, m), 7.13 (1H, d, J = 7.6 Hz), 4.27 (3H, s), 3.77-3.57 (5H, m), 2.50-2.49 (2H, m), 1.15 (2H, s), 1.06 (3H, t, J = 6.9 Hz). |
| 115 | | | | free | 501.3 | 1H-NMR (DMSO-D6) δ: 8.16-8.14 (1H, m), 7.79-7.72 (2H, m), 7.70 (1H, d, J = 9.2 Hz), 7.66 (1H, s), 7.62 (1H, d, J = 7.6 Hz), 7.47-7.43 (1H, m), 7.14-7.12 (1H, m), 4.28 (3H, s), 3.74-3.52 (6H, m), 2.13-2.03 (1H, m), 1.81-1.72 (1H, m), 1.07-0.96 (6H, m). |

TABLE 15

| | | | | | | |
|---|---|---|---|---|---|---|
| 116 | (aryl nitrile) | (cyclobutylamino pyrrolidine) | (fluoro benzotriazole) | (acyl) | free | 513.2 | 1H-NMR (DMSO-D6) δ: 8.14-8.13 (1H, m), 7.78-7.61 (5H, m), 7.45 (1H, dd, J = 9.9, 4.7 Hz), 7.13 (1H, dd, J = 7.9, 1.5 Hz), 4.27 (3H, s), 3.68-3.48 (6H, m), 2.18-1.95 (4H, m), 1.79-1.58 (4H, m). |
| 117 | | (diaminopyrrolidine) | (indoline) | | free | 441.2 | 1H-NMR (DMSO-D6) δ: 7.84 (1H, t, J = 7.5 Hz), 7.65-7.60 (1H, m), 7.55 (1H, s), 7.50 (1H, d, J = 8.2 Hz), 7.39-7.34 (1H, m), 7.12 (1H, d, J = 7.3 Hz), 6.88 (1H, s), 6.69 (1H, d, J = 8.2 Hz), 6.38 (1H, d, J = 7.9 Hz), 3.93-3.54 (6H, m), 3.20-3.15 (1H, m), 2.82 (2H, t, J = 8.1 Hz), 2.69 (3H, s), 2.30-2.18 (1H, m), 2.06-1.92 (1H, m). |
| 118 | | (aminopyrrolidine) | (benzoxazine) | | free | 457.2 | 1H-NMR (DMSO-D6) δ: 7.86 (1H, t, J = 7.5 Hz), 7.64-7.60 (1H, m), 7.54 (1H, s), 7.50 (1H, d, J = 7.9 Hz), 7.42-7.36 (1H, m), 7.17-7.11 (1H, m), 6.58 (1H, d, J = 8.5 Hz), 6.47 (1H, d, J = 2.1 Hz), 4.22-4.17 (2H, m), 3.94-3.53 (4H, m), 3.30-3.21 (3H, m), 2.81 (3H, s), 2.29-2.15 (1H, m), 2.02-1.89 (1H, m). |
| 119 | | (aminopyrrolidine) | (benzoxazolone) | | free | 457.2 | 1H-NMR (DMSO-D6) δ: 7.82 (1H, t, J = 7.5 Hz), 7.71-7.67 (1H, m), 7.62-7.57 (2H, m), 7.41 (1H, t, J = 10.7 Hz), 7.22 (1H, s), 7.18 (1H, d, J = 8.2 Hz), 7.13-7.08 (1H, m), 6.94 (1H, d, J = 9.5 Hz), 3.96-3.56 (4H, m), 3.30-3.26 (3H, m), 3.24-3.17 (1H, m), 2.31-2.18 (1H, m), 2.07-1.95 (1H, m). |
| 120 | | (aminopyrrolidine) | (benzothiazolone) | | free | 473.2 | 1H-NMR (DMSO-D6) δ: 7.82 (1H, t, J = 7.5 Hz), 7.69 (1H, t, J = 6.1 Hz), 7.63-7.56 (3H, m), 7.44 (1H, t, J = 9.2 Hz), 7.22 (1H, d, J = 8.2 Hz), 7.11-7.07 (1H, m), 7.07-7.04 (1H, m), 3.84-3.52 (4H, m), 3.31-3.28 (3H, m), 3.28-3.23 (1H, m), 2.21-2.12 (1H, m), 1.94-1.85 (1H, m). |

TABLE 15-continued

| 121 | [structure: 2-fluoro-4-substituted benzonitrile] | [structure: 3-aminopyrrolidine] | [structure: 2,3-dihydro-1,4-benzodioxine] | [structure: C=O] | free | 444.1 | 1H-NMR (DMSO-D6) δ: 7.85 (1H, t, J = 7.5 Hz), 7.67-7.63 (1H, m), 7.57 (1H, s), 7.53 (1H, d, J = 7.6 Hz), 7.42-7.35 (1H, m), 7.14-7.11 (1H, m), 6.76 (1H, d, J = 8.5 Hz), 6.72 (1H, d, J = 2.1 Hz), 6.50 (1H, d, J = 7.3 Hz), 4.25-4.20 (4H, m), 3.98-3.56 (4H, m), 3.30-3.25 (1H, m), 2.33-2.15 (1H, m), 2.07-1.95 (1H, m). |
| --- | --- | --- | --- | --- | --- | --- | --- |
| 122 | [structure: 2-fluoro-4-substituted benzonitrile] | [structure: 3-aminopyrrolidine] | [structure: 1,3-benzodioxole] | [structure: C=O] | free | 430.2 | 1H-NMR (DMSO-D6) δ: 7.83 (1H, t, J = 7.5 Hz), 7.68-7.62 (1H, m), 7.59-7.55 (1H, m), 7.53 (1H, d, J = 7.9 Hz), 7.40-7.34 (1H, m), 7.14-7.10 (1H, m), 6.84 (1H, d, J = 7.9 Hz), 6.74 (1H, d, J = 1.5 Hz), 6.56 (1H, d, J = 7.9 Hz), 6.01 (2H, s), 4.23-3.74 (4H, m), 3.36-3.28 (1H, m), 2.30-2.14 (1H, m), 2.11-1.95 (1H, m). |
| 123 | [structure: 2-fluoro-4-substituted benzonitrile] | [structure: azabicyclic amine with NH2] | [structure: 6-fluoro-1-methylindole] | [structure: C=O] | free | 497.2 | 1H-NMR (DMSO-D6) δ: 7.74 (1H, t, J = 7.5 Hz), 7.60 (1H, dd, J = 7.9, 1.8 Hz), 7.55-7.49 (3H, m), 7.37-7.33 (2H, m), 7.21 (1H, dd, J = 11.0 Hz), 7.10 (1H, dd, J = 8.2, 1.5 Hz), 6.45 (1H, d, J = 3.1 Hz), 4.59 (1H, s), 4.09 (1H, s), 3.75-3.69 (3H, m), 2.22-1.50 (9H, m). |

TABLE 16
| | | | | | |
|---|---|---|---|---|---|
| 124 | 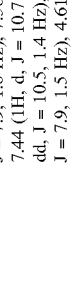 | | | free | 498.2 | 1H-NMR (DMSO-D6) δ: 8.09 (1H, d, J = 0.9 Hz), 7.79 (1H, d, J = 7.3 Hz), 7.75 (1H, t, J = 7.5 Hz), 7.63 (1H, dd, J = 7.9, 1.8 Hz), 7.58-7.54 (2H, m), 7.44 (1H, d, J = 10.7 Hz), 7.39 (1H, dd, J = 10.5, 1.4 Hz), 7.10 (1H, dd, J = 7.9, 1.5 Hz), 4.61 (1H, s), 4.10 (1H, s), 3.98 (3H, s), 2.61-2.57 (2H, m), 2.47-2.42 (1H, m), 2.27-1.52 (6H, m). |
| 125 | | | | free | 499.2 | 1H-NMR (DMSO-D6) δ: 8.12 (1H, d, J = 6.4 Hz), 7.74 (1H, t, J = 7.5 Hz), 7.69-7.65 (1H, m), 7.62 (1H, d, J = 7.9 Hz), 7.58 (1H, d, J = 1.5 Hz), 7.44 (2H, dd, J = 10.5, 1.4 Hz), 7.13 (1H, dd, J = 7.9, 1.5 Hz), 4.64 (1H, s), 4.25 (3H, s), 4.11 (1H, s), 2.34-2.10 (3H, m), 2.07-1.94 (3H, m), 1.93-1.52 (3H, m). |
| 126 | | | | free | 516.2 | 1H-NMR (DMSO-D6) δ: 8.25 (1H, s), 7.76 (1H, m), 7.66-7.63 (1H, m), 7.60-7.56 (2H, m), 7.45-7.41 (2H, m), 7.12 (1H, dd, J = 7.9, 1.5 Hz), 4.61 (1H, s), 4.10 (1H, s), 3.96 (3H, s), 2.30-2.17 (2H, m), 2.14-2.04 (1H, m), 2.01-1.51 (6H, m). |
| 127 | | | | free | 516.2 | 1H-NMR (DMSO-D6) δ: 7.83 (1H, t, J = 7.5 Hz), 7.56 (2H, d, J = 0.9 Hz), 7.48 (1H, d, J = 0.9 Hz), 7.34 (1H, dd, J = 10.5, 1.4 Hz), 7.25 (1H, t, J = 7.9 Hz), 7.13-7.10 (2H, m), 7.04-6.99 (1H, m), 4.78-4.72 (1H, m), 3.97-3.92 (1H, m), 3.54 (2H, t, J = 8.5 Hz), 3.29-3.28 (1H, m), 3.23 (3H, s), 2.82 (2H, t, J = 6.7 Hz), 2.07-1.56 (10H, m). |

TABLE 16-continued
| | | | | | |
|---|---|---|---|---|---|
| 128 | 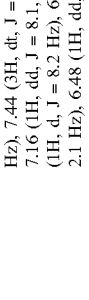 | 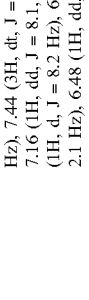 | 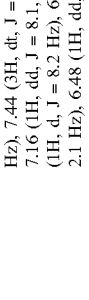 | 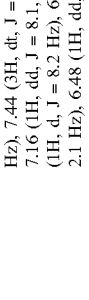 | free | 497.2 | 1H-NMR (DMSO-D6) δ: 7.84 (1H, t, J = 7.5 Hz), 7.54 (1H, dt, J = 7.9, 1.5 Hz), 7.44 (3H, dd, J = 17.3, 7.9 Hz), 7.16 (1H, dd, J = 8.1, 1.4 Hz), 6.59 (1H, d, J = 8.2 Hz), 6.53 (1H, d, J = 2.1 Hz), 6.48 (1H, dd, J = 8.2, 2.1 Hz), 4.58 (1H, s), 4.20 (2H, t, J = 4.4 Hz), 4.10 (1H, s), 3.24 (2H, t, J = 4.4 Hz), 2.82 (3H, s), 2.40-1.90 (7H, m), 1.60-1.52 (2H, m). |
| 129 | | | | | free | 516.2 | 1H-NMR (DMSO-D6) δ: 7.82 (1H, t, J = 7.5 Hz), 7.54 (2H, s), 7.48 (1H, s), 7.34 (1H, d, J = 10.7 Hz), 7.25 (1H, t, J = 7.9 Hz), 7.16-7.08 (2H, m), 7.01 (1H, d, J = 11.0 Hz), 4.91-4.84 (1H, m), 4.07-4.01 (1H, m), 3.54 (2H, t, J = 6.6 Hz), 3.24 (3H, s), 2.93-2.86 (1H, m), 2.82 (2H, t, J = 6.6 Hz), 2.31-1.96 (3H, m), 1.67-1.50 (4H, m), 1.43-1.24 (3H, m). |
| 130 | | | | | free | 498.1 | 1H-NMR (DMSO-D6) δ: 8.28 (1H, s), 7.77-7.73 (1H, m), 7.64 (2H, dd, J = 9.8, 7.9 Hz), 7.58 (2H, d, J = 7.9 Hz), 7.42 (2H, d, J = 9.8 Hz), 7.11 (1H, d, J = 7.9 Hz), 4.69 (1H, s), 4.18 (1H, s), 3.80 (3H, s), 2.45-2.28 (3H, m), 2.13-2.02 (2H, m), 1.88-1.80 (2H, m), 1.73-1.59 (2H, m). |
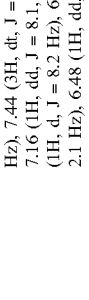

TABLE 17

| 131 | [4-cyano-2-fluorophenyl] | [8-azabicyclo[3.2.1]octan-3-amine, exo] | [5-(dimethylamino)pyridin-2-yl] | acetyl | free | 470.2 | 1H-NMR (DMSO-D6) δ: 7.91 (1H, d, J = 2.4 Hz), 7.87 (1H, t, J = 7.5 Hz), 7.79-7.74 (1H, m), 7.60 (1H, d, J = 7.9 Hz), 7.55-7.46 (2H, m), 7.22 (1H, d, J = 7.9 Hz), 7.17 (1H, d, J = 7.9 Hz), 6.60-6.56 (1H, m), 4.66 (1H, s), 4.17 (1H, s), 3.02 (6H, s), 2.40-2.25 (3H, m), 2.10-2.01 (2H, m), 1.84-1.78 (2H, m), 1.70-1.59 (2H, m). |
| --- | --- | --- | --- | --- | --- | --- | --- |
| 132 | [4-cyano-2-fluorophenyl] | [8-azabicyclo[3.2.1]octan-3-amine] | [1,3,3-trimethyl-2-oxoindolin-5-yl] | acetyl | free | 523.2 | 1H-NMR (DMSO-D6) δ: 7.80 (1H, t, J = 7.5 Hz), 7.62-7.55 (2H, m), 7.51 (1H, d, J = 1.5 Hz), 7.36 (1H, d, J = 10.4 Hz), 7.22 (1H, dd, J = 7.9, 1.8 Hz), 7.09 (1H, dd, J = 8.1, 1.4 Hz), 7.02 (1H, d, J = 8.2 Hz), 6.90 (1H, d, J = 1.8 Hz), 4.58 (1H, s), 4.07 (1H, s), 3.13 (3H, s), 2.25-1.84 (7H, m), 1.63-1.48 (2H, m), 1.07 (6H, s). |
| 133 | [4-cyano-2-fluorophenyl] | [8-azabicyclo[3.2.1]octan-3-amine] | [3-methyl-2-oxo-2,3-dihydrobenzo[d]thiazol-6-yl] | acetyl | free | 513.1 | 1H-NMR (DMSO-D6) δ: 7.81 (1H, t, J = 7.6 Hz), 7.62-7.58 (2H, m), 7.55 (1H, d, J = 7.9 Hz), 7.51 (1H, d, J = 1.8 Hz), 7.46 (1H, dd, J = 10.5, 1.4 Hz), 7.22 (1H, d, J = 8.2 Hz), 7.10 (1H, dd, J = 8.2, 1.5 Hz), 7.06 (1H, dd, J = 8.2, 1.8 Hz), 4.58 (1H, s), 4.07 (1H, s), 3.27-3.24 (3H, m), 2.27-1.84 (7H, m), 1.63-1.48 (2H, m). |
| 134 | [4-cyano-2-fluorophenyl] | [pyrrolidin-3-amine] | [5-fluoro-1-methyl-1H-indol-6-yl] | acetyl | free | 457.1 | 1H-NMR (DMSO-D6) δ: 7.79-7.73 (1H, m), 7.72-7.66 (1H, m), 7.65-7.59 (1H, m), 7.58-7.49 (2H, m), 7.39-7.32 (2H, m), 7.22 (1H, d, J = 11.0 Hz), 7.14-7.09 (1H, m), 6.45 (1H, d, J = 3.1 Hz), 3.74 (3H, s), 3.69-3.60 (5H, m), 2.04-1.94 (1H, m), 1.71-1.65 (1H, m). |

| | | | | | |
|---|---|---|---|---|---|
| 135 | ![benzonitrile with F] | ![pyrrolidine with NH2] | ![fluoroindazole] | ![acetyl] | free | 458.1 | 1H-NMR (DMSO-D6) δ: 8.10 (1H, s), 7.81-7.75 (2H, m), 7.71 (1H, t, J = 7.0 Hz), 7.66 (1H, d, J = 5.2 Hz), 7.59 (1H, d, J = 7.9 Hz), 7.46 (1H, d, J = 10.4 Hz), 7.42-7.38 (1H, m), 7.10 (1H, d, J = 8.2 Hz), 4.00 (3H, s), 3.79-3.66 (5H, m), 2.16-2.09 (1H, m), 1.88-1.80 (1H, m). |
| 136 | ![benzonitrile with F] | ![bicyclic amine NH2] | ![fluoroindole with CH2C(CH3)2OH] | ![acetyl] | free | 555.1 | 1H-NMR (DMSO-D6) δ: 7.74 (1H, t, J = 7.6 Hz), 7.61 (1H, dd, J = 7.9, 1.8 Hz), 7.58-7.53 (2H, m), 7.48 (1H, d, J = 7.6 Hz), 7.33 (3H, dd, J = 21.4, 7.0 Hz), 7.13 (1H, dd, J = 7.9, 1.5 Hz), 6.45 (1H, d, J = 3.1 Hz), 4.64 (1H, s), 4.62-4.57 (1H, m), 4.13-4.08 (1H, m), 4.02 (2H, s), 2.25-2.14 (2H, m), 2.03-1.86 (3H, m), 1.80-1.68 (1H, m), 1.63-1.51 (2H, m), 1.46-1.33 (1H, m), 1.06 (6H, s). |
| 137 | ![benzonitrile with F] | ![bicyclic amine NH2] | ![dihydroisobenzofuran] | ![acetyl] | free | 468.1 | 1H-NMR (DMSO-D6) δ: 7.81 (1H, t, J = 7.5 Hz), 7.61 (1H, d, J = 9.8 Hz), 7.56-7.50 (2H, m), 7.42 (1H, d, J = 10.7 Hz), 7.22 (1H, d, J = 7.9 Hz), 7.18 (1H, s), 7.11 (1H, d, J = 8.2 Hz), 6.98 (1H, d, J = 7.9 Hz), 4.99 (2H, s), 4.95 (2H, s), 4.62-4.56 (1H, m), 4.12-4.07 (1H, m), 2.23-2.10 (2H, m), 2.05-1.86 (3H, m), 1.82-1.69 (1H, m), 1.63-1.50 (2H, m), 1.45-1.34 (1H, m). |

TABLE 18

| | | | | | | |
|---|---|---|---|---|---|---|
| 138 | (4-cyano-3-fluorophenyl) | (8-amino-3-azabicyclo) | (3-isopropyl-2-oxo-2,3-dihydrobenzothiazol-6-yl) | acetyl | free | 541.1 | 1H-NMR (DMSO-D6) δ: 7.82 (1H, t, J = 7.6 Hz), 7.62 (1H, d, J = 7.9 Hz), 7.58-7.54 (2H, m), 7.52 (1H, s), 7.48 (1H, d, J = 10.7 Hz), 7.40 (1H, d, J = 8.5 Hz), 7.12 (1H, d, J = 7.9 Hz), 7.04 (1H, d, J = 8.5 Hz), 4.78-4.71 (1H, m), 4.65-4.58 (1H, m), 4.14-4.08 (1H, m), 2.28-2.19 (1H, m), 2.15-1.90 (3H, m), 1.87-1.70 (2H, m), 1.65-1.52 (3H, m), 1.47 (6H, d, J = 7.0 Hz). |
| 139 | | | | acetyl | free | 541.2 | 1H-NMR (DMSO-D6) δ: 8.13 (1H, d, J = 7.0 Hz), 7.93 (1H, d, J = 10.4 Hz), 7.77 (1H, t, J = 7.6 Hz), 7.67-7.62 (2H, m), 7.59 (1H, s), 7.48 (1H, d, J = 10.7 Hz), 7.15 (1H, dd, J = 8.1, 1.4 Hz), 4.66-4.59 (1H, m), 4.14-4.08 (1H, m), 2.24-2.05 (4H, m), 2.01-1.86 (3H, m), 1.77 (9H, s), 1.66-1.53 (2H, m). |
| 140 | | | | acetyl | free | 428.1 | 1H-NMR (DMSO-D6) δ: 7.82 (1H, t, J = 7.6 Hz), 7.69 (1H, t, J = 7.6 Hz), 7.61 (1H, d, J = 6.4 Hz), 7.55 (1H, d, J = 7.9 Hz), 7.45-7.38 (1H, m), 7.23 (1H, d, J = 7.9 Hz), 7.18 (1H, s), 7.10 (1H, d, J = 7.6 Hz), 6.98 (1H, d, J = 6.4 Hz), 4.99 (2H, s), 4.95 (2H, s), 3.82-3.67 (5H, m), 2.13-2.06 (1H, m), 1.85-1.78 (1H, m). |
| 141 | | | | acetyl | free | 491 | 1H-NMR (DMSO-D6) δ: 7.82 (1H, t, J = 7.3 Hz), 7.75 (1H, d, J = 7.0 Hz), 7.72-7.69 (1H, m), 7.64 (1H, t, J = 4.7 Hz), 7.54 (1H, d, J = 7.9 Hz), 7.45 (1H, d, J = 10.4 Hz), 7.24 (1H, d, J = 10.7 Hz), 7.12 (1H, dd, J = 8.2, 1.5 Hz), 3.67-3.48 (5H, m), 3.37 (3H, s), 2.02-1.91 (1H, m), 1.69-1.61 (1H, m). |

TABLE 18-continued

| | | | | | |
|---|---|---|---|---|---|
| 142 | 4-cyano-3-fluorophenyl | 8-azabicyclo amine | 2-(5-fluoro-6-methyl-indazol-1-yl)-2-methylpropan-1-ol derivative | O | free | 556.1 | 1H-NMR (DMSO-D6) δ: 8.10 (1H, d, J = 0.9 Hz), 7.79-7.74 (2H, m), 7.63 (1H, dd, J = 7.8, 1.7 Hz), 7.59-7.55 (2H, m), 7.45 (1H, d, J = 11.0 Hz), 7.39 (1H, dd, J = 10.7, 1.5 Hz), 7.13 (1H, dd, J = 8.2, 1.5 Hz), 4.62 (1H, s), 4.60-4.56 (1H, m), 4.26 (2H, s), 4.08-4.05 (1H, m), 2.35-2.21 (2H, m), 2.12-2.06 (1H, m), 1.99-1.83 (3H, m), 1.64-1.48 (3H, m), 1.11 (6H, s). |
| 143 | 4-cyano-3-fluorophenyl | 8-azabicyclo amine Racemate Relative configuration | 3,4-difluoro-phenethyl methyl ether | O | free | 448.1 | 1H-NMR (DMSO-D6) δ: 7.82 (1H, t, J = 7.5 Hz), 7.73-7.58 (2H, m), 7.53 (1H, d, J = 7.9 Hz), 7.39-7.33 (1H, m), 7.25 (1H, t, J = 7.9 Hz), 7.16-7.10 (2H, m), 7.01 (1H, d, J = 11.3 Hz), 4.49-3.86 (3H, m), 3.54 (2H, t, J = 6.6 Hz), 3.23 (3H, s), 2.82 (2H, t, J = 6.6 Hz), 2.22-2.10 (2H, m), 1.89-1.70 (1H, m), 1.64-1.48 (2H, m), 0.91 (1H, dd, J = 12.2, 4.3 Hz). |
| 144 | 4-cyano-3-fluorophenyl | 8-azabicyclo amine | 2,3-difluoro-4-methylphenyl | O | free | 476.0 | 1H-NMR (DMSO-D6) δ: 7.83 (1H, dd, J = 7.9, 7.0 Hz), 7.63 (1H, dd, J = 7.8, 1.7 Hz), 7.57-7.53 (2H, m), 7.43 (1H, dd, J = 10.5, 1.4 Hz), 7.13-7.10 (2H, m), 7.03-6.99 (1H, m), 4.59 (1H, s), 4.05 (1H, s), 2.27 (3H, d, J = 1.2 Hz), 2.23-2.09 (3H, m), 2.04-1.85 (3H, m), 1.63-1.49 (3H, m). |

TABLE 19

| | | | | | NMR |
|---|---|---|---|---|---|
| 145 | (2-fluoro-4-cyanophenyl) | (8-azabicyclo, NH2) | (difluoro-methyl-benzotriazole) | C(=O) | 517.0 free | 1H-NMR (DMSO-D6) δ: 7.97 (1H, d, J = 4.6 Hz), 7.78 (1H, dd, J = 7.9, 7.0 Hz), 7.67 (1H, dd, J = 7.9, 1.8 Hz), 7.63 (1H, d, J = 7.6 Hz), 7.59 (1H, d, J = 1.5 Hz), 7.50 (1H, dd, J = 10.5, 1.4 Hz), 7.16 (1H, d, J = 7.9, 1.5 Hz), 4.61 (1H, s), 4.40 (3H, s), 4.06 (1H, s), 2.24-1.86 (6H, m), 1.66-1.51 (3H, m). |
| 146 | (2-fluoro-4-cyanophenyl) | (pyrrolidine, NH2) | (fluoro-indole with hydroxyisobutyl) | C(=O) | 515.0 free | 1H-NMR (DMSO-D6) δ: 7.74 (1H, t, J = 7.5 Hz), 7.68 (1H, t, J = 7.2 Hz), 7.62 (1H, d, J = 8.5 Hz), 7.55 (1H, d, J = 7.9 Hz), 7.47 (1H, d, J = 7.6 Hz), 7.35 (1H, d, J = 3.1 Hz), 7.30 (2H, d, J = 11.9 Hz), 7.11 (1H, t, J = 4.7 Hz), 6.44 (1H, d, J = 3.1 Hz), 4.62 (1H, s), 4.01 (2H, s), 3.78-3.58 (4H, m), 3.13-2.96 (1H, m), 2.03-1.93 (1H, m), 1.72-1.61 (1H, m), 1.05 (6H, s). |
| 147 | (2-fluoro-4-cyanophenyl) | (pyrrolidine, NH2) | (fluoro-indazole with hydroxyisobutyl) | C(=O) | 516.0 free | 1H-NMR (DMSO-D6) δ: 8.10 (1H, d, J = 0.9 Hz), 7.77-7.74 (2H, m), 7.71-7.69 (1H, m), 7.64 (1H, dd, J = 7.8, 1.7 Hz), 7.57-7.57 (1H, m), 7.44 (1H, d, J = 11.0 Hz), 7.37 (1H, d, J = 10.7 Hz), 7.11 (1H, dd, J = 8.1, 1.7 Hz), 4.61 (1H, s), 4.25 (2H, s), 3.69-3.57 (2H, m), 3.56-3.43 (2H, m), 3.24-3.14 (1H, m), 2.02-1.90 (1H, m), 1.68-1.61 (1H, m, s). |
| 148 | (2-fluoro-4-cyanophenyl) | (8-azabicyclo, NH2) | (quinoxaline) | C(=O) | 478.1 free | 1H-NMR (DMSO-D6) δ: 8.97 (2H, s), 8.03-7.98 (2H, m), 7.80-7.74 (2H, m), 7.70 (1H, dd, J = 7.9, 1.5 Hz), 7.62 (1H, dd, J = 1.5 Hz), 7.57-7.52 (2H, m), 7.15 (1H, dd, J = 8.1, 1.7 Hz), 4.69-4.62 (1H, m), 4.20-4.13 (1H, m), 2.33-1.91 (7H, m), 1.74-1.53 (2H, m). |
| 149 | (2-fluoro-4-cyanophenyl) | (8-azabicyclo, NH2) | (isoquinoline) | C(=O) | 477.0 free | 1H-NMR (DMSO-D6) δ: 9.40-9.31 (1H, m), 8.60-8.53 (1H, m), 8.07-7.95 (2H, m), 7.78-7.68 (4H, m), 7.62 (1H, s), 7.51 (1H, d, J = 9.8 Hz), 7.39-7.30 (1H, m), 7.09 (1H, d, J = 7.6 Hz), 4.76-4.63 (1H, m), 4.24-4.15 (1H, m), 2.36-1.81 (7H, m), 1.78-1.58 (2H, m). |

TABLE 19-continued

| | | | | | | |
|---|---|---|---|---|---|---|
| 150 | (2-fluoro-4-cyanophenyl) | (8-azabicyclo-NH2) | (isoquinoline) | (C=O) | free | 477.0 | 1H-NMR (DMSO-D6) δ: 9.37-9.31 (1H, m), 8.56-8.52 (1H, m), 8.13-8.08 (1H, m), 7.92-7.85 (2H, m), 7.76-7.70 (3H, m), 7.62 (1H, s), 7.50 (1H, d, J = 10.4 Hz), 7.46-7.40 (1H, m), 7.10 (1H, d, J = 7.9 Hz), 4.73-4.66 (1H, m), 4.24-4.17 (1H, m), 2.34-2.00 (5H, m), 1.92-1.57 (4H, m). |
| 151 | | | (quinoline) | | free | 477.0 | 1H-NMR (DMSO-D6) δ: 8.93 (1H, d, J = 4.3 Hz), 8.36 (1H, d, J = 8.5 Hz), 7.94 (1H, s), 7.90 (1H, d, J = 8.5 Hz), 7.76-7.69 (3H, m), 7.61 (1H, d, J = 1.5 Hz), 7.60-7.55 (1H, m), 7.51 (1H, d, J = 10.4 Hz), 7.40 (1H, d, J = 9.2 Hz), 7.10 (1H, dd, J = 7.9, 1.5 Hz), 4.74-4.65 (1H, m), 4.25-4.16 (1H, m), 2.31-1.58 (9H, m). |
| 152 | | | (quinazoline) | | free | 478.0 | 1H-NMR (DMSO-D6) δ: 9.60 (1H, s), 8.06 (1H, d, J = 8.5 Hz), 7.93 (1H, s), 7.75-7.74 (1H, m), 7.73-7.69 (1H, m), 7.63 (1H, s), 7.58-7.52 (2H, m), 7.45-7.41 (1H, m), 7.15-7.12 (2H, m), 4.72-4.63 (1H, m), 4.22-4.15 (1H, m), 2.13-2.04 (2H, m), 1.88-1.60 (7H, m). |

TABLE 20

| | | | | | 1H-NMR |
|---|---|---|---|---|---|
| 153 | (benzonitrile-F) | (bicyclic amine NH2) | (methylquinoline) | (acetyl) | free | 478.0 | 1H-NMR (DMSO-D6) δ: 9.32 (1H, s), 8.12 (1H, d, J = 2.7 Hz), 7.90 (1H, d, J = 8.5 Hz), 7.75-7.71 (3H, m), 7.69-7.62 (3H, m), 7.53 (1H, d, J = 10.1 Hz), 7.11-7.09 (1H, m), 4.73-4.65 (1H, m), 4.24-4.15 (1H, m), 2.14-2.01 (3H, m), 1.87-1.65 (6H, m). |
| 154 | | | (methylphthalazine) | | free | 478.0 | 1H-NMR (DMSO-D6) δ: 9.66 (2H, d, J = 3.4 Hz), 8.20 (1H, s), 8.12 (1H, s), 8.03 (1H, d, J = 8.5 Hz), 7.75-7.66 (4H, m), 7.62 (1H, s), 7.51 (1H, d, J = 9.2 Hz), 7.07 (1H, dd, J = 7.9, 1.5 Hz), 4.66-4.58 (1H, m), 4.15-4.07 (1H, m), 2.31-1.88 (7H, m), 1.67-1.50 (2H, m). |
| 155 | | isomer-B Relative configuration | (F-methoxyethyl phenyl) | | free | 488.0 | 1H-NMR (DMSO-D6) δ: 7.81 (1H, t, J = 7.5 Hz), 7.73-7.56 (2H, m), 7.52 (1H, d, J = 7.9 Hz), 7.35 (1H, d, J = 10.4 Hz), 7.24 (1H, t, J = 7.9 Hz), 7.14-7.09 (2H, m), 7.01 (1H, d, J = 11.3 Hz), 4.42-3.89 (3H, m), 3.53 (2H, t, J = 6.6 Hz), 3.23 (3H, s), 2.81 (2H, t, J = 6.6 Hz), 2.25-2.08 (2H, m), 1.79-1.68 (1H, m), 1.64-1.44 (2H, m), 0.91-0.87 (1H, m). |
| 156 | | isomer-A Relative configuration | (F-methoxyethyl phenyl) | | free | 488.0 | 1H-NMR (DMSO-D6) δ: 7.81 (H, t, J = 7.5 Hz), 7.73-7.56 (2H, m), 7.52 (1H, d, J = 7.6 Hz), 7.35 (1H, d, J = 10.7 Hz), 7.24 (1H, t, J = 7.9 Hz), 7.15-7.09 (2H, m), 7.01 (1H, d, J = 11.0 Hz), 4.46-3.85 (3H, m), 3.53 (2H, t, J = 6.7 Hz), 3.23 (3H, S), 2.81 (2H, t, J = 6.6 Hz), 2.21-2.10 (2H, m), 1.79-1.68 (1H, m), 1.64-1.46 (2H, m), 0.93-0.87 (1H, m). |
| 157 | | | (methylimidazopyridine) | | free | 480.0 | 1H-NMR (DMSO-D6) δ: 7.87 (1H, t, J = 7.5 Hz), 7.78 (3H, s), 7.65 (2H, s), 7.59-7.51 (3H, m), 7.24 (1H, d, J = 7.0 Hz), 4.67 (1H, s), 4.16 (1H, s), 2.52 (3H, s), 2.34-2.22 (2H, m), 2.14-2.02 (3H, m), 1.89-1.80 (3H, m), 1.76-1.57 (3H, m). |

TABLE 20-continued

| | | | | | |
|---|---|---|---|---|---|
| 158 | (4-cyano-3-fluorophenyl) | (bicyclic amine with NH2) | (pyrazolo[1,5-a]pyrimidine with methyl) | free | 481.1 | 1H-NMR (DMSO-D6) δ: 9.04 (1H, d, J = 2.1 Hz), 8.11 (1H, d, J = 0.6 Hz), 8.02 (1H, d, J = 2.1 Hz), 7.85 (1H, t, J = 7.5 Hz), 7.75 (1H, d, J = 7.9 Hz), 7.67 (1H, dd, J = 1.7 Hz), 7.62 (1H, dd, J = 10.4, 1.2 Hz), 7.59 (1H, d, J = 1.5 Hz), 7.28 (1H, dd, J = 7.9, 1.5 Hz), 4.62 (1H, s), 4.08 (1H, s), 2.26 (3H, s), 2.15-1.91 (6H, m), 1.68-1.51 (3H, m). |
| 159 | (4-cyano-3-fluorophenyl) | (bicyclic amine with NH2) | (fluoroindazole with 2-hydroxy-2-methylpropyl) | free | 556.0 | 1H-NMR (DMSO-D6) δ: 8.37 (1H, d, J = 0.9 Hz), 7.81-7.75 (2H, m), 7.62 (1H, dd, J = 7.9, 1.8 Hz), 7.58-7.54 (2H, m), 7.41 (1H, d, J = 10.7, 1.5 Hz), 7.26 (1H, d, J = 11.6 Hz), 7.14 (1H, dd, J = 8.2, 1.5 Hz), 4.87 (1H, s), 4.59 (1H, s), 4.32 (2H, s), 4.08 (1H, s), 2.28-2.10 (3H, m), 2.02-1.83 (3H, m), 1.63-1.49 (3H, m), 1.11 (6H, s). |
| 160 | (4-cyano-3-fluorophenyl) | (bicyclic amine with NH2) | (fluorobenzotriazole with ethyl) | free | 513.0 | 1H-NMR (DMSO-D6) δ: 8.14 (1H, d, J = 6.4 Hz), 7.77-7.74 (2H, m), 7.62 (3H, ddd, J = 29.6, 12.8, 3.2 Hz), 7.46 (1H, dd, J = 10.5, 1.4 Hz), 7.14 (1H, dd, J = 7.9, 1.5 Hz), 4.68 (2H, q, J = 7.3 Hz), 4.61 (1H, s), 4.09 (1H, s), 2.23-1.88 (6H, m), 1.65-1.52 (3H, m), 1.49 (3H, t, J = 7.2 Hz). |

TABLE 21

| # | | | | | | NMR |
|---|---|---|---|---|---|---|
| 161 | (4-cyano-3-fluorophenyl) | (8-azabicyclo NH2) | (difluoro-methyl-benzotriazole with OH) | acetyl | free | 575.0 | 1H-NMR (DMSO-D6) δ: 7.97 (1H, d, J = 4.6 Hz), 7.76 (1H, t, J = 7.6 Hz), 7.67-7.64 (2H, m), 7.59 (1H, d, J = 0.9 Hz), 7.48 (1H, dd, J = 10.5, 1.4 Hz), 7.16 (1H, dd, J = 7.9, 1.5 Hz), 4.81 (1H, s), 4.61 (2H, s), 4.57 (1H, s), 4.05 (1H, s), 2.34-2.21 (2H, m), 2.12-2.05 (1H, m), 1.99-1.83 (3H, m), 1.62-1.46 (3H, m), 1.15 (6H, s). |
| 162 | | (pyrrolidine NH2) | (difluoro-methyl-benzotriazole with OH) | acetyl | free | 535.0 | 1H-NMR (DMSO-D6) δ: 7.97 (1H, d, J = 5.2 Hz), 7.78-7.64 (4H, m), 7.46 (1H, d, J = 10.4 Hz), 7.15 (1H, dd, J = 8.2, 1.5 Hz), 4.81 (1H, s), 4.61 (2H, s), 3.69-3.57 (2H, m), 3.55-3.46 (2H, m), 3.23-3.15 (1H, m), 2.04-1.90 (1H, m), 1.68-1.56 (6H, m), 1.15 (6H, s). |
| 163 | | piperazine | (fluorophenyl-ethyl-methoxy) | acetyl | free | 462.0 | 1H-NMR (DMSO-D6) δ: 7.82 (1H, t, J = 7.5 Hz), 7.63-7.60 (1H, m), 7.57-7.53 (2H, m), 7.34 (1H, d, J = 10.4 Hz), 7.26-7.21 (1H, m), 7.13-7.09 (2H, m), 7.01 (1H, d, J = 11.3 Hz), 3.76-3.42 (8H, m), 3.23 (3H, s), 3.13-2.92 (2H, m), 2.81 (2H, t, J = 6.7 Hz). |
| 164 | | (piperidine NH2) | (fluorophenyl-ethyl-methoxy) | acetyl | free | 476.1 | 1H-NMR (DMSO-D6) δ: 7.82 (1H, t, J = 7.5 Hz), 7.59 (1H, dd, J = 7.8, 1.7 Hz), 7.56-7.52 (2H, m), 7.32 (1H, dd, J = 10.5, 1.4 Hz), 7.24 (1H, t, J = 7.9 Hz), 7.11 (2H, dd, J = 7.9, 1.5 Hz), 7.01 (1H, d, J = 11.3 Hz), 4.34-3.71 (2H, m), 3.53 (2H, t, J = 6.6 Hz), 3.23 (3H, s), 3.12-2.94 (2H, m), 2.82 (2H, t, J = 6.7 Hz), 1.99-1.91 (1H, m), 1.81-1.64 (1H, m), 1.56-1.41 (2H, m), 0.88-0.80 (1H, m). |
| 165 | | (azepane NH2) | (fluorophenyl-ethyl-methoxy) | acetyl | free | 490.1 | 1H-NMR (DMSO-D6) δ: 7.81 (1H, t, J = 7.5 Hz), 7.57-7.48 (3H, m), 7.35-7.31 (1H, m), 7.24 (1H, t, J = 7.9 Hz), 7.11 (2H, dd, J = 8.1, 1.4 Hz), 7.01 (1H, d, J = 11.3 Hz), 3.92-3.62 (2H, m), 3.58-3.41 (4H, m), 3.23 (3H, s), 2.81 (2H, t, J = 6.7 Hz), 2.14-2.03 (1H, m), 1.91-1.49 (5H, m), 0.88-0.80 (1H, m). |

TABLE 21-continued

| | | | | | |
|---|---|---|---|---|---|
| 166 | (2-fluoro-4-cyano-phenyl) | (azabicyclic NH2, isomer-B Relative configuration) | (3-fluoro-4-(2-hydroxy-2-methylpropyl)phenyl with C=O) | free | 502.0 | 1H-NMR (DMSO-D6) δ: 7.80 (1H, t, J = 7.6 Hz), 7.68 (1H, s), 7.60 (1H, s), 7.53 (1H, d, J = 7.9 Hz), 7.29 (1H, t, J = 5.3 Hz), 7.21 (1H, t, J = 7.9 Hz), 7.15 (1H, dd, J = 8.2, 1.5 Hz), 7.07 (1H, d, J = 7.9 Hz), 6.95 (1H, d, J = 11.6 Hz), 4.46-3.86 (3H, m), 2.65 (2H, s), 2.25-2.10 (2H, m), 1.74-1.49 (4H, m), 1.04 (6H, s), 0.87 (1H, dd, J = 12.2, 4.6 Hz). |
| 167 | (2-fluoro-4-cyano-phenyl) | (pyrrolidine NH2) | (methyl-benzotriazole with 2F) | free | 477.0 | 1H-NMR (DMSO-D6) δ: 7.99-7.96 (1H, m), 7.80-7.73 (2H, m), 7.69-7.67 (1H, m), 7.64 (1H, d, J = 7.9 Hz), 7.50-7.46 (1H, m), 7.18-7.14 (1H, m), 4.40 (3H, d, J = 6.7 Hz), 3.70-3.64 (2H, m), 3.58-3.48 (2H, m), 3.25-3.16 (1H, m), 2.08-2.04 (1H, m), 1.78-1.74 (1H, m). |
| 168 | (2-fluoro-4-cyano-phenyl) | (azabicyclic NH2) | (propyl-benzotriazole with F) | free | 527.0 | 1H-NMR (DMSO-D6) δ: 8.14 (1H, d, J = 6.7 Hz), 7.77-7.74 (2H, m), 7.68-7.59 (3H, m), 7.45 (1H, dd, J = 10.4, 1.5 Hz), 7.14 (1H, dd, J = 7.9, 1.5 Hz), 4.64-4.60 (3H, m), 4.14-4.07 (1H, m), 2.30-1.87 (9H, m), 1.66-1.55 (2H, m), 0.84 (3H, t, J = 7.3 Hz). |

TABLE 22

| # | | | | | | NMR |
|---|---|---|---|---|---|---|
| 169 | | | | | free | 521.0 | 1H-NMR (DMSO-D6) δ: 7.99 (1H, d, J = 4.9 Hz), 7.79-7.73 (2H, m), 7.70-7.64 (2H, m), 7.48-7.45 (1H, m), 7.16 (1H, dd, J = 8.2, 1.5 Hz), 4.91 (2H, t, J = 5.2 Hz), 3.81 (2H, t, J = 5.0 Hz), 3.69-3.45 (4H, m), 3.18-3.16 (4H, m), 2.01-1.94 (1H, m), 1.68-1.63 (1H, m). |
| 170 | | | | | free | 487.0 | 1H-NMR (DMSO-D6) δ: 7.75 (1H, dd, J = 7.8, 7.2 Hz), 7.69-7.66 (1H, m), 7.62 (1H, dd, J = 7.9, 1.5 Hz), 7.51 (2H, dd, J = 18.9, 7.5 Hz), 7.39-7.35 (2H, m), 7.25 (1H, d, J = 11.3 Hz), 7.11 (1H, dd, J = 3.1, 0.6 Hz), 6.44 (1H, dd, J = 3.1, 0.6 Hz), 4.86 (1H, t, J = 5.2 Hz), 4.15 (2H, t, J = 5.3 Hz), 3.69-3.59 (4H, m), 3.54-3.47 (2H, m), 3.22-3.18 (1H, m), 1.99-1.94 (1H, m), 1.73-1.66 (1H, m). |
| 171 | | | | | free | 541.0 | 1H-NMR (DMSO-D6) δ: 7.74 (1H, t, J = 7.5 Hz), 7.68 (1H, d, J = 7.9 Hz), 7.61-7.55 (2H, m), 7.47 (1H, d, J = 7.6 Hz), 7.36-7.29 (3H, m), 7.13 (1H, dd, J = 7.9, 1.5 Hz), 6.44 (1H, d, J = 3.4 Hz), 4.62 (1H, s), 4.48-3.87 (5H, m), 2.19-2.14 (2H, m), 1.78-1.73 (1H, m), 1.62-1.49 (2H, m), 1.05 (6H, s), 0.88 (1H, dd, J = 12.1, 4.7 Hz). |
| 172 | | | | | free | 533.0 | 1H-NMR (DMSO-D6) δ: 7.76 (1H, t, J = 7.6 Hz), 7.71-7.68 (1H, m), 7.66-7.64 (1H, m), 7.59 (1H, d, J = 7.9 Hz), 7.38 (1H, d, J = 3.4 Hz), 7.35-7.30 (2H, m), 7.12 (1H, dd, J = 7.9, 1.5 Hz), 6.51 (1H, t, J = 2.4 Hz), 4.70 (1H, s), 4.13 (2H, s), 3.70-3.55 (4H, m), 3.24-3.18 (1H, m), 2.01-1.99 (1H, m), 1.71-1.67 (1H, m), 1.05 (6H, s). |
| 173 | | | | | free | 541.0 | 1H-NMR (DMSO-D6) δ: 7.76-7.53 (5H, m), 7.50-7.44 (1H, m), 7.35-7.28 (2H, m), 7.15-7.08 (1H, m), 6.44 (1H, t, J = 2.7 Hz), 4.62 (1H, s), 4.30-3.84 (3H, m), 3.78-3.59 (1H, m), 3.20-3.15 (1H, m), 3.09-3.04 (1H, m), 2.25-1.50 (5H, m), 1.05 (6H, dd, J = 12.4, 4.7 Hz). |

TABLE 22-continued

| | | | | | |
|---|---|---|---|---|---|
| 174 | ![structure] | ![structure] | ![structure] | free | 502.1 | 1H-NMR (DMSO-D6) δ: 7.83-7.77 (1H, m), 7.67-7.49 (3H, m), 7.28-7.12 (3H, m), 7.09-7.05 (1H, m), 6.98-6.93 (1H, m), 4.40 (1H, d, J = 3.1 Hz), 4.11-3.72 (1H, m), 3.61-3.48 (1H, m), 3.22-3.16 (1H, m), 3.10-3.03 (1H, m), 2.66 (2H, s), 2.21-1.55 (5H, m), 1.04 (6H, s). |
| 175 | ![structure] | ![structure] isomer-B Relative configuration | ![structure] | free | 503.0 | 1H-NMR (DMSO-D6) δ: 7.98 (1H, d, J = 5.2 Hz), 7.78 (1H, t, J = 7.5 Hz), 7.75-7.70 (1H, m), 7.63 (2H, d, J = 7.6 Hz), 7.55-7.48 (1H, m), 7.17 (1H, dd, J = 8.2, 1.5 Hz), 4.48-3.88 (6H, m), 2.24-2.12 (2H, m), 1.75-1.51 (3H, m), 0.89 (1H, dd, J = 12.1, 4.7 Hz). |
| 176 | ![structure] | ![structure] isomer-B Relative configuration | ![structure] | free | 542.0 | 1H-NMR (DMSO-D6) δ: 8.10 (1H, d, J = 0.9 Hz), 7.80-7.74 (2H, m), 7.73-7.67 (1H, m), 7.64-7.56 (2H, m), 7.45 (1H, d, J = 11.0 Hz), 7.40 (1H, dd, J = 10.5, 1.4 Hz), 7.13 (1H, dd, J = 7.9, 1.5 Hz), 4.61 (1H, s), 4.49-3.89 (5H, m), 2.26-2.13 (2H, m), 1.81-1.50 (4H, m), 1.10 (6H, s). |

TABLE 23

| 177 | | isomer-B Relative configuration | | | free | 561.0 | 1H-NMR (DMSO-D6) δ: 7.97 (1H, d, J = 5.2 Hz), 7.78-7.73 (2H, m), 7.66 (2H, d, J = 7.6 Hz), 7.49 (1H, dd, J = 10.4 1.2 Hz), 7.17 (1H, dd, J = 8.2, 1.5 Hz), 4.81 (1H, s), 4.61 (2H, s), 4.49-3.87 (3H, m), 2.28-2.11 (2H, m), 1.80-1.51 (3H, m) 1.15 6H, s), 0.89 (1H, dd, J = 11.7, 4.7 Hz). |
|---|---|---|---|---|---|---|---|
| 178 | | | | | free | 635.9 | 1H-NMR (DMSO-D6) δ,7.77 (1H, t, J = 7.5 Hz), 7.64-7.56 (4H, m), 7.51 (1H, d, J = 10.7 Hz), 7.44 (1H, d, J = 11.6 Hz), 7.14) 1H, d, J = 9.2 Hz), 4.64 (1H, s), 4.58 (1H, s), 4.25 (2H, s), 4.05 (1H, s), 2.34-1.85 (6H, m), 1.64-1.44 (2H, m), 1.16-1.15 (1H, m), 1.13 1.08 (6H, m). |
| 179 | | | | | free | 499.0 | 1H-NMR (DMSO-D6) δ: 7.84 (1H, d, J = 5.2 Hz), 7.78 (1H, t, J = 7.5 Hz), 7.69-7.64 (2H, m), 7.63-7.58 (2H, m), 7.47 (1H, d, J = 10.4 Hz), 7.13 (1H, dd, J = 8.2, 1.5 Hz), 4.63-4.57 (1H, m), 4.11-4.02 (1H, m), 2.53 (3H, s), 2.24-1.90 (7H, m), 1.64-1.48 (2H, m). |
| 180 | | | | | free | 459.0 | 1H-NMR (DMSO-D6) δ: 7.83 (1H, d, J = 5.5 Hz), 7.79 (2H, t, J = 6.7 Hz), 7.74 (1H, t, J = 6.7Hz), 7.70-7.62 3H, m), 7.45 (1H, t, J = 9.0 Hz), 7.12 (1H, d, J = 8.9 Hz), 3.82-3.49 (5H, m), 2.53 (3H, s), 2.20-2.12 (1H, m), 1.94-1.84 (1H, m). |
| 181 | | | | | free | 570.0 | 1H-NMR (DMSO-D6) δ: 7.80-7.73 (2H, m), 7.66-7.52 (3H, m), 7.39 (1H, d, J = 10.7 Hz), 7.32 (1H, d, J = 11.3 Hz) 7.12 (1H, dd, J = 8.2, 1.5 Hz), 4.62-4.55 (2H, m), 6.18-4.11 (2H, m), 4.10-4.03 (1H, m), 2.47 (3H, s), 2.35-1.84 (7H, m), 1.64-1.49 (2H, m), 1.10 (6H, s). |
| 182 | | Racemate Relative configuration | | | free | 502.0 | 1H-NMR (DMSO-D6) δ: 7.83-7.64 (3H, m), 7.51 (1H, d, J = 7.3 Hz), 7.30-7.25 (1H, m), 7.21 (1H, t, J = 7.9 Hz), 7.16 (1H, dd, J = 8.2, 1.5 Hz), 7.07 (1H, dd, J = 7.9, 1.2 Hz), 6.95 (1H, d, J = 11.6 Hz), 4.51-3.85 (3H, m), 3.08-2.95 (1H, m), 2.65 (2H, s), 1.82-1.68 (2H, m), 1.36-1.23 (4H, m), 1.04 (6H, s). |
| 183 | | | | | free | 573.1 | 1H-NMR (DMSO-D6) δ: 7.76 (1H, t, J = 7.6 Hz), 7.62 (1H, dd, J = 7.9, 1.5 Hz), 7.59 (1H, d, J = 7.9 Hz), 7.56 (1H, d, J = 1.5 Hz), 7.35 (1H, d = (3.1 Hz), 7.34 (1H, dd, J = 10.5, 1.4 Hz), 7.31 (1H, d, J = 5.8 Hz), 7.13 (1H, dd, J = 7.9, 1.5 Hz), 6.51 (1H, t, J = 2.4 Hz), 4.70 (1H, s), 4.59 (1H, s), 4.13 (2H, s), 4.09 (1H, s), 2.27-2.15 (3H, m), 2.03-1.85 (4H, m), 1.64-1.48 (2H, m), 1.05 (6H, s). |

TABLE 23-continued

| | | | | | | |
|---|---|---|---|---|---|---|
| 184 | | Racemate Relative configuration | | free | 541.1 | 1H-NMR (DMSO-D6) δ: 7.79-7.72 (3H, m), 7.60-7.53 (1H, m), 7.47 (2H, d, J = 7.3 Hz), 7.37-7.28 (3H, m), 7.14-7.12 (1H, m), 6.45 (1H, d, J = 2.4 Hz), 4.62 (1H, s), 4.53 3.89 (4H, m), 3.10 3.04 (1H, m), 2.45-2.39 (1H, m), 1.87-1.79 (1H, m), 1.72-1.69 (2H, m), 1.41-1.17 (2H, m), 1.05 (6H, s). |

TABLE 24

| | | | | | | |
|---|---|---|---|---|---|---|
| 185 | | Racemate Relative configuration | | free | 503 | 1H-NMR (DMSO-D6) δ: 7.98 (1H, d, J = 5.2 Hz), 7.78 (1H, t, J = 7.5 Hz), 7.75-7.70 (1H, m), 7.63 (2H, d, J = 7.5 Hz), 7.55-7.48 (1H, m), 7.17 (1H, dd, J = 8.2, 1.5 Hz), 4.48-3.88 (6H, m), 2.24-2.12 (2H, m), 1.7501.51 (3H, m), 0.89 (1H, dd, J = 12.1, 4.7 Hz). |
| 186 | | | | free | 586.1 | 1H-NMR (DMSO-D6) δ: 8.12 (1H, s), 7.76 (1H, t, J = 7.6 Hz), 7.65-7.50 (2H, m), 7.57 (1H, d, J = 1.2 Hz), 7.50 (1H, d, J = 6.1 Hz), 7.36 (1H, dd, J = 10.5, 1.4 Hz), 7.12 (1H, dd, J = 8.1, 1.7 Hz), 4.62 (1H, s), 4.58 (1H, s), 4.41 (2H, s), 4.05 (1H, s), 3.72 (3H, d, J = 1.5 Hz), 2.30-2.18 (2H, m), 2.14-2.08 (1H, m), 2.00-1.84 (3H, m),1.62-1.49 (3H, m), 1.09 (6H, s). |
| 187 | | | | free | 534.1 | 1H-NMR (DMSO-D6) δ: 8.19 (1H, d, J = 1.8 Hz), 7.76-7.75 (1H, m), 7.73-7.70 (1H, m), 7.66 (1H, dd, J = 8.5, 1.5 Hz), 7.62-7.58 (2H, m), 7.42-7.39 (1H, m), 7.12 (1H, dd, J = 7.9, 1.5 Hz), 4.68 (1H, s), 4.33 (2H, s), 3.72-3.59 (4H, m), 3.20-3.15 (1H, m), 2.01-1.94 (1H, m), 1.69-1.63 (1H, m), 1.10 (6H, s). |
| 188 | | | | free | 574.1 | 1H-NMR (DMSO-D6) δ: 8.19 (1H, d, J = 1.8 Hz), 7.76 (1H, dd, J = 8.1, 7.2 Hz), 7.64 (1H, dd, J = 7.9, 1.5 Hz), 7.61-7.57 (3H, m), 7.42 (1H, dd, J = 10.5, 1.4 Hz), 7.14-7.11 (1H, m), 4.68 (1H, s), 4.57 (1H, s), 4.33 (2H, s), 4.05 (1H, s), 2.33-2.20 (2H, m), 2.12 2.07 (1H, m), 1.97-1.83 (3H, m), 1.61-1.48 (3H, m), 1.10 (6H, s). |
| 189 | | Racemate Relative configuration | | free | 542.1 | 1H-NMR (DMSO-D6) δ: 8.10 (1H, d, J = 0.9 Hz), 7.80-7.74 (2H, m), 7.73 7.67 (1H, m), 7.64-7.56 (2H, m), 7.45 (1H, d, J = 11.0 Hz), 7.40 (1H, dd, J = 10.5 1.4 Hz), 7.13 (1H, dd, J = 7.9 1.5 Hz), 4.61 (1H, s), 4.49-3.89 (5H, m), 2.26-2.13 (2H, m), 1.81-1.50 (4H, m), 1.10 (6H, s). |
| 190 | | | | free | 529.2 | 1H-NMR (DMSO-D6) δ: 7.76-7.73 (1H, m), 7.70 7.60 (2H, m), 7.56-7.54 (1H, m), 7.47 (1H, d, J = 7.3 Hz), 7.35 (1H, d, J = 3.1 Hz), 7.32-7.28 (2H, m), 7.11 (1H, d, J = 8.2 Hz), 5.44 (1H, d, J = 3.1 Hz), 4.62 (1H, s), 4.01 (2H, s), 3.75-3.50 (4H, m), 1.77-1.73 (2H, m), 1.25-1.16 (3H, m), 1.08 (6H, s). |

TABLE 24-continued

| # | Ar1 | Amine | Ar2 | X | Salt | MS | 1H-NMR |
|---|---|---|---|---|---|---|---|
| 191 | 4-CN, 2-F phenyl | 3-methyl-3-amino pyrrolidine | 6,7-diF benzotriazole with 2-hydroxy-2-methylpropyl | C=O | free | 549.1 | 1H-NMr (DMSO-D6) δ: 7.98-7.95 (1H, m), 7.78-7.64 (4H, m), 7.48-7.44 (1H, m), 7.17-7.14 (1H, m), 4.82-4.81 (1H, m), 4.63-4.60 (2H, m), 3.72-3.50 (4H, m), 1.80-1.73 (2H, m), 1.26-1.15 (9H, m). |
| 192 | 4-CN, 2-F phenyl | azabicyclic amine (Racemate Relative configuration) | 6,7-diF benzotriazole with 2-hydroxy-2-methylpropyl | C=O | free | 561.1 | 1H-NMR (DMSO-D6) δ: 7.97 (1H, d, J = 5.2 Hz), 7.76-7.73 (2H, m), 7.66 (2H, d, J = 7.6 Hz), 7.49 (1H, dd, J = 10.4, 1.2 Hz), 7.17 (1H, dd, J = 8.2, 1.5 Hz), 4.81 (1H, s), 4.61 (2H, s), 4.49-3.87 (3H, m), 2.28-2.11 (2H, m), 1.80-1.51 (3H, m), 1.15 (6H, s), 0.89 (1H, dd, J = 11.7, 4.7 Hz). |

TABLE 25

| # | Ar1 | Amine | Ar2 | X | Salt | MS | 1H-NMR |
|---|---|---|---|---|---|---|---|
| 193 | 4-CN, 2-F phenyl | azabicyclic amine (Racemate Relative configuration) | 3-F phenyl with 2-hydroxy-2-methylpropyl | C=O | free | 502.2 | 1H-NMR (DMSO-D6) δ: 7.80 (1H, t, J = 7.6 Hz), 7.68 (1H, s), 7.60 (1H, s), 7.53 (1H, d, J = 7.9 Hz), 7.29 (1H, t, J = 5.3 Hz), 7.21 (1H, t, J = 7.9 Hz), 7.15 (1H, dd, J = 8.2, 1.5 Hz), 7.07 11.6 Hz), 4.46 3.86 (3H, m), 2.65 (2H, s), 2.25-2.10 (2H, m), 1.74-1.49 (4H, m), 1.04 (6H, s), 0.87 (1H, dd, J = 12.2, 4.6 Hz). |
| 194 | 4-CN, 2-F phenyl | azabicyclic amine | 5-F indazole with 3-hydroxy-3-methylbutyl | C=O | free | 570.2 | 1H-NMR (DMSO-D6) δ: 8.09 (1H, d, J = 0.64 Hz), 7.79-7.74 (2H, m), 7.63 (1H, dd, J = 7.9, 1.5 Hz), 7.57-7.55 (2H, m), 7.43 (1H, d, J = 10.7 Hz), 7.39 (1H, dd, J = 10.5. 1.4 Hz), 7.12 (1H, dd, J = 8.2, 1.5 Hz), 4.59 (1H, s), 4.48 (1H, s), 4.42-4.38 (2H, m), 4.08 (1H, s), 2.23-2.12 (3H, m), 1.98-1.87 (5H, m), 1.62-1.51 (3H, m), 1.12 (6H, s). |
| 195 | 4-CN, 2-F phenyl | azabicyclic amine (Racemate Relative configuration) | 5,6-diF indazole with 2-hydroxy-2-methylpropyl | C=O | free | 560.1 | 1H-NMR (DMSO-D6) δ: 8.19 (1H, d, J = 1.8 Hz), 7.79-7.75 (!H, m), 7.73-7.70 (1H, m), 7.64-7.57 (3H, m), 7.43 (1H, dd, J = 10.5, 1.4 Hz), 7.14 (1H, dd, J = 8.1, 1.7 Hz), 4.69 (1H, s), 4.33-3.66 (5H, m), 2.20-2.14 (2H, m), 1.78-1.72 (1H, m), 1.65-1.50 (2H, m), 1.10 (6H, s), 0.93-0.89 (1H, m). |
| 196 | 4-CN, 2-F phenyl | azabicyclic amine (Racemate Relative configuration) | 5,6-diF indole with 2-hydroxy-2-methylpropyl | C=O | free | 559.1 | 1H-NMr (DMSO-D6) δ: 7.76 (1H, t, J = 7.6 Hz), 7.62-7.58 (2H, m), 7.38-7.30 (4H, m), 7.14 (1H, dd, J = 8.2, 1.5 Hz), 5.52-6.50 (1H, m), 4.71 (1H, s), 4.44-3.93 (5H, m), 2.19-2.13 (2H, m), 1.78-1.72 (1H, m), 1.64-1.50 (2H, m), 1.04 (6H, s), 0.92-0.88 (1H, m). |
| 197 | 4-CN, 2-F phenyl | 3-methyl-3-amino pyrrolidine | 5,6-diF indazole with 2-hydroxy-2-methylpropyl | C=O | free | 548.2 | 1H-NMR (DMSO-D6) δ: 8.19 (1H, d, J = 1.8 Hz), 7.79-7.69 (3H, m), 7.64-7.58 (2H, m), 7.40 (1H, dd, J = 9.9, 4.1 Hz), 7.12 (1H, dd, J = 8.1, 1.7 Hz), 4.69 (1H, s), 4.33 (2H, s), 3.75-3.64 (4H, m), 1.80 (2H, t, J = 7.3 Hz), 1.30-1.18 (3H, m), 1.10 (6H, s). |
| 198 | 4-CN, 2-F phenyl | 3-methyl-3-amino pyrrolidine | 5,6-diF indole with 2-hydroxy-2-methylpropyl | C=O | free | 547.2 | 1H- NMR (DMSO-D6) δ: 7.76 (1H, t, J = 7.5 Hz), 7.71-7.58 (3H, m), 7.37 (1H, d, J = 3.1 Hz), 7.31-7.29 (1H, m), 7.12 (1H, dd, J = 8.1, 1.3 Hz), 6.56 (1H, s), 6.52-6.50 (1H, m), 4.71 (1H, s), 4.13 (2H, s), 3.74-3.63 (4H, m), 1.81-1.78 *2H, m), 1.29-1.17 (3H, m), 1.04 (6H, s). |

TABLE 25-continued

| 199 | | | | | free | 542.1 | 1H-NMR (DMSO-D6) δ: 8.10 (1H, d, J = 3.7 Hz), 7.77-7.74 (2H, m), 7.72-7.69 (1H, m), 7.65 (1H, d, J = 9.2 Hz), 7.58 (1H, dd, J = 12.5, 7.9 Hz), 7.45 (1H, dd, J = 10.7, 4.6 Hz), 7.40-7.36 (1H, m), 7.13-7.09 (1H, m), 4.61 (1H, s), 4.25 (2H, s), 3.82-3.52 (8H, m), 2.13-2.07 (2H, m), 1.10 (6H, s). |
| 200 | | | | | free | 559.1 | 1H-NMR (DMSO-D6) δ: 7.78-7.74 (1H, m), 7.72-7.68 (1H, m), 7.66-7.64 (1H, m), 7.62-7.58 (1H, m), 7.39-7.29 (3H, m), 7.14-7.10 (1H, m), 6.51 (1H, s), 4.71 (1H, s), 4.13 (2H, s), 3.76-3.50 (8H, m), 2.11-2.07 (2H, m), 2.05 (6H, s). |

TABLE 26

| 201 | | | | | free | 573.2 | 1H-NMR (DMSO-D6) δ: 7.82 (1H, dd, J = 7.9, 1.8 Hz), 7.77 (1H, t, J = 7.5 Hz), 7.74 (1H, d, J = 1.8 Hz), 7.65 (1H, d, J = 7.9 Hz), 7.38 (1H, d, J = 3.1 Hz), 7.34 7.29 (2H, m), 7.12 (1H, dd, J = 7.9, 1.5 Hz), 6.52-6.50 (1H, m), 4.71 (1H, s), 4.13-4.04 (4H, m), 3.75 (2H, dd, J = 46.2, 9.9 Hz), 3.25-3.16 (2H, m), 2.86-2.81 (2H, m), 1.73-1.68 (2H, m), 1.47-1.41 (2H, m), 1.04 (6H, s). |
| 202 | | isomer-X Relative configuration | | | free | 485.2 | 1H-NMR (DMSO-D6) δ: 7.83 (1H, d, J = 5.5 Hz), 7.78 (1H, t, J = 7.5 Hz), 7.74-7.72 (1H, m), 7.66-7.61 (3H, m), 7.47 (1H, dd, J = 10.5, 1.4 Hz), 7.14 (1H, dd, J = 7.9, 1.5 Hz), 4.48-3.90 (2H, m), 3.22-3.16 (1H, m), 2.52 (3H, s), 2.21-2.12 (2H, m), 1.78-1.72 (1H, m), 1.64-1.50 (2H, m), 0.93-0.90 (1H, m). |
| 203 | | | | | free | 559.1 | 1H-NMR (DMSO-D6) δ: 7.76 (1H, t, J = 7.5 Hz), 7.67 (1H, dd, J = 7.9, 1.8 Hz), 7.62-7.56 (2H, m), 7.38 (1H, d, J = 3.1 Hz), 7.33 (1H, dd, J = 10.5. 1.4 Hz), 7.30 (1H, d, J = 5.8 Hz), 7.12 (1H, dd, J = 7.9, 1.5 Hz), 6.52-6.50 (1H, m), 4.70 (1H, s), 4.13 (2H, s), 3.85-3.70 (4H, m), 3.07 2.75 (6H, m), 1.05 (6H, s). |
| 204 | | | | | free | 544.2 | 1H-NMR (DMSO-D6) δ: 8.10 (1H, d, J = 0.6 Hz), 7.77-7.74 (2H, m), 7.71-7.68 (1H, m), 7.65-7.63 (1H, m), 7.57 (1H, d, J = 8.2 Hz), 7.43 (1H, d, J = 11.0 Hz), 7.37 (1H, dd, J = 10.5, 2.3 Hz), 7.12 (1H, dd, J = 8.2, 1.5 Hz), 4.33 (1H, s), 4.24 (2H, s), 3.66-3.60 4H, m), 3.21-3.18 (1H, m), 2.04-1.99 (1H, m), 1.74-1.67 (1H, m), 1.38-1.30 (4H, m), 0.85 (6H, t, J = 7.3 Hz). |
| 205 | | | | | free | 584.2 | 1H-NMR (DMSO-D6) δ: 8.10 (1H, d, J = 0.6 Hz), 7.77-7.74 (2H, m), 7.63 (1H, dd, J = 7.9, 1.8 Hz), 7.58-7.55 (2H, m), 7.44 (1H, d, J = 11.0 Hz), 7.38 (1H, dd, J = 10.7, 1.2 Hz), 7.12 (1H, dd, J = 8.1, 1.4 Hz), 4.59 (1H, s), 4.34 (1H, s), 4.24 (2H, s), 4.08 (1H, s), 2.23-2.13 (3H, m), 2.02-1.86 (3H, m), 1.83-1.50 (3H, m), 1.39-1.31 (4H, m), 0.85 (6H, t, J = 7.5 Hz). |

TABLE 26-continued

| | | | | | | |
|---|---|---|---|---|---|---|
| 206 | 4-cyano-3-fluorophenyl | 2-azabicyclic-NH₂ isomer-X Relative configuration | 2-ethyl-2-hydroxybutyl-(5-fluoro-6-fluoro)indazole | C=O | free | 570.2 | 1H-NMR (DMSO-D6) δ: 8.10 (1H, d, J = 0.9 Hz), 7.77-7.74 (2H, m), 7.72-7.69 (1H, m), 7.62-7.56 (2H, m), 7.44 (1H, d, J = 11.0 Hz), 7.39 (1H, dd, J = 10.5, 1.4 Hz), 7.13 (1H, dd, J = 8.2, 1.5 Hz), 4.45-3.64 (6H, m), 2.39-2.13 (2H, m), 1.79-1.73 (1H, m), 1.65-1.51(2H, m), 1.37-1.31 (4H, m), 0.92 (1H, dd, J = 12.1, 4.1 Hz), 0.85 (6H, t, J = 7.3 Hz). |
| 207 | 4-cyano-3-fluorophenyl | 2-azabicyclic-NH₂ isomer-X Relative configuration | (5-fluoro-6-fluoroindol-1-yl)acetic acid | C=O | free | 527.2 | 1H-NMR (DMSO-D6) δ: 7.75 (1H, t, J = 7.5 Hz), 7.79 (1H, d, J = 7.9 Hz), 7.61 (1H, s), 7.54 (1H, d, J = 7.9 Hz), 7.48 (1H, d, J = 7.3 Hz), 7.38 (1H, d, J = 10.1 Hz), 7.33 (1H, d, J = 3.1 Hz), 7.15 (1H, d, J = 11.0 Hz), 7.12 (1H, d, J = 8.9 Hz), 6.43 (1H, d, J = 2.7 Hz), 4.79 (2H, s), 4.46 3.48 (3H, m), 2.24 2.05 (2H, m), 1.80-1.76 (1H, m), 1.59-1.64 (1H, m), 1.57-1.53 (1H, m), 1.06-1.01 (1H, m). |

TABLE 27

| | | | | | | |
|---|---|---|---|---|---|---|
| 208 | 4-cyano-3-fluorophenyl | 2-azabicyclic-NH₂ isomer-X Relative configuration | 4-fluorophenylacetic acid | C=O | free | 488.2 | 1H-NMR (DMSO-D6) δ: 7.80 (1H, t, J = 7.5 H), 7.71-7.68 (1H, m), 7.61-7.58 (1H, m), 7.53 (1H, d, J = 7.9 Hz), 7.37 (1H, dd, J = 10.5, 1.4 Hz), 7.26 (1H, t, J = 7.9 Hz), 7.14-7.11 (2H, m), 7.03 (1H, d, J = 11.3 Hz), 4.43-3.57 (5H, m), 2.19-2.13 (2H, m), 1.78-1.72 (1H, m), 1.59-1.50 (2H, m), 0.90 (1H, dd, J = 11.9, 4.3 Hz). |
| 209 | 4-cyano-3-fluorophenyl | 2-azabicyclic-NH₂ isomer-X Relative configuration | 2-hydroxy-2-methylpropyl-(7-chloro-6-fluoro-5-fluoro)benzotriazole | C=O | free | 577.2 579.2 | 1H-NMR (DMSO-D6) δ: 8.10 (1H, d, J = 6.1 Hz), 7.74 7.69 (2H, m), 7.63-7.59 (2H, m), 7.44 (1H, d, J = 10.4 Hz), 7.11 (1H, dd, J = 7.9, 1.5 Hz), 4.78 (2H, s), 4.71 (1H, s), 4.41-3.56 (3H, m), 2.18-2.10 (2H, m), 1.75-1.68 (1H, m), 1.60-1.54 (1H, m), 1.51-1.46 (1H, m), 1.13 (6H, s), 0.86 (1H, dd, J = 12.1, 4.7 Hz). |
| 210 | 4-cyano-3-fluorophenyl | (S)-3-aminopyrrolidine | 2-hydroxy-2-methylpropyl-(7-chloro-6-fluoro-5-fluoro)benzotriazole | C=O | free | 551.2 553.2 | 1H-NMR (DMSO-D6) δ: 8.10 (1H, d, J = 6.1 Hz), 7.73-7.68 (2H, m), 7.65-7.61 (2H, m), 7.43-7.40 (1H, m), 7.10 (1H, dd, J = 8.1, 1.4 Hz), 4.78 (2H, s), 4.71 (1H, s), 3.65-3.45 (4H, m), 3.24-3.23 (1H, m), 1.98-1.93 (1H, m), 1.63-1.59 (1H, m), 1.13 (6H, s). |
| 211 | 4-cyano-3-fluorophenyl | 8-azabicyclic-NH₂ isomer | 2-hydroxy-2-methylpropyl-(7-chloro-6-fluoro-5-fluoro)benzotriazole | C=O | free | 591.2 593.2 | 1H-NMR (DMSO-D6) δ: 8.10 (1H, d, J = 6.1 Hz), 7.71 (1H, t, J = 7.5 Hz), 7.62-7.60 (2H, m), 7.55 (1H, s), 7.42 (1H, dd, J = 10.5, 1.4 Hz), 7.10 (1H, dd, J = 7.9, 3.5 Hz), 4.77 (2H, s), 4.70 (1H, s), 4.53 (1H, s), 4.01 (1H, s), 2.22-2.04 (3H, m), 1.82-1.80 (3H, m), 1.56-1.45 (3H, m), 1.12 (6H, s). |
| 212 | 4-cyano-3-fluorophenyl | 2-azabicyclic-NH₂ isomer-X Relative configuration | 1-(2-hydroxy-2-methylpropyl)-6-fluoro-5-fluoroindazole-3-carboxylic acid | C=O | free | 586.2 | 1H-NMR (DMSO-D6) δ: 8.10 (1H, d, J = 7.3 Hz), 7.76-7.70 (2H, m), 7.63 7.58 (2H, m), 7.48 (1H, d, J = 10.7 Hz), 7.41 (1H, d, J = 10.4 Hz), 7.12 (1H, dd, J = 7.9, 1.5 Hz), 4.67 (1H, s), 4.46-3.50 (5H, m), 2.21-2.12 (2H, m), 1.80-1.74 (1H, m), 1.66-1.60 (1H, m), 1.56-1.51 (1H, m), 1.11 (6H, s), 0.98-0.93 (1H, m). |

TABLE 27-continued

| # | Ar | Amine | Benzotriazole | | Salt | MS | 1H-NMR |
|---|---|---|---|---|---|---|---|
| 213 | 4-CN-2-F-phenyl | 2-azabicyclic-NH2, Racemate Relative configuration | Cl,F-benzotriazole with CH2-C(CH3)2-OH | C=O | free | 577.3 579.2 | 1H-NMR (DMSO-D6) δ: 8.14 (1H, d, 6.1 Hz), 7.78-7.73 (2H, m), 7.68-7.63 (2H, m), 7.48 (1H, d, J = 9.2 Hz), 7.15 (1H, dd, J = 8.1, 1.1 Hz), 4.81 (2H, s), 4.75 (1H, s), 4.45-3.82 (3H, m), 2.22-2.12 (2H, m), 1.79-1.73 (1H, m), 1.64-1.59 (1H, m), 1.55-1.50 (1H, m), 1.17 (6H, s), 0.91 (1H, dd, J = 11.7, 4.4 Hz). |
| 214 | 4-CN-2-F-phenyl | 2-azabicyclic-NH2, isomer-X Relative configuration | F,F-benzotriazole with CH2-C(Et)(OH)-Et | C=O | free | 589.3 | 1H-NMR (DMSO-D6) δ: 7.97 (1H, d, J = 5.2 Hz), 7.79-7.72 (2H, m), 7.66-7.63 (2H, m), 7.49 (1H, dd, J = 10.4, 1.2 Hz), 7.17 (1H, dd, J = 7.9, 1.5 Hz), 4.61 (2H, s), 4.45 (1H, s), 4.33-3.50 (3H, m), 2.21-2.15 (2H, m), 1.79-1.72 (1H, m), 1.64-1.50 (2H, m), 1.44-1.35 (4H, m), 0.91-0.87 (7H, m). |
| 215 | 4-CN-2-F-phenyl | pyrrolidine-NH2 | F,F-benzotriazole with CH2-C(Et)(OH)-Et | C=O | free | 563.3 | 1H-NMR (DMSO-D6) δ: 7.97 (1H, d, J = 4.9 Hz), 7.78-7.72 (2H, m), 7.68 (1H, d, J = 8.2 Hz), 7.64 (1H, d, J = 7.6 Hz), 7.47 (1H, d, J = 10.4 Hz), 7.15 (1H, dd, J = 7.9, 1.5 Hz), 4.61 (2H, s), 4.46 (1H, s), 3.67-3.43 (4H, m), 3.22-3.16 (1H, m), 2.04-1.90 (1H, m), 1.70-1.62 (1H, m), 1.44-1.35 (4H, m), 0.89 (6H, t, J = 7.5 Hz). |

TABLE 28

| # | Ar | Amine | Benzotriazole | | Salt | MS | 1H-NMR |
|---|---|---|---|---|---|---|---|
| 216 | 4-CN-2-F-phenyl | 8-azabicyclic-NH2 | F,F-benzotriazole with CH2-C(Et)(OH)-Et | C=O | free | 603.3 | 1H-NMR (DMSO-D6) δ: 7.97 (1H, d, J = 5.2 Hz), 7.77 (1H, t, J = 7.5 Hz), 7.57-7.59 (3H, m), 7.48 (1H, d, J = 11.3 Hz), 7.16 (1H, d, J = 8.9 Hz), 4.61 (2H, s), 4.58 (1H, s), 4.46 (1H, s), 4.05 (1H, s), 2.33-2.20 (2H, m), 2.12-2.07 (1H, m), 1.96-1.84 (3H, m), 1.61-1.49 (3H, m), 1.42-1.37 (4H, m), 0.89 (5H, t, J = 7.3 Hz). |
| 217 | 4-CN-2-F-phenyl | 2-azabicyclic-NH2, Racemate Relative configuration | F,F-benzotriazole with CH2-C(Et)(OH)-Et | C=O | free | 589.3 | 1H-NMR (DMSO-D6) δ: 7.97 (1H, d. J = 5.2 Hz), 7.79-7.72 (2H, m), 7.66-7.63 (2H, m), 7.49 (1H, dd, J = 10.4, 1.2 Hz), 7.17 (1H, dd, J = 7.9, 1.5 Hz), 4.61 (2H, s), 4.45 (1H, s), 4.33-3.50 (3H, m), 2.25-2.15 (2H, m), 1.79-1.72 (1H, m), 1.64-1.50 (2H, m), 1.44-1.35 (4H, m), 0.91-0.87 (7H, m). |
| 218 | 4-CN-2-F-phenyl | 2-azabicyclic-NH2, isomer-X Relative configuration | Cl,F-benzotriazole with CH2-C(Et)(OH)-Et | C=O | free | 605.2 607.2 | 1H-NMR (DMSO-D6) δ: 8.14 (1H, d, J = 6.1 Hz), 7.79-7.72 (2H, m), 7.67-7.63 (2H, m), 7.50-7.48 (1H, m), 7.15 (1H, dd, J = 7.9, 1.5 Hz), 4.81 (2H, s), 4.45-3.92 (4H, m), 2.22-2.13 (2H, m), 1.79-1.73 (1H, m), 1.64-1.59 (1H, m), 1.55-1.37 (5H, m), 0.93-0.87 (7H, m). |
| 219 | 4-CN-2-F-phenyl | pyrrolidine-NH2 | Cl,F-benzotriazole with CH2-C(Et)(OH)-Et | C=O | free | 579.2 581.3 | 1H-NMR (DMSO-D6) δ: 8.14 (1H, d, J = 5.5 Hz), 7.78-7.72 (2H, m), 7.68 (1H, d, J = 7.9 Hz), 7.65 (1H, d, J = 7.9 Hz), 7.47 (1H, dd, J = 10.4, 3.7 Hz), 7.14 (1H, d, J = 7.9 Hz), 4.82 (2H, s), 4.37 (1H, s), 3.69-3.49 (4H, m), 3.23-3.20 (1H, m), 2.06-1.97 (1H, m), 1.75-1.67 (1H, m), 1.52-1.35 (4H, m), 0.90 (6H, t, J = 7.3 Hz). |
| 220 | 4-CN-2-F-phenyl | 8-azabicyclic-NH2 | Cl,F-benzotriazole with CH2-C(Et)(OH)-Et | C=O | free | 619.3 621.2 | 1H-NMR (DMSO-D6) δ: 8.14 (1H, d, J = 6.1 Hz), 7.78-7.74 (1H, m), 7.68-7.59 (3H, m), 7.50-7.47 (1H, m), 7.14 (1H, dd, J = 7.9, 1.5 Hz), 4.82 (2H, s), 4.60 (1H, s), 4.37 (1H, s), 4.07 (1H, s), 2.24-2.13 (3H, m), 2.02-1.88 (3H, m), 1.63-1.38 (7H, m), 0.90 (6H, t, J = 7.5 Hz). |

TABLE 28-continued

| | | | | | | | |
|---|---|---|---|---|---|---|---|
| 221 | (4-cyano-2-fluorophenyl) | bicyclic amine NH2, Racemate Relative configuration | chloro-fluoro-benzotriazole with HO-ethyl side chain | C=O | free | 605.2 607.2 | 1H-NMR (DMSO-D6) δ: 8.14 (1H, d, J = 6.1 Hz), 7.79-7.72 (2H, m), 7.67-7.63 (2H, m), 7.50-7.48 (1H, m), 7.15 (1H, dd, J = 7.9, 1.5 Hz), 4.81 (2H, s), 4.45-3.92 (4H, m), 2.22-2.13 (2H, m), 1.79-1.73 (1H, m), 1.64-1.59 (1H, m), 1.55-1.37 (5H, m), 0.93-0.87 (7H, m). |
| 222 | (4-cyano-2-fluorophenyl) | bicyclic amine NH2, isomer-X Relative configuration | F-indole-N-CH2C(CH3)2OH, COOH | C=O | free | 585.3 | 1H-NMR (DMSO-D6) δ: 8.14 (1H, d, J = 7.94 (1H, d, J = 7.6 Hz), 7.76-7.68 (2H, m), 7.62-7.58 (2H, m), 7.46 (1H, d, J = 11.3 Hz), 7.34 (1H, t, J = 5.3 Hz), 7.11 (1H, dd, J = 7.9, 1.5 Hz), 4.73 (1H, s), 4.44-3.51 (5H, m), 2.21-2.13 (2H, m), 1.78-1.72 (1H, m), 1.60-1.50 (2H, m), 1.96 (6H, s), 0.89 (1H, dd, J = 12.1, 4.4 Hz). |
| 223 | (4-cyano-2-fluorophenyl) | bicyclic amine NH2, isomer-X Relative configuration | F-indazole-N-CH3, COOH | C=O | free | 528.2 | 1H-NMR (DMSO-D6) δ: 8.16 (1H, d, J = 7.3 Hz), 7.77-7.70 (2H, m), 7.62-7.60 (1H, m), 7.57 )1H, d, J = 7.9 Hz), 7.43 (2H, d, J = 10.4 Hz), 7.09 (1H, dd, J = 7.9, 1.5 Hz), 4.44-3.50 (6H, m), 2.19-2.14 (2H, m), 1.79-1.74 (1H, m), 1.64-1.59 (1H, m), 1.55-1.50 (1H, (m), 0.94-0.90 (1H, m). |

TABLE 29

| | | | | | | | |
|---|---|---|---|---|---|---|---|
| 224 | (4-cyano-2-fluorophenyl) | bicyclic amine NH2, isomer-X Relative configuration | F-indole-N-CH3, COOH | C=O | free | 527.2 | 1H-NMR (DMSO-D6) δ: 8.07 (1H, s), 7.96 (1H, d, J = 7.3 Hz), 7.77-7.69 (2H, m), 7.41 (1H, dd, J = 10.5, 1.4 Hz), 7.36 (1H, d, J = 10.7 Hz), 7.10 (1H, dd, J = 8.2, 1.5 Hz), 4.44-3.51 (6H, m), 2.20-2.13 (2H, m), 1.79-1.73 (1H, m), 1.60-1.50 (2H, m), 0.91 (1H, dd, J = 12.2, 4.6 Hz). |
| 225 | (4-cyano-2-fluorophenyl) | bicyclic amine NH2, Racemate Relative configuration | F-indazole-N-CH2C(Et)(OH)- | C=O | free | 570.3 | 1H-NMR (DMSO-D6) δ: 8.10 (1H, d, J = 0.9 Hz), 7.77-7.74 (2H, m), 7.72 7.69 (1H, m), 7.62-7.56 (2H, m), 7.44 (1H, d, J = 11.0 Hz), 7.39 (1H, dd, J = 10.5, 1.4 Hz), 7.13 (1H, dd, J = 8.2, 1.5 Hz), 4.45-3.64 (6H, m), 2.19-2.13 (2H, m), 1.79-1.73 (1H, m), 1.65-1.51 (2H, m), 1.37-1.31 (4H, m), 0.92 (1H, dd, J = 12.1, 4.1 Hz), 0.85 (6H, t, J = 7.3 Hz). |
| 226 | (4-cyano-2-fluorophenyl) | bicyclic amine NH2, isomer-X Relative configuration | F-dihydroisobenzofuran with C(CH3)2OH | C=O | free | 544.3 | 1H-NMR (DMSO-D6) δ: 7.83-7.80 (1H, m), 7.70-7.67 (1H, m), 7.61-7.58 (1H, m), 7.53 (1H, d, J = 7.9 Hz), 7.41-7.38 (1H, m), 7.28 (1H, d, J = 6.7 Hz), 7.13 (1H, d, J = 7.9 Hz), 7.02 (1H, d, J = 4.99-4.87 (2H, m), 4.44-3.53 (4H, m), 2.21-2.11 (2H, m), 1.92-1.88 (1H, m), 1.77 1.49 (4H, m), 1.23-1.18 (6H, m), 0.88 (1H, dd, J = 12.1, 4.7 Hz). |
| 227 | (4-cyano-2-fluorophenyl) | (S)-pyrrolidine-N-, 3-NH2 | F-dihydroisobenzofuran with C(CH3)2OH | C=O | free | 518.2 | 1H-NMR (DMSO-D6) δ: 7.83-7.80 (1H, m), 7.70-7.67 (1H, m), 7.64-7.62 (1H, m), 7.52 (1H, dd, J = 7.9, 2.1 Hz), 7.37 (1H, d, J = 9.5 Hz), 7.29 (1H, d, J = 6.4 Hz), 7.11 (1H, dd, J = 7.9, 1.5 Hz), 7.01 (1H, d, J = 9.8 Hz), 5.30 (1H, d, J = 7.3 Hz), 4.99-4.88 (2H, m), 4.35-4.33 (1H, m), 3.67-3.50 (4H, m), 3.17-3.12 (1H, m), 2.01-1.88 (2H, m), 1.71-1.62 (2H, m), 1.22-1.19 (6H, m). |

TABLE 29-continued

| | | | | | | | |
|---|---|---|---|---|---|---|---|
| 228 | 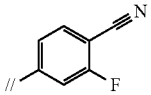 | 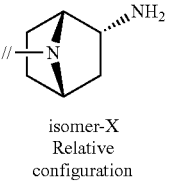 isomer-X Relative configuration | 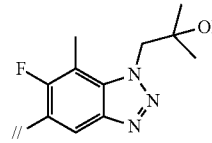 |  | free | 557.2 | 1H-NMR (DMSO-D6) δ: 7.87 (1H, d, J = 6.1 Hz), 7.79-7.68 (2H, m), 7.65-7.56 (2H, m), 7.46 (1H, d, J = 10.4 Hz), 7.15 (1H, dd, J = 8.2, 1.5 Hz), 4.78 (1H, s), 4.69 (2H, s), 4.49-3.87 (3H, m), 2.49 (3H, s), 2.24-2.11 (2H, m), 1.81-1.48 (3H, m), 1.20 (6H, s), 0.90 (1H, dd, J = 12.2, 4.3 Hz). |
| 229 | 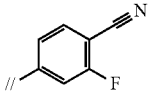 | 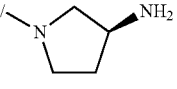 | 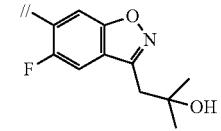 |  | free | 517.2 | 1H-NMR (DMSO-D6) δ: 7.81-7.52 (6H, m), 7.44 (1H, d, J = 8.9 Hz), 7.16-7.13 (1H, m), 4.70 (1H, s), 3.73-3.51 (5H, m), 3.03 (2H, s), 2.03-1.93 (1H, m), 1.70-1.61 (1H, m), 1.18 (6H, s). |
| 230 | 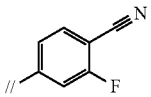 | 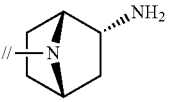 Racemate Relative configuration | 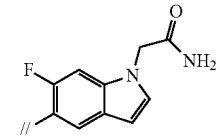 |  | free | 526.2 | 1H-NMR (DMSO-D6) δ: 8.34 (2H, s), 7.76 (1H, t, J = 7.5 Hz), 7.53 (3H, dd, J = 15.4, 7.5 Hz), 7.40 (1H, d, J = 10.4 Hz), 7.34 (1H, d, J = 3.1 Hz), 7.24 (1H, s), 7.14 (2H, dd, J = 12.8, 6.1 Hz), 6.47 (1H, d, J = 3.4 Hz), 4.76 (2H, s), 4.45-3.94 (3H, m), 2.26-2.14 (2H, m), 1.82-1.70 (1H, m), 1.66-1.46 (2H, m), 0.90 (1H, dd, J = 12.2, 4.6 Hz). |

TABLE 30

| | | | | | | | |
|---|---|---|---|---|---|---|---|
| 231 | 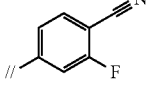 |  Racemate Relative configuration | 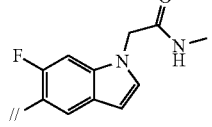 |  | free | 540.2 | 1H-NMR (DMSO-D6) δ: 8.03 (1H, d, J = 4.6 Hz), 7.91 (1H, d, J = 7.0 Hz), 7.76 (1H, t, J = 7.5 Hz), 7.56-7.48 (2H, m), 7.47-7.38 (2H, m), 7.34 (1H, d, J = 3.1 Hz), 7.20-7.09 (2H, m), 6.47 (1H, d, J = 2.7 Hz), 4.76 (2H, s), 4.48-3.92 (3H, m), 2.61 (3H, d, J = 4.6 Hz), 2.26-2.13 (2H, m), 1.82-1.72 (1H, m), 1.68-1.46 (2H, m), 0.90 (1H, dd, J = 12.1, 4.4 Hz). |
| 232 | 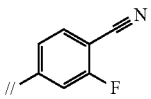 | 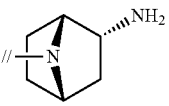 Racemate Relative configuration | 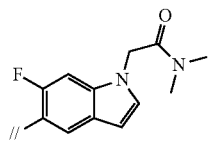 |  | free | 554.2 | 1H-NMR (DMSO-D6) δ: 7.93 (1H, t, J = 4.1 Hz), 7.77 (1H, t, J = 7.6 Hz), 7.53 (2H, dd, J = 19.1, 7.5 Hz), 7.47 (1H, d, J = 7.9 Hz), 7.39 (1H, d, J = 10.4 Hz), 7.27 (2H, d, J = 3.1 Hz), 7.15 (2H, dt, J = 13.2, 6.0 Hz), 6.46 (1H, d, J = 3.4 Hz), 5.11 (2H, s), 4.46-3.87 (3H, m), 3.08 (3H, d, J = 12.2 Hz), 2.85 (3H, s), 2.25-2.15 (2H, m), 1.82-1.71 (1H, m), 1.67-1.50 (2H, m), 0.95-0.87 (1H, m). |
| 233 | 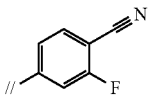 | 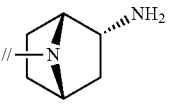 Racemate Relative configuration | 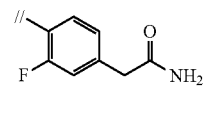 |  | free | 487.2 | 1H-NMR (DMSO-D6) δ: 7.83 (1H, dd, J = 23.7, 7.2 Hz), 7.72-7.56 (1H, m), 7.52 (1H, t, J = 7.5 Hz), 7.33 (3H, ddd, J = 33.5, 19.8, 8.0 Hz), 7.05 (3H, dq, J = 53.3, 15.3 Hz), 4.40-3.87 (3H, m), 3.01 (2H, s), 2.22-2.14 (2H, m), 1.83-1.57 (3H, m), 0.91-0.85 (1H, m). |
| 234 | 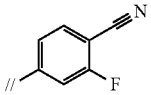 | 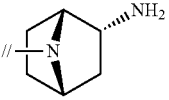 Racemate Relative configuration | 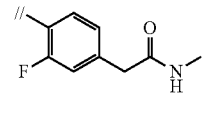 |  | free | 501.2 | 1H-NMR (DMSO-D6) δ: 7.83-7.79 (2H, m), 7.56-7.45 (2H, m), 7.38 (1H, d, J = 10.7 Hz), 7.27 (1H, t, J = 7.9 Hz), 7.12 (2H, td, J = 9.1, 3.7 Hz), 7.00 (1H, d, J = 11.0 Hz), 4.45-4.07 (3H, m), 3.02 (2H, s), 2.58 (3H, d, J = 4.6 Hz), 2.21-2.15 (2H, m), 1.79-1.72 (1H, m), 1.64-1.51 (2H, m), 0.93-0.65 (1H, m). |

TABLE 30-continued

| | Ar1 | Amine | Ar2 | | Salt | MS | 1H-NMR |
|---|---|---|---|---|---|---|---|
| 235 | 4-CN-2-F-phenyl | Racemate Relative configuration | 4-F-phenyl-CH2-C(O)N(CH3)2 | | free | 515.2 | 1H-NMR (DMSO-D6) δ: 7.96-7.91 (1H, m), 7.82 (1H, t, J = 7.6 Hz), 7.54 (1H, d, J = 7.9 Hz), 7.49-7.44 (1H, m), 7.5 (1H, d, J = 10.7 Hz), 7.27 (1H, t, J = 7.9 Hz), 7.15 (1H, dd, J = 8.2, 1.5 Hz), 7.08 (1H, d, J = 7.6 Hz), 6.97 (1H, d, J = 11.3 Hz), 4.47-3.89 (3H, m), 3.72 (2H, s), 3.00 (3H, s), 2.84 (3H, s), 2.22-2.13 (2H, m), 1.79-1.72 (1H, m), 1.67-1.48 (2H, m), 0.89 (1H, s). |
| 236 | 4-CN-2-F-phenyl | isomer-X Relative configuration | F-indole-C(O)NH2 | | free | 526.2 | 1H-NMR (DMSO-D6) δ: 8.14 (1H, d, J = 7.6 Hz), 8.01 (1H, s), 7.76 (1H, t, J = 7.6 Hz), 7.72-7.69 (1H, m). 7.60 (1H, s), 7.56 (1H, d, J = 7.9 Hz), 7.40 (1H, d, J = 10.4 Hz), 7.30 (1H, d, J = 10.7 Hz), 7.11 (1H, dd, J = 7.9, 1.5 Hz), 4.45-3.93 (3H, m), 3.77 (3H, s), 2.25-2.14 (2H, m), 1.81-1.72 (1H, m), 1.67-1.49 (2H, m), 0.93-0.86 (1H, m). |
| 237 | 4-CN-2-F-phenyl | isomer-X Relative configuration | F-indole-C(O)NHCH3 | | free | 540.2 | 1H-NMR (DMSO-D6) δ: 8.13 (1H, d, J = 7.6 Hz), 7.94 (1H, s), 7.92-7.89 (1H, m), 7.78-7.55 (4H, m), 7.39 (1H, d, J = 9.2 Hz), 7.30 (1H, d, J = 10.7 Hz), 7.12 (1H, d, J = 7.9 Hz), 4.47-3.91 (3H, m), 3.77 (3H, s), 2.76 (3H, d, J = 4.6 Hz), 2.23-2.15 (2H, m), 1.80-1.74 (1H, m), 1.66-1.50 (2H, m), 0.90 (1H, dd, J = 12.1, 4.7 Hz). |

TABLE 31

| | Ar1 | Amine | Ar2 | | Salt | MS | 1H-NMR |
|---|---|---|---|---|---|---|---|
| 238 | 4-CN-2-F-phenyl | isomer-X Relative configuration | F-indazole-C(O)N(CH3)2 | | free | 554.2 | 1H-NMR (DMSO-D6) δ: 7.83 (1H, s), 7.80-7.75 (2H, m), 7.73-7.68 (1H, m), 7.57 (2H, t, J = 18.3 Hz), 7.40 (1H, dd, J = 10.7, 1.5 Jz), 7.32 (1H, d, J = 11.0 Hz), 7.11 (1H, dd, J = 7.9, 1.5 Hz), 4.48-3.92 (3H, m), 3.80 (3H, d, J = 7.0 Hz), 3.06 (6H, s), 2.25-2.14 (2H, m), 1.80-1.70 (1H, m), 1.65-1.48 (2H, m), 0.90 (1H, t, J = 8.4 Hz). |
| 239 | 4-CN-2-F-phenyl | (S)-pyrrolidin-3-amine | F-benzotriazole-CH2C(CH3)2OH | | free | 531.1 | 1H-NMR (DMSO-D6) δ: 7.87 (1H, d, J = 6.7 Hz), 7.80-7.64 ((3H, m), 7.58 (1H, d, J = 7.9 Hz), 7.44 (1H, d, J = 10.4 Hz), 7.13 (1H, dd, J = 8.2, 1.5 Hz), 4.78 (1H, s), 4.69 (2H, s), 3.75-3.58 (5H, m), 2.49 (3H, s), 2.04-1.93 (1H, m), 1.74-1.64 (1H, m), 1.20 (6H, s). |
| 240 | 4-CN-2-F-phenyl | tropane-amine | F-benzotriazole-CH2C(CH3)2OH | | free | 571.2 | 1H-NMR (DMSO-D6) δ: 7.87 (1H, d, J = 6.7 Hz), 7.75 (1H, t, J = 7.5 Hz). 7.63 (1H, d = 7.3 Hz), 7.60-7.55 (2H, m), 7.45 (1H, d, J = 10.4 Hz), 7.14 (1H, d, J = 7.9 Hz), 4.78 (1H, s), 4.69 (2H, s), 4.64-4.56 (1H, m), 4.11-4.04 (1H, m), 2.49 (3H, s), 2.34-2.20 (2H, m), 2.13-2.06 (1H, m), 1.99-1.85 (3H, m), 1.66-1.47 (3H, m), 1.20 (6H, s). |
| 241 | 4-CN-2-F-phenyl | Racemate Relative configuration | F-benzotriazole-CH2C(CH3)2OH | | free | 557.2 | 1H-NMR (DMSO-D6) δ: 7.87 (1H, d, J = 6.1 Hz), 7.79-7.68 (2H, m), 7.65-7.56 (2H, m), 7.46 (1H, d, J = 10.4 Hz), 7.15 (1H, dd, J = 8.2, 1.5 Hz), 4.78 (1H, s), 4.69 (2H, s), 4.49-3.87 (3H, m), 2.49 (3H, s), 2.24-2.11 (2H, m), 1.81-1.48 (3H, m), 1.20 (6H, s), 0.90 (1H, dd, J = 12.2, 4.3 Hz). |

TABLE 31-continued

| | | | | | | |
|---|---|---|---|---|---|---|
| 242 | (4-cyano-3-fluorophenyl) | Racemate Relative configuration (bicyclic amine with NH₂) | 6-fluoro-1-methyl-indole-3-carboxylic acid | ketone | free | 527.1 | 1H-NMR (DMSO-D6) δ: 8.07 (1H, s), 7.96 (1H, d, J = 7.3 Hz), 7.77-7.69 (2H, m), 7.62-7.55 (2H, m), 7.41 (1H, dd, J = 10.5, 1.4 Hz), 7.36 (1H, d, J = 10.7 Hz), 7.10 (1H, d, J = 8.2, 1.5 Hz), 4.44-3.51 (6H, m), 2.20-2.13 (2H, m), 1.79-1.73 (1H, m), 1.60-1.50 (2H, m), 0.91 (1H, dd, J = 12.2, 4.6 Hz). |
| 243 | (4-cyano-3-fluorophenyl) | Racemate Relative configuration | 6-fluoro-1-methyl-indazole-3-N-methylcarboxamide | ketone | free | 540.3 | 1H-NMR (DMSO-D6) δ: 8.13 (1H, d, J = 7.6 Hz), 7.94 (1H, s), 7.92-7.89 (1H, m), 7.78-7.55 (4H, m), 7.39 (1H, d, J = 9.2 Hz), 7.30 (1H, d, J = 10.7 Hz), 7.12 (1H, d, J = 7.9 Hz), 4.47-3.91 (3H, m), 3.77 (2H, s), 2.76 (3H, d, J = 4.6 Hz), 2.23-2.15 (2H, m), 1.80-1.74 (1H, m), 1.66-1.50 (2H, m), 0.90 (1H, dd, J = 12.1, 4.7 Hz). |
| 244 | (4-cyano-3-fluorophenyl) | Racemate Relative configuration | 6-fluoro-1-methyl-indole-3-N,N-dimethylcarboxamide | ketone | free | 554.2 | 1H-NMR (DMSO-D6) δ: 7.83 (1H, s), 78.0-7.75 (2H, m), 7.73-7.68 (1H, m), 7.57 (2H, t, J = 18.3 Hz), 7.40 (1H, dd, J = 10.7, 1.5 Hz), 7.32 (1H, d, J = 11.0 Hz), 7.11 (1H, dd, J = 7.9, 1.5 Hz), 4.48-3.92 (3H, m), 3.80 (3H, d, J = 7.0 Hz), 3.06 (6H, s), 2.25-2.14 (2H, m), 1.80-1.70 (1H, m), 1.65-1.8 (2H, m), 0.90 (1H, t, J = 8.4 Hz). |

TABLE 32

| | | | | | | |
|---|---|---|---|---|---|---|
| 245 | (4-cyano-3-fluorophenyl) | Racemate Relative configuration | 6-fluoro-1-methyl-indole-3-carboxamide | ketone | free | 526.3 | 1H-NMR (DMSO-D6) δ: 8.14 (1H, d, J = 7.6 Hz), 8.51 (1H, s), 7.76 (1H, t, J = 7.6 Hz), 7.72=7.69 (1H, m), 7.60 (1H, s), 7.56 (1H, d, J = 7.9 Hz), 7.40 (1H, d, J = 10.4 Hz), 7.30 (1H, d, J = 10.7 Hz), 7.11 (1H, dd, J = 7.9, 1.5 Hz), 4.46-3.93 (3H, m), 3.77 (3H, s), 2.25-2.14 (2H, m), 1.81-1.72 (1H, m), 1.67-1.49 (2H, m), 0.93-0.86 (1H, m). |
| 246 | (4-cyano-3-fluorophenyl) | isomer-X Relative configuration | 4-(difluoromethyl)-5-fluoro-1-(2-hydroxy-2-methylpropyl)benzotriazole | ketone | free | 593.3 | 1H-NMR (DMSO-D6) δ: 8.40 (1H, d, J = 6.1 Hz), 7.80-7.62 (5H, m), 7.51-7.42 (1H, m), 7.15 (1H. dd, J = 8.1, 1.4 Hz), 5.03 (1H, s), 4.75 (2H, s), 4.48-3.87 (3H, m), 2.27-2.12 (2H, m), 1.81-1.72 (1H, m), 1.68 1.50 (2H, m), 1.16 (6H, s), 0.91-0.86 (1H, m). |
| 247 | (4-cyano-3-fluorophenyl) | isomer-X Relative configuration | 4-cyano-5-fluoro-1-(2-hydroxy-2-methylpropyl)benzotriazole | ketone | free | 568.3 | 1H,NMR (DMSO-D6) δ: 8.55 (1H, d, J = 6.7 Hz), 7.80-7.67 (4H, m), 7.53 (1H, d, J = 9.2 Hz), 7.19 (1H, dd, J = 8.2, 1.5 Hz), 4.83 (1H, s), 4.73 (2H, s), 4.52-3.87 (3H, m), 2.29-2.10 (2H, m), 1.83-1.72 (1H, m), 1.69-1.49 (2H, m), 1.22 (6H, s), 0.95 0.86 (1H, m). |
| 248 | (4-cyano-3-fluorophenyl) | (3-aminopyrrolidine) | 4-(difluoromethyl)-5-fluoro-1-(2-hydroxy-2-methylpropyl)benzotriazole | ketone | free | 567.3 | 1H-NMR (DMSO-D6) δ: 8.40 (1H, d, J = 5.5 Hz), 7.87-7.62 (5H, m), 7.43 (1H, d, J = 10.4 Hz), 7.14 (1H, dd, J = 8.1, 1.4 Hz), 5.03 (1H, s), 4.75 (2H, s), 3.79-3.60 (5H, m), 2.06-1.92 (1H, m), 1.75-1.62 (1H, m), 1.17 (6H, s). |
| 249 | (4-cyano-3-fluorophenyl) | (3-aminopyrrolidine) | 4-cyano-5-fluoro-1-(2-hydroxy-2-methylpropyl)benzotriazole | ketone | free | 542.3 | 1H-NMR (DMSO-D6) δ: 8.56 (1H, d, J = 6.4 Hz), 7.83-7.65 (4H, m), 7.51 (1H, d, J = 10.4 Hz), 7.22-7.14 (1H, m), 4.83 (1H, s), 4.73 (2H, s), 3.80-3.60 (5H, m), 2.06-1.92 (1H, m), 1.77-1.59 (1H, m), 1.22 (6H, s) |

TABLE 32-continued

| # | | | | | | MS | NMR |
|---|---|---|---|---|---|---|---|
| 250 | (structure) | (structure) | (structure) | (structure) | free | 607.3 | 1H-NMR (DMSO-D6) δ: 8.41 (1H, d, J = 6.1 Hz), 7.90-7.59 (5H, m), 7.45 (1H, d, J = 10.4 Hz), 7.15 (1H, dd, J = 7.9, 1.5 Hz), 5.03 (2H, s), 4.75 (2H, s), 4.64 4.56 (1H, m), 4.11-4.02 (1H, m), 2.33-1.84 (6H, m), 1.66-1.46 (3H, m), 1.17 (6H, s). |
| 251 | (structure) | (structure) | (structure) | (structure) | free | 582.3 | 1H-NMR (DMSO-D6) δ: 8.56 (1H, d, J = 6.4 Hz), 7.64- 7.76 (1H, m), 7.68 (2H, s), 7.61 (1H, s), 7.52 (1H, d, J = 10.4 Hz), 7.19 (1H, dd, J = 8.1, 1.4 Hz), 4.83 (1H, s), 4.73 (2H, s), 4.63-4.55 (1H, m), 4.11-4.02 (1H, m), 2.33-1.82 (6H, m), 1.65-1.46 (3H, m), 1.22 (6H, s). |
| 252 | (structure) | (structure) Racemate Relative configuration | (structure) | (structure) | free | 593.3 | 1H-NMR (DMSO-D6) δ: 8.40 (1H, d, J = 6.1 Hz), 7.80-7.52 (5H, m), 7.51-7.42 (1H, m), 7.15 (1H, dd, J = 8.1, 1.4 Hz), 5.03 (1H, s), 4.75 (2H, s), 4.48-3.87 (3H, m), 2.21 2.12 (2H, m), 1.81-1.72 (1H, m), 1.68-1.50 (2H, m), 1.16 (6H, s), 0.91-0.86 (1H, m). |
| 253 | (structure) | (structure) Racemate Relative configuration | (structure) | (structure) | free | 568.3 | 1H-NMR (DMSO-D6) δ: 8.55 (1H, d, J = 6.7 Hz), 7.80-7.67 (4H, m), 7.53 (1H, d, J = 9.2 Hz), 7.19 (1H, dd, J = 8.2, 1.5 Hz), 4.83 (1H, s), 4.73 (2H, s), 4.52-3.87 (3H, m), 2.29-2.10 (2H, m), 1.83-1.72 (1H, m), 1.59-1.49 (2H, m), 1.22 (6H, s), 0.95-0.86 (1H, m). |
| 254 | (structure) | (structure) isomer-X Relative configuration | (structure) | (structure) | free | 573.2 | 1H-NMR (DMSO-D6) δ: 7.96 (1H, d, J = 5.5 Hz), 7.83-7.61 (4H, m), 7.50 (1H, d, J = 10.4 Hz), 7.17 (1H, d, J = 7.9 Hz), 5.43 (1H, s), 4.78 (2H, s), 4.49-3.87 (3H, m), 2.21-1.96 (6H, m), 1.82-1.50 (5H, m), 0.99-0.79 (1H, m). |

TABLE 33

| # | | | | | | MS | NMR |
|---|---|---|---|---|---|---|---|
| 255 | (structure) | (structure) | (structure) | (structure) | free | 547.3 | 1H-NMR (DMSO-D6) δ: 7.96 (1H, d, J = 4.9 Hz), 7.81-7.72 (2H, m), 7.70-7.63 (2H, m), 7.48 (1H, d, J = 10.7 Hz), 7.16 (1H, d, J = 8.5 Hz), 5.43 (1H, s), 4.78 (2H, s), 3.75-3.59 (5H, m), 2.26-2.17 (2H, m), 2.04-1.91 (3H, m), 1.77-1.59 (3H, m). |
| 256 | (structure) | (structure) | (structure) | (structure) | free | 587.2 | 1HNMR (DMSO-D6) δ: 7.97 (1H, d, J = 5.2 Hz), 7.77 (1H, t, J = 7.5 Hz), 7.69-7.63 (2H, m), 7.59 (1H, s), 7.49 (1H, d, J = 10.7 Hz), 7.17 (1H, d, J = 8.5 Hz), 5.44 (1H, s), 4.76 (2H, s), 4.62-4.55 (1H, m), 4.07-4.01 (1H, m), 2.32-1.50 (15H, m). |
| 257 | (structure) | (structure) isomer-X Relative configuration | (structure) | (structure) | free | 589.2 591.2 | 1H-NMR (DMSO-D6) δ: 8.14 (1H, d, J = 5.8 Hz), 7.79-7.63 (4H, m), 7.50 (1H, d, J = 9.8 Hz), 7.16 (1H, d, J = 8.5 Hz), 5.38 (1H, s), 4.97 (2H, s), 4.49-3.87 (3H, m), 2.25-1.97 (6H, m), 1.76-1.50 (5H, m), 0.95-0.83 (1H, m). |

TABLE 33-continued

| | | | | | | | |
|---|---|---|---|---|---|---|---|
| 258 | | | | | free | 563.2 565.2 | 1H-NMR (DMSO-D6) δ: 8.14 (1H, d, J = 6.4 Hz), 7.78-7.73 (2H, m), 7.71-7.64 (2H, m), 7.47 (1H, d, J = 9.8 Hz), 7.14 (1H, d, J = 8.2 Hz), 5.38 (1H, s), 4.97 (2H, s), 3.68-3.59 (5H, m), 2.31-2.21 (2H, m), 2.10-1.93 (3H, m), 1.76-1.55 (3H, m). |
| 259 | | | | | free | 603.2 605.2 | 1H-NMR (DMSO-D6) δ: 8.14 (1H, d, J = 5.8 Hz), 7.77 (1H, t, J = 7.6 Hz), 7.69-7.59 (3H, m), 7.49 (1H, d, J = 10.4 Hz), 7.15 (1H, d, J = 8.2 Hz), 5.38 (1H, s), 4.97 (2H, s), 4.63-4.57 (1H, m), 4.08-4.02 (1H, m), 2.33-1.47 (15H, m). |
| 260 | | | isomer-X Relative configuration | | free | 605.2 | 1H-NMR (DMSO-D6) δ: 8.40 (1H, d, J = 5.8 Hz), 7.85-7.59 (5H, m), 7.47 (1H, d, J = 10.4 Hz), 77.15 (1H, d, J = 7.9 Hz), 5.77 (1H, s), 4.92 (2H, s), 4.50-3.89 (3H, m), 2.17-1.45 (11H, m), 0.90 (1H, dd, J = 12.1, 4.4 Hz). |
| 261 | | | | | free | 579.3 | 1H-NMR (DMSO-D6) δ: 8.40 (1H, d, 5.2 Hz), 7.82-7.52 (5H, m), 7.44 (1H, d, J = 10.7 Hz), 7.14 (1H, d, J = 7.9 Hz), 5.77 (1H, s), 4.92 (2H, s), 3.63-3.39 (5H, m), 2.21-1.66 (8H, m). |
| 262 | | | | | free | 619.3 | 1H-NMR (DMSO-D6) δ: 8.40 (1H, d, 6.1 Hz), 7.84-7.59 (5H, m), 7.46 (1H, d, J = 10.7 Hz), 7.15 (1H, dd, J = 8.1, 1.4 Hz), 5.78 (1H, s), 4.92 (2H, s), 4.65-4.54 (1H, m), 4.11-4.02 (1H, m), 2.29-1.47 (15H, m). |
| 263 | | | Racemate Relative configuration | | free | 605.2 | 1H-NMR (DMSO-D6) δ: 8.40 (1H, d, J = 5.8 Hz), 7.85-7.59 (5H, m), 2.47 (1H, d, J = 10.4 Hz), 7.15 (1H, d, J = 7.9 Hz), 5.77 (1H, s), 4.92 (2H, s), 4.50-3.89 (3H, m), 2.17-1.45 (11H, m), 0.90 (1H, dd, J = 12.1, 4.4 Hz). |
| 264 | | | isomer-X Relative configuration | | free | 580.2 | 1H-NMR (DMSO-D6) δ: 8.54 (1H, d, J = 6.7 Hz), 7.91-7.38 (5H, m), 7.19 (1H, dd, J = 7.9, 1.5 Hz), 5.56 (1H, s), 4.89 (2H, s), 4.47-3.88 (3H, m), 2.27-1.48 (11H, m), 0.96-0.85 (1H, m). |
| 265 | | | | | free | 554.2 | 1H-NMR (DMSO-D6) δ: 8.55 (1H, d, J = 6.4 Hz), 7.80-7.68 (4H, m), 7.57-7.49 (1H, m), 7.18 (1H, dd, J = 8.1, 1.4 Hz), 5.55 (1H, s), 4.89 (2H, s), 3.67-3.46 (5H, m), 2.26-1.67 (8H, m). |

TABLE 34

| | | | | | | | |
|---|---|---|---|---|---|---|---|
| 266 | | | | | free | 594.2 | 1H-NMR (DMSO-D6) δ: 8.55 (1H, d, J = 6.4 Hz), 7.78 (1H, t, J = 7.5 Hz), 7.70-7.60 (3H, m), 7.53 (1H, dd, J = 10.4, 1.5 Hz), 7.21-7.16 (1H, m), 5.55 (1H, s), 4.89 (2H, s), 4.61-4.55 (1H, m), 4.08-4.02 (1H, m), 2.31-1.50 (15H, m). |

TABLE 34-continued

| | | | | | | |
|---|---|---|---|---|---|---|
| 267 | 2-F, 4-CN phenyl | azabicyclic NH2, Racemate Relative configuration | F-CN-benzotriazole-CH2-cyclobutanol-OH | acetyl | free | 580.2 | 1H-NMR (DMSO-D6) δ: 8.54 (1H, d, J = 6.7 Hz), 7.91-7.38 (5H, m), 7.19 (1H, dd, J = 7.9, 1.5 H), 5.56 (1H, s), 4.89 (2H, s), 4.47-3.88 (3H, m), 2.27-1.48 (11H, m), 0.96-0.85 (1H, m). |
| 268 | 2-F, 4-CN phenyl | azabicyclic NH2, Racemate Relative configuration | F-benzotriazole-CH2-cyclobutanol-OH | acetyl | free | 573.2 | 1H-NMR (DMSO-D6) δ: 7.96 (1H, d, J = 5.5 Hz), 7.83 7.61 (4H, m), 7.50 (1H, d, J = 10.4 Hz), 7.17 (1H, d, J = 7.9 Hz), 5.43 (1H, s), 4.78 (2H, s), 4.49-3.87 (3H, m), 2.21-1.96 (6H, m), 1.82-1.50 (5H, m), 0.99-0.79 (1H, m). |
| 269 | 2-F, 4-CN phenyl | azabicyclic NH2, Racemate Relative configuration | Cl,F-benzotriazole-CH2-cyclobutanol-OH | acetyl | free | 589.2 591.4 | 1H-NMR (DMSO-D6) δ: 8.14 (1H, d, J = 5.8 Hz), 7.79-7.63 (4H, m), 7.50 (1H, d, J = 9.8 Hz), 7.15 (1H, d, J = 8.5 Hz), 5.38 (1H, s), 4.97 (2H, s), 4.49-3.87 (3H, m), 2.25-1.97 (6H, m), 1.76-1.50 (5H, m), 0.95-0.83 (1H, m. |
| 270 | 2-F, 4-CN phenyl | azabicyclic NH2, isomer-X Relative configuration | F,Me-benzotriazole-CH2-cyclobutanol-OH | acetyl | free | 569.4 | 1H-NMR (DMSO-D6) δ: 7.86 (1H, d, 6.4 Hz), 7.79-7.57 (4H, m), 7.46 (1H, dd, J = 10.5, 1.4 Hz), 7.17-7.14 (1H, m), 5.52 (1H, s), 4.84 (2H, s), 4.45 3.89 (3H, m), 2.54 (3H, s), 2.30 1.96 (6H, m), 1.79-1.51 (5H, m), 3.89 (1H, dd, J = 11.9, 4.6 Hz). |
| 271 | 2-F, 4-CN phenyl | (S)-pyrrolidin-3-amine | F,Me-benzotriazole-CH2-cyclobutanol-OH | acetyl | free | 543.2 | 1H-NMR (DMSO-D6) δ: 7.56 (1H, d, J = 6.4 Hz), 7.76-7.69 (2H, m), 7.68-7.63 (1H, m), 7.63-7.56 (1H, m), 7.44 (1H, d, J = 10.7 Hz), 7.13 (1H, dd, J = 8.2, 1.5 Hz), 5.52 (1H, s), 4.84 (2H, s), 3.68-3.49 (5H, m), 2.52 (3H, s), 2.30-2.24 (2H, m), 2.02-1.93 (3H, m), 1.75-1.60 (3H, m). |
| 272 | 2-F, 4-CN phenyl | azabicyclic NH2 | F,Me-benzotriazole-CH2-cyclobutanol-OH | acetyl | free | 583.2 | 1H-NMR (DMSO-D6) δ: 7.67 (1H, d, J = 6.4 Hz), 7.75 (1H, t, J = 7.6 Hz), 7.63 (1H, dd, J = 7.8, 1.7 Hz), 7.60 7.53 (2H, m), 7.45 (1H, dd, J = 10.5, 1.4 Hz), 7.14 (1H, dd, J = 7.9, 1.5 Hz), 5.52 (1H, s), 4.84 (2H, s), 4.64-4.54 (1H, m), 4.11-4.01 (1H, m), 2.52 (3H, s), 2.28-1.50 (15H. m). |
| 273 | 2-F, 4-CN phenyl | azabicyclic NH2, isomer-X Relative configuration | Br,F-benzotriazole-CH2-C(Me)2-OH | acetyl | free | 621.1 623.1 | 1H-NMR (DMSO-D6) δ: 8.17 (1H, d, J = 6.1 Hz), 7.80-7.62 (4H, m), 7.47 (1H, d, J = 9.5 Hz), 7.15 (1H, d, J = 8.2 Hz), 4.88 (2H, s, 4.74 (1H, s), 4.49-3.86 (3H, m), 2.27-2.12 (2H, m), 1.79-1.50 (3H, m), 1.18 (6H, s), 0.89 (1H, dd, J = 12.4, 4.4 Hz). |
| 274 | 2-F, 4-CN phenyl | (S)-pyrrolidin-3-amine | Br,F-benzotriazole-CH2-C(Me)2-OH | acetyl | free | 595.1 597.1 | 1H-NMR (DMSO-D6) δ: 8.21-8.16 (1H, m), 7.78-7.65 (4H, m), 7.45 (1H, d, J = 10.7 Hz), 7.13 (1H, dd, J = 8.2, 1.5 Hz), 4.88 (2H, s), 4.74 (1H, s), 3.70-3.48 (5H, m), 2.03-1.94 (1H, m), 1.71-1.63 (1H, m), 1.18 (6H, s). |

TABLE 34-continued

| 275 | | | | | free | 635.1 637.1 | 1H-NMR (DMSO-D6) δ: 8.18 (1H, d, J = 6.1 Hz), 7.76 (1H, t, J = 7.5 Hz), 7.68-7.59 (3H, m), 7.46 (1H, dd, J = 10.5, 1.4 Hz), 7.14 (1H, dd, J = 7.9, 1.5 Hz), 4.88 (2H, s), 4.74 (1H, s), 4.62-4.55 (1H, m), 4.10-4.02 (1H, m), 2.26-1.88 (6H, m), 1.65-1.47 (3H, m), 1.18 (6H, s). |

TABLE 35

| 276 | | Racemate Relative configuration | | | free | 559.4 | 1H-NMR (DMSO-D6) δ: 7.85 (1H, d, 6.4 Hz), 7.79-7.57 (4H, m), 7.46 (1H, dd, J = 10.5, 1.4 Hz), 7.17-7.14 (1H, m), 5.52 (1H, s), 4.84 (2H, s), 4.45-3.89 (3H, m), 2.54 (3H, s), 2.30-1.96 (6H, m), 1.79-1.51 (5H, m), 0.89 (1H, dd, J = 11.9, 4.6 Hz). |
| 277 | | Racemate Relative configuration | | | free | 621.1 623.1 | 1H-NMR (DMSO-D6) δ: 8.17 (1H, d, J = 6.1 Hz), 7.80-7.62 (4H, m), 7.47 (1H, d, J = 9.5 Hz), 7.15 (1H, d, J = 8.2 Hz), 4.88 (2H, s), 4.74 (1H, s), 4.49-3.85 (3H, m), 2.27-2.12 (2H, m), 1.79-1.50 (3H, m), 1.18 (6H, s), 0.89 (1H, dd, J = 12.4, 4.4 Hz). |
| 278 | | Racemate Relative configuration | 13 | | free | 583.4 | 1H-NMR (DMSO-D6) δ: 7.99 (1H, d, J = 5.8 Hz), 7.83-7.58 (4H, m), 7.38 (1H, dd, J = 10.5, 1.4 Hz), 7.09 (1H, dd, J = 8.2, 1.5 Hz), 5.10-4.83 (2H, m), 4.72 (1H, s), 4.53-4.88 (3H, m), 2.29-2.13 (3H, m), 1.80 1.50 (3H, m), 1.15 (6H, s), 1.02-0.96 (2H, m), 0.89 (1H, dd, J = 11.9, 4.6 Hz), 0.53-0.12 (2H, m). |
| 279 | | isomer-X Relative configuration | | | free | 583.4 | 1H-NMR (DMSO-D6) δ: 7.99 (1H, d, J = 5.6 Hz), 7.83-7.58 (4H, m), 7.38 (1H, dd, J = 10.5, 1.4 Hz), 7.09 (1H, dd, J = 8.2, 1.5 Hz), 5.10-4.83 (2H, m), 4.72 (1H, s), 4.53-3.88 (3H, m), 2.29-2.63 (3H, m), 1.80-1.50 (3H, m), 1.15 (6H, s), 1.02-0.96 (2H, m), 0.89 (1H, dd, J = 11.9, 4.6 Hz), 0.53-0.12 (2H, m). |
| 280 | | | | | free | 557.4 | 1H-NMR (DMSO-D6) δ: 7.99 (1H, d, J = 5.5 Hz), 7.76 7.64 (4H, m), 7.36 (1H, dd, J = 10.5, 2.9 Hz), 7.07 (1H, dd, J = 8.2, 1.5 Hz), 5.05-4.81 (2H, m), 4.72 (1H, s), 3.70-3.44 (5H, m), 2.26-2.17 (1H, m), 2.11-1.97 (1H, m), 1.78 1.67 (1H, m), 1.15 (6H, s), 1.03 0.95 (2H, m), 0.40-0.15 (2H, m). |
| 281 | | | | | free | 597.5 | 1H-NMR (DMSO-D6) δ: 7.99 (1H, d, J = 6.1 Hz), 7.74 (1H, t, J = 7.5 Hz), 7.68-7.56 (3H, m), 7.37 (11H, d, J = 10.7 Hz), 7.08 (1H, d, J = 7.9 Hz), 5.04-4.81 (2H, m), 4.72 (1H, s), 4.65-4.57 (1H, m), 4.13-4.05 (1H, m), 2.24-1.51 (10H, m), 1.15 (6H, s), 1.02-0.94 (2H, m), 0.42-0.16 (2H, m). |
| 282 | | | | //—CH2—// | free | 368.2 | 1H-NMR (DMSO-D6) δ: 8.23-7.56 (5H, m), 7.37-7.28 (2H, m), 7.17-7.09 (2H, m), 7.02-6.89 *2H, m), 5.76 (2H, s), 4.65-3.85 (5H, m), 2.28 (3H, s), 1.99-1.64 (2H, m). |

TABLE 35-continued

| 283 |  |  isomer-X Relative configuration |  | //—CH2—// | free | 430.1 | 1H-NMR (DMSO-D6) δ: 7.80 (1H, t, J = 7.3 Hz), 7.53 (1H, d, J = 7.9 Hz), 7.44 (1H, s), 7.36 (1H, d, J= 7.6 Hz), 7.29 (1H, , J = 10.4 Hz), 7.18 (1H, t, J = 7.8 Hz), 7.09 (1H, d, J = 7.9 Hz), 7.03 (1H, d, J = 7.9 Hz), 6.93 (1H, d, J = 11.3 Hz), 3.62 (2H, s), 3.29-3.25 (1H, m), 3.15-3.10 (1H, m), 3.05-2.99 (1H, m), 2.30 (3H, s), 2.06-1.96 (2H, m), 1.89-1.76 (1H, m), 1.66-1.56 (1H, m), 1.39-1.29 (1H, m), 0.64 (1H, dd, J = 11.6, 4.0 Hz). |

TABLE 36

| 284 |  |  |  | //—CH2—// | free | 418.2 | 1H-NMR (DMSO-D6) δ: 7.81 (1H, t, J = 7.5 Hz), 7.52 (1H, d, J = 7.6 Hz), 7.47 (1H, s), 7.39 (1H, d, J = 7.9 Hz), 7.31 (1H, d, J = 10.4 Hz), 7.18 (1H, t, J = 8.1 Hz), 7.09 (1H, d, J = 7.9 Hz), 7.03 (1H, d, J = 7.3 Hz), 6.93 (1H, d, J = 11.0 Hz), 3.70 (2H, dd, J = 37.4, 13.6 Hz), 2.89-2.78 (1H, m), 2.64-2.60 (2H, m), 2.38-2.34 (1H, m), 2.31 (3H, s), 1.86-1.73 (2H, m), 1.28 (3H, s). |
| 285 |  |  isomer-X Relative configuration | 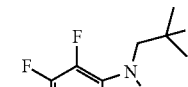 | //—CH2—// | 2HCl | 547.2 | 1H-NMR (DMSO-D6) δ: 7.94-7.72 (5H, m), 7.54-7.43 (1H, m), 7.22-7.09 (1H, m), 4.90-4.74 (1H, m), 4.63 (2H, s), 4.53-4.40 (1H, m), 4.29-3.98 (3H, m), 2.24-1.33 (5H, m), 1.16 (6H, s), 0.93-0.81 (1H, m). |
| 286 |  | 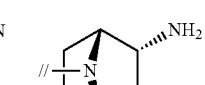 isomer-X Relative configuration | 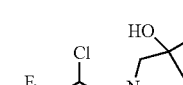 | //—CH2—// | 2HCl | 575.1 576.1 | 1H-NMR (DMSO-D6) δ: 8.09 (1H, d, J = 5.8 Hz), 7.91-7.51 (5H, m), 7.15 (1H, d, J = 8.2 Hz), 5.45-5.34 (1H, m), 4.98 (2H, s), 4.49-4.03 (5H, m), 2.34-2.21 (3H, m), 2.05-1.87 (3H, m), 1.79-1.49 (3H, m), 1.28-1.23 (1H, m), 1.04 (1H, d, J = 6.1 Hz), 0.92-0.81 (1H, m). |
| 287 |  | 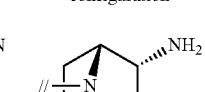 isomer-X Relative configuration |  | //—CH2—// | 2HCl | 528.2 | 1H-NMR (DMSO-D6) δ: 8.16-8.08 (1H, m), 8.01-7.31 (8H, m), 7.19-6.98 (1H, m), 4.77-4.39 (3H, m), 4.30-3.96 (6H, m), 2.13-1.39 (4H, m), 1.11 (6H, s). |
| 288 |  |  isomer-X Relative configuration | 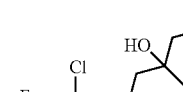 | //—CH2—// | 2HCl | 591.1 592.0 | 1H-NMR (DMSO-D6) δ: 8.10 (1H, s), 7.97-7.36 (5H, m), 7.18-7.13 (1H, m), 4.82 (2H, s), 4.52-3.95 (6H, m), 2.33-1.37 (9H, m), 0.90 (6H, t, J = 7.3 Hz). |
| 289 |  |  isomer-X Relative configuration |  | //—CH2—// | 2HCl | 527.1 | 1H-NMR (DMSO-D6) δ: 7.91-7.75 (3H, m), 7.64-7.59 (1H, m), 7.53-7.31 (4H, m), 7.17-7.11 (1H, m), 6.48-6.43 (1H, m), 4.70-3.94 (9H, m), 2.18-1.50 (4H, m), 1.06 (6H, s). |

TABLE 36-continued

| | | | | | | |
|---|---|---|---|---|---|---|
| 290 | [benzonitrile with F structure] | [bicyclic amine NH2, isomer-X Relative configuration] | [HO-phenyl-F with gem-dimethyl] | //—CH2—// | 2HCl 488.2 | 1H-NMR (DMSO-D6) δ: 7.97-7.80 (3H, m), 7.66-7.54 (1H, m), 7.35-6.93 (5H, m), 4.53-3.92 (7H, m), 2.32-1.48 (6H, m), 1.05 (6H, s). |
| 291 | [benzonitrile with F] | [pyrrolidine NH2] | [F-phenyl with OH group] | //—CH2—// | 2HCl 462.2 | 1H-NMR (DMSO-D6) δ: 7.72 (4H, t, J = 62.6 Hz), 7.12 (5H, ddd, J = 96.0, 48.2, 18.5 Hz), 4.58-3.75 (6H, m), 2.66 (2H, s), 2.30-1.99 (2H, m), 1.29-1.16 (1H, m), 1.05 (6H, s). |
| 292 | [benzonitrile with F] | [bicyclic amine NH2, isomer-X Relative configuration] | [methyl-F-phenyl] | //—CH2—// | 2HCl 444.1 | 1H-NMR (DMSO-D6) δ: 7.97-6.93 (9H, m), 4.63-4.49 (1H, m), 4.23-3.86 (3H, m), 2.32 (3H, s), 2.21-1.97 (2H, m), 1.83-1.64 (3H, m), 1.31-1.24 (2H, m), 1.07-0.82 (2H, m). |

TABLE 37

| | | | | | | |
|---|---|---|---|---|---|---|
| 293 | [benzonitrile with F] | [bicyclic amine NH2, isomer-X Relative configuration] | [F,F-benzotriazole with HO-ethyl branch] | //—CH2—// | 2HCl 575 | 1H-NMR (DMSO-D6) δ: 7.94-7.49 (6H, m), 7.18-7.11 (1H, m), 4.63 (2H, 5), 4.52-4.40 (2H, m), 4.19-3.70 (4H, m), 2.32-1.66 (5H, m), 1.44-1.35 (4H, m), 0.90 (6H, t, J = 7.3 Hz). |
| 294 | [benzonitrile with F] | [bicyclic amine NH2, isomer-X Relative configuration] | [Br,F-benzotriazole with OH branch] | //—CH2—// | 2HCl 607.0 609.0 | 1H-NMR (DMSO-D6) δ: 8.13 (1H, d, J = 5.8 Hz), 8.00-7.71 (4H, m), 7.50-7.44 (1H, m, 7.19-7.10 (1H m), 4.88 (2H, s), 4.75 (1H, s), 4.51-3.98 (5H, m), 2.30-1.64 (5H, m), 1.18 (6H, 5), 0.92-0.82 (1H, m). |
| 295 | [benzonitrile with F] | [bicyclic amine NH2, isomer-X Relative configuration] | [Br,F-benzotriazole with HO-ethyl branch] | //—CH2—// | 2HCl 635.1 637.0 | 1H-NMR (DMSO-D6) δ: 8.13 (1H, d, J = 5.8 Hz), 7.96-7.69 (4H, m), 7.52-7.46 (1H, m), 7.14 (1H, d, J = 7.9 Hz), 4.89 (2H, s), 4.48-4.01 (5H, m), 2.14-1.24 (11H, m), 0.91 (6H, t, J = 7.5 Hz). |

Test Example 1: Measurement of LSD1 Inhibitory Activity (In Vitro)

The conditions for measuring inhibitory activity of compounds against LSD1 activity were determined with reference to a document available from the website of PerkinElmer (U-TRF #38) and a patent of GlaxoSmithKline (WO2012135113).

To measure the inhibitory activity, first, the Example compound was serially diluted in dimethylsulfoxide (DMSO). Sequentially, the serially diluted solution of the Example compound in DMSO (final concentration of DMSO: 5%) and human LSD1 protein (Abcam, ab80379) were added to a reaction buffer (25 mM Tris-HCl (pH 7.5), 50 mM KCl, 2 mM CHAPS, 1 mM DTT, 0.02% BSA). The mixture was preincubated at 25° C. for 30 minutes. Thereafter, a H3K4 (Mel)-biotin-labeled peptide (Anaspec #64355) (final concentration: 200 nM) was added thereto and reacted for 60 minutes. Tranylcypromine (final concentration: 3 mM) was then added thereto to terminate the reaction. Thereafter, a detection solution containing an Eu-labeled anti-H3K4 antibody (PerkinElmer, TRF0404) and Streptavidin Alexa Fluor 647 (Thermo Fisher Scientific, S21374) was added thereto, and the mixture was allowed to stand at room temperature for 1 hour. Finally, the intensity of fluorescence under the excitation light with a wavelength of 337 nm was measured with a PHERAstar FS (BMG Labtech) at two wavelengths: 620 nm and 665 nm. The demethylation level was calculated from the ratio of the fluorescence intensity at the two wavelengths, and the compound concentration at which demethylation was inhibited by 50% was defined as IC50 (nM). The following tables show the results.

TABLE 38

| Example No. | LSD1 Inhibitory activity IC50 (nM) |
|---|---|
| 1 | 7.02 |
| 3 | 10.6 |
| 4 | 4.93 |
| 5 | 1.59 |
| 6 | 10.7 |
| 7 | 0.78 |
| 8 | 5.92 |
| 9 | 4.45 |
| 10 | 3.74 |
| 11 | 17.4 |
| 12 | 5.83 |
| 13 | 14.9 |
| 14 | 11.0 |
| 15 | 2.41 |
| 16 | 1.97 |
| 17 | 3.51 |
| 18 | 0.40 |
| 19 | 2.67 |
| 20 | 1.31 |
| 21 | 0.87 |
| 22 | 1.18 |
| 23 | 0.18 |
| 24 | 0.29 |
| 25 | 1.83 |
| 26 | 0.45 |
| 27 | 11.4 |
| 28 | 0.57 |
| 29 | 19.8 |
| 30 | 4.31 |
| 31 | 16.0 |
| 32 | 17.7 |
| 33 | 11.0 |
| 34 | 15.1 |
| 35 | 10.0 |
| 36 | 1.04 |
| 37 | 2.40 |
| 38 | 16.0 |
| 39 | 1.91 |
| 40 | 5.96 |
| 41 | 1.57 |
| 42 | 11.6 |
| 45 | 7.71 |
| 46 | 19.7 |
| 47 | 9.15 |
| 48 | 17.9 |
| 49 | 5.51 |
| 51 | 11.0 |
| 52 | 8.31 |
| 53 | 10.9 |
| 54 | 4.58 |
| 55 | 20.0 |
| 56 | 11.3 |
| 57 | 3.42 |
| 58 | 13.5 |
| 59 | 6.78 |
| 60 | 13.8 |
| 61 | 15.5 |
| 62 | 6.34 |
| 63 | 3.48 |
| 64 | 6.69 |
| 65 | 2.80 |
| 66 | 6.99 |
| 67 | 10.4 |
| 68 | 17.3 |
| 69 | 11.1 |
| 70 | 3.68 |
| 71 | 3.04 |
| 72 | 7.57 |
| 73 | 9.23 |
| 74 | 1.53 |
| 75 | 1.54 |
| 76 | 2.09 |
| 77 | 1.54 |
| 78 | 9.65 |
| 79 | 17.9 |
| 80 | 12.8 |
| 81 | 3.30 |
| 82 | 3.04 |
| 83 | 9.29 |
| 84 | 9.33 |
| 85 | 6.27 |
| 86 | 6.58 |
| 87 | 5.12 |
| 89 | 11.2 |
| 90 | 14.0 |
| 91 | 4.85 |
| 92 | 2.78 |
| 93 | 20.3 |
| 94 | 5.10 |
| 95 | 0.75 |
| 96 | 0.49 |
| 97 | 10.1 |
| 98 | 2.18 |
| 100 | 3.13 |
| 101 | 3.70 |
| 102 | 0.63 |
| 103 | 9.65 |
| 104 | 0.44 |
| 105 | 0.51 |
| 106 | 0.34 |
| 107 | 1.05 |
| 103 | 0.21 |
| 109 | 0.28 |
| 110 | 0.47 |
| 111 | 9.45 |
| 112 | 1.80 |
| 113 | 1.56 |
| 114 | 1.42 |
| 115 | 2.81 |
| 116 | 3.03 |
| 117 | 1.97 |
| 118 | 1.57 |
| 119 | 1.98 |
| 120 | 0.90 |
| 121 | 9.46 |
| 122 | 8.61 |
| 123 | 0.12 |
| 124 | 0.36 |
| 125 | 0.29 |
| 126 | 0.41 |
| 127 | 17.0 |
| 128 | 0.62 |
| 130 | 0.29 |
| 131 | 1.81 |
| 132 | 10.8 |
| 133 | 0.91 |
| 134 | 0.21 |
| 135 | 0.30 |
| 136 | 0.30 |
| 137 | 3.18 |
| 138 | 2.83 |
| 139 | 1.68 |
| 140 | 5.98 |
| 141 | 0.25 |
| 142 | 0.38 |
| 143 | 0.25 |
| 144 | 0.51 |
| 145 | 0.38 |
| 146 | 0.42 |
| 147 | 0.35 |
| 148 | 19.8 |
| 150 | 2.99 |
| 151 | 5.02 |
| 155 | 0.51 |
| 156 | 12.8 |
| 158 | 6.35 |
| 159 | 17.7 |
| 160 | 0.92 |

TABLE 38-continued

| Example No. | LSD1 Inhibitory activity IC50 (nM) |
|---|---|
| 161 | 0.74 |
| 162 | 1.09 |
| 164 | 12.8 |
| 165 | 11.2 |
| 166 | 0.63 |
| 167 | 1.79 |
| 168 | 1.05 |
| 169 | 0.90 |
| 170 | 0.72 |
| 171 | 0.35 |
| 172 | 0.55 |
| 173 | 1.84 |
| 174 | 13.8 |
| 175 | 0.33 |
| 176 | 0.30 |
| 177 | 0.23 |
| 178 | 1.24 |
| 179 | 0.69 |
| 180 | 0.88 |
| 181 | 2.70 |
| 182 | 17.6 |
| 183 | 0.67 |
| 184 | 0.25 |
| 185 | 0.14 |
| 186 | 0.43 |
| 187 | 0.25 |
| 168 | 0.61 |
| 189 | 0.33 |
| 190 | 0.15 |
| 191 | 0.22 |
| 192 | 0.40 |
| 193 | 2.35 |
| 194 | 0.34 |
| 195 | 0.20 |
| 196 | 0.14 |
| 197 | 0.11 |
| 198 | 0.18 |
| 199 | 1.00 |
| 200 | 0.91 |
| 201 | 0.40 |
| 202 | 0.09 |
| 203 | 0.24 |
| 204 | 0.45 |
| 205 | 1.28 |
| 206 | 0.30 |
| 207 | 6.89 |
| 208 | 16.8 |
| 209 | 0.06 |
| 210 | 0.15 |
| 211 | 0.14 |
| 213 | 0.15 |
| 214 | 0.10 |

TABLE 39

| Example No. | LSD1 Inhibitory activity IC50 (nM) |
|---|---|
| 215 | 0.25 |
| 216 | 0.50 |
| 217 | 0.21 |
| 218 | 0.07 |
| 219 | 0.10 |
| 220 | 0.12 |
| 221 | 0.20 |
| 222 | 8.31 |
| 224 | 0.49 |
| 225 | 0.20 |

TABLE 39-continued

| Example No. | LSD1 Inhibitory activity IC50 (nM) |
|---|---|
| 226 | 0.54 |
| 227 | 11.7 |
| 228 | 0.11 |
| 229 | 0.43 |
| 230 | 0.94 |
| 231 | 0.65 |
| 232 | 0.63 |
| 233 | 4.88 |
| 234 | 2.43 |
| 235 | 2.09 |
| 237 | 0.20 |
| 238 | 2.35 |
| 239 | 0.59 |
| 240 | 0.34 |
| 241 | 0.29 |
| 242 | 2.69 |
| 243 | 0.65 |
| 244 | 6.54 |
| 245 | 0.39 |
| 246 | 0.17 |
| 247 | 0.23 |
| 248 | 0.46 |
| 249 | 0.88 |
| 250 | 0.38 |
| 251 | 0.96 |
| 252 | 0.36 |
| 254 | 0.13 |
| 255 | 0.23 |
| 256 | 0.24 |
| 257 | 0.12 |
| 258 | 0.13 |
| 259 | 0.14 |
| 260 | 0.14 |
| 261 | 0.37 |
| 262 | 0.30 |
| 263 | 0.52 |
| 264 | 0.24 |
| 265 | 0.43 |
| 266 | 0.35 |
| 267 | 0.49 |
| 268 | 0.29 |
| 269 | 0.41 |
| 270 | 0.15 |
| 271 | 0.23 |
| 272 | 0.32 |
| 273 | 0.19 |
| 274 | 0.32 |
| 275 | 0.21 |
| 276 | 0.39 |
| 277 | 0.42 |
| 278 | 0.87 |
| 279 | 0.46 |
| 280 | 2.13 |
| 281 | 2.62 |
| 282 | 3.51 |
| 283 | 0.062 |
| 284 | 0.74 |
| 285 | 0.091 |
| 286 | 0.093 |
| 287 | 0.10 |
| 288 | 0.075 |
| 289 | 0.18 |
| 290 | 0.23 |
| 291 | 0.80 |
| 292 | 0.36 |
| 293 | 0.076 |
| 294 | 0.14 |
| 295 | 0.15 |

The results of the test clarified that the biphenyl compound represented by Formula (I) exhibits LSD1 inhibitory activity.

Test Example 2: Cell-Growth Inhibition Test

Under the following conditions, an in vitro cell-growth inhibition test was performed with respect to HEL cells (human acute myelocytic leukemia cell lines), NCI-H1417 cells (human small-cell lung cancer cell lines), and NCI-H146 cells (human small-cell lung cancer cell lines).

HEL cells (JCRB, Cat #: JCRB0062), NCI-H1417 cells (ATCC, Cat #: CRL-5869), or NCI-H146 cells (ATCC, Cat #: HTB-173) cultured in a 10% FBS-containing RPMI1640 medium (Thermo Fisher Scientific, Cat #: A10491-01) were seeded in a 96-well flat-bottom microplate (Thermo Fisher Scientific, Cat #: 165305) so that each well contained 1500 HEL cells (100 μL), 5000 NCI-H1417 cells (100 μL), or 1200 NCI-H146 cells (100 μL). The Example compound was serially diluted in dimethylsulfoxide to a concentration that was 500 times higher than the final concentration. The serially diluted Example compound or dimethylsulfoxide alone was added to a 10% FBS-containing RPMI1640 medium to a concentration that was 2 times higher than the final concentration, and the resulting product was added in an amount of 100 μL to each well of the culture plate containing HEL cells, NCI-H1417 cells, or NCI-H146 cells, so that the final concentrations of the Example compound were 3000, 1000, 300, 100, 30, 10, 3, 1, 0.3, 0.1, 0.03, and 0.01 nM. The final concentration of dimethylsulfoxide was adjusted to 0.2%. The cells with the Example compound or with dimethylsulfoxide alone were cultured at 37° C. in a 5% carbon-dioxide-containing incubator for 5 days (HEL cells) or 10 days (NCI-H1417 cells and NCI-H146 cells). After culture, the plate was allowed to stand at room temperature for 30 minutes, and 100 μL of the supernatant was removed from each well to leave 100 μL of the cell culture solution. To each well containing the remaining 100 μL of the cell culture solution, the same amount of CellTiter-Glo 2.0 Assay (Promega, Cat #: G9242) was added. The microplate was shaken with a plate mixer for 1 minute and then allowed to stand in a dark place for 10 minutes. Thereafter, the luminescence intensity of viable cells in each well was measured using a microplate reader (PerkinElmer, EnSpire). The cell growth rate was determined in accordance with the following equation, and the concentration at which the cell growth rate was 50%, i.e.; the concentration of each test compound at which the cell growth was inhibited by 50% (IC50 (nM)) was determined.

Cell growth rate (%)=T/C×100

T: The luminescence intensity in a well to which the test compound was added (count per second)

C: The luminescence intensity in a well to which dimethylsulfoxide alone was added (count per second)

The tables below show the results.

TABLE 40

| Cell-Growth Inhibition Test: HEL Cells | |
|---|---|
| Ex. No. | IC50 (nM) |
| 1 | 39.8 |
| 4 | 28.9 |
| 5 | 34.5 |
| 7 | 14.8 |
| 8 | 42.7 |
| 9 | 38.7 |
| 10 | 31.7 |
| 12 | 36.7 |
| 15 | 17.3 |
| 16 | 34.3 |

TABLE 40-continued

| Cell-Growth Inhibition Test: HEL Cells | |
|---|---|
| Ex. No. | IC50 (nM) |
| 18 | 3.56 |
| 19 | 24.4 |
| 20 | 7.73 |
| 21 | 8.34 |
| 22 | 3.51 |
| 23 | 0.73 |
| 24 | 3.50 |
| 25 | 4.72 |
| 26 | 4.83 |
| 27 | 24.7 |
| 28 | 18.7 |
| 30 | 27.1 |
| 36 | 15.4 |
| 37 | 10.1 |
| 38 | 34.0 |
| 39 | 17.4 |
| 40 | 27.2 |
| 41 | 4.95 |
| 47 | 29.8 |
| 48 | 28.9 |
| 49 | 32.1 |
| 59 | 53.0 |
| 63 | 28.3 |
| 65 | 23.9 |
| 69 | 29.9 |
| 71 | 19.5 |
| 74 | 20.4 |
| 75 | 5.78 |
| 77 | 13.6 |
| 80 | 45.6 |
| 81 | 11.7 |
| 82 | 11.1 |
| 84 | 41.7 |
| 85 | 32.2 |
| 86 | 13.4 |
| 87 | 17.4 |
| 92 | 9.91 |
| 94 | 28.4 |
| 98 | 11.0 |
| 102 | 12.8 |
| 104 | 41.7 |
| 106 | 5.74 |
| 108 | 35.4 |
| 109 | 15.1 |
| 110 | 7.41 |
| 113 | 9.00 |
| 117 | 8.54 |
| 120 | 7.50 |
| 123 | 1.89 |
| 124 | 2.84 |
| 125 | 7.57 |
| 126 | 5.39 |
| 128 | 5.70 |
| 130 | 22.2 |
| 131 | 15.2 |
| 133 | 17.7 |
| 134 | 1.08 |
| 135 | 2.37 |
| 138 | 0.90 |
| 139 | 16.9 |
| 141 | 1.50 |
| 142 | 3.80 |
| 143 | 0.95 |
| 144 | 0.37 |
| 145 | 1.81 |
| 146 | 1.15 |
| 147 | 3.04 |
| 155 | 0.83 |
| 160 | 7.03 |
| 161 | 9.88 |
| 162 | 0.62 |
| 166 | 0.62 |
| 167 | 4.05 |
| 168 | 5.29 |
| 170 | 3.44 |

TABLE 40-continued

Cell-Growth Inhibition Test: HEL Cells

| Ex. No. | IC50 (nM) |
|---|---|
| 171 | 0.050 |
| 172 | 0.47 |
| 173 | 1.65 |
| 175 | 0.20 |
| 176 | 0.20 |
| 177 | 0.38 |
| 178 | 3.57 |
| 179 | 1.52 |
| 180 | 1.18 |
| 181 | 9.06 |
| 182 | 22.4 |
| 183 | 0.54 |
| 184 | 2.28 |
| 185 | 0.68 |
| 186 | 5.30 |
| 187 | 1.59 |
| 188 | 1.95 |
| 189 | 0.59 |
| 190 | 0.41 |
| 191 | 3.91 |
| 192 | 1.11 |
| 193 | 2.31 |
| 194 | 15.8 |
| 195 | 0.45 |
| 196 | 0.32 |
| 197 | 1.0 |
| 198 | 0.43 |
| 199 | 22.0 |
| 200 | 3.72 |
| 201 | 1.95 |
| 202 | 0.24 |
| 203 | 2.48 |
| 204 | 2.14 |
| 205 | 4.95 |
| 206 | 0.40 |

TABLE 41

Cell-Growth Inhibition Test: HEL Cells

| Ex. No. | IC50 (nM) |
|---|---|
| 209 | 0.24 |
| 210 | 3.30 |
| 211 | 1.41 |
| 213 | 0.65 |
| 214 | 0.44 |
| 215 | 4.91 |
| 216 | 4.19 |
| 217 | 0.86 |
| 218 | 0.22 |
| 219 | 1.70 |
| 220 | 1.09 |
| 221 | 0.49 |
| 222 | 38.0 |
| 224 | 48.2 |
| 225 | 0.69 |
| 226 | 2.56 |
| 227 | 23.6 |
| 228 | 0.68 |
| 229 | 2.55 |
| 231 | 13.4 |
| 232 | 2.04 |
| 234 | 42.6 |
| 235 | 8.42 |
| 237 | 28.5 |
| 238 | 26.1 |
| 239 | 12.5 |
| 240 | 4.20 |
| 241 | 2.54 |
| 246 | 0.37 |

TABLE 41-continued

Cell-Growth Inhibition Test: HEL Cells

| Ex. No. | IC50 (nM) |
|---|---|
| 247 | 3.02 |
| 248 | 5.94 |
| 249 | 41.6 |
| 250 | 2.36 |
| 251 | 23.9 |
| 252 | 0.77 |
| 253 | 6.11 |
| 254 | 0.20 |
| 255 | 2.73 |
| 256 | 1.31 |
| 257 | 0.13 |
| 258 | 1.27 |
| 259 | 0.58 |
| 260 | 0.13 |
| 261 | 2.67 |
| 262 | 0.93 |
| 263 | 0.39 |
| 264 | 0.64 |
| 265 | 17.6 |
| 266 | 4.63 |
| 267 | 1.98 |
| 268 | 0.40 |
| 269 | 0.29 |
| 270 | 0.26 |
| 271 | 4.29 |
| 272 | 1.52 |
| 273 | 0.27 |
| 274 | 3.15 |
| 275 | 0.99 |
| 276 | 0.62 |
| 277 | 0.65 |
| 278 | 3.76 |
| 279 | 1.59 |
| 280 | 36.6 |
| 281 | 23.9 |
| 282 | 40.7 |
| 283 | 0.79 |
| 284 | 5.78 |
| 285 | 0.046 |
| 286 | 0.036 |
| 287 | 0.045 |
| 288 | 0.062 |
| 289 | 0.038 |
| 290 | 0.16 |

TABLE 42

Cell-Growth Inhibition Test: NCI-H1417 Cells

| Ex. No. | IC50 (nM) |
|---|---|
| 7 | 28.0 |
| 18 | 4.73 |
| 20 | 17.4 |
| 21 | 32.8 |
| 22 | 8.20 |
| 23 | 0.99 |
| 24 | 0.97 |
| 25 | 13.4 |
| 26 | 3.15 |
| 27 | 22.5 |
| 28 | 4.40 |
| 37 | 19.2 |
| 39 | 22.7 |
| 41 | 8.12 |
| 65 | 47.6 |
| 74 | 20.7 |
| 75 | 14.1 |
| 76 | 43.3 |
| 77 | 16.5 |
| 81 | 26.7 |

TABLE 42-continued

Cell-Growth Inhibition Test:
NCI-H1417 Cells

| Ex. No. | IC50 (nM) |
|---|---|
| 82 | 26.6 |
| 86 | 26.4 |
| 87 | 49.9 |
| 88 | 40.5 |
| 91 | 30.3 |
| 92 | 26.6 |
| 95 | 11.8 |
| 96 | 7.14 |
| 100 | 42.8 |
| 101 | 53.2 |
| 102 | 4.99 |
| 104 | 49.8 |
| 105 | 11.7 |
| 106 | 6.15 |
| 107 | 16.2 |
| 108 | 3.99 |
| 109 | 1.81 |
| 110 | 3.54 |
| 112 | 20.5 |
| 113 | 13.7 |
| 114 | 30.6 |
| 117 | 38.1 |
| 118 | 29.5 |
| 119 | 23.8 |
| 120 | 15.7 |
| 123 | 3.57 |
| 124 | 9.02 |
| 125 | 8.43 |
| 126 | 5.02 |
| 130 | 8.25 |
| 131 | 36.8 |
| 133 | 17.9 |
| 134 | 6.93 |
| 135 | 9.08 |
| 136 | 2.39 |
| 141 | 2.95 |
| 142 | 3.79 |
| 143 | 4.88 |
| 145 | 3.29 |
| 146 | 1.42 |
| 147 | 1.66 |
| 155 | 2.80 |
| 160 | 9.20 |
| 161 | 2.49 |
| 162 | 4.80 |
| 166 | 1.42 |
| 167 | 4.46 |
| 168 | 7.20 |
| 169 | 3.20 |
| 170 | 2.51 |
| 171 | 0.15 |
| 172 | 0.70 |
| 173 | 3.61 |
| 175 | 3.61 |
| 176 | 0.27 |
| 177 | 0.24 |
| 178 | 3.03 |
| 179 | 3.36 |
| 180 | 3.12 |
| 181 | 4.60 |
| 183 | 1.01 |
| 184 | 2.73 |
| 185 | 1.43 |
| 186 | 5.95 |
| 187 | 1.52 |
| 188 | 1.96 |
| 189 | 0.71 |
| 190 | 0.56 |
| 191 | 1.98 |
| 192 | 0.75 |
| 193 | 6.66 |
| 194 | 5.63 |
| 195 | 0.79 |
| 196 | 0.78 |
| 197 | 0.92 |

TABLE 42-continued

Cell-Growth Inhibition Test:
NCI-H1417 Cells

| Ex. No. | IC50 (nM) |
|---|---|
| 198 | 0.61 |
| 199 | 4.55 |
| 200 | 1.23 |
| 201 | 2.23 |
| 202 | 0.62 |
| 203 | 2.14 |
| 204 | 1.99 |
| 205 | 5.25 |
| 206 | 0.95 |
| 209 | 0.18 |
| 210 | 1.27 |
| 211 | 0.79 |
| 213 | 0.57 |
| 214 | 0.47 |
| 215 | 2.67 |
| 216 | 4.40 |
| 217 | 1.10 |
| 218 | 0.21 |
| 219 | 1.11 |
| 220 | 1.03 |
| 221 | 0.64 |
| 222 | 41.8 |
| 225 | 1.99 |
| 226 | 5.36 |
| 227 | 26.5 |

TABLE 43

Cell-Growth Inhibition Test:
NCI-H1417 Cells

| Ex. No. | IC50 (nM) |
|---|---|
| 228 | 0.30 |
| 229 | 1.30 |
| 230 | 16.4 |
| 231 | 7.11 |
| 232 | 1.55 |
| 233 | 36.5 |
| 234 | 14.8 |
| 235 | 6.99 |
| 236 | 11.0 |
| 237 | 6.63 |
| 238 | 10.8 |
| 239 | 3.8 |
| 240 | 2.55 |
| 241 | 2.89 |
| 246 | 0.81 |
| 247 | 1.4 |
| 248 | 6.06 |
| 249 | 16.1 |
| 250 | 1.2 |
| 251 | 2.7 |
| 252 | 0.5 |
| 253 | 1.47 |
| 254 | 0.15 |
| 255 | 1.52 |
| 256 | 0.94 |
| 257 | 0.12 |
| 258 | 0.65 |
| 259 | 0.46 |
| 260 | 0.13 |
| 261 | 1.30 |
| 262 | 0.70 |
| 263 | 0.38 |
| 264 | 0.30 |
| 265 | 4.40 |
| 266 | 1.85 |
| 267 | 0.86 |
| 268 | 0.30 |
| 269 | 0.27 |
| 270 | 0.18 |

TABLE 43-continued

Cell-Growth Inhibition Test:
NCI-H1417 Cells

| Ex. No. | IC50 (nM) |
| --- | --- |
| 271 | 1.42 |
| 272 | 0.81 |
| 273 | 0.19 |
| 274 | 1.25 |
| 275 | 0.59 |
| 276 | 0.50 |
| 277 | 0.53 |
| 278 | 2.68 |
| 279 | 0.90 |
| 280 | 9.11 |
| 281 | 8.50 |
| 283 | 2.10 |
| 284 | 13.0 |
| 285 | 0.090 |
| 286 | 0.083 |
| 287 | 0.10 |
| 288 | 0.22 |
| 289 | 0.094 |
| 290 | 1.06 |

TABLE 44

Cell-Growth Inhibition Test:
NCI-H146 Cells

| Ex. No. | IC50 (nM) |
| --- | --- |
| 18 | 8.13 |
| 22 | 15.0 |
| 23 | 9.33 |
| 24 | 4.04 |
| 37 | 10.1 |
| 41 | 9.76 |
| 123 | 1.39 |
| 146 | 3.15 |
| 161 | 1.09 |
| 166 | 2.37 |
| 171 | 0.19 |
| 172 | 0.52 |
| 175 | 0.16 |
| 176 | 0.27 |
| 177 | 0.11 |
| 178 | 1.22 |
| 179 | 1.05 |
| 180 | 0.94 |
| 181 | 2.93 |
| 182 | 13.2 |
| 183 | 0.25 |
| 184 | 2.51 |
| 185 | 1.32 |
| 186 | 3.21 |
| 187 | 1.06 |
| 188 | 1.58 |
| 189 | 0.33 |
| 190 | 1.17 |
| 191 | 3.84 |
| 192 | 0.83 |
| 193 | 5.33 |
| 194 | 11.3 |
| 195 | 1.26 |
| 196 | 0.82 |
| 197 | 1.82 |
| 198 | 1.10 |
| 199 | 5.45 |
| 200 | 2.31 |
| 201 | 3.25 |
| 202 | 0.73 |
| 203 | 4.73 |
| 205 | 15.1 |
| 206 | 1.09 |
| 209 | 0.22 |
| 210 | 4.26 |

TABLE 44-continued

Cell-Growth Inhibition Test:
NCI-H146 Cells

| Ex. No. | IC50 (nM) |
| --- | --- |
| 211 | 1.40 |
| 213 | 0.87 |
| 214 | 2.58 |
| 215 | 6.99 |
| 216 | 5.02 |
| 217 | 1.32 |
| 218 | 0.33 |
| 219 | 1.45 |
| 220 | 1.81 |
| 221 | 0.94 |
| 225 | 5.47 |
| 226 | 10.1 |
| 228 | 0.51 |
| 229 | 1.26 |
| 231 | 16.7 |
| 233 | 41.4 |
| 234 | 19.1 |
| 235 | 8.12 |
| 236 | 28.5 |
| 237 | 5.14 |
| 238 | 17.7 |
| 239 | 5.39 |
| 240 | 4.81 |
| 241 | 2.89 |
| 246 | 1.32 |
| 247 | 3.84 |
| 248 | 10.3 |
| 249 | 24.7 |
| 250 | 9.30 |
| 251 | 13.2 |
| 252 | 1.46 |
| 253 | 7.59 |
| 254 | 0.36 |
| 255 | 4.41 |
| 256 | 2.54 |
| 257 | 0.39 |
| 258 | 1.83 |
| 259 | 2.08 |
| 260 | 0.46 |
| 261 | 3.35 |
| 262 | 3.1 |
| 263 | 0.62 |
| 264 | 0.96 |
| 265 | 24.6 |
| 266 | 17.5 |
| 267 | 3.14 |
| 268 | 0.94 |
| 269 | 0.53 |
| 270 | 0.37 |
| 271 | 3.08 |
| 272 | 3.17 |
| 273 | 0.63 |
| 274 | 2.23 |
| 275 | 1.78 |
| 276 | 0.89 |
| 277 | 1.81 |
| 278 | 6.18 |
| 279 | 3.36 |
| 280 | 16.8 |
| 281 | 32.3 |
| 283 | 11.1 |
| 284 | 21.9 |
| 285 | 0.49 |
| 286 | 0.17 |
| 287 | 0.20 |
| 288 | 1.29 |
| 289 | 0.97 |
| 290 | 2.12 |

The results of this test revealed that the biphenyl compound represented by Formula (I) exhibits in vitro cell growth inhibitory effects, and that this compound not only inhibits the activity of recombinant human LSD1 protein but also inhibits cancer cell growth, suggesting that this compound is useful as an antitumor agent.

Test Example 3: Antitumor Effect Test Using NCI-H146 Cells (Human Small-Cell Lung Cancer Cell Lines)

NCI-H146 cells, $3.5 \times 10^6$ cells (100 μL), were subcutaneously implanted into BALB/cAJcl-nu/nu mice, and mice with a tumor volume within a range of 100 to 300 mm³ were divided into groups so that the groups had a uniform average tumor volume. To 5 mice in each group, a vehicle (0.5% hydroxymethylpropylcellulose containing 0.1 N HCL) or each Example compound was orally administered. The administration was performed once a day for 21 consecutive days (Example compound 41) or 28 consecutive days (Example compounds 37, 161, 166, 175, 176, and 177). The major axis and the minor axis of each tumor were measured twice a week with an electric caliper to calculate the tumor volume (TV). According to the tumor volumes thus obtained, a relative tumor volume (RTV) and a relative tumor volume change (T/C (%)) were calculated. The TV, RTV, and T/C (%) were calculated using the following equations.

Tumor volume TV (mm³)=(major axis, mm)×(minor axis, mm)×(minor axis, mm)/2

Relative tumor volume RTV=TV/(TV on the grouping day)

T/C (%)=(average RTV of administration group)/(average RTV of vehicle administration group)×100.

The table below shows the results.

TABLE 45

| Example compound No. | Dose (mg/kg) | T/C (%) |
| --- | --- | --- |
| 37 | 50 | 22 |
| 41 | 25 | 19 |
| 161 | 40 | 14 |
| 166 | 20 | 19 |
| 175 | 2 | 41 |
| 176 | 20 | 27 |
| 177 | 10 | 22 |

The final measurement day was the day following the final administration day. The biphenyl compound represented by Formula (I) showed an antitumor effect on the above models for efficacy evaluation, and the percentage of body weight reduction on the final measurement day was less than 20% of the body weight before administration (day 0).

The results revealed that the biphenyl compound represented by Formula (I) or a salt thereof exhibits excellent LSD1 inhibitory activity, shows a cancer cell growth inhibitory effect, has low toxicity, and is orally administrable. Therefore, the biphenyl compound represented by Formula (I) or a salt thereof is useful as an agent for preventing and/or treating cancer.

Test Example 4: Combination of Biphenyl Compounds and Other Antitumor Agents Using Human AML Cell Line or Human Myelodysplastic Syndrome (MDS) Cell Line (In Vitro)

The following tables show the source of reagents, the source of tumor cell lines, the media used, and the number of seeded cells.

TABLE 46

| Reagent | Source |
| --- | --- |
| Fetal bovine serum (FBS) | Biological Industries |
| RPMI-1640 medium | Wako Pure Chemical Industries, Ltd. |
| RPMI-1640 medium (ATCC-formulated medium: containing L-glutamine, HEPES, sodium pyruvate) | Wako Pure Chemical Industries, Ltd. |
| Human recombinant IL-3 | Peprotech |
| 2-Mercaptoethanol (2-ME) | SIGMA |
| Cytarabine | SIGMA-ALDRICH |
| Decitabine | SIGMA-ALDRICH |
| Azacitidine | SIGMA-ALDRICH |
| ATRA | KareBay Biochem |
| Daunorubicin | CALBIOCHEM |

TABLE 47

| Tumor cell line (origin) | Source of cell line | Medium | Number of seeded cells per well (cells) |
| --- | --- | --- | --- |
| Kasumi-1 (human AML cell line) | ATCC | RPMI-1640 medium containing 20% FBS (ATCC-formulated medium) | 1000 |
| MDS-L (human MDS cell line) | Dr. Kaoru Tohyama, Kawasaki Medical University | RPMI-1640 medium containing 10% FBS, 10 ng/mL IL-3, and 50 μM 2-ME | 100 |

Cells were seeded at 20 μL/well in a 384-well culture plate (Corning). The plate seeded with cells was cultured in an incubator set at 37° C. and 5% $CO_2$. On the day of seeding, drug solutions containing a combination of one of the biphenyl compounds and one of other compounds having an antitumor effect mixed at various concentrations were each added to the cells. Specifically, using an RPMI-1640 medium containing 20% FBS (ATCC-formulated medium) or an RPMI-1640 medium containing 10% FBS, 10 ng/mL IL-3, and 50 μM 2-ME, ten-step serial dilutions (including 0 nM) of the biphenyl compounds (Example compounds 37, 41, 166, 177, 214, 273, and 285) were prepared, and eight-step serial dilutions (including 0 nM) of other compounds having an antitumor effect were prepared. Solutions in which the same amount of serial dilution of each compound was dispensed were mixed at a ratio of 1:1, and a total of 80 mixed drug solutions were prepared with brute-force combinations. The table below shows the maximum concentration (expressed as the final concentration) and geometric ratio of each compound. Each of these mixed solutions was added to the plate at 5 μL/well (N=4), and further cultured at 37° C. under 5% $CO_2$ conditions for 10 days. Ten days later, CellTiter-Glo 2.0 Assay (Promega, Cat #: G9242) was added at 25 μL/well, and chemiluminescence was measured with a plate reader (EnSpire (registered trademark) Multimode Plate Reader, PerkinElmer Japan Co., Ltd.).

TABLE 48

| Other compound having antitumor effect | | | Biphenyl compound | | | |
|---|---|---|---|---|---|---|
| Name | Maximum concentration (nM) | Geometric ratio | Name | Maximum concentration (nM) | Geometric ratio | Tumor cell line |
| Cytarabine | 200 | 2 | Example compound 37 | 100 | 2 | Kasumi-1, MDS-L |
| | | | Example compound 166 | 10 | 2 | |
| | | | Example compound 177 | 1 | 2 | |
| | | | Example compound 273 | 1 | 2 | |
| Decitabine | 200 | 2 | Example compound 37 | 100 | 2 | Kasumi-1, MDS-L |
| | | | Example compound 166 | 10 | 2 | |
| | | | Example compound 177 | 1 | 2 | |
| | | | Example compound 273 | 1 | 2 | |
| | | | Example compound 41 | 100 | 2 | Kasumi-1 |
| | | | Example compound 214 | 1 | 2 | |
| | | | Example compound 285 | 0.1 | 2 | |
| Azacitidine | 10000 | 2 | Example compound 37 | 100 | 2 | Kasumi-1, MDS-L |
| | | | Example compound 166 | 10 | 2 | |
| | | | Example compound 177 | 1 | 2 | |
| | | | Example compound 273 | 1 | 2 | |
| Tretinoin (ATRA) | 10000 | 5 | Example compound 37 | 100 | 2 | Kasumi-1 |
| | | | Example compound 166 | 10 | 2 | |
| | | | Example compound 177 | 1 | 2 | |
| | | | Example compound 273 | 1 | 2 | |
| Daunorubicin | 10 | 2 | Example compound 37 | 100 | 2 | Kasumi-1 |
| | | | Example compound 166 | 10 | 2 | |
| | | | Example compound 177 | 1 | 2 | |
| | | | Example compound 273 | 1 | 2 | |

The effect potentiated by the combined use of drugs was evaluated according to the methods described in known documents (Trends Pharmacol. Sci., 4, 450-454, 1983; Pharmacol Rev., 58 (3), 621-81, 2006).

Specifically, normalized cell viability T/C (treatment/control ratio, %) was determined by comparing the cells treated with each single agent of the biphenyl compounds and other compounds having an antitumor effect with control cells. From the obtained T/C values, the half maximal inhibitory concentration (IC50) of each drug was determined by a curve fitting regression analysis tool using a regression analysis tool XLfit 5.3 (IDBS Ltd.).

The IC50 ratio of each single agent was calculated by the following equation.

IC50 ratio=[IC50 of biphenyl compound]:[IC50 of other compound having antitumor effect].

Regarding the concentration ratio combination of two compounds actually used in the experiment, the half maximal inhibitory concentration (ED50) when both compounds were used in combination was determined using their T/C. The combination index (CI) and fraction affected (Fa) in ED50 were determined. For the calculation of CI, median effect analysis software CalcuSyn 2.0 (CalcuSyn, Inc.) calculating the median-effect method was used.

The effect of combined use was determined as shown in the following table (Pharmacol Rev., 58 (3), pp. 621-81, 2006).

TABLE 49

| Range of CI (upper limit) | Explanation |
|---|---|
| 0.1 | Very strong synergism |
| 0.3 | Strong synergism |
| 0.7 | Synergism |
| 0.85 | Moderate synergism |
| 0.9 | Slight synergism |
| 1.0 | Almost additive |
| 1.2 | Slight antagonism |
| 1.45 | Moderate antagonism |

TABLE 49-continued

| Range of CI (upper limit) | Explanation |
|---|---|
| 3.3 | Antagonism |
| 10 | Strong antagonism |
| >10 | Very strong antagonism |

The following tables show the results.

TABLE 50

Other antitumor agent:cytarabine, cell line:Kasumi-1

| Example compound 37 (nM) | Other antitumor agent (nM) | Fa | CI | Combination ratio (Example compound 37:other antitumor agent) |
|---|---|---|---|---|
| 1.563 | 50 | 0.971 | 0.872 | 1:32 |
| 1.563 | 100 | 0.994 | 0.875 | 1:64 |
| 3.125 | 25 | 0.886 | 0.852 | 1:8 |
| 3.125 | 50 | 0.971 | 0.874 | 1:16 |
| 6.25 | 6.25 | 0.732 | 0.795 | 1:1 |
| 12.5 | 6.25 | 0.794 | 0.890 | 1:0.5 |
| 12.5 | 12.5 | 0.855 | 0.799 | 1:1 |
| 12.5 | 25 | 0.936 | 0.720 | 1:2 |
| 12.5 | 50 | 0.984 | 0.689 | 1:4 |
| 12.5 | 100 | 0.995 | 0.832 | 1:8 |
| 25 | 12.5 | 0.886 | 0.892 | 1:0.5 |
| 25 | 25 | 0.960 | 0.608 | 1:1 |
| 25 | 50 | 0.982 | 0.747 | 1:2 |
| 50 | 25 | 0.957 | 0.761 | 1:0.5 |
| 50 | 50 | 0.984 | 0.731 | 1:1 |
| 50 | 100 | 0.994 | 0.891 | 1:2 |
| 100 | 50 | 0.985 | 0.775 | 1:0.5 |
| 100 | 100 | 0.995 | 0.893 | 1:1 |

TABLE 51

Other antitumor agent:cytarabine, cell line:Kasumi-1

| Example compound 166 (nM) | Other antitumor agent (nM) | Fa | CI | Combination ratio (Example compound 166:other antitumor agent) |
|---|---|---|---|---|
| 0.1563 | 50 | 0.968 | 0.894 | 1:320 |
| 0.3125 | 50 | 0.968 | 0.896 | 1:160 |
| 0.3125 | 100 | 0.994 | 0.891 | 1:320 |
| 0.625 | 25 | 0.904 | 0.805 | 1:40 |
| 0.625 | 50 | 0.978 | 0.776 | 1:80 |
| 1.25 | 25 | 0.955 | 0.589 | 1:20 |
| 1.25 | 50 | 0.987 | 0.632 | 1:40 |
| 2.5 | 12.5 | 0.894 | 0.857 | 1:5 |
| 2.5 | 25 | 0.942 | 0.779 | 1:10 |
| 2.5 | 50 | 0.981 | 0.763 | 1:20 |
| 5 | 25 | 0.961 | 0.740 | 1:5 |
| 5 | 50 | 0.988 | 0.668 | 1:10 |
| 5 | 100 | 0.997 | 0.738 | 1:20 |
| 5 | 200 | 0.999 | 0.900 | 1:40 |
| 10 | 50 | 0.986 | 0.776 | 1:5 |
| 10 | 100 | 0.996 | 0.786 | 1:10 |

TABLE 52

Other antitumor agent:cytarabine, cell line:Kasumi-1

| Example compound 177 (nM) | Other antitumor agent (nM) | Fa | CI | Combination ratio (Example compound 177:other antitumor agent) |
|---|---|---|---|---|
| 0.00781 | 200 | 0.999 | 0.823 | 1:25600 |
| 0.01563 | 200 | 0.999 | 0.823 | 1:12800 |
| 0.03125 | 100 | 0.996 | 0.794 | 1:3200 |
| 0.0625 | 25 | 0.951 | 0.699 | 1:400 |
| 0.0625 | 50 | 0.983 | 0.800 | 1:800 |
| 0.0625 | 100 | 0.996 | 0.795 | 1:1600 |
| 0.0625 | 200 | 0.999 | 0.824 | 1:3200 |
| 0.125 | 3.125 | 0.788 | 0.693 | 1:25 |
| 0.125 | 6.25 | 0.787 | 0.877 | 1:50 |
| 0.125 | 25 | 0.952 | 0.730 | 1:200 |
| 0.125 | 50 | 0.984 | 0.787 | 1:400 |
| 0.125 | 100 | 0.995 | 0.887 | 1:800 |
| 0.25 | 12.5 | 0.894 | 0.888 | 1:50 |
| 0.25 | 25 | 0.954 | 0.778 | 1:100 |
| 0.25 | 50 | 0.986 | 0.748 | 1:200 |
| 0.25 | 100 | 0.996 | 0.801 | 1:400 |
| 0.25 | 200 | 0.999 | 0.825 | 1:800 |
| 0.5 | 12.5 | 0.927 | 0.900 | 1:25 |
| 0.5 | 25 | 0.969 | 0.703 | 1:50 |
| 0.5 | 50 | 0.992 | 0.605 | 1:100 |
| 0.5 | 100 | 0.996 | 0.819 | 1:200 |
| 0.5 | 200 | 0.999 | 0.826 | 1:400 |
| 1 | 25 | 0.974 | 0.769 | 1:25 |
| 1 | 50 | 0.990 | 0.705 | 1:50 |
| 1 | 100 | 0.997 | 0.726 | 1:100 |

TABLE 53

Other antitumor agent:cytarabine, cell line:Kasumi-1

| Example compound 273 (nM) | Other antitumor agent (nM) | Fa | CI | Combination ratio (Example compound 273:other antitumor agent) |
|---|---|---|---|---|
| 0.00391 | 100 | 0.993 | 0.794 | 1:25600 |
| 0.00781 | 200 | 0.999 | 0.685 | 1:25600 |
| 0.01563 | 50 | 0.968 | 0.782 | 1:3200 |
| 0.01563 | 100 | 0.993 | 0.810 | 1:6400 |
| 0.01563 | 200 | 0.999 | 0.685 | 1:12800 |
| 0.03125 | 25 | 0.859 | 0.827 | 1:800 |
| 0.03125 | 50 | 0.968 | 0.785 | 1:1600 |
| 0.03125 | 100 | 0.991 | 0.897 | 1:3200 |
| 0.0625 | 25 | 0.878 | 0.817 | 1:400 |
| 0.0625 | 50 | 0.960 | 0.887 | 1:800 |
| 0.0625 | 100 | 0.991 | 0.893 | 1:1600 |
| 0.125 | 25 | 0.925 | 0.692 | 1:200 |
| 0.125 | 50 | 0.979 | 0.679 | 1:400 |
| 0.125 | 100 | 0.993 | 0.808 | 1:800 |
| 0.25 | 100 | 0.993 | 0.822 | 1:400 |
| 0.5 | 25 | 0.954 | 0.774 | 1:50 |
| 0.5 | 50 | 0.984 | 0.684 | 1:100 |
| 0.5 | 100 | 0.995 | 0.761 | 1:200 |
| 1 | 50 | 0.984 | 0.813 | 1:50 |
| 1 | 100 | 0.995 | 0.808 | 1:100 |
| 1 | 200 | 0.999 | 0.819 | 1:200 |

TABLE 54

Other antitumor agent:cytarabine, cell line:MDS-L

| Example compound 37 (nM) | Other antitumor agent (nM) | Fa | CI | Combination ratio (Example compound 37:other antitumor agent) |
|---|---|---|---|---|
| 0.391 | 3.125 | 0.201 | 0.816 | 1:8 |
| 0.391 | 6.25 | 0.467 | 0.696 | 1:16 |
| 0.781 | 3.125 | 0.264 | 0.730 | 1:4 |
| 0.781 | 6.25 | 0.455 | 0.734 | 1:8 |
| 1.563 | 3.125 | 0.357 | 0.611 | 1:2 |
| 1.563 | 6.25 | 0.416 | 0.863 | 1:4 |
| 3.125 | 3.125 | 0.409 | 0.631 | 1:1 |
| 12.5 | 200 | 0.999 | 0.834 | 1:16 |
| 25 | 200 | 0.999 | 0.834 | 1:8 |
| 50 | 200 | 0.999 | 0.834 | 1:4 |
| 100 | 200 | 0.999 | 0.872 | 1:2 |

TABLE 55

Other antitumor agent:cytarabine, cell line:MDS-L

| Example compound 166 (nM) | Other antitumor agent (nM) | Fa | CI | Combination ratio (Example compound 166:other antitumor agent) |
|---|---|---|---|---|
| 0.0391 | 3.125 | 0.220 | 0.721 | 1:80 |
| 0.0391 | 6.25 | 0.452 | 0.712 | 1:160 |
| 0.0781 | 3.125 | 0.252 | 0.746 | 1:40 |
| 0.0781 | 6.25 | 0.443 | 0.748 | 1:80 |
| 0.1563 | 3.125 | 0.328 | 0.668 | 1:20 |
| 0.3125 | 3.125 | 0.429 | 0.569 | 1:10 |
| 5 | 200 | 0.999 | 0.858 | 1:40 |
| 10 | 200 | 0.999 | 0.896 | 1:20 |

TABLE 56

Other antitumor agent:cytarabine, cell line:MDS-L

| Example compound 177 (nM) | Other antitumor agent (nM) | Fa | CI | Combination ratio (Example compound 177:other antitumor agent) |
|---|---|---|---|---|
| 0.00781 | 3.125 | 0.291 | 0.599 | 1:400 |
| 0.00781 | 6.25 | 0.481 | 0.669 | 1:800 |
| 0.01563 | 3.125 | 0.377 | 0.513 | 1:200 |

TABLE 56-continued

Other antitumor agent:cytarabine, cell line:MDS-L

| Example compound 177 (nM) | Other antitumor agent (nM) | Fa | CI | Combination ratio (Example compound 177:other antitumor agent) |
|---|---|---|---|---|
| 0.01563 | 6.25 | 0.448 | 0.755 | 1:400 |
| 0.03125 | 3.125 | 0.447 | 0.480 | 1:100 |
| 0.03125 | 6.25 | 0.430 | 0.867 | 1:200 |
| 0.0625 | 3.125 | 0.429 | 0.668 | 1:50 |
| 0.0625 | 6.25 | 0.517 | 0.763 | 1:100 |
| 0.125 | 200 | 0.998 | 0.864 | 1:1600 |
| 0.5 | 200 | 0.998 | 0.864 | 1:400 |
| 1 | 6.25 | 0.747 | 0.784 | 1:6.25 |

TABLE 57

Other antitumor agent:cytarabine, cell line:MDS-L

| Example compound 273 (nM) | Other antitumor agent (nM) | Fa | CI | Combination ratio (Example compound 273:other antitumor agent) |
|---|---|---|---|---|
| 0.00391 | 3.125 | 0.245 | 0.772 | 1:800 |
| 0.00391 | 6.25 | 0.477 | 0.718 | 1:1600 |
| 0.00781 | 3.125 | 0.328 | 0.609 | 1:400 |
| 0.00781 | 6.25 | 0.474 | 0.741 | 1:800 |
| 0.01563 | 3.125 | 0.392 | 0.548 | 1:200 |
| 0.01563 | 6.25 | 0.454 | 0.823 | 1:400 |
| 0.03125 | 3.125 | 0.474 | 0.493 | 1:100 |
| 0.0625 | 3.125 | 0.510 | 0.556 | 1:50 |
| 0.0625 | 6.25 | 0.588 | 0.680 | 1:100 |
| 0.125 | 200 | 0.997 | 0.381 | 1:1600 |
| 0.25 | 200 | 0.998 | 0.288 | 1:800 |
| 0.5 | 200 | 0.998 | 0.289 | 1:400 |
| 1 | 200 | 0.999 | 0.191 | 1:200 |

TABLE 58

Other antitumor agent:decitabine, cell line:Kasumi-1

| Example compound 37 (nM) | Other antitumor agent (nM) | Fa | CI | Combination ratio (Example compound 37:other antitumor agent) |
|---|---|---|---|---|
| 0.391 | 6.25 | 0.326 | 0.674 | 1:16 |
| 0.391 | 12.5 | 0.404 | 0.897 | 1:32 |
| 0.391 | 25 | 0.758 | 0.657 | 1:64 |
| 0.391 | 50 | 0.872 | 0.827 | 1:128 |
| 0.781 | 25 | 0.788 | 0.615 | 1:32 |
| 0.781 | 50 | 0.879 | 0.806 | 1:64 |
| 0.781 | 100 | 0.958 | 0.833 | 1:128 |
| 1.563 | 3.125 | 0.410 | 0.776 | 1:2 |
| 1.563 | 6.25 | 0.433 | 0.879 | 1:4 |
| 1.563 | 12.5 | 0.544 | 0.861 | 1:8 |
| 1.563 | 25 | 0.788 | 0.660 | 1:16 |
| 1.563 | 50 | 0.943 | 0.512 | 1:32 |
| 1.563 | 100 | 0.973 | 0.643 | 1:64 |
| 1.563 | 200 | 0.991 | 0.687 | 1:128 |
| 3.125 | 3.125 | 0.580 | 0.665 | 1:1 |
| 3.125 | 6.25 | 0.592 | 0.754 | 1:2 |
| 3.125 | 12.5 | 0.660 | 0.778 | 1:4 |
| 3.125 | 25 | 0.806 | 0.691 | 1:8 |
| 3.125 | 50 | 0.943 | 0.527 | 1:16 |
| 3.125 | 100 | 0.982 | 0.514 | 1:32 |
| 3.125 | 200 | 0.992 | 0.640 | 1:64 |
| 6.25 | 3.125 | 0.697 | 0.696 | 1:0.5 |
| 6.25 | 6.25 | 0.715 | 0.724 | 1:1 |
| 6.25 | 12.5 | 0.779 | 0.664 | 1:2 |
| 6.25 | 25 | 0.905 | 0.456 | 1:4 |
| 6.25 | 50 | 0.958 | 0.458 | 1:8 |
| 6.25 | 100 | 0.982 | 0.524 | 1:16 |

TABLE 58-continued

Other antitumor agent:decitabine, cell line:Kasumi-1

| Example compound 37 (nM) | Other antitumor agent (nM) | Fa | CI | Combination ratio (Example compound 37:other antitumor agent) |
|---|---|---|---|---|
| 6.25 | 200 | 0.995 | 0.518 | 1:32 |
| 12.5 | 3.125 | 0.819 | 0.620 | 1:0.25 |
| 12.5 | 6.25 | 0.850 | 0.543 | 1:0.5 |
| 12.5 | 12.5 | 0.868 | 0.569 | 1:1 |
| 12.5 | 25 | 0.951 | 0.331 | 1:2 |
| 12.5 | 50 | 0.978 | 0.326 | 1:4 |
| 12.5 | 100 | 0.987 | 0.444 | 1:8 |
| 12.5 | 200 | 0.996 | 0.439 | 1:16 |
| 25 | 3.125 | 0.872 | 0.747 | 1:0.125 |
| 25 | 6.25 | 0.886 | 0.694 | 1:0.25 |
| 25 | 12.5 | 0.894 | 0.726 | 1:0.5 |
| 25 | 25 | 0.955 | 0.409 | 1:1 |
| 25 | 50 | 0.979 | 0.355 | 1:2 |
| 25 | 100 | 0.991 | 0.371 | 1:4 |
| 25 | 200 | 0.995 | 0.506 | 1:8 |
| 50 | 6.25 | 0.923 | 0.804 | 1:0.125 |
| 50 | 12.5 | 0.933 | 0.751 | 1:0.25 |
| 50 | 25 | 0.970 | 0.405 | 1:0.5 |
| 50 | 50 | 0.988 | 0.287 | 1:1 |
| 50 | 100 | 0.995 | 0.279 | 1:2 |
| 50 | 200 | 0.997 | 0.385 | 1:4 |
| 100 | 25 | 0.967 | 0.705 | 1:0.25 |
| 100 | 50 | 0.985 | 0.438 | 1:0.5 |
| 100 | 100 | 0.992 | 0.418 | 1:1 |
| 100 | 200 | 0.997 | 0.433 | 1:2 |

TABLE 59

Other antitumor agent:decitabine, cell line:Kasumi-1

| Example compound 166 (nM) | Other antitumor agent (nM) | Fa | CI | Combination ratio (Example compound 166:other antitumor agent) |
|---|---|---|---|---|
| 0.0391 | 3.125 | 0.369 | 0.775 | 1:80 |
| 0.0391 | 6.25 | 0.511 | 0.712 | 1:160 |
| 0.0781 | 100 | 0.979 | 0.650 | 1:1280 |
| 0.0781 | 200 | 0.992 | 0.664 | 1:2560 |
| 0.156 | 50 | 0.953 | 0.585 | 1:320 |
| 0.156 | 100 | 0.985 | 0.522 | 1:640 |
| 0.156 | 200 | 0.993 | 0.606 | 1:1280 |
| 0.3125 | 25 | 0.901 | 0.562 | 1:80 |
| 0.3125 | 50 | 0.953 | 0.595 | 1:160 |
| 0.3125 | 100 | 0.991 | 0.356 | 1:320 |
| 0.3125 | 200 | 0.994 | 0.558 | 1:640 |
| 0.625 | 3.125 | 0.758 | 0.699 | 1:5 |
| 0.625 | 6.25 | 0.813 | 0.569 | 1:10 |
| 0.625 | 12.5 | 0.843 | 0.625 | 1:20 |
| 0.625 | 25 | 0.906 | 0.597 | 1:40 |
| 0.625 | 50 | 0.970 | 0.439 | 1:80 |
| 0.625 | 100 | 0.991 | 0.364 | 1:160 |
| 0.625 | 200 | 0.996 | 0.434 | 1:320 |
| 1.25 | 3.125 | 0.829 | 0.717 | 1:2.5 |
| 1.25 | 6.25 | 0.863 | 0.592 | 1:5 |
| 1.25 | 12.5 | 0.882 | 0.624 | 1:10 |
| 1.25 | 25 | 0.942 | 0.453 | 1:20 |
| 1.25 | 50 | 0.977 | 0.376 | 1:40 |
| 1.25 | 100 | 0.993 | 0.308 | 1:80 |
| 1.25 | 200 | 0.996 | 0.414 | 1:160 |
| 2.5 | 3.125 | 0.876 | 0.810 | 1:1.25 |
| 2.5 | 6.25 | 0.909 | 0.571 | 1:2.5 |
| 2.5 | 12.5 | 0.919 | 0.595 | 1:5 |
| 2.5 | 25 | 0.959 | 0.402 | 1:10 |
| 2.5 | 50 | 0.984 | 0.306 | 1:20 |
| 2.5 | 100 | 0.994 | 0.281 | 1:40 |
| 2.5 | 200 | 0.997 | 0.341 | 1:80 |
| 5 | 3.125 | 0.924 | 0.743 | 1:0.625 |
| 5 | 6.25 | 0.935 | 0.639 | 1:1.25 |
| 5 | 12.5 | 0.947 | 0.562 | 1:2.5 |

TABLE 59-continued

Other antitumor agent:decitabine, cell line:Kasumi-1

| Example compound 166 (nM) | Other antitumor agent (nM) | Fa | CI | Combination ratio (Example compound 166:other antitumor agent) |
|---|---|---|---|---|
| 5 | 25 | 0.976 | 0.307 | 1:5 |
| 5 | 50 | 0.987 | 0.285 | 1:10 |
| 5 | 100 | 0.993 | 0.325 | 1:20 |
| 5 | 200 | 0.998 | 0.260 | 1:40 |
| 10 | 12.5 | 0.958 | 0.710 | 1:1.25 |
| 10 | 25 | 0.975 | 0.457 | 1:2.5 |
| 10 | 50 | 0.988 | 0.317 | 1:5 |
| 10 | 100 | 0.996 | 0.235 | 1:10 |
| 10 | 200 | 0.998 | 0.309 | 1:20 |

TABLE 60

Other antitumor agent:decitabine, cell line:Kasumi-1

| Example compound 177 (nM) | Other antitumor agent (nM) | Fa | CI | Combination ratio (Example compound 177:other antitumor agent) |
|---|---|---|---|---|
| 0.00781 | 25 | 0.744 | 0.878 | 1:3200 |
| 0.00781 | 50 | 0.893 | 0.893 | 1:6400 |
| 0.01563 | 50 | 0.941 | 0.605 | 1:3200 |
| 0.01563 | 100 | 0.976 | 0.672 | 1:6400 |
| 0.01563 | 200 | 0.992 | 0.666 | 1:12800 |
| 0.03125 | 25 | 0.776 | 0.877 | 1:800 |
| 0.03125 | 50 | 0.941 | 0.618 | 1:1600 |
| 0.03125 | 100 | 0.983 | 0.538 | 1:3200 |
| 0.03125 | 200 | 0.996 | 0.447 | 1:6400 |
| 0.0625 | 25 | 0.844 | 0.734 | 1:400 |
| 0.0625 | 50 | 0.957 | 0.522 | 1:800 |
| 0.0625 | 100 | 0.983 | 0.549 | 1:1600 |
| 0.0625 | 200 | 0.995 | 0.501 | 1:3200 |
| 0.125 | 3.125 | 0.719 | 0.758 | 1:25 |
| 0.125 | 6.25 | 0.767 | 0.705 | 1:50 |
| 0.125 | 12.5 | 0.843 | 0.612 | 1:100 |
| 0.125 | 25 | 0.945 | 0.393 | 1:200 |
| 0.125 | 50 | 0.967 | 0.471 | 1:400 |
| 0.125 | 100 | 0.987 | 0.477 | 1:800 |
| 0.125 | 200 | 0.997 | 0.368 | 1:1600 |
| 0.25 | 3.125 | 0.844 | 0.716 | 1:12.5 |
| 0.25 | 6.25 | 0.882 | 0.595 | 1:25 |
| 0.25 | 12.5 | 0.899 | 0.617 | 1:50 |
| 0.25 | 25 | 0.956 | 0.418 | 1:100 |
| 0.25 | 50 | 0.981 | 0.359 | 1:200 |
| 0.25 | 100 | 0.99 | 0.425 | 1:400 |
| 0.25 | 200 | 0.996 | 0.450 | 1:800 |
| 0.5 | 12.5 | 0.932 | 0.706 | 1:25 |
| 0.5 | 25 | 0.972 | 0.412 | 1:50 |
| 0.5 | 50 | 0.989 | 0.301 | 1:100 |
| 0.5 | 100 | 0.992 | 0.409 | 1:200 |
| 0.5 | 200 | 0.996 | 0.468 | 1:400 |
| 1 | 25 | 0.974 | 0.603 | 1:25 |
| 1 | 50 | 0.988 | 0.420 | 1:50 |
| 1 | 100 | 0.992 | 0.477 | 1:100 |
| 1 | 200 | 0.995 | 0.571 | 1:200 |

TABLE 61

Other antitumor agent:decitabine, cell line:Kasumi-1

| Example compound 273 (nM) | Other antitumor agent (nM) | Fa | CI | Combination ratio (Example compound 273:other antitumor agent) |
|---|---|---|---|---|
| 0.00391 | 3.125 | 0.223 | 0.781 | 1:800 |
| 0.00781 | 100 | 0.971 | 0.813 | 1:12800 |
| 0.00781 | 200 | 0.989 | 0.839 | 1:25600 |
| 0.01563 | 50 | 0.932 | 0.752 | 1:3200 |
| 0.01563 | 100 | 0.972 | 0.799 | 1:6400 |
| 0.01563 | 200 | 0.993 | 0.620 | 1:12800 |
| 0.03125 | 50 | 0.932 | 0.768 | 1:1600 |
| 0.03125 | 100 | 0.984 | 0.550 | 1:3200 |
| 0.03125 | 200 | 0.996 | 0.419 | 1:6400 |
| 0.0625 | 25 | 0.859 | 0.775 | 1:400 |
| 0.0625 | 50 | 0.952 | 0.620 | 1:800 |
| 0.0625 | 100 | 0.984 | 0.555 | 1:1600 |
| 0.0625 | 200 | 0.996 | 0.436 | 1:3200 |
| 0.125 | 3.125 | 0.717 | 0.817 | 1:25 |
| 0.125 | 6.25 | 0.781 | 0.710 | 1:50 |
| 0.125 | 12.5 | 0.817 | 0.780 | 1:100 |
| 0.125 | 25 | 0.941 | 0.443 | 1:200 |
| 0.125 | 50 | 0.961 | 0.571 | 1:400 |
| 0.125 | 100 | 0.989 | 0.440 | 1:800 |
| 0.125 | 200 | 0.996 | 0.432 | 1:1600 |
| 0.25 | 3.125 | 0.836 | 0.774 | 1:12.5 |
| 0.25 | 6.25 | 0.849 | 0.790 | 1:25 |
| 0.25 | 12.5 | 0.899 | 0.644 | 1:50 |
| 0.25 | 25 | 0.942 | 0.551 | 1:100 |
| 0.25 | 50 | 0.978 | 0.419 | 1:200 |
| 0.25 | 100 | 0.992 | 0.369 | 1:400 |
| 0.25 | 200 | 0.996 | 0.440 | 1:800 |
| 0.5 | 6.25 | 0.914 | 0.781 | 1:12.5 |
| 0.5 | 12.5 | 0.941 | 0.619 | 1:25 |
| 0.5 | 25 | 0.974 | 0.386 | 1:50 |
| 0.5 | 50 | 0.985 | 0.375 | 1:100 |
| 0.5 | 100 | 0.994 | 0.333 | 1:200 |
| 0.5 | 200 | 0.997 | 0.374 | 1:400 |
| 1 | 25 | 0.976 | 0.543 | 1:25 |
| 1 | 50 | 0.987 | 0.434 | 1:50 |
| 1 | 100 | 0.995 | 0.339 | 1:100 |
| 1 | 200 | 0.997 | 0.407 | 1:200 |

TABLE 62

Other antitumor agent:decitabine, cell line:Kasumi-1

| Example compound 41 (nM) | Other antitumor agent (nM) | Fa | CI | Combination ratio (Example compound 41:other antitumor agent) |
|---|---|---|---|---|
| 0.391 | 50 | 0.757 | 0.717 | 1:128 |
| 0.781 | 25 | 0.617 | 0.709 | 1:32 |
| 0.781 | 50 | 0.764 | 0.713 | 1:64 |
| 0.781 | 200 | 0.955 | 0.540 | 1:256 |
| 1.563 | 25 | 0.617 | 0.808 | 1:16 |
| 1.563 | 50 | 0.866 | 0.409 | 1:32 |
| 1.563 | 200 | 0.972 | 0.356 | 1:128 |
| 3.125 | 3.125 | 0.547 | 0.654 | 1:1 |
| 3.125 | 6.25 | 0.636 | 0.501 | 1:2 |
| 3.125 | 12.5 | 0.587 | 0.799 | 1:4 |
| 3.125 | 25 | 0.744 | 0.564 | 1:8 |
| 3.125 | 50 | 0.866 | 0.447 | 1:16 |
| 3.125 | 100 | 0.944 | 0.350 | 1:32 |
| 3.125 | 200 | 0.978 | 0.291 | 1:64 |
| 6.25 | 3.125 | 0.692 | 0.590 | 1:0.5 |
| 6.25 | 6.25 | 0.783 | 0.380 | 1:1 |
| 6.25 | 12.5 | 0.797 | 0.417 | 1:2 |
| 6.25 | 25 | 0.865 | 0.340 | 1:4 |
| 6.25 | 50 | 0.929 | 0.268 | 1:8 |
| 6.25 | 100 | 0.944 | 0.375 | 1:16 |
| 6.25 | 200 | 0.989 | 0.158 | 1:32 |
| 12.5 | 3.125 | 0.826 | 0.467 | 1:0.25 |
| 12.5 | 6.25 | 0.853 | 0.395 | 1:0.5 |
| 12.5 | 12.5 | 0.885 | 0.325 | 1:1 |
| 12.5 | 25 | 0.914 | 0.289 | 1:2 |
| 12.5 | 50 | 0.957 | 0.198 | 1:4 |

TABLE 62-continued

Other antitumor agent:decitabine, cell line:Kasumi-1

| Example compound 41 (nM) | Other antitumor agent (nM) | Fa | CI | Combination ratio (Example compound 41:other antitumor agent) |
|---|---|---|---|---|
| 12.5 | 100 | 0.945 | 0.416 | 1:8 |
| 12.5 | 200 | 0.989 | 0.168 | 1:16 |
| 25 | 6.25 | 0.888 | 0.514 | 1:0.25 |
| 25 | 12.5 | 0.913 | 0.402 | 1:0.5 |
| 25 | 25 | 0.920 | 0.421 | 1:1 |
| 25 | 50 | 0.967 | 0.201 | 1:2 |
| 25 | 100 | 0.967 | 0.303 | 1:4 |
| 25 | 200 | 0.995 | 0.089 | 1:8 |
| 50 | 12.5 | 0.919 | 0.678 | 1:0.25 |
| 50 | 25 | 0.958 | 0.333 | 1:0.5 |
| 50 | 50 | 0.969 | 0.278 | 1:1 |
| 50 | 100 | 0.970 | 0.368 | 1:2 |
| 50 | 200 | 0.995 | 0.099 | 1:4 |
| 100 | 25 | 0.957 | 0.621 | 1:0.25 |
| 100 | 50 | 0.971 | 0.433 | 1:0.5 |
| 100 | 100 | 0.972 | 0.509 | 1:1 |
| 100 | 200 | 0.992 | 0.202 | 1:2 |

TABLE 63

Other antitumor agent:decitabine, cell line:Kasumi-1

| Example compound 214 (nM) | Other antitumor agent (nM) | Fa | CI | Combination ratio (Example compound 214:other antitumor agent) |
|---|---|---|---|---|
| 0.00391 | 100 | 0.867 | 0.693 | 1:25600 |
| 0.00781 | 100 | 0.865 | 0.704 | 1:12800 |
| 0.01563 | 100 | 0.873 | 0.671 | 1:6400 |
| 0.01563 | 200 | 0.932 | 0.744 | 1:12800 |
| 0.03125 | 100 | 0.904 | 0.521 | 1:3200 |
| 0.0625 | 100 | 0.904 | 0.532 | 1:1600 |
| 0.0625 | 200 | 0.957 | 0.503 | 1:3200 |
| 0.125 | 50 | 0.722 | 0.890 | 1:400 |
| 0.125 | 100 | 0.910 | 0.526 | 1:800 |
| 0.125 | 200 | 0.96 | 0.486 | 1:1600 |
| 0.25 | 100 | 0.884 | 0.727 | 1:400 |
| 0.5 | 3.125 | 0.745 | 0.561 | 1:6.25 |
| 0.5 | 6.25 | 0.692 | 0.743 | 1:12.5 |
| 0.5 | 12.5 | 0.791 | 0.560 | 1:25 |
| 0.5 | 50 | 0.884 | 0.549 | 1:100 |
| 0.5 | 100 | 0.966 | 0.284 | 1:200 |
| 0.5 | 200 | 0.985 | 0.243 | 1:400 |
| 1 | 12.5 | 0.904 | 0.477 | 1:12.5 |
| 1 | 25 | 0.856 | 0.780 | 1:25 |
| 1 | 50 | 0.930 | 0.506 | 1:50 |
| 1 | 100 | 0.964 | 0.396 | 1:100 |
| 1 | 200 | 0.986 | 0.265 | 1:200 |

TABLE 64

Other antitumor agent:decitabine, cell line:Kasumi-1

| Example compound 285 (nM) | Other antitumor agent (nM) | Fa | CI | Combination ratio (Example compound 285:other antitumor agent) |
|---|---|---|---|---|
| 0.000781 | 50 | 0.569 | 0.814 | 1:64000 |
| 0.00156 | 25 | 0.222 | 0.894 | 1:16000 |
| 0.00156 | 50 | 0.614 | 0.747 | 1:32000 |
| 0.00313 | 50 | 0.617 | 0.754 | 1:16000 |
| 0.00625 | 50 | 0.617 | 0.774 | 1:8000 |
| 0.00625 | 100 | 0.848 | 0.810 | 1:16000 |
| 0.0125 | 25 | 0.418 | 0.688 | 1:2000 |
| 0.0125 | 50 | 0.722 | 0.638 | 1:4000 |
| 0.0125 | 100 | 0.848 | 0.829 | 1:8000 |
| 0.025 | 25 | 0.516 | 0.667 | 1:1000 |
| 0.025 | 50 | 0.795 | 0.566 | 1:2000 |
| 0.025 | 100 | 0.911 | 0.635 | 1:4000 |
| 0.025 | 200 | 0.962 | 0.777 | 1:8000 |
| 0.05 | 12.5 | 0.803 | 0.293 | 1:250 |
| 0.05 | 25 | 0.709 | 0.548 | 1:500 |
| 0.05 | 50 | 0.938 | 0.315 | 1:1000 |
| 0.05 | 100 | 0.920 | 0.643 | 1:2000 |
| 0.05 | 200 | 0.990 | 0.404 | 1:4000 |
| 0.1 | 3.125 | 0.676 | 0.596 | 1:31.3 |
| 0.1 | 6.25 | 0.792 | 0.432 | 1:62.5 |
| 0.1 | 12.5 | 0.724 | 0.621 | 1:125 |
| 0.1 | 25 | 0.884 | 0.404 | 1:250 |
| 0.1 | 50 | 0.967 | 0.269 | 1:500 |
| 0.1 | 100 | 0.977 | 0.362 | 1:1000 |
| 0.1 | 200 | 0.977 | 0.656 | 1:2000 |
| 0.2 | 6.25 | 0.881 | 0.520 | 1:31.3 |
| 0.2 | 12.5 | 0.870 | 0.601 | 1:62.5 |
| 0.2 | 25 | 0.919 | 0.498 | 1:125 |
| 0.2 | 50 | 0.972 | 0.331 | 1:250 |
| 0.2 | 100 | 0.985 | 0.342 | 1:500 |
| 0.2 | 200 | 0.993 | 0.381 | 1:1000 |

TABLE 65

Other antitumor agent:decitabine, cell line:MDS-L

| Example compound 37 (nM) | Other antitumor agent (nM) | Fa | CI | Combination ratio (Example compound 37:other antitumor agent) |
|---|---|---|---|---|
| 0.391 | 6.25 | 0.434 | 0.708 | 1:16 |
| 0.781 | 6.25 | 0.446 | 0.711 | 1:8 |
| 1.563 | 100 | 0.984 | 0.852 | 1:64 |
| 3.125 | 100 | 0.983 | 0.879 | 1:32 |
| 6.25 | 6.25 | 0.498 | 0.867 | 1:1 |
| 6.25 | 12.5 | 0.685 | 0.817 | 1:2 |
| 12.5 | 6.25 | 0.604 | 0.733 | 1:0.5 |
| 12.5 | 12.5 | 0.754 | 0.695 | 1:1 |
| 12.5 | 25 | 0.847 | 0.891 | 1:2 |
| 12.5 | 50 | 0.951 | 0.829 | 1:4 |
| 12.5 | 100 | 0.984 | 0.842 | 1:8 |
| 25 | 6.25 | 0.729 | 0.546 | 1:0.25 |
| 25 | 12.5 | 0.823 | 0.564 | 1:0.5 |
| 25 | 25 | 0.877 | 0.784 | 1:1 |
| 25 | 50 | 0.971 | 0.608 | 1:2 |
| 25 | 100 | 0.990 | 0.638 | 1:4 |
| 50 | 6.25 | 0.779 | 0.560 | 1:0.125 |
| 50 | 12.5 | 0.835 | 0.607 | 1:0.25 |
| 50 | 25 | 0.932 | 0.536 | 1:0.5 |
| 50 | 50 | 0.977 | 0.531 | 1:1 |
| 50 | 100 | 0.990 | 0.657 | 1:2 |
| 50 | 200 | 0.995 | 0.849 | 1:4 |
| 100 | 6.25 | 0.827 | 0.574 | 1:0.0625 |
| 100 | 12.5 | 0.904 | 0.427 | 1:0.125 |
| 100 | 25 | 0.949 | 0.459 | 1:0.25 |
| 100 | 50 | 0.979 | 0.503 | 1:0.5 |
| 100 | 100 | 0.992 | 0.577 | 1:1 |
| 100 | 200 | 0.995 | 0.849 | 1:2 |

TABLE 66

Other antitumor agent:decitabine, cell line:MDS-L

| Example compound 166 (nM) | Other antitumor agent (nM) | Fa | CI | Combination ratio (Example compound 166:other antitumor agent) |
|---|---|---|---|---|
| 0.0391 | 100 | 0.986 | 0.706 | 1:2560 |
| 0.0781 | 6.25 | 0.467 | 0.742 | 1:80 |
| 0.1563 | 6.25 | 0.448 | 0.835 | 1:40 |
| 0.3125 | 200 | 0.994 | 0.866 | 1:640 |
| 0.625 | 6.25 | 0.566 | 0.720 | 1:10 |
| 0.625 | 12.5 | 0.674 | 0.891 | 1:20 |
| 1.25 | 6.25 | 0.654 | 0.615 | 1:5 |
| 1.25 | 12.5 | 0.765 | 0.681 | 1:10 |
| 1.25 | 25 | 0.856 | 0.860 | 1:20 |
| 1.25 | 50 | 0.951 | 0.797 | 1:40 |
| 1.25 | 100 | 0.985 | 0.737 | 1:80 |
| 2.5 | 6.25 | 0.762 | 0.454 | 1:2.5 |
| 2.5 | 12.5 | 0.825 | 0.557 | 1:5 |
| 2.5 | 25 | 0.925 | 0.541 | 1:10 |
| 2.5 | 50 | 0.956 | 0.750 | 1:20 |
| 2.5 | 100 | 0.987 | 0.673 | 1:40 |
| 5 | 3.125 | 0.669 | 0.862 | 1:0.625 |
| 5 | 6.25 | 0.792 | 0.491 | 1:1.25 |
| 5 | 12.5 | 0.848 | 0.544 | 1:2.5 |
| 5 | 25 | 0.927 | 0.544 | 1:5 |
| 5 | 50 | 0.971 | 0.570 | 1:10 |
| 5 | 100 | 0.990 | 0.584 | 1:20 |
| 5 | 200 | 0.995 | 0.734 | 1:40 |
| 10 | 6.25 | 0.820 | 0.559 | 1:0.625 |
| 10 | 12.5 | 0.886 | 0.475 | 1:1.25 |
| 10 | 25 | 0.935 | 0.520 | 1:2.5 |
| 10 | 50 | 0.976 | 0.505 | 1:5 |
| 10 | 100 | 0.990 | 0.560 | 1:10 |
| 10 | 200 | 0.994 | 0.788 | 1:20 |

TABLE 67

Other antitumor agent:decitabine, cell line:MDS-L

| Example compound 177 (nM) | Other antitumor agent (nM) | Fa | CI | Combination ratio (Example compound 177:other antitumor agent) |
|---|---|---|---|---|
| 0.00391 | 50 | 0.953 | 0.828 | 1:12800 |
| 0.00781 | 3.125 | 0.374 | 0.539 | 1:400 |
| 0.00781 | 6.25 | 0.409 | 0.870 | 1:800 |
| 0.01563 | 3.125 | 0.417 | 0.537 | 1:200 |
| 0.03125 | 3.125 | 0.499 | 0.475 | 1:100 |
| 0.0625 | 3.125 | 0.458 | 0.784 | 1:50 |
| 0.125 | 12.5 | 0.705 | 0.859 | 1:100 |
| 0.125 | 50 | 0.952 | 0.840 | 1:400 |
| 0.125 | 100 | 0.984 | 0.848 | 1:800 |
| 0.25 | 3.125 | 0.633 | 0.649 | 1:12.5 |
| 0.25 | 6.25 | 0.698 | 0.618 | 1:25 |
| 0.25 | 12.5 | 0.817 | 0.578 | 1:50 |
| 0.25 | 25 | 0.871 | 0.829 | 1:100 |
| 0.25 | 50 | 0.965 | 0.694 | 1:200 |
| 0.5 | 3.125 | 0.698 | 0.662 | 1:6.25 |
| 0.5 | 6.25 | 0.780 | 0.497 | 1:12.5 |
| 0.5 | 12.5 | 0.853 | 0.515 | 1:25 |
| 0.5 | 25 | 0.925 | 0.575 | 1:50 |
| 0.5 | 50 | 0.973 | 0.581 | 1:100 |
| 0.5 | 100 | 0.989 | 0.690 | 1:200 |
| 0.5 | 200 | 0.995 | 0.837 | 1:400 |
| 1 | 6.25 | 0.812 | 0.535 | 1:6.25 |
| 1 | 12.5 | 0.879 | 0.480 | 1:12.5 |
| 1 | 25 | 0.931 | 0.557 | 1:25 |
| 1 | 50 | 0.977 | 0.533 | 1:50 |
| 1 | 100 | 0.993 | 0.526 | 1:100 |
| 1 | 200 | 0.995 | 0.837 | 1:200 |

TABLE 68

Other antitumor agent:decitabine, cell line:MDS-L

| Example compound 273 (nM) | Other antitumor agent (nM) | Fa | CI | Combination ratio (Example compound 273:other antitumor agent) |
|---|---|---|---|---|
| 0.00391 | 50 | 0.945 | 0.884 | 1:12800 |
| 0.00391 | 100 | 0.984 | 0.836 | 1:25600 |
| 0.00781 | 50 | 0.961 | 0.720 | 1:6400 |
| 0.00781 | 100 | 0.983 | 0.866 | 1:12800 |
| 0.01563 | 3.125 | 0.365 | 0.527 | 1:200 |
| 0.125 | 6.25 | 0.530 | 0.858 | 1:50 |
| 0.125 | 12.5 | 0.682 | 0.856 | 1:100 |
| 0.125 | 25 | 0.852 | 0.860 | 1:200 |
| 0.25 | 6.25 | 0.665 | 0.633 | 1:25 |
| 0.25 | 12.5 | 0.817 | 0.549 | 1:50 |
| 0.25 | 25 | 0.855 | 0.867 | 1:100 |
| 0.25 | 50 | 0.956 | 0.771 | 1:200 |
| 0.25 | 100 | 0.986 | 0.772 | 1:400 |
| 0.5 | 3.125 | 0.618 | 0.899 | 1:6.25 |
| 0.5 | 6.25 | 0.736 | 0.593 | 1:12.5 |
| 0.5 | 12.5 | 0.849 | 0.509 | 1:25 |
| 0.5 | 25 | 0.891 | 0.728 | 1:50 |
| 0.5 | 50 | 0.975 | 0.550 | 1:100 |
| 0.5 | 100 | 0.991 | 0.605 | 1:200 |
| 0.5 | 200 | 0.996 | 0.735 | 1:400 |
| 1 | 6.25 | 0.808 | 0.525 | 1:6.25 |
| 1 | 12.5 | 0.899 | 0.402 | 1:12.5 |
| 1 | 25 | 0.910 | 0.666 | 1:25 |
| 1 | 50 | 0.971 | 0.605 | 1:50 |
| 1 | 100 | 0.992 | 0.566 | 1:100 |

TABLE 69

Other antitumor agent:azacitidine, cell line:Kasumi-1

| Example compound 37 (nM) | Other antitumor agent (nM) | Fa | CI | Combination ratio (Example compound 37:other antitumor agent) |
|---|---|---|---|---|
| 0.391 | 5000 | 0.548 | 0.844 | 1:12800 |
| 0.781 | 5000 | 0.646 | 0.729 | 1:6400 |
| 0.781 | 10000 | 0.783 | 0.863 | 1:12800 |
| 1.563 | 1250 | 0.575 | 0.621 | 1:800 |
| 1.563 | 2500 | 0.661 | 0.564 | 1:1600 |
| 1.563 | 5000 | 0.752 | 0.605 | 1:3200 |
| 1.563 | 10000 | 0.903 | 0.521 | 1:6400 |
| 3.125 | 1250 | 0.709 | 0.560 | 1:400 |
| 3.125 | 2500 | 0.661 | 0.852 | 1:800 |
| 3.125 | 5000 | 0.915 | 0.293 | 1:1600 |
| 3.125 | 10000 | 0.927 | 0.465 | 1:3200 |
| 6.25 | 1250 | 0.827 | 0.465 | 1:200 |
| 6.25 | 2500 | 0.786 | 0.723 | 1:400 |
| 6.25 | 5000 | 0.915 | 0.361 | 1:800 |
| 6.25 | 10000 | 0.955 | 0.367 | 1:1600 |
| 12.5 | 156.25 | 0.827 | 0.769 | 1:12.5 |
| 12.5 | 312.5 | 0.839 | 0.702 | 1:25 |
| 12.5 | 625 | 0.818 | 0.860 | 1:50 |
| 12.5 | 1250 | 0.913 | 0.342 | 1:100 |
| 12.5 | 2500 | 0.931 | 0.308 | 1:200 |
| 12.5 | 5000 | 0.948 | 0.312 | 1:400 |
| 12.5 | 10000 | 0.980 | 0.240 | 1:800 |
| 25 | 156.25 | 0.895 | 0.748 | 1:6.25 |
| 25 | 1250 | 0.917 | 0.588 | 1:50 |
| 25 | 2500 | 0.940 | 0.442 | 1:100 |
| 25 | 5000 | 0.955 | 0.394 | 1:200 |
| 25 | 10000 | 0.982 | 0.260 | 1:400 |
| 50 | 1250 | 0.952 | 0.560 | 1:25 |
| 50 | 2500 | 0.963 | 0.446 | 1:50 |
| 50 | 5000 | 0.976 | 0.328 | 1:100 |
| 50 | 10000 | 0.987 | 0.255 | 1:200 |
| 100 | 1250 | 0.966 | 0.700 | 1:12.5 |

TABLE 69-continued

Other antitumor agent:azacitidine, cell line:Kasumi-1

| Example compound 37 (nM) | Other antitumor agent (nM) | Fa | CI | Combination ratio (Example compound 37:other antitumor agent) |
|---|---|---|---|---|
| 100 | 2500 | 0.977 | 0.458 | 1:25 |
| 100 | 5000 | 0.976 | 0.539 | 1:50 |
| 100 | 10000 | 0.989 | 0.295 | 1:100 |

TABLE 70

Other antitumor agent:azacitidine, cell line:Kasumi-1

| Example compound 166 (nM) | Other antitumor agent (nM) | Fa | CI | Combination ratio (Example compound 166:other antitumor agent) |
|---|---|---|---|---|
| 0.0391 | 156.25 | 0.370 | 0.325 | 1:4000 |
| 0.0391 | 312.5 | 0.296 | 0.629 | 1:8000 |
| 0.0781 | 1250 | 0.484 | 0.729 | 1:16000 |
| 0.0781 | 2500 | 0.591 | 0.717 | 1:32000 |
| 0.0781 | 5000 | 0.733 | 0.591 | 1:64000 |
| 0.0781 | 10000 | 0.877 | 0.351 | 1:128000 |
| 0.1563 | 2500 | 0.829 | 0.213 | 1:16000 |
| 0.1563 | 5000 | 0.844 | 0.302 | 1:32000 |
| 0.1563 | 10000 | 0.931 | 0.177 | 1:64000 |
| 0.3125 | 156.25 | 0.643 | 0.535 | 1:500 |
| 0.3125 | 312.5 | 0.675 | 0.478 | 1:1000 |
| 0.3125 | 625 | 0.667 | 0.545 | 1:2000 |
| 0.3125 | 1250 | 0.753 | 0.395 | 1:4000 |
| 0.3125 | 2500 | 0.829 | 0.297 | 1:8000 |
| 0.3125 | 5000 | 0.893 | 0.225 | 1:16000 |
| 0.3125 | 10000 | 0.946 | 0.150 | 1:32000 |
| 0.625 | 156.25 | 0.757 | 0.565 | 1:250 |
| 0.625 | 312.5 | 0.794 | 0.457 | 1:500 |
| 0.625 | 625 | 0.748 | 0.638 | 1:1000 |
| 0.625 | 1250 | 0.799 | 0.502 | 1:2000 |
| 0.625 | 2500 | 0.860 | 0.355 | 1:4000 |
| 0.625 | 5000 | 0.893 | 0.318 | 1:8000 |
| 0.625 | 10000 | 0.980 | 0.056 | 1:16000 |
| 1.25 | 156.25 | 0.836 | 0.644 | 1:125 |
| 1.25 | 312.5 | 0.861 | 0.524 | 1:250 |
| 1.25 | 625 | 0.845 | 0.617 | 1:500 |
| 1.25 | 1250 | 0.893 | 0.402 | 1:1000 |
| 1.25 | 2500 | 0.925 | 0.279 | 1:2000 |
| 1.25 | 5000 | 0.961 | 0.146 | 1:4000 |
| 1.25 | 10000 | 0.980 | 0.083 | 1:8000 |
| 2.5 | 156.25 | 0.906 | 0.628 | 1:62.5 |
| 2.5 | 312.5 | 0.918 | 0.535 | 1:125 |
| 2.5 | 625 | 0.889 | 0.786 | 1:250 |
| 2.5 | 1250 | 0.946 | 0.332 | 1:500 |
| 2.5 | 2500 | 0.954 | 0.285 | 1:1000 |
| 2.5 | 5000 | 0.963 | 0.240 | 1:2000 |
| 2.5 | 10000 | 0.979 | 0.141 | 1:4000 |
| 5 | 1250 | 0.952 | 0.570 | 1:250 |
| 5 | 2500 | 0.966 | 0.387 | 1:500 |
| 5 | 5000 | 0.979 | 0.229 | 1:1000 |
| 5 | 10000 | 0.988 | 0.131 | 1:2000 |
| 10 | 1250 | 0.963 | 0.833 | 1:125 |
| 10 | 2500 | 0.976 | 0.511 | 1:250 |
| 10 | 5000 | 0.986 | 0.284 | 1:500 |
| 10 | 10000 | 0.993 | 0.135 | 1:1000 |

TABLE 71

Other antitumor agent:azacitidine, cell line:Kasumi-1

| Example compound 177 (nM) | Other antitumor agent (nM) | Fa | CI | Combination ratio (Example compound 177:other antitumor agent) |
|---|---|---|---|---|
| 0.00391 | 156.25 | 0.324 | 0.309 | 1:40000 |
| 0.00391 | 312.5 | 0.225 | 0.643 | 1:80000 |
| 0.00781 | 10000 | 0.834 | 0.225 | 1:1280000 |
| 0.01563 | 2500 | 0.545 | 0.632 | 1:160000 |
| 0.01563 | 5000 | 0.720 | 0.365 | 1:320000 |
| 0.01563 | 10000 | 0.852 | 0.222 | 1:640000 |
| 0.03125 | 5000 | 0.880 | 0.153 | 1:160000 |
| 0.03125 | 10000 | 0.868 | 0.241 | 1:320000 |
| 0.0625 | 2500 | 0.732 | 0.667 | 1:40000 |
| 0.0625 | 5000 | 0.880 | 0.244 | 1:80000 |
| 0.0625 | 10000 | 0.936 | 0.136 | 1:160000 |
| 0.125 | 1250 | 0.830 | 0.611 | 1:10000 |
| 0.125 | 2500 | 0.851 | 0.530 | 1:20000 |
| 0.125 | 5000 | 0.934 | 0.201 | 1:40000 |
| 0.125 | 10000 | 0.973 | 0.078 | 1:80000 |
| 0.25 | 1250 | 0.903 | 0.576 | 1:5000 |
| 0.25 | 2500 | 0.897 | 0.626 | 1:10000 |
| 0.25 | 5000 | 0.965 | 0.175 | 1:20000 |
| 0.25 | 10000 | 0.980 | 0.096 | 1:40000 |
| 0.5 | 1250 | 0.939 | 0.638 | 1:2500 |
| 0.5 | 2500 | 0.947 | 0.539 | 1:5000 |
| 0.5 | 5000 | 0.976 | 0.217 | 1:10000 |
| 0.5 | 10000 | 0.984 | 0.139 | 1:20000 |
| 1 | 5000 | 0.976 | 0.422 | 1:5000 |
| 1 | 10000 | 0.984 | 0.265 | 1:10000 |

TABLE 72

Other antitumor agent:azacitidine, cell line:Kasumi-1

| Example compound 273 (nM) | Other antitumor agent (nM) | Fa | CI | Combination ratio (Example compound 273:other antitumor agent) |
|---|---|---|---|---|
| 0.00391 | 156.25 | 0.206 | 0.316 | 1:40000 |
| 0.00391 | 312.5 | 0.295 | 0.283 | 1:80000 |
| 0.00781 | 1250 | 0.384 | 0.588 | 1:160000 |
| 0.00781 | 2500 | 0.437 | 0.794 | 1:320000 |
| 0.00781 | 5000 | 0.635 | 0.558 | 1:640000 |
| 0.00781 | 10000 | 0.747 | 0.556 | 1:1280000 |
| 0.01563 | 1250 | 0.384 | 0.733 | 1:80000 |
| 0.01563 | 2500 | 0.644 | 0.356 | 1:160000 |
| 0.01563 | 5000 | 0.691 | 0.463 | 1:320000 |
| 0.01563 | 10000 | 0.849 | 0.279 | 1:640000 |
| 0.03125 | 156.25 | 0.476 | 0.459 | 1:5000 |
| 0.03125 | 312.5 | 0.425 | 0.595 | 1:10000 |
| 0.03125 | 625 | 0.404 | 0.743 | 1:20000 |
| 0.03125 | 1250 | 0.492 | 0.659 | 1:40000 |
| 0.03125 | 2500 | 0.644 | 0.475 | 1:80000 |
| 0.03125 | 5000 | 0.858 | 0.193 | 1:160000 |
| 0.03125 | 10000 | 0.914 | 0.160 | 1:320000 |
| 0.0625 | 156.25 | 0.563 | 0.656 | 1:2500 |
| 0.0625 | 312.5 | 0.640 | 0.514 | 1:5000 |
| 0.0625 | 625 | 0.561 | 0.730 | 1:10000 |
| 0.0625 | 1250 | 0.704 | 0.463 | 1:20000 |
| 0.0625 | 2500 | 0.724 | 0.498 | 1:40000 |
| 0.0625 | 5000 | 0.858 | 0.279 | 1:80000 |
| 0.0625 | 10000 | 0.934 | 0.159 | 1:160000 |
| 0.125 | 156.25 | 0.785 | 0.534 | 1:1250 |
| 0.125 | 312.5 | 0.771 | 0.579 | 1:2500 |
| 0.125 | 625 | 0.683 | 0.870 | 1:5000 |
| 0.125 | 1250 | 0.781 | 0.590 | 1:10000 |
| 0.125 | 2500 | 0.860 | 0.393 | 1:20000 |
| 0.125 | 5000 | 0.910 | 0.281 | 1:40000 |
| 0.125 | 10000 | 0.951 | 0.180 | 1:80000 |
| 0.25 | 156.25 | 0.874 | 0.618 | 1:625 |
| 0.25 | 312.5 | 0.869 | 0.645 | 1:1250 |
| 0.25 | 625 | 0.839 | 0.799 | 1:2500 |
| 0.25 | 1250 | 0.903 | 0.497 | 1:5000 |

TABLE 72-continued

Other antitumor agent:azacitidine, cell line:Kasumi-1

| Example compound 273 (nM) | Other antitumor agent (nM) | Fa | CI | Combination ratio (Example compound 273:other antitumor agent) |
|---|---|---|---|---|
| 0.25 | 2500 | 0.936 | 0.345 | 1:10000 |
| 0.25 | 5000 | 0.963 | 0.220 | 1:20000 |
| 0.25 | 10000 | 0.979 | 0.141 | 1:40000 |
| 0.5 | 1250 | 0.933 | 0.695 | 1:2500 |
| 0.5 | 2500 | 0.943 | 0.606 | 1:5000 |
| 0.5 | 5000 | 0.968 | 0.375 | 1:10000 |
| 0.5 | 10000 | 0.985 | 0.197 | 1:20000 |
| 1 | 5000 | 0.973 | 0.628 | 1:5000 |
| 1 | 10000 | 0.985 | 0.383 | 1:10000 |

TABLE 73

Other antitumor agent:azacitidine, cell line:MDS-L

| Example compound 37 (nM) | Other antitumor agent (nM) | Fa | CI | Combination ratio (Example compound 37:other antitumor agent) |
|---|---|---|---|---|
| 0.391 | 312.5 | 0.376 | 0.547 | 1:800 |
| 0.391 | 625 | 0.451 | 0.720 | 1:1600 |
| 0.391 | 1250 | 0.706 | 0.403 | 1:3200 |
| 0.391 | 2500 | 0.724 | 0.722 | 1:6400 |
| 0.781 | 156.25 | 0.245 | 0.789 | 1:200 |
| 0.781 | 312.5 | 0.368 | 0.624 | 1:400 |
| 0.781 | 625 | 0.451 | 0.753 | 1:800 |
| 0.781 | 1250 | 0.663 | 0.515 | 1:1600 |
| 0.781 | 2500 | 0.706 | 0.804 | 1:3200 |
| 1.563 | 1250 | 0.663 | 0.532 | 1:800 |
| 12.5 | 156.25 | 0.509 | 0.840 | 1:12.5 |
| 25 | 312.5 | 0.615 | 0.870 | 1:12.5 |

TABLE 74

Other antitumor agent:azacitidine, cell line:MDS-L

| Example compound 166 (nM) | Other antitumor agent (nM) | Fa | CI | Conbination ratio (Example compound 166:other antitumor agent) |
|---|---|---|---|---|
| 0.0391 | 312.5 | 0.219 | 0.897 | 1:8000 |
| 0.0391 | 625 | 0.433 | 0.604 | 1:16000 |
| 0.0781 | 312.5 | 0.338 | 0.543 | 1:4000 |
| 0.0781 | 625 | 0.433 | 0.636 | 1:8000 |
| 0.1563 | 312.5 | 0.445 | 0.391 | 1:2000 |
| 0.1563 | 625 | 0.455 | 0.637 | 1:4000 |
| 0.3125 | 156.25 | 0.344 | 0.712 | 1:500 |
| 0.3125 | 312.5 | 0.367 | 0.793 | 1:1000 |
| 0.625 | 1250 | 0.571 | 0.884 | 1:2000 |
| 0.625 | 2500 | 0.719 | 0.844 | 1:4000 |
| 1.25 | 312.5 | 0.540 | 0.657 | 1:250 |
| 1.25 | 625 | 0.589 | 0.646 | 1:500 |
| 1.25 | 1250 | 0.674 | 0.637 | 1:1000 |
| 1.25 | 2500 | 0.788 | 0.623 | 1:2000 |
| 1.25 | 5000 | 0.853 | 0.793 | 1:4000 |
| 2.5 | 312.5 | 0.604 | 0.722 | 1:125 |
| 2.5 | 625 | 0.695 | 0.487 | 1:250 |
| 2.5 | 1250 | 0.793 | 0.380 | 1:500 |
| 2.5 | 2500 | 0.848 | 0.448 | 1:1000 |
| 2.5 | 5000 | 0.896 | 0.566 | 1:2000 |
| 2.5 | 10000 | 0.936 | 0.691 | 1:4000 |
| 5 | 312.5 | 0.711 | 0.568 | 1:62.5 |
| 5 | 625 | 0.770 | 0.419 | 1:125 |
| 5 | 1250 | 0.818 | 0.393 | 1:250 |
| 5 | 2500 | 0.867 | 0.422 | 1:500 |
| 5 | 5000 | 0.938 | 0.346 | 1:1000 |
| 5 | 10000 | 0.959 | 0.459 | 1:2000 |

TABLE 74-continued

Other antitumor agent:azacitidine, cell line:MDS-L

| Example compound 166 (nM) | Other antitumor agent (nM) | Fa | CI | Conbination ratio (Example compound 166:other antitumor agent) |
|---|---|---|---|---|
| 10 | 625 | 0.790 | 0.564 | 1:62.5 |
| 10 | 1250 | 0.827 | 0.499 | 1:125 |
| 10 | 2500 | 0.878 | 0.445 | 1:250 |
| 10 | 5000 | 0.911 | 0.535 | 1:500 |
| 10 | 10000 | 0.962 | 0.438 | 1:1000 |

TABLE 75

Other antitumor agent:azacitidine, cell line:MDS-L

| Example compound 177 (nM) | Other antitumor agent (nM) | Fa | CI | Combination ratio (Example compound 177:other antitumor agent) |
|---|---|---|---|---|
| 0.00781 | 156.25 | 0.250 | 0.452 | 1:20000 |
| 0.00781 | 312.5 | 0.357 | 0.439 | 1:40000 |
| 0.01563 | 156.25 | 0.337 | 0.357 | 1:10000 |
| 0.01563 | 312.5 | 0.344 | 0.539 | 1:20000 |
| 0.01563 | 625 | 0.414 | 0.691 | 1:40000 |
| 0.03125 | 156.25 | 0.297 | 0.662 | 1:5000 |
| 0.03125 | 312.5 | 0.369 | 0.599 | 1:10000 |
| 0.0625 | 156.25 | 0.394 | 0.569 | 1:2500 |
| 0.125 | 312.5 | 0.471 | 0.722 | 1:2500 |
| 0.125 | 625 | 0.552 | 0.641 | 1:5000 |
| 0.125 | 1250 | 0.639 | 0.681 | 1:10000 |
| 0.125 | 2500 | 0.765 | 0.675 | 1:20000 |
| 0.125 | 5000 | 0.840 | 0.839 | 1:40000 |
| 0.25 | 312.5 | 0.584 | 0.602 | 1:1250 |
| 0.25 | 625 | 0.643 | 0.549 | 1:2500 |
| 0.25 | 1250 | 0.739 | 0.485 | 1:5000 |
| 0.25 | 2500 | 0.796 | 0.609 | 1:10000 |
| 0.25 | 5000 | 0.890 | 0.579 | 1:20000 |
| 0.25 | 10000 | 0.945 | 0.578 | 1:40000 |
| 0.5 | 156.25 | 0.608 | 0.814 | 1:313 |
| 0.5 | 312.5 | 0.721 | 0.405 | 1:625 |
| 0.5 | 625 | 0.777 | 0.332 | 1:1250 |
| 0.5 | 1250 | 0.821 | 0.346 | 1:2500 |
| 0.5 | 2500 | 0.844 | 0.484 | 1:5000 |
| 0.5 | 5000 | 0.917 | 0.451 | 1:10000 |
| 0.5 | 10000 | 0.955 | 0.482 | 1:20000 |
| 1 | 312.5 | 0.749 | 0.568 | 1:313 |
| 1 | 625 | 0.788 | 0.471 | 1:625 |
| 1 | 1250 | 0.822 | 0.458 | 1:1250 |
| 1 | 2500 | 0.897 | 0.339 | 1:2500 |
| 1 | 5000 | 0.923 | 0.438 | 1:5000 |
| 1 | 10000 | 0.958 | 0.462 | 1:10000 |

TABLE 76

Other antitumor agent: azacitidine, cell line:MDS-L

| Example compound 273 (nM) | Other antitumor agent (nM) | Fa | CI | Combination ratio (Example compound 273:other antitumor agent) |
|---|---|---|---|---|
| 0.00781 | 156.25 | 0.215 | 0.537 | 1:20000 |
| 0.00781 | 312.5 | 0.381 | 0.383 | 1:40000 |
| 0.00781 | 625 | 0.374 | 0.733 | 1:80000 |
| 0.01563 | 2500 | 0.696 | 0.801 | 1:160000 |
| 0.01563 | 5000 | 0.818 | 0.852 | 1:320000 |
| 0.03125 | 156.25 | 0.296 | 0.627 | 1:5000 |
| 0.03125 | 312.5 | 0.391 | 0.518 | 1:10000 |
| 0.0625 | 156.25 | 0.442 | 0.423 | 1:2500 |
| 0.125 | 625 | 0.561 | 0.614 | 1:5000 |
| 0.125 | 1250 | 0.616 | 0.741 | 1:10000 |
| 0.125 | 2500 | 0.768 | 0.622 | 1:20000 |

TABLE 76-continued

Other antitumor agent: azacitidine, cell line:MDS-L

| Example compound 273 (nM) | Other antitumor agent (nM) | Fa | CI | Combination ratio (Example compound 273:other antitumor agent) |
|---|---|---|---|---|
| 0.125 | 5000 | 0.827 | 0.833 | 1:40000 |
| 0.125 | 10000 | 0.920 | 0.720 | 1:80000 |
| 0.25 | 312.5 | 0.641 | 0.453 | 1:1250 |
| 0.25 | 625 | 0.645 | 0.564 | 1:2500 |
| 0.25 | 1250 | 0.724 | 0.527 | 1:5000 |
| 0.25 | 2500 | 0.810 | 0.527 | 1:10000 |
| 0.25 | 5000 | 0.921 | 0.369 | 1:20000 |
| 0.5 | 156.25 | 0.611 | 0.875 | 1:313 |
| 0.5 | 312.5 | 0.663 | 0.680 | 1:625 |
| 0.5 | 625 | 0.745 | 0.463 | 1:1250 |
| 0.5 | 1250 | 0.809 | 0.395 | 1:2500 |
| 0.5 | 2500 | 0.853 | 0.439 | 1:5000 |
| 0.5 | 5000 | 0.929 | 0.348 | 1:10000 |
| 0.5 | 10000 | 0.965 | 0.327 | 1:20000 |
| 1 | 312.5 | 0.711 | 0.893 | 1:313 |
| 1 | 625 | 0.801 | 0.489 | 1:625 |
| 1 | 1250 | 0.824 | 0.497 | 1:1250 |
| 1 | 2500 | 0.905 | 0.309 | 1:2500 |
| 1 | 5000 | 0.930 | 0.367 | 1:5000 |
| 1 | 10000 | 0.967 | 0.315 | 1:10000 |

TABLE 77

Other antitumor agent:ATRA, cell line:Kasumi-1

| Example compound 37 (nM) | Other antitumor agent (nM) | Fa | CI | Combination ratio (Example compound 37:other antitumor agent) |
|---|---|---|---|---|
| 0.391 | 2000 | 0.635 | 0.566 | 1:5120 |
| 3.13 | 3.2 | 0.564 | 0.877 | 1:1.02 |
| 3.13 | 16 | 0.579 | 0.824 | 1:5.11 |
| 6.25 | 80 | 0.786 | 0.530 | 1:12.8 |

TABLE 78

Other antitumor agent:ATRA, cell line:Kasumi-1

| Example compound 166 (nM) | Other antitumor agent (nM) | Fa | CI | Combination ratio (Example compound 166:other antitumor agent) |
|---|---|---|---|---|
| 0.0391 | 2000 | 0.528 | 0.869 | 1:51200 |
| 0.313 | 0.64 | 0.529 | 0.852 | 1:2.05 |
| 0.625 | 0.64 | 0.713 | 0.730 | 1:1.02 |
| 0.625 | 3.2 | 0.732 | 0.660 | 1:5.12 |
| 0.625 | 16 | 0.701 | 0.779 | 1:25.6 |
| 0.625 | 80 | 0.695 | 0.807 | 1:128 |

TABLE 79

Other antitumor agent:ATRA, cell line:Kasumi-1

| Example compound 177 (nM) | Other antitumor agent (nM) | Fa | CI | Combination ratio (Example compound 177:other antitumor agent) |
|---|---|---|---|---|
| 0.00391 | 16 | 0.166 | 0.737 | 1:4090 |
| 0.0313 | 3.2 | 0.440 | 0.824 | 1:102 |
| 0.0625 | 80 | 0.651 | 0.703 | 1:1280 |

TABLE 80

Other antitumor agent:ATRA, cell line:Kasumi-1

| Example compound 273 (nM) | Other antitumor agent (nM) | Fa | CI | Combination ratio (Example compound 273:other antitumor agent) |
|---|---|---|---|---|
| 0.00391 | 3.2 | 0.265 | 0.304 | 1:818 |
| 0.00391 | 16 | 0.292 | 0.369 | 1:4090 |
| 0.00391 | 80 | 0.314 | 0.770 | 1:20500 |
| 0.00781 | 3.2 | 0.258 | 0.597 | 1:410 |

TABLE 81

Other antitumor agent:daunorubicin, cell line:Kasumi-1

| Example compound 37 (nM) | Other antitumor agent (nM) | Fa | CI | Combination ratio (Example compound 37:other antitumor agent) |
|---|---|---|---|---|
| 0.781 | 10 | 0.992 | 0.283 | 1:12.8 |
| 1.563 | 2.5 | 0.703 | 0.654 | 1:1.6 |
| 1.563 | 5 | 0.773 | 0.893 | 1:3.2 |
| 1.563 | 10 | 0.987 | 0.360 | 1:6.4 |
| 3.125 | 2.5 | 0.703 | 0.869 | 1:0.8 |
| 3.125 | 5 | 0.894 | 0.611 | 1:1.6 |
| 3.125 | 10 | 0.994 | 0.256 | 1:3.2 |
| 6.25 | 5 | 0.894 | 0.733 | 1:0.8 |
| 6.25 | 10 | 0.996 | 0.214 | 1:1.6 |
| 12.5 | 1.25 | 0.853 | 0.851 | 1:0.1 |
| 12.5 | 2.5 | 0.878 | 0.834 | 1:0.2 |
| 12.5 | 5 | 0.942 | 0.616 | 1:0.4 |
| 12.5 | 10 | 0.997 | 0.191 | 1:0.8 |
| 25 | 2.5 | 0.929 | 0.832 | 1:0.1 |
| 25 | 5 | 0.966 | 0.572 | 1:0.2 |
| 25 | 10 | 0.998 | 0.165 | 1:0.4 |
| 50 | 5 | 0.971 | 0.751 | 1:0.1 |
| 50 | 10 | 0.999 | 0.124 | 1:0.2 |
| 100 | 10 | 0.998 | 0.250 | 1:0.1 |

TABLE 82

Other antitumor agent:daunorubicin, cell line:Kasumi-1

| Example compound 166 (nM) | Other antitumor agent (nM) | Fa | CI | Combination ratio (Example compound 166:other antitumor agent) |
|---|---|---|---|---|
| 0.0781 | 10 | 0.986 | 0.823 | 1:128 |
| 0.1563 | 10 | 0.986 | 0.824 | 1:64 |
| 0.3125 | 5 | 0.894 | 0.771 | 1:16 |
| 0.3125 | 10 | 0.995 | 0.622 | 1:32 |
| 0.625 | 0.625 | 0.706 | 0.875 | 1:1 |
| 0.625 | 1.25 | 0.751 | 0.767 | 1:2 |
| 0.625 | 2.5 | 0.801 | 0.778 | 1:4 |
| 0.625 | 5 | 0.893 | 0.830 | 1:8 |
| 0.625 | 10 | 0.995 | 0.645 | 1:16 |
| 1.25 | 0.1563 | 0.835 | 0.517 | 1:0.125 |
| 1.25 | 0.3125 | 0.828 | 0.581 | 1:0.25 |
| 1.25 | 0.625 | 0.827 | 0.640 | 1:0.5 |
| 1.25 | 1.25 | 0.838 | 0.681 | 1:1 |
| 1.25 | 2.5 | 0.870 | 0.701 | 1:2 |
| 1.25 | 5 | 0.940 | 0.697 | 1:4 |
| 1.25 | 10 | 0.996 | 0.594 | 1:8 |
| 2.5 | 0.1563 | 0.866 | 0.705 | 1:0.0625 |
| 2.5 | 0.3125 | 0.886 | 0.562 | 1:0.125 |
| 2.5 | 0.625 | 0.879 | 0.664 | 1:0.25 |
| 2.5 | 1.25 | 0.905 | 0.554 | 1:0.5 |
| 2.5 | 2.5 | 0.925 | 0.582 | 1:1 |
| 2.5 | 5 | 0.960 | 0.638 | 1:2 |
| 2.5 | 10 | 0.996 | 0.596 | 1:4 |
| 5 | 0.1563 | 0.912 | 0.692 | 1:0.0313 |
| 5 | 0.3125 | 0.928 | 0.523 | 1:0.0625 |

TABLE 82-continued

Other antitumor agent:daunorubicin, cell line:Kasumi-1

| Example compound 166 (nM) | Other antitumor agent (nM) | Fa | CI | Combination ratio (Example compound 166:other antitumor agent) |
|---|---|---|---|---|
| 5 | 0.625 | 0.916 | 0.705 | 1:0.125 |
| 5 | 1.25 | 0.931 | 0.609 | 1:0.25 |
| 5 | 2.5 | 0.943 | 0.634 | 1:0.5 |
| 5 | 5 | 0.968 | 0.648 | 1:1 |
| 5 | 10 | 0.995 | 0.636 | 1:2 |
| 10 | 0.313 | 0.934 | 0.880 | 1:0.0313 |
| 10 | 0.625 | 0.944 | 0.721 | 1:0.0625 |
| 10 | 1.25 | 0.942 | 0.834 | 1:0.125 |
| 10 | 2.5 | 0.947 | 0.886 | 1:0.25 |
| 10 | 5 | 0.969 | 0.756 | 1:0.5 |
| 10 | 10 | 0.997 | 0.558 | 1:1 |

TABLE 83

Other antitumor agent:daunorubicin, cell line:Kasumi-1

| Example compound 177 (nM) | Other antitumor agent (nM) | Fa | CI | Combination ratio (Example compound 177:other antitumor agent) |
|---|---|---|---|---|
| 0.01563 | 10 | 0.950 | 0.859 | 1:640 |
| 0.03125 | 5 | 0.768 | 0.826 | 1:160 |
| 0.03125 | 10 | 0.967 | 0.779 | 1:320 |
| 0.0625 | 10 | 0.980 | 0.697 | 1:160 |
| 0.125 | 0.3125 | 0.730 | 0.795 | 1:2.5 |
| 0.125 | 0.625 | 0.729 | 0.842 | 1:5 |
| 0.125 | 1.25 | 0.756 | 0.849 | 1:10 |
| 0.25 | 10 | 0.987 | 0.708 | 1:40 |
| 0.5 | 10 | 0.992 | 0.687 | 1:20 |
| 1 | 10 | 0.993 | 0.814 | 1:10 |

TABLE 84

Other antitumor agent:daunorubicin, cell line:Kasumi-1

| Example compound 273 (nM) | Other antitumor agent (nM) | Fa | CI | Combination ratio (Example compound 273:other antitumor agent) |
|---|---|---|---|---|
| 0.00781 | 10 | 0.974 | 0.790 | 1:1280 |
| 0.01563 | 10 | 0.983 | 0.702 | 1:640 |
| 0.03125 | 10 | 0.977 | 0.778 | 1:320 |
| 0.0625 | 10 | 0.983 | 0.724 | 1:160 |
| 0.125 | 10 | 0.990 | 0.635 | 1:80 |
| 0.25 | 5 | 0.937 | 0.873 | 1:20 |
| 0.25 | 10 | 0.995 | 0.533 | 1:40 |
| 0.5 | 10 | 0.997 | 0.481 | 1:20 |
| 1 | 10 | 0.994 | 0.713 | 1:10 |

These results indicated that the antitumor effects of the biphenyl compounds were synergistically potentiated when used in combination with an antimetabolite (cytarabine, decitabine, or azacitidine), an all-trans retinoic acid (tretinoin (ATRA)), or an antitumor antibiotic (daunorubicin).

Test Example 5: Combination of Biphenyl Compounds and Other Antitumor Agents Using Human Small-Cell Lung Cancer Cell Line (In Vitro)

The following tables show the source of reagents, the source of tumor cell lines, the media used, and the number of seeded cells.

TABLE 85

| Reagent | Source |
|---|---|
| Fetal bovine serum (FBS) | Biological Industries |
| RPMI-1640 medium | GIBCO |
| F-12K medium | GIBCO |
| Cisplatin | SIGMA-ALDRICH |
| Carboplatin | SIGMA-ALDRICH |
| Etoposide | SIGMA-ALDRICH |
| Paclitaxel | Wako Pure Chemical Industries, Ltd. |
| SN-38 | Tokyo Chemical Industry Co., Ltd. |

TABLE 86

| Tumor cell line (origin) | Source of cell line | Medium | Number of seeded cells per well (cells) |
|---|---|---|---|
| NCI-H1417 (human small-cell lung cancer) | ATCC | RPMI-1640 medium containing 10% FBS | 5000 |
| NCI-H510A (human small-cell lung cancer) | ATCC | F-12K medium containing 10% FBS | 7500 |

Cells were seeded at 100 µL/well in a 96-well culture plate (NUNC). The plate seeded with cells was cultured in an incubator set at 37° C. and 5% 002. On the day after seeding, drug solutions containing a combination of biphenyl compounds and other compounds having an antitumor effect mixed at various concentrations were each added to the cells. Specifically, using an RPMI-1640 medium containing 10% FBS or an F-12K medium containing 10% FBS, eight-step serial dilutions (including 0 nM) of the biphenyl compounds (Example compounds 37, 166, 177, and 273) were prepared, and eight-step serial dilutions (including 0 nM) of other compounds having an antitumor effect were also prepared. Drug solutions in which the same amount of serial dilution of each compound was dispensed were mixed at a ratio of 1:1, and a total of 64 mixed drug solutions were prepared with brute-force combinations. The table below shows the maximum concentration (expressed as the final concentration) and geometric ratio of each drug. Each of these mixed drug solutions was added to the plate at 100 µL/well (N=1), and further cultured at 37° C. under 5% $CO_2$ conditions for 10 days. Ten days later, 100 µL of the culture supernatant was removed from each well to leave 100 µL of the cell culture solution. CellTiter-Glo 2.0 Assay (Promega, Cat #: G9242) was added at 100 µL/well to the remaining 100 µL of the cell culture solution. The chemiluminescence measurement was the same as in Test Example 4.

TABLE 87

| Other compound having antitumor effect | | Biphenyl compound | | | |
|---|---|---|---|---|---|
| Name | Maximum concentration (nM) | Geometric ratio | Name | Maximum concentration (nM) | Geometric ratio | Tumor cell line |
| Cisplatin | 500 | 2 | Example compound 37 | 30 | 2 | NCI-H1417, |
|  |  |  | Example compound 166 | 10 | 2 | NCI-H510A |
|  |  |  | Example compound 177 | 1 | 2 |  |
|  |  |  | Example compound 273 | 1 | 2 |  |
| Carboplatin | 25000 | 2 | Example compound 37 | 30 | 2 | NCI-H510A |
|  |  |  | Example compound 166 | 3 | 2 |  |
|  |  |  | Example compound 177 | 1 | 2 |  |
|  |  |  | Example compound 273 | 1 | 2 |  |
| SN-38 | 1 | 2 | Example compound 37 | 30 | 2 | NCI-H1417, |
|  |  |  | Example compound 166 | 10 | 2 | NCI-H510A |
|  |  |  | Example compound 177 | 1 | 2 |  |
|  |  |  | Example compound 273 | 1 | 2 |  |
| Etoposide | 100 | 2 | Example compound 37 | 30 | 2 | NCI-H1417 |
|  |  |  | Example compound 166 | 10 | 2 |  |
|  |  |  | Example compound 177 | 1 | 2 |  |
|  |  |  | Example compound 273 | 1 | 2 |  |
| Paclitaxel | 10 | 2 | Example compound 37 | 30 | 2 | NCI-H1417 |
|  | 4 | 1.25 | Example compound 166 | 3 | 2 |  |
|  | 4 |  | Example compound 177 | 1 | 2 |  |
|  | 4 |  | Example compound 273 | 1 | 2 |  |

The effect potentiated by the combined use of drugs was evaluated according to the methods described in known documents (Trends Pharmacol. Sci., 4, 450-454, 1983; Pharmacol Rev., 58 (3), 621-81, 2006).

The specific method and the method for determining the effect of combined use were the same as in Test Example 4.

The following tables show the results.

TABLE 88

Other antitumor agent:cisplatin, cell line:NCI-H1417

| Example compound 37 (nM) | Other antitumor agent (nM) | Fa | CI | Combination ratio (Example compound 37:other antitumor agent) |
|---|---|---|---|---|
| 0.938 | 250 | 0.52 | 0.437 | 1:267 |
| 0.938 | 500 | 0.70 | 0.195 | 1:533 |
| 1.88 | 250 | 0.54 | 0.475 | 1:133 |
| 1.88 | 500 | 0.75 | 0.166 | 1:267 |
| 3.75 | 125 | 0.46 | 0.784 | 1:33.3 |
| 3.75 | 250 | 0.61 | 0.450 | 1:66.7 |
| 3.75 | 500 | 0.82 | 0.143 | 1:133 |
| 7.50 | 250 | 0.73 | 0.398 | 1:33.3 |
| 7.50 | 500 | 0.89 | 0.134 | 1:66.7 |
| 15 | 125 | 0.74 | 0.679 | 1:8.33 |
| 15 | 250 | 0.83 | 0.409 | 1:16.7 |
| 15 | 500 | 0.93 | 0.156 | 1:33.3 |
| 30 | 125 | 0.87 | 0.587 | 1:4.17 |
| 30 | 250 | 0.89 | 0.492 | 1:8.33 |
| 30 | 500 | 0.96 | 0.175 | 1:16.7 |

TABLE 89

Other antitumor agent:cisplatin, cell line:NCI-H1417

| Example compound 166 (nM) | Other antitumor agent (nM) | Fa | CI | Combination ratio (Example compound 166:other antitumor agent) |
|---|---|---|---|---|
| 0.313 | 7.81 | 0.20 | 0.830 | 1:25 |
| 0.313 | 15.6 | 0.26 | 0.700 | 1:50 |
| 0.625 | 125 | 0.56 | 0.696 | 1:200 |
| 0.625 | 250 | 0.70 | 0.566 | 1:400 |
| 0.625 | 500 | 0.88 | 0.288 | 1:800 |

TABLE 89-continued

Other antitumor agent:cisplatin, cell line:NCI-H1417

| Example compound 166 (nM) | Other antitumor agent (nM) | Fa | CI | Combination ratio (Example compound 166:other antitumor agent) |
|---|---|---|---|---|
| 1.25 | 7.81 | 0.58 | 0.706 | 1:6.25 |
| 1.25 | 15.6 | 0.55 | 0.804 | 1:12.5 |
| 1.25 | 31.3 | 0.60 | 0.710 | 1:25 |
| 1.25 | 62.5 | 0.58 | 0.838 | 1:50 |
| 1.25 | 125 | 0.68 | 0.670 | 1:100 |
| 1.25 | 250 | 0.80 | 0.477 | 1:200 |
| 1.25 | 500 | 0.92 | 0.243 | 1:400 |
| 2.5 | 7.81 | 0.70 | 0.899 | 1:3.12 |
| 2.5 | 15.6 | 0.73 | 0.804 | 1:6.25 |
| 2.5 | 31.3 | 0.71 | 0.894 | 1:12.5 |
| 2.5 | 62.5 | 0.73 | 0.859 | 1:25 |
| 2.5 | 125 | 0.78 | 0.737 | 1:50 |
| 2.5 | 250 | 0.88 | 0.444 | 1:100 |
| 2.5 | 500 | 0.94 | 0.272 | 1:200 |
| 5 | 250 | 0.90 | 0.659 | 1:50 |
| 5 | 500 | 0.95 | 0.384 | 1:100 |
| 10 | 500 | 0.96 | 0.568 | 1:50 |

TABLE 90

Other antitumor agent:cisplatin, cell line:NCI-H1417

| Example compound 177 (nM) | Other antitumor agent (nM) | Fa | CI | Combination ratio (Example compound 177:other antitumor agent) |
|---|---|---|---|---|
| 0.0156 | 31.3 | 0.19 | 0.751 | 1:2000 |
| 0.0625 | 500 | 0.78 | 0.478 | 1:8000 |
| 0.125 | 250 | 0.65 | 0.732 | 1:2000 |
| 0.125 | 500 | 0.89 | 0.259 | 1:4000 |
| 0.25 | 62.5 | 0.68 | 0.756 | 1:250 |
| 0.25 | 125 | 0.71 | 0.716 | 1:500 |
| 0.25 | 250 | 0.84 | 0.389 | 1:1000 |
| 0.25 | 500 | 0.95 | 0.146 | 1:2000 |
| 0.5 | 15.6 | 0.79 | 0.747 | 1:31.3 |
| 0.5 | 31.3 | 0.80 | 0.710 | 1:62.5 |
| 0.5 | 62.5 | 0.78 | 0.831 | 1:125 |
| 0.5 | 125 | 0.85 | 0.535 | 1:250 |

TABLE 90-continued

Other antitumor agent:cisplatin, cell line:NCI-H1417

| Example compound 177 (nM) | Other antitumor agent (nM) | Fa | CI | Combination ratio (Example compound 177:other antitumor agent) |
|---|---|---|---|---|
| 0.5 | 250 | 0.87 | 0.501 | 1:500 |
| 0.5 | 500 | 0.95 | 0.211 | 1:1000 |
| 1 | 125 | 0.90 | 0.615 | 1:125 |
| 1 | 250 | 0.92 | 0.506 | 1:250 |
| 1 | 500 | 0.96 | 0.266 | 1:500 |

TABLE 91

Other antitumor agent:cisplatin, cell line:NCI-H1417

| Example compound 273 (nM) | Other antitumor agent (nM) | Fa | CI | Combination ratio (Example compound 273:other antitumor agent) |
|---|---|---|---|---|
| 0.0313 | 500 | 0.73 | 0.321 | 1:16000 |
| 0.0625 | 250 | 0.55 | 0.791 | 1:4000 |
| 0.0625 | 500 | 0.83 | 0.181 | 1:5000 |
| 0.125 | 250 | 0.78 | 0.314 | 1:2000 |
| 0.125 | 500 | 0.90 | 0.133 | 1:4000 |
| 0.25 | 7.81 | 0.70 | 0.698 | 1:31.3 |
| 0.25 | 15.6 | 0.68 | 0.768 | 1:62.5 |
| 0.25 | 31.3 | 0.73 | 0.621 | 1:125 |
| 0.25 | 62.5 | 0.70 | 0.733 | 1:250 |
| 0.25 | 125 | 0.78 | 0.511 | 1:500 |
| 0.25 | 250 | 0.86 | 0.315 | 1:1000 |
| 0.25 | 500 | 0.94 | 0.133 | 1:2000 |
| 0.5 | 31.3 | 0.80 | 0.851 | 1:62.5 |
| 0.5 | 62.5 | 0.82 | 0.760 | 1:125 |
| 0.5 | 125 | 0.82 | 0.773 | 1:250 |
| 0.5 | 250 | 0.89 | 0.460 | 1:500 |
| 0.5 | 500 | 0.95 | 0.209 | 1:1000 |
| 1 | 125 | 0.89 | 0.889 | 1:125 |
| 1 | 250 | 0.92 | 0.647 | 1:250 |
| 1 | 500 | 0.96 | 0.328 | 1:500 |

TABLE 92

Other antitumor agent:cisplatin, cell line:NCI-H510A

| Example compound 37 (nM) | Other antitumor agent (nM) | Fa | CI | Combination ratio (Example compound 37:other antitumor agent) |
|---|---|---|---|---|
| 0.938 | 500 | 0.54 | 0.169 | 1:533 |
| 1.875 | 250 | 0.37 | 0.606 | 1:133 |
| 1.875 | 500 | 0.68 | 0.165 | 1:267 |
| 3.75 | 250 | 0.57 | 0.496 | 1:66.7 |
| 3.75 | 500 | 0.80 | 0.180 | 1:133 |
| 7.5 | 125 | 0.63 | 0.775 | 1:16.7 |
| 7.5 | 250 | 0.75 | 0.464 | 1:33.3 |
| 8 | 500 | 0.90 | 0.172 | 1:66.7 |
| 15 | 250 | 0.87 | 0.448 | 1:16.7 |
| 15 | 500 | 0.93 | 0.241 | 1:33.3 |
| 30 | 125 | 0.87 | 0.896 | 1:4.17 |
| 30 | 250 | 0.88 | 0.825 | 1:8.33 |
| 30 | 500 | 0.96 | 0.283 | 1:16.7 |

TABLE 93

Other antitumor agent:cisplatin, cell line:NCI-H510A

| Example compound 166 (nM) | Other antitumor agent (nM) | Fa | CI | Combination ratio (Example compound 166:other antitumor agent) |
|---|---|---|---|---|
| 0.313 | 250 | 0.47 | 0.483 | 1:800 |
| 0.313 | 500 | 0.77 | 0.129 | 1:1600 |
| 0.625 | 7.81 | 0.42 | 0.667 | 1:12.5 |
| 0.625 | 15.6 | 0.36 | 0.842 | 1:25 |
| 0.625 | 31.3 | 0.57 | 0.408 | 1:80 |
| 0.625 | 62.5 | 0.49 | 0.563 | 1:100 |
| 0.625 | 125 | 0.55 | 0.481 | 1:200 |
| 0.625 | 250 | 0.69 | 0.295 | 1:400 |
| 0.625 | 500 | 0.82 | 0.162 | 1:800 |
| 1.25 | 7.81 | 0.61 | 0.691 | 1:6.25 |
| 1.25 | 15.6 | 0.62 | 0.669 | 1:12.5 |
| 1.25 | 31.3 | 0.66 | 0.581 | 1:25 |
| 1.25 | 62.5 | 0.70 | 0.502 | 1:50 |
| 1.25 | 125 | 0.74 | 0.430 | 1:100 |
| 1.25 | 250 | 0.85 | 0.241 | 1:200 |
| 1.25 | 500 | 0.93 | 0.118 | 1:400 |
| 2.5 | 7.81 | 0.73 | 0.871 | 1:3.12 |
| 2.5 | 15.6 | 0.73 | 0.872 | 1:6.24 |
| 2.5 | 31.3 | 0.77 | 0.730 | 1:12.5 |
| 2.5 | 62.5 | 0.79 | 0.664 | 1:25 |
| 2.5 | 125 | 0.85 | 0.472 | 1:50 |
| 2.5 | 250 | 0.90 | 0.320 | 1:100 |
| 2.5 | 500 | 0.95 | 0.171 | 1:200 |
| 5 | 62.5 | 0.86 | 0.876 | 1:12.5 |
| 5 | 125 | 0.87 | 0.816 | 1:25 |
| 5 | 250 | 0.91 | 0.578 | 1:50 |
| 5 | 500 | 0.96 | 0.280 | 1:100 |
| 10 | 500 | 0.96 | 0.558 | 1:50 |

TABLE 94

Other antitumor agent:cisplatin, cell line:NCI-H510A

| Example compound 177 (nM) | Other antitumor agent (nM) | Fa | CI | Combination ratio (Example compound 177:other antitumor agent) |
|---|---|---|---|---|
| 0.0313 | 250 | 0.34 | 0.741 | 1:8000 |
| 0.0313 | 500 | 0.53 | 0.342 | 1:16000 |
| 0.0625 | 500 | 0.74 | 0.194 | 1:8000 |
| 0.125 | 125 | 0.58 | 0.630 | 1:1000 |
| 0.125 | 250 | 0.68 | 0.446 | 1:2000 |
| 0.125 | 500 | 0.89 | 0.144 | 1:4000 |
| 0.25 | 15.6 | 0.67 | 0.880 | 1:62.5 |
| 0.25 | 31.3 | 0.70 | 0.786 | 1:125 |
| 0.25 | 62.5 | 0.73 | 0.698 | 1:250 |
| 0.25 | 125 | 0.79 | 0.533 | 1:500 |
| 0.25 | 250 | 0.86 | 0.357 | 1:1000 |
| 0.25 | 500 | 0.94 | 0.165 | 1:2000 |
| 0.5 | 62.5 | 0.85 | 0.758 | 1:125 |
| 0.5 | 125 | 0.86 | 0.710 | 1:250 |
| 0.5 | 250 | 0.92 | 0.425 | 1:500 |
| 0.5 | 500 | 0.96 | 0.232 | 1:1000 |
| 1 | 250 | 0.94 | 0.658 | 1:250 |
| 1 | 500 | 0.97 | 0.363 | 1:500 |

TABLE 95

Other antitumor agent:cisplatin, cell line:NCI-H510A

| Example compound 273 (nM) | Other antitumor agent (nM) | Fa | CI | Combination ratio (Example compound 273:other antitumor agent) |
|---|---|---|---|---|
| 0.0313 | 250 | 0.26 | 0.895 | 1:8000 |
| 0.0313 | 500 | 0.57 | 0.162 | 1:16000 |

TABLE 95-continued

Other antitumor agent:cisplatin, cell line:NCI-H510A

| Example compound 273 (nM) | Other antitumor agent (nM) | Fa | CI | Combination ratio (Example compound 273:other antitumor agent) |
|---|---|---|---|---|
| 0.0625 | 250 | 0.42 | 0.526 | 1:4000 |
| 0.0625 | 500 | 0.74 | 0.164 | 1:8000 |
| 0.125 | 31.3 | 0.51 | 0.705 | 1:250 |
| 0.125 | 62.5 | 0.56 | 0.603 | 1:500 |
| 0.125 | 125 | 0.57 | 0.587 | 1:1000 |
| 0.125 | 250 | 0.72 | 0.348 | 1:2000 |
| 0.125 | 500 | 0.89 | 0.142 | 1:4000 |
| 0.25 | 7.81 | 0.69 | 0.777 | 1:31.3 |
| 0.25 | 15.6 | 0.71 | 0.722 | 1:62.5 |
| 0.25 | 31.3 | 0.66 | 0.865 | 1:125 |
| 0.25 | 62.5 | 0.74 | 0.642 | 1:250 |
| 0.25 | 125 | 0.80 | 0.492 | 1:500 |
| 0.25 | 250 | 0.85 | 0.375 | 1:1000 |
| 0.25 | 500 | 0.94 | 0.170 | 1:2000 |
| 0.5 | 125 | 0.86 | 0.704 | 1:250 |
| 0.5 | 250 | 0.90 | 0.523 | 1:500 |
| 0.5 | 500 | 0.96 | 0.244 | 1:1000 |
| 1 | 500 | 0.97 | 0.386 | 1:500 |

TABLE 96

Other antitumor agent:carboplatin, cell line:NCI-H510A

| Example compound 37 (nM) | Other antitumor agent (nM) | Fa | CI | Combination ratio (Example compound 37:other antitumor agent) |
|---|---|---|---|---|
| 0.938 | 1563 | 0.94 | 0.824 | 1:1670 |
| 1.88 | 1563 | 0.96 | 0.716 | 1:831 |
| 3.75 | 781 | 0.75 | 0.853 | 1:208 |
| 3.75 | 1563 | 0.97 | 0.653 | 1:417 |
| 7.5 | 391 | 0.64 | 0.869 | 1:52 |
| 7.5 | 781 | 0.88 | 0.648 | 1:104 |
| 7.5 | 1563 | 0.99 | 0.447 | 1:208 |
| 15 | 391 | 0.79 | 0.773 | 1:26 |
| 15 | 781 | 0.92 | 0.611 | 1:52 |
| 15 | 1563 | 0.99 | 0.458 | 1:104 |
| 30 | 781 | 0.95 | 0.581 | 1:26 |
| 30 | 1563 | 0.99 | 0.479 | 1:52 |

TABLE 97

Other antitumor agent:carboplatin, cell line:NCI-H510A

| Example compound 166 (nM) | Other antitumor agent (nM) | Fa | CI | Combination ratio (Example compound 166:other antitumor agent) |
|---|---|---|---|---|
| 0.0938 | 391 | 0.42 | 0.880 | 1:4160 |
| 0.0938 | 781 | 0.71 | 0.849 | 1:8330 |
| 0.0938 | 1563 | 0.97 | 0.622 | 1:16700 |
| 0.188 | 391 | 0.60 | 0.747 | 1:2080 |
| 0.188 | 781 | 0.85 | 0.647 | 1:4160 |
| 0.188 | 1563 | 0.99 | 0.421 | 1:8310 |
| 0.375 | 391 | 0.76 | 0.634 | 1:1040 |
| 0.375 | 781 | 0.91 | 0.554 | 1:2080 |
| 0.375 | 1563 | 0.99 | 0.425 | 1:4170 |
| 0.75 | 391 | 0.84 | 0.644 | 1:521 |
| 0.75 | 781 | 0.93 | 0.562 | 1:1041 |
| 0.75 | 1563 | 0.99 | 0.436 | 1:2080 |
| 1.5 | 391 | 0.88 | 0.771 | 1:260 |
| 1.5 | 781 | 0.95 | 0.573 | 1:521 |
| 1.5 | 1563 | 0.99 | 0.456 | 1:1040 |
| 3 | 781 | 0.96 | 0.666 | 1:260 |

TABLE 98

Other antitumor agent:carboplatin, cell line:NCI-H510A

| Example compound 177 (nM) | Other antitumor agent (nM) | Fa | CI | Combination ratio (Example compound 177:other antitumor agent) |
|---|---|---|---|---|
| 0.0313 | 3125 | 0.99 | 0.880 | 1:100000 |
| 0.0625 | 1563 | 0.95 | 0.780 | 1:25000 |
| 0.125 | 781 | 0.76 | 0.865 | 1:6250 |
| 0.125 | 1563 | 0.98 | 0.581 | 1:12500 |
| 0.25 | 391 | 0.76 | 0.743 | 1:1560 |
| 0.25 | 781 | 0.90 | 0.670 | 1:3120 |
| 0.25 | 1563 | 0.99 | 0.478 | 1:6250 |
| 0.5 | 391 | 0.83 | 0.897 | 1:781 |
| 0.5 | 781 | 0.94 | 0.664 | 1:1560 |
| 0.5 | 1563 | 0.99 | 0.514 | 1:3130 |
| 1 | 781 | 0.95 | 0.840 | 1:781 |
| 1 | 1563 | 0.99 | 0.587 | 1:1560 |

TABLE 99

Other antitumor agent:carboplatin, cell line:NCI-H510A

| Example compound 273 (nM) | Other antitumor agent (nM) | Fa | CI | Combination ratio (Example compound 273:other antitumor agent) |
|---|---|---|---|---|
| 0.0625 | 1563 | 0.95 | 0.790 | 1:250000 |
| 0.125 | 781 | 0.79 | 0.868 | 1:6250 |
| 0.125 | 1563 | 0.98 | 0.558 | 1:12500 |
| 0.25 | 391 | 0.78 | 0.739 | 1:1560 |
| 0.25 | 781 | 0.90 | 0.648 | 1:3130 |
| 0.25 | 1563 | 0.99 | 0.436 | 1:6250 |
| 0.5 | 391 | 0.86 | 0.724 | 1:781 |
| 0.5 | 781 | 0.94 | 0.574 | 1:1560 |
| 0.5 | 1563 | 0.99 | 0.448 | 1:3130 |
| 1 | 781 | 0.95 | 0.650 | 1:781 |
| 1 | 1563 | 0.99 | 0.471 | 1:1560 |

TABLE 100

Other antitumor agent:SN-38, cell line:NCI-H1417

| Example compound 37 (nM) | Other antitumor agent (nM) | Fa | CI | Combination ratio (Example compound 37:other antitumor agent) |
|---|---|---|---|---|
| 0.938 | 1 | 0.968 | 0.302 | 1:1.07 |
| 1.88 | 1 | 0.978 | 0.217 | 1:0.532 |
| 3.75 | 0.5 | 0.862 | 0.688 | 1:0.133 |
| 3.75 | 1 | 0.986 | 0.148 | 1:0.267 |
| 7.5 | 1 | 0.992 | 0.092 | 1:0.133 |
| 15 | 0.0313 | 0.785 | 0.805 | 1:0.00209 |
| 15 | 0.0625 | 0.806 | 0.743 | 1:0.00417 |
| 15 | 0.125 | 0.860 | 0.545 | 1:0.00833 |
| 15 | 0.25 | 0.907 | 0.425 | 1:0.0167 |
| 15 | 0.5 | 0.972 | 0.179 | 1:0.0333 |
| 30 | 0.0313 | 0.915 | 0.420 | 1:0.00104 |
| 30 | 0.0625 | 0.866 | 0.813 | 1:0.00208 |
| 30 | 0.125 | 0.907 | 0.548 | 1:0.00417 |
| 30 | 0.25 | 0.954 | 0.281 | 1:0.00833 |
| 30 | 0.5 | 0.980 | 0.160 | 1:0.0167 |
| 30 | 1 | 0.996 | 0.056 | 1:0.0333 |

TABLE 101

Other antitumor agent:SN-38, cell line:NCI-H1417

| Example compound 166 (nM) | Other antitumor agent (nM) | Fa | CI | Combination ratio (Example compound 166:other antitumor agent) |
|---|---|---|---|---|
| 0.313 | 0.5 | 0.815 | 0.715 | 1:1.6 |
| 0.313 | 1 | 0.983 | 0.159 | 1:3.19 |
| 0.625 | 0.5 | 0.910 | 0.394 | 1:0.8 |
| 0.625 | 1 | 0.989 | 0.115 | 1:1.6 |
| 1.25 | 0.125 | 0.729 | 0.799 | 1:0.1 |
| 1.25 | 0.25 | 0.830 | 0.602 | 1:0.2 |
| 1.25 | 0.5 | 0.949 | 0.276 | 1:0.4 |
| 1.25 | 1 | 0.993 | 0.084 | 1:0.8 |
| 2.5 | 0.25 | 0.874 | 0.659 | 1:0.1 |
| 2.5 | 0.5 | 0.958 | 0.300 | 1:0.2 |
| 2.5 | 1 | 0.993 | 0.095 | 1:0.4 |
| 5 | 0.5 | 0.967 | 0.346 | 1:0.2 |
| 5 | 1 | 0.994 | 0.103 | 1:0.2 |
| 10 | 0.5 | 0.974 | 0.443 | 1:0.05 |
| 10 | 1 | 0.995 | 0.120 | 1:0.1 |

TABLE 102

Other antitumor agent:SN-38, cell line:NCI-H1417

| Example compound 177 (nM) | Other antitumor agent (nM) | Fa | CI | Combination ratio (Example compound 177:other antitumor agent) |
|---|---|---|---|---|
| 0.0313 | 1 | 0.956 | 0.227 | 1:32 |
| 0.0625 | 0.5 | 0.778 | 0.826 | 1:8 |
| 0.0625 | 1 | 0.977 | 0.141 | 1:16 |
| 0.125 | 0.5 | 0.883 | 0.498 | 1:4 |
| 0.125 | 1 | 0.989 | 0.101 | 1:8 |
| 0.25 | 0.5 | 0.938 | 0.421 | 1:2 |
| 0.25 | 1 | 0.990 | 0.147 | 1:4 |
| 0.5 | 0.5 | 0.951 | 0.598 | 1:1 |
| 0.5 | 1 | 0.992 | 0.222 | 1:2 |
| 1 | 1 | 0.994 | 0.351 | 1:1 |

TABLE 103

Other antitumor agent:SN-38, cell line:NCI-H1417

| Example compound 273 (nM) | Other antitumor agent (nM) | Fa | CI | Combination ratio (Example compound 273:other antitumor agent) |
|---|---|---|---|---|
| 0.0313 | 1 | 0.960 | 0.228 | 1:32 |
| 0.0625 | 0.5 | 0.833 | 0.546 | 1:8 |
| 0.0625 | 1 | 0.985 | 0.098 | 1:16 |
| 0.125 | 0.125 | 0.625 | 0.831 | 1:1 |
| 0.125 | 0.25 | 0.752 | 0.654 | 1:2 |
| 0.125 | 0.5 | 0.914 | 0.322 | 1:4 |
| 0.125 | 1 | 0.990 | 0.073 | 1:8 |
| 0.25 | 0.0313 | 0.764 | 0.617 | 1:0.125 |
| 0.25 | 0.0625 | 0.759 | 0.675 | 1:0.25 |
| 0.25 | 0.125 | 0.760 | 0.755 | 1:0.5 |
| 0.25 | 0.25 | 0.851 | 0.537 | 1:1 |
| 0.25 | 0.5 | 0.960 | 0.199 | 1:2 |
| 0.25 | 1 | 0.992 | 0.070 | 1:4 |
| 0.5 | 0.25 | 0.876 | 0.721 | 1:0.5 |
| 0.5 | 0.5 | 0.959 | 0.295 | 1:1 |
| 0.5 | 1 | 0.992 | 0.089 | 1:2 |
| 1 | 0.25 | 0.935 | 0.662 | 1:0.25 |
| 1 | 0.5 | 0.973 | 0.321 | 1:0.5 |
| 1 | 1 | 0.993 | 0.113 | 1:1 |

TABLE 104

Other antitumor agent:SN-38, cell line:NCI-H510A

| Example compound 37 (nM) | Other antitumor agent (nM) | Fa | CI | Combination ratio (Example compound 37:other antitumor agent) |
|---|---|---|---|---|
| 0.938 | 1 | 0.516 | 0.337 | 1:1.07 |
| 1.88 | 1 | 0.615 | 0.419 | 1:0.532 |
| 3.75 | 1 | 0.775 | 0.379 | 1:0.267 |
| 7.5 | 1 | 0.874 | 0.371 | 1:0.133 |
| 15 | 0.5 | 0.860 | 0.840 | 1:0.0333 |
| 15 | 1 | 0.937 | 0.340 | 1:0.0667 |
| 30 | 0.5 | 0.924 | 0.835 | 1:0.0167 |
| 30 | 1 | 0.968 | 0.328 | 1:0.0333 |

TABLE 105

Other antitumor agent:SN-38, cell line:NCI-H510A

| Example compound 166 (nM) | Other antitumor agent (nM) | Fa | CI | Combination ratio (Example compound 166:other antitumor agent) |
|---|---|---|---|---|
| 0.313 | 1 | 0.629 | 0.363 | 1:3.19 |
| 0.625 | 0.25 | 0.503 | 0.735 | 1:0.4 |
| 0.625 | 0.5 | 0.551 | 0.660 | 1:0.8 |
| 0.625 | 1 | 0.809 | 0.215 | 1:1.6 |
| 1.25 | 0.0156 | 0.651 | 0.702 | 1:0.0125 |
| 1.25 | 0.0313 | 0.625 | 0.792 | 1:0.025 |
| 1.25 | 0.0625 | 0.662 | 0.674 | 1:0.05 |
| 1.25 | 0.125 | 0.661 | 0.686 | 1:0.1 |
| 1.25 | 0.25 | 0.701 | 0.581 | 1:0.2 |
| 1.25 | 0.5 | 0.771 | 0.419 | 1:0.4 |
| 1.25 | 1 | 0.872 | 0.222 | 1:0.8 |
| 2.5 | 0.0156 | 0.760 | 0.804 | 1:0.00624 |
| 2.5 | 0.0313 | 0.758 | 0.815 | 1:0.0125 |
| 2.5 | 0.0625 | 0.786 | 0.692 | 1:0.025 |
| 2.5 | 0.125 | 0.781 | 0.719 | 1:0.05 |
| 2.5 | 0.25 | 0.785 | 0.711 | 1:0.1 |
| 2.5 | 0.5 | 0.827 | 0.551 | 1:0.2 |
| 2.5 | 1 | 0.934 | 0.187 | 1:0.4 |
| 5 | 0.25 | 0.863 | 0.792 | 1:0.05 |
| 5 | 0.5 | 0.865 | 0.789 | 1:0.1 |
| 5 | 1 | 0.954 | 0.237 | 1:0.2 |
| 10 | 1 | 0.959 | 0.406 | 1:0.1 |

TABLE 106

Other antitumor agent:SN-38, cell line:NCI-H510A

| Example compound 177 (nM) | Other antitumor agent (nM) | Fa | CI | Combination ratio (Example compound 177:other antitumor agent) |
|---|---|---|---|---|
| 0.0313 | 1 | 0.367 | 0.205 | 1:32 |
| 0.0625 | 0.5 | 0.260 | 0.553 | 1:8 |
| 0.0625 | 1 | 0.514 | 0.271 | 1:16 |
| 0.125 | 0.0156 | 0.361 | 0.767 | 1:0.125 |
| 0.125 | 0.0313 | 0.321 | 0.852 | 1:0.25 |
| 0.125 | 0.0625 | 0.321 | 0.853 | 1:0.5 |
| 0.125 | 0.125 | 0.308 | 0.886 | 1:1 |
| 0.125 | 0.25 | 0.403 | 0.694 | 1:2 |
| 0.125 | 0.5 | 0.496 | 0.556 | 1:4 |
| 0.125 | 1 | 0.785 | 0.258 | 1:8 |
| 0.25 | 0.0156 | 0.677 | 0.714 | 1:0.0625 |
| 0.25 | 0.0313 | 0.616 | 0.834 | 1:0.125 |
| 0.25 | 0.0625 | 0.619 | 0.828 | 1:0.25 |
| 0.25 | 0.125 | 0.609 | 0.849 | 1:0.5 |
| 0.25 | 0.25 | 0.699 | 0.672 | 1:1 |
| 0.25 | 0.5 | 0.725 | 0.624 | 1:2 |
| 0.25 | 1 | 0.906 | 0.293 | 1:4 |
| 0.5 | 0.5 | 0.855 | 0.781 | 1:1 |

TABLE 106-continued

Other antitumor agent:SN-38, cell line:NCI-H510A

| Example compound 177 (nM) | Other antitumor agent (nM) | Fa | CI | Combination ratio (Example compound 177:other antitumor agent) |
|---|---|---|---|---|
| 0.5 | 1 | 0.924 | 0.512 | 1:2 |
| 1 | 1 | 0.954 | 0.750 | 1:1 |

TABLE 107

Other antitumor agent:SN-38, cell line:NCI-H510A

| Example compound 273 (nM) | Other antitumor agent (nM) | Fa | CI | Combination ratio (Example compound 273:other antitumor agent) |
|---|---|---|---|---|
| 0.0313 | 1 | 0.486 | 0.255 | 1:32 |
| 0.0625 | 0.5 | 0.326 | 0.800 | 1:8 |
| 0.0625 | 1 | 0.614 | 0.271 | 1:16 |
| 0.125 | 0.25 | 0.446 | 0.886 | 1:2 |
| 0.125 | 0.5 | 0.607 | 0.516 | 1:4 |
| 0.125 | 1 | 0.824 | 0.204 | 1:8 |
| 0.25 | 0.0625 | 0.707 | 0.698 | 1:0.25 |
| 0.25 | 0.125 | 0.682 | 0.770 | 1:0.5 |
| 0.25 | 0.25 | 0.706 | 0.702 | 1:1 |
| 0.25 | 0.5 | 0.791 | 0.483 | 1:2 |
| 0.25 | 1 | 0.903 | 0.229 | 1:4 |
| 0.5 | 0.5 | 0.858 | 0.654 | 1:1 |
| 0.5 | 1 | 0.942 | 0.289 | 1:2 |
| 1 | 1 | 0.947 | 0.535 | 1:1 |

TABLE 108

Other antitumor agent:etoposide, cell line:NCI-H1417

| Example compound 37 (nM) | Other antitumor agent (nM) | Fa | CI | Combination ratio (Example compound 37:other antitumor agent) |
|---|---|---|---|---|
| 0.938 | 100 | 0.56 | 0.588 | 1:106 |
| 1.88 | 100 | 0.64 | 0.472 | 1:53.2 |
| 3.75 | 100 | 0.68 | 0.518 | 1:26.7 |
| 7.5 | 50 | 0.62 | 0.833 | 1:6.67 |
| 7.5 | 100 | 0.80 | 0.423 | 1:13.3 |
| 15 | 50 | 0.78 | 0.748 | 1:3.33 |
| 15 | 100 | 0.89 | 0.388 | 1:6.67 |
| 30 | 25 | 0.86 | 0.875 | 1:0.833 |
| 30 | 50 | 0.88 | 0.766 | 1:1.67 |
| 30 | 100 | 0.95 | 0.348 | 1:3.33 |

TABLE 109

Other antitumor agent:etoposide, cell line:NCI-H1417

| Example compound 166 (nM) | Other antitumor agent (nM) | Fa | CI | Combination ratio (Example compound 166:other antitumor agent) |
|---|---|---|---|---|
| 0.156 | 25 | 0.35 | 0.792 | 1:160 |
| 0.156 | 50 | 0.41 | 0.729 | 1:320 |
| 0.313 | 50 | 0.50 | 0.674 | 1:160 |
| 0.313 | 100 | 0.65 | 0.353 | 1:320 |
| 0.625 | 50 | 0.57 | 0.819 | 1:80 |
| 0.625 | 100 | 0.74 | 0.344 | 1:160 |
| 1.25 | 50 | 0.79 | 0.442 | 1:40 |
| 2.5 | 25 | 0.79 | 0.862 | 1:10 |
| 2.5 | 50 | 0.84 | 0.589 | 1:20 |
| 2.5 | 100 | 0.92 | 0.238 | 1:40 |

TABLE 109-continued

Other antitumor agent:etoposide, cell line:NCI-H1417

| Example compound 166 (nM) | Other antitumor agent (nM) | Fa | CI | Combination ratio (Example compound 166:other antitumor agent) |
|---|---|---|---|---|
| 5 | 25 | 0.88 | 0.791 | 1:5 |
| 5 | 50 | 0.88 | 0.793 | 1:10 |
| 5 | 100 | 0.94 | 0.330 | 1:20 |
| 10 | 50 | 0.93 | 0.794 | 1:5 |

TABLE 110

Other antitumor agent:etoposide, cell line:NCI-H1417

| Example compound 177 (nM) | Other antitumor agent (nM) | Fa | CI | Combination ratio (Example compound 177:other antitumor agent) |
|---|---|---|---|---|
| 0.0625 | 100 | 0.62 | 0.817 | 1:1600 |
| 0.125 | 50 | 0.60 | 0.779 | 1:400 |
| 0.125 | 100 | 0.73 | 0.697 | 1:800 |
| 0.25 | 50 | 0.80 | 0.606 | 1:200 |
| 0.25 | 100 | 0.89 | 0.443 | 1:400 |
| 0.5 | 50 | 0.86 | 0.786 | 1:100 |
| 0.5 | 100 | 0.92 | 0.562 | 1:200 |

TABLE 111

Other antitumor agent:etoposide, cell line:NCI-H1417

| Example compound 273 (nM) | Other antitumor agent (nM) | Fa | CI | Combination ratio (Example compound 273:other antitumor agent) |
|---|---|---|---|---|
| 0.0156 | 50 | 0.31 | 0.887 | 1:3200 |
| 0.0313 | 100 | 0.51 | 0.531 | 1:3200 |
| 0.0625 | 100 | 0.63 | 0.404 | 1:1600 |
| 0.125 | 25 | 0.48 | 0.797 | 1:200 |
| 0.125 | 50 | 0.64 | 0.527 | 1:400 |
| 0.125 | 100 | 0.80 | 0.308 | 1:800 |
| 0.25 | 1.56 | 0.71 | 0.728 | 1:6025 |
| 0.25 | 3.13 | 0.69 | 0.776 | 1:12.5 |
| 0.25 | 6.25 | 0.66 | 0.853 | 1:25 |
| 0.25 | 12.5 | 0.67 | 0.836 | 1:50 |
| 0.25 | 25 | 0.72 | 0.726 | 1:100 |
| 0.25 | 50 | 0.80 | 0.550 | 1:200 |
| 0.25 | 100 | 0.89 | 0.349 | 1:400 |
| 0.5 | 50 | 0.87 | 0.767 | 1:100 |
| 0.5 | 100 | 0.93 | 0.492 | 1:200 |
| 1 | 100 | 0.95 | 0.775 | 1:100 |

TABLE 112

Other antitumor agent:paclitaxel, cell line:NCI-H1417

| Example compound 37 (nM) | Other antitumor agent (nM) | Fa | CI | Combination ratio (Example compound 37:other antitumor agent) |
|---|---|---|---|---|
| 0.469 | 2.5 | 0.556 | 0.455 | 1:5.33 |
| 0.469 | 5 | 0.910 | 0.615 | 1:10.7 |
| 0.938 | 2.5 | 0.548 | 0.512 | 1:2.67 |
| 0.938 | 5 | 0.909 | 0.626 | 1:5.33 |
| 1.88 | 2.5 | 0.589 | 0.584 | 1:1.33 |
| 1.88 | 5 | 0.920 | 0.632 | 1:2.66 |
| 3.75 | 2.5 | 0.586 | 0.777 | 1:0.667 |
| 3.75 | 5 | 0.931 | 0.648 | 1:1.333 |
| 7.5 | 2.5 | 0.769 | 0.749 | 1:0.333 |

TABLE 112-continued

Other antitumor agent:paclitaxel, cell line:NCI-H1417

| Example compound 37 (nM) | Other antitumor agent (nM) | Fa | CI | Combination ratio (Example compound 37:other antitumor agent) |
|---|---|---|---|---|
| 7.5 | 5 | 0.942 | 0.685 | 1:0.667 |
| 15.0 | 5 | 0.958 | 0.723 | 1:0.333 |
| 15.0 | 10 | 0.987 | 0.989 | 1:0.667 |

TABLE 113

Other antitumor agent:paclitaxel, cell line:NCI-H1417

| Example compound 166 (nM) | Other antitumor agent (nM) | Fa | CI | Combination ratio (Example compound 166:other antitumor agent) |
|---|---|---|---|---|
| 0.0469 | 1.05 | 0.829 | 0.365 | 1:22.4 |
| 0.0469 | 2.05 | 0.882 | 0.621 | 1:43.70 |
| 0.0938 | 1.05 | 0.851 | 0.368 | 1:11.20 |
| 0.0938 | 2.05 | 0.897 | 0.607 | 1:21.90 |
| 0.0938 | 4 | 0.905 | 1.158 | 1:42.60 |
| 0.188 | 1.05 | 0.896 | 0.344 | 1:5.59 |
| 0.188 | 2.05 | 0.918 | 0.582 | 1:10.9 |
| 0.188 | 4 | 0.921 | 1.112 | 1:21.3 |
| 0.375 | 1.05 | 0.574 | 1.423 | 1:2.80 |
| 0.375 | 2.05 | 0.933 | 0.571 | 1:5.47 |
| 0.375 | 4 | 0.946 | 1.007 | 1:10.7 |
| 0.75 | 1.64 | 0.731 | 1.459 | 1:2.19 |
| 0.75 | 2.05 | 0.872 | 0.924 | 1:2.73 |
| 1.5 | 1.05 | 0.785 | 1.519 | 1:0.70 |
| 1.5 | 2.05 | 0.963 | 0.547 | 1:1.37 |
| 1.5 | 2.56 | 0.941 | 0.831 | 1:1.71 |
| 1.5 | 3.2 | 0.963 | 0.819 | 1:2.13 |
| 1.5 | 4 | 0.963 | 1.021 | 1:2.67 |
| 3 | 1.31 | 0.805 | 2.445 | 1:0.44 |
| 3 | 1.64 | 0.845 | 1.967 | 1:0.55 |
| 3 | 2.05 | 0.920 | 1.146 | 1:0.68 |
| 3 | 4 | 0.967 | 1.036 | 1:1.33 |

TABLE 114

Other antitumor agent: paclitaxel, cell line:NCI-H1417

| Example compound 177 (nM) | Other antitumor agent (nM) | Fa | CI | Combination ratio (Example compound 177:other antitumor agent) |
|---|---|---|---|---|
| 0.0157 | 1.05 | 0.878 | 0.347 | 1:66.9 |
| 0.0157 | 2.05 | 0.890 | 0.661 | 1:131.0 |
| 0.0313 | 1.05 | 0.865 | 0.358 | 1:33.5 |
| 0.0313 | 2.05 | 0.884 | 0.660 | 1:65.5 |
| 0.0313 | 4 | 0.919 | 1.168 | 1:128.0 |
| 0.0625 | 1.05 | 0.878 | 0.370 | 1:16.8 |
| 0.0625 | 2.05 | 0.893 | 0.670 | 1:32.8 |
| 0.0625 | 4 | 0.906 | 1.255 | 1:64.0 |
| 0.125 | 1.05 | 0.365 | 2.248 | 1:8.4 |
| 0.125 | 2.05 | 0.910 | 0.652 | 1:16.1 |
| 0.125 | 4 | 0.924 | 1.186 | 1:32.0 |
| 0.25 | 1.05 | 0.924 | 0.368 | 1:4.2 |
| 0.25 | 1.31 | 0.621 | 1.525 | 1:5.24 |
| 0.25 | 1.64 | 0.685 | 1.383 | 1:6.56 |
| 0.25 | 2.05 | 0.849 | 0.943 | 1:8.20 |
| 0.25 | 4 | 0.946 | 1.093 | 1:16.00 |
| 0.5 | 1.05 | 0.754 | 1.274 | 1:2.10 |
| 0.5 | 2.05 | 0.953 | 0.589 | 1:4.10 |

TABLE 114-continued

Other antitumor agent: paclitaxel, cell line:NCI-H1417

| Example compound 177 (nM) | Other antitumor agent (nM) | Fa | CI | Combination ratio (Example compound 177:other antitumor agent) |
|---|---|---|---|---|
| 0.5 | 2.56 | 0.940 | 0.808 | 1:5.12 |
| 0.5 | 3.2 | 0.953 | 0.909 | 1:6.40 |
| 0.5 | 4 | 0.954 | 1.129 | 1:8.00 |
| 1 | 1.31 | 0.832 | 1.436 | 1:1.31 |
| 1 | 1.64 | 0.841 | 1.472 | 1:1.64 |
| 1 | 2.05 | 0.920 | 0.946 | 1:2.05 |
| 1 | 4 | 0.964 | 1.057 | 1:4.00 |

TABLE 115

Other antitumor agent:paclitaxel, cell line:NCI-H1417

| Example compound 273 (nM) | Other antitumor agent (nM) | Fa | CI | Combination ratio (Example compound 273:other antitumor agent) |
|---|---|---|---|---|
| 0.0157 | 1.05 | 0.846 | 0.387 | 1:66.9 |
| 0.0157 | 2.05 | 0.880 | 0.694 | 1:130.0 |
| 0.0313 | 1.05 | 0.844 | 0.395 | 1:33.5 |
| 0.0313 | 2.05 | 0.859 | 0.726 | 1:65.5 |
| 0.0313 | 4 | 0.895 | 1.285 | 1:128.0 |
| 0.0625 | 1.05 | 0.864 | 0.41 | 1:16.8 |
| 0.0625 | 2.05 | 0.885 | 0.711 | 1:32.8 |
| 0.0625 | 4 | 0.909 | 1.266 | 1:64.0 |
| 0.125 | 1.05 | 0.365 | 2.212 | 1:8.40 |
| 0.125 | 2.05 | 0.915 | 0.667 | 1:16.4 |
| 0.125 | 4 | 0.936 | 1.144 | 1:32.0 |
| 0.25 | 1.05 | 0.934 | 0.382 | 1:4.20 |
| 0.25 | 1.31 | 0.727 | 1.170 | 1 5.24 |
| 0.25 | 1.64 | 0.733 | 1.307 | 1 6.56 |
| 0.25 | 2.05 | 0.860 | 0.985 | 1 8.20 |
| 0.25 | 4 | 0.949 | 1.101 | 1 16.00 |
| 0.5 | 1.05 | 0.729 | 1.559 | 1 2.10 |
| 0.5 | 2.05 | 0.948 | 0.677 | 1 4.10 |
| 0.5 | 2.56 | 0.934 | 0.918 | 1 5.12 |
| 0.5 | 3.2 | 0.948 | 1.003 | 1 6.40 |
| 0.5 | 4 | 0.959 | 1.130 | 1 8.00 |
| 1 | 1.31 | 0.794 | 2.169 | 1 1.31 |
| 1 | 1.64 | 0.804 | 2.185 | 1 1.64 |
| 1 | 4 | 0.961 | 1.182 | 1 4.00 |

These results indicated that the antitumor effects of the biphenyl compounds were synergistically potentiated when used in combination with a platinum-based drug (cisplatin or carboplatin) or a plant alkaloid-based drug (SN-38 (active metabolite of irinotecan)), etoposide, or paclitaxel).

Test Example 6: Combination of Biphenyl Compounds and Other Antitumor Agents Using Human AML Cell Line (In Vitro)

The following tables show the source of reagents, the source of tumor cell lines, the media used, and the number of seeded cells.

TABLE 116

| Reagent | Source |
| --- | --- |
| Fetal bovine serum (FBS) | Biological Industries |
| RPMI-1640 medium | GIBCO |
| Guadecitabine | AdooQ Bioscience |
| RG7388 | ChemScene |

TABLE 117

| Tumor cell line (origin) | Source of cell line | Medium | Number of seeded cells per well (cells) |
| --- | --- | --- | --- |
| MOLM-13 (human AML cell line) | DSMZ | RPMI-1640 medium containing 10% FBS | 100 |

Cells were seeded at 100 μL/well in a 96-well culture plate (NUNC). The plate seeded with cells was cultured in an incubator set at 37° C. and 5% $CO_2$. On the day of seeding, drug solutions containing a combination of biphenyl compounds and other compounds having an antitumor effect mixed at various concentrations were each added to the cells. Specifically, using an RPMI-1640 medium containing 10% FBS, eight-step serial dilutions (including 0 nM) of the biphenyl compounds (Example compounds 37, 166, 177, and 273) were prepared, and eight-step serial dilutions (including 0 nM) of other compounds having an antitumor effect were also prepared. The table below shows the maximum concentration (expressed as the final concentration) and geometric ratio of each drug.

The procedures after production of the serial dilutions were the same as in Test Example 5.

The effect potentiated by the combined use of drugs was evaluated according to the methods described in known documents (Trends Pharmacol. Sci., 4, 450-454, 1983; Pharmacol Rev., 58 (3), 621-81, 2006).

The specific method and the method for determining the effect of combined use were the same as in Test Example 4.

The following tables show the results.

TABLE 119

| Other antitumor agent:RG7388, cell line:MOLM-13 | | | | |
| --- | --- | --- | --- | --- |
| Example compound 37 (nM) | Other antitumor agent (nM) | Fa | CI | Combination ratio (Example compound 37:other antitumor agent) |
| 3.13 | 2.63 | 0.373 | 0.683 | 1:0.842 |
| 6.25 | 5.27 | 0.801 | 0.465 | 1:0.843 |

TABLE 120

| Other antitumor agent:RG7388, cell line:MOLM-13 | | | | |
| --- | --- | --- | --- | --- |
| Example compound 166 (nM) | Other antitumor agent (nM) | Fa | CI | Combination ratio (Example compound 166:other antitumor agent) |
| 0.156 | 1.32 | 0.244 | 0.605 | 1:8.46 |
| 0.313 | 2.63 | 0.572 | 0.553 | 1:8.4 |
| 0.625 | 5.26 | 0.927 | 0.320 | 1:8.42 |

TABLE 121

| Other antitumor agent:RG7388, cell line:MOLM-13 | | | | |
| --- | --- | --- | --- | --- |
| Example compound 177 (nM) | Other antitumor agent (nM) | Fa | CI | Combination ratio (Example compound 177:other antitumor agent) |
| 0.125 | 2.63 | 0.797 | 0.209 | 1:21 |

TABLE 118

| Other compound having antitumor effect | | | Biphenyl compound | | | |
| --- | --- | --- | --- | --- | --- | --- |
| Name | Maximum concentration (nM) | Geometric ratio | Name | Maximum concentration (nM) | Geometric ratio | Tumor cell line |
| RG7388 | 15 | 1.5 | Example compound 37 | 50 | 2 | MOLM-13 |
| | | | Example compound 166 | 5 | 2 | |
| | | | Example compound 177 | 1 | 2 | |
| | | | Example compound 273 | 1 | 2 | |
| Guadecitabine | 10 | 2 | Example compound 37 | 100 | 2 | MOLM-13 |
| | | | Example compound 166 | 10 | 2 | |
| | | | Example compound 177 | 3 | 2 | |
| | | | Example compound 273 | 3 | 2 | |

TABLE 122

Other antitumor agent:RG7388, cell line:MOLM-13

| Example compound 273 (nM) | Other antitumor agent (nM) | Fa | CI | Combination ratio (Example compound 273:other antitumor agent) |
|---|---|---|---|---|
| 0.0625 | 2.63 | 0.477 | 0.712 | 1:42.1 |

TABLE 123

Other antitumor agent:guadecitabine, cell line:MOLM-13

| Example compound 37 (nM) | Other antitumor agent (nM) | Fa | CI | Combination ratio (Example compound 37:other antitumor agent) |
|---|---|---|---|---|
| 1.56 | 2.5 | 0.290 | 0.872 | 1:1.6 |
| 1.56 | 5 | 0.734 | 0.807 | 1:3.2 |
| 3.13 | 2.5 | 0.648 | 0.520 | 1:0.8 |
| 3.13 | 5 | 0.749 | 0.810 | 1:1.6 |
| 3.13 | 10 | 0.992 | 0.452 | 1:3.2 |
| 6.25 | 1.25 | 0.592 | 0.425 | 1:0.2 |
| 6.25 | 2.5 | 0.706 | 0.526 | 1:0.4 |
| 6.25 | 5 | 0.833 | 0.705 | 1:0.8 |
| 6.25 | 10 | 0.995 | 0.388 | 1:1.6 |
| 12.5 | 1.25 | 0.680 | 0.475 | 1:0.1 |
| 12.5 | 2.5 | 0.969 | 0.201 | 1:0.2 |
| 12.5 | 5 | 0.987 | 0.275 | 1:0.4 |
| 12.5 | 10 | 0.998 | 0.288 | 1:0.8 |
| 25 | 2.5 | 0.898 | 0.415 | 1:0.1 |
| 25 | 5 | 0.997 | 0.169 | 1:0.2 |
| 25 | 10 | 0.993 | 0.443 | 1:0.4 |
| 50 | 1.25 | 0.899 | 0.426 | 1:0.025 |
| 50 | 2.5 | 0.968 | 0.277 | 1:0.05 |
| 50 | 5 | 0.963 | 0.488 | 1:0.1 |
| 100 | 1.25 | 0.969 | 0.280 | 1:0.0125 |
| 100 | 2.5 | 0.997 | 0.105 | 1:0.025 |
| 100 | 5 | 0.999 | 0.123 | 1:0.05 |

TABLE 124

Other antitumor agent:guadecitabine, cell line:MOLM-13

| Example compound 166 (nM) | Other antitumor agent (nM) | Fa | CI | Combination ratio (Example compound 166:other antitumor agent) |
|---|---|---|---|---|
| 0.156 | 2.5 | 0.543 | 0.786 | 1:16 |
| 0.156 | 5 | 0.829 | 0.311 | 1:32 |
| 0.313 | 5 | 0.870 | 0.227 | 1:16 |
| 0.313 | 10 | 0.985 | 0.037 | 1:32 |
| 0.625 | 1.25 | 0.519 | 0.892 | 1:2 |
| 0.625 | 2.5 | 0.729 | 0.412 | 1:4 |
| 0.625 | 5 | 0.931 | 0.111 | 1:8 |
| 0.625 | 10 | 0.992 | 0.019 | 1:16 |
| 1.25 | 1.25 | 0.750 | 0.349 | 1:1 |
| 1.25 | 2.5 | 0.935 | 0.068 | 1:2 |
| 1.25 | 5 | 0.950 | 0.083 | 1:4 |
| 1.25 | 10 | 0.999 | 0.002 | 1:8 |
| 2.5 | 0.625 | 0.679 | 0.848 | 1:0.25 |
| 2.5 | 1.25 | 0.702 | 0.806 | 1:0.5 |
| 2.5 | 2.5 | 0.964 | 0.041 | 1:1 |
| 2.5 | 5 | 0.981 | 0.030 | 1:2 |
| 2.5 | 10 | 0.998 | 0.004 | 1:4 |
| 5 | 0.625 | 0.785 | 0.720 | 1:0.125 |
| 5 | 1.25 | 0.955 | 0.063 | 1:0.25 |
| 5 | 2.5 | 0.937 | 0.127 | 1:0.5 |
| 5 | 5 | 0.991 | 0.014 | 1:1 |
| 5 | 10 | 0.999 | 0.002 | 1:2 |
| 10 | 1.25 | 0.962 | 0.087 | 1:0.125 |
| 10 | 2.5 | 0.996 | 0.005 | 1:0.25 |
| 10 | 5 | 0.991 | 0.019 | 1:0.5 |

TABLE 125

Other antitumor agent:guadecitabine, cell line:MOLM-13

| Example compound 177 (nM) | Other antitumor agent (nM) | Fa | CI | Combination ratio (Example compound 177:other antitumor agent) |
|---|---|---|---|---|
| 0.0469 | 2.5 | 0.555 | 0.602 | 1:53.3 |
| 0.0469 | 5 | 0.735 | 0.518 | 1:107 |
| 0.0934 | 2.5 | 0.611 | 0.549 | 1:26.8 |
| 0.0934 | 5 | 0.836 | 0.308 | 1:53.5 |
| 0.0934 | 10 | 0.980 | 0.065 | 1:107 |
| 0.188 | 0.625 | 0.395 | 0.895 | 1:3.32 |
| 0.188 | 1.25 | 0.542 | 0.631 | 1:6.65 |
| 0.188 | 2.5 | 0.690 | 0.486 | 1:13.3 |
| 0.188 | 5 | 0.961 | 0.075 | 1:26.6 |
| 0.188 | 10 | 0.998 | 0.007 | 1:53.2 |
| 0.375 | 1.25 | 0.679 | 0.553 | 1:3.33 |
| 0.375 | 2.5 | 0.928 | 0.119 | 1:6.67 |
| 0.375 | 5 | 0.990 | 0.024 | 1:13.3 |
| 0.375 | 10 | 0.999 | 0.004 | 1:26.7 |
| 0.75 | 2.5 | 0.991 | 0.022 | 1:3.33 |
| 0.75 | 5 | 0.990 | 0.032 | 1:6.67 |
| 1.5 | 1.25 | 0.880 | 0.500 | 1:0.833 |
| 1.5 | 2.5 | 0.879 | 0.552 | 1:1.67 |
| 3 | 2.5 | 0.950 | 0.384 | 1:0.833 |

TABLE 126

Other antitumor agent:guadecitabine, cell line:MOLM-13

| Example compound 273 (nM) | Other antitumor agent (nM) | Fa | CI | Combination ratio (Example compound 273:other antitumor agent) |
|---|---|---|---|---|
| 0.0469 | 5 | 0.854 | 0.806 | 1:107 |
| 0.0934 | 5 | 0.910 | 0.492 | 1:53.3 |
| 0.0934 | 10 | 0.987 | 0.157 | 1:107 |
| 0.188 | 1.25 | 0.631 | 0.809 | 1:6.67 |
| 0.188 | 2.5 | 0.936 | 0.180 | 1:13.3 |
| 0.188 | 5 | 0.972 | 0.161 | 1:26.7 |
| 0.188 | 10 | 0.999 | 0.015 | 1:53.3 |
| 0.375 | 0.156 | 0.576 | 0.684 | 1:0.417 |
| 0.375 | 0.313 | 0.712 | 0.321 | 1:0.833 |
| 0.375 | 0.625 | 0.701 | 0.460 | 1:1.67 |
| 0.375 | 1.25 | 0.653 | 0.895 | 1:3.33 |
| 0.375 | 2.5 | 0.838 | 0.506 | 1:6.67 |
| 0.375 | 5 | 0.976 | 0.140 | 1:13.3 |
| 0.375 | 10 | 0.998 | 0.028 | 1:26.7 |
| 0.75 | 0.156 | 0.665 | 0.683 | 1:0.208 |
| 0.75 | 0.313 | 0.794 | 0.271 | 1:0.417 |
| 0.75 | 0.625 | 0.745 | 0.506 | 1:0.833 |
| 0.75 | 1.25 | 0.727 | 0.780 | 1:1.67 |
| 0.75 | 2.5 | 0.897 | 0.327 | 1:3.33 |
| 0.75 | 5 | 0.973 | 0.158 | 1:6.67 |
| 0.75 | 10 | 0.999 | 0.015 | 1:13.3 |
| 1.5 | 2.5 | 0.964 | 0.115 | 1:1.67 |
| 1.5 | 5 | 0.994 | 0.039 | 1:3.33 |

TABLE 126-continued

| Other antitumor agent:guadecitabine, cell line:MOLM-13 | | | | |
|---|---|---|---|---|
| Example compound 273 (nM) | Other antitumor agent (nM) | Fa | CI | Combination ratio (Example compound 273:other antitumor agent) |
| 3 | 2.5 | 0.958 | 0.154 | 1:0.833 |
| 3 | 5 | 0.993 | 0.046 | 1:1.67 |
| 3 | 10 | 0.999 | 0.015 | 1:3.33 |

These results indicated that the antitumor effects of the biphenyl compounds were synergistically potentiated when used in combination with a human MDM2 (HDM2) inhibitor (RG7388) or a DNA methylation inhibitor (guadecitabine).

As described above, the biphenyl compounds represented by Formula (I) showed an effect of potentiating their antitumor effects when used in combination with various other antitumor agents.

The invention claimed is:

1. A method for inhibiting LSD1 activity in a patient with a tumor, comprising administering a combination of a biphenyl compound or a salt thereof in combination with one or more antitumor agents in an amount effective for inhibiting LSD1 activity to a patient, wherein said biphenyl compound is selected from the group consisting of:
   1) 4-[5-[(3S)-3-aminopyrrolidine-1-carbonyl]-2-[2-fluoro-4-(2-hydroxy-2-methyl-propyl)phenyl]phenyl]-2-fluoro-benzonitrile;
   2) 4-[5-[(3-endo)-3-amino-8-azabicyclo[3.2.1]octane-8-carbonyl]-2-[2-fluoro-4-(2-hydroxy-2-methyl-propyl) phenyl]phenyl]-2-fluoro-benzonitrile;
   3) 5'-((1S,2S,4R)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile-isomer-B;
   4) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
   5) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
   6) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X; and
   7) 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.

2. A method for inhibiting LSD1 activity in a patient with a tumor, comprising administering a biphenyl compound or a salt thereof in an amount effective for inhibiting LSD1 activity, to a cancer patient, wherein said biphenyl compound is administered in combination with one or more antitumor agents, and wherein said biphenyl compound is selected from the group consisting of:
   (1) 4-[5-[(3S)-3-aminopyrrolidine-1-carbonyl]-2-[2-fluoro-4-(2-hydroxy-2-methyl-propyl)phenyl]phenyl]-2-fluoro-benzonitrile;
   (2) 4-[5-[(3-endo)-3-amino-8-azabicyclo[3.2.1]octane-8-carbonyl]-2-[2-fluoro-4-(2-hydroxy-2-methyl-propyl) phenyl]phenyl]-2-fluoro-benzonitrile;
   (3) 5'-((1S,2S,4R)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile-isomer-B;
   (4) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
   (5) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
   (6) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X; and
   (7) 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.

3. The method according to claim 1, wherein said biphenyl compound or salt thereof and said one or more other antitumor agents are administered simultaneously, sequentially, or at an interval.

4. The method according to claim 1, wherein said one or more antitumor agents are at least one member selected from the group consisting of cytarabine, azacitidine, decitabine, guadecitabine, daunorubicin, tretinoin (ATRA), RG7388, carboplatin, cisplatin, paclitaxel, irinotecan (SN-38), and etoposide.

5. The method according to claim 2, wherein said one or more antitumor agents are at least one member selected from the group consisting of cytarabine, azacitidine, decitabine, guadecitabine, daunorubicin, tretinoin (ATRA), RG7388, carboplatin, cisplatin, paclitaxel, irinotecan (SN-38), and etoposide.

6. A method for treating a tumor associated with LSD1 activity, comprising administering a combination of a biphenyl compound or a salt thereof in combination with one or more antitumor agents, in an amount effective for inhibiting LSD1 activity, to a patient with a tumor associated with LSD1 activity,
wherein the biphenyl compound is selected from the group consisting of:
   (1) 4-[5-[(3S)-3-aminopyrrolidine-1-carbonyl]-2-[2-fluoro-4-(2-hydroxy-2-methyl-propyl)phenyl]phenyl]-2-fluoro-benzonitrile;
   (2) 4-[5-[(3-endo)-3-amino-8-azabicyclo[3.2.1]octane-8-carbonyl]-2-[2-fluoro-4-(2-hydroxy-2-methyl-propyl) phenyl]phenyl]-2-fluoro-benzonitrile;
   (3) 5'-((1S,2S,4R)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile-isomer-B;
   (4) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
   (5) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
   (6) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X; and (7) 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.

7. A method for treating a tumor associated with LSD1 activity, comprising administering a biphenyl compound or a salt thereof in an amount effective for inhibiting LSD1 activity, to a cancer patient, wherein said biphenyl compound is administered in combination with one or more antitumor agents,
wherein the biphenyl compound is selected from the group consisting of:
- (1) 4-[5-[(3S)-3-aminopyrrolidine-1-carbonyl]-2-[2-fluoro-4-(2-hydroxy-2-methyl-propyl)phenyl]phenyl]-2-fluoro-benzonitrile;
- (2) 4-[5-[(3-endo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile;
- (3) 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile-isomer-B;
- (4) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
- (5) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
- (6) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X, and
- (7) 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.

8. A method for treating a cancer patient with a tumor associated with LSD1 activity, comprising administering to a cancer patient, an LSD1 inhibiting agent comprising a biphenyl compound or a salt thereof in combination with one or more antitumor agents, wherein the biphenyl compound is selected from the group consisting of
- 1) 4-[5-[(3S)-3-aminopyrrolidine-1-carbonyl]-2-[2-fluoro-4-(2-hydroxy-2-methyl-propyl)phenyl]phenyl]-2-fluoro-benzonitrile;
- 2) 4-[5-[(3-endo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile;
- 3) 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile-isomer-B;
- 4) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
- 5) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
- 6) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X; and
- 7) 5'-(((1S,2S,4R)-rel-2-amino-7-azabicyclo[2.2.1]heptan-7-yl)methyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-X.

\* \* \* \* \*